US012703858B2

(12) United States Patent
Tachikawa et al.

(10) Patent No.: US 12,703,858 B2
(45) **Date of Patent: *Aug. 11, 2026**

(54) THERAPEUTICS FOR GLYCOGEN STORAGE DISEASE TYPE III

(71) Applicant: Ultragenyx Pharmaceutical Inc., Novato, CA (US)

(72) Inventors: Kiyoshi Tachikawa, San Diego, CA (US); Carlos Gustavo Perez-Garcia, San Diego, CA (US); Padmanabh Chivukula, La Jolla, CA (US); Hari Bhaskaran, Oceanside, CA (US); Christian W. Cobaugh, Boston, MA (US); Sean Christopher Daugherty, Petaluma, CA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 1135 days.

This patent is subject to a terminal disclaimer.

(21) Appl. No.: 17/736,798

(22) Filed: May 4, 2022

(65) Prior Publication Data

US 2022/0340886 A1 Oct. 27, 2022

Related U.S. Application Data

(63) Continuation of application No. 16/617,431, filed as application No. PCT/US2018/035477 on May 31, 2018, now Pat. No. 11,377,643.

(60) Provisional application No. 62/513,350, filed on May 31, 2017.

(51) Int. Cl.

| | |
|---|---|
| ***C12N 9/10*** | (2006.01) |
| ***A61K 48/00*** | (2006.01) |
| ***A61P 3/00*** | (2006.01) |
| ***C12N 9/44*** | (2006.01) |
| ***C12N 15/11*** | (2006.01) |

(52) U.S. Cl.

CPC .............. *C12N 9/1051* (2013.01); *A61P 3/00* (2018.01); *C12N 9/2451* (2013.01); *C12N 15/11* (2013.01); *C12Y 204/01025* (2013.01); *C12Y 302/01033* (2013.01); *A61K 48/00* (2013.01); *C12N 2310/334* (2013.01); *C12N 2310/335* (2013.01)

(58) Field of Classification Search

CPC ................ C12N 9/1051; C12N 9/2451; C12N 2310/335; A61P 3/00; C12Y 204/01025; C12Y 302/01033; A61K 48/00

See application file for complete search history.

(56) References Cited

U.S. PATENT DOCUMENTS

| | | | |
|---|---|---|---|
| 8,058,069 | B2 | 11/2011 | Yaworski et al. |
| 8,093,367 | B2 | 1/2012 | Kore et al. |
| 8,158,601 | B2 | 4/2012 | Chen et al. |
| 8,278,036 | B2 | 10/2012 | Kariko et al. |
| 8,304,529 | B2 | 11/2012 | Kore et al. |
| 8,492,359 | B2 | 7/2013 | Yaworski et al. |
| 8,691,966 | B2 | 4/2014 | Kariko et al. |
| 8,748,089 | B2 | 6/2014 | Kariko et al. |
| 8,822,668 | B2 | 9/2014 | Yaworski et al. |
| 9,006,191 | B2 | 4/2015 | MacLachlan et al. |
| 9,006,417 | B2 | 4/2015 | Yaworski et al. |
| 9,364,435 | B2 | 6/2016 | Yaworski et al. |
| 9,404,127 | B2 | 8/2016 | Yaworski et al. |
| 9,428,535 | B2 | 8/2016 | de Fougerolles et al. |
| 9,518,272 | B2 | 12/2016 | Yaworski et al. |
| 9,572,874 | B2 | 2/2017 | Fotin-Mleczek et al. |
| 9,750,824 | B2 | 9/2017 | Kariko et al. |
| 9,751,925 | B2 | 9/2017 | Hoge et al. |
| 9,896,413 | B2 | 2/2018 | Payne et al. |
| 10,072,057 | B2 | 9/2018 | Hoge et al. |
| 10,143,758 | B2 | 12/2018 | Guild et al. |
| 10,188,748 | B2 | 1/2019 | Von Der Mulbe et al. |
| 10,201,620 | B2 | 2/2019 | Meis et al. |
| 10,227,302 | B2 | 3/2019 | Payne et al. |
| 10,232,055 | B2 | 3/2019 | Kariko et al. |

(Continued)

FOREIGN PATENT DOCUMENTS

| | | | |
|---|---|---|---|
| CA | 3063907 | A1 | 12/2018 |
| WO | WO 2004/03941 | A2 | 5/2004 |

(Continued)

OTHER PUBLICATIONS

Andries, O. et al. "N(1)-methylpseudouridine-incorporated mRNA outperforms pseudouridine-incorporated mRNA by providing enhanced protein expression and reduced immunogenicity in mammalian cell lines and mice", J Control Release 217:337-344. (Nov. 10, 2015). Epub Sep. 3, 2015.

(Continued)

*Primary Examiner* — Tracy Vivlemore

(74) *Attorney, Agent, or Firm* — COOLEY LLP

(57) ABSTRACT

This invention provides a range of translatable polynucleotide and oligomer molecules for expressing a human amylo-alpha-1, 6-glucosidase, 4-alpha-glucanotransferase (AGL), or a fragment thereof having AGL activity. The polynucleotide and oligomer molecules are expressible to provide the human AGL or a fragment thereof having AGL activity. The molecules can be used as active agents to express an active polypeptide or protein in cells or subjects. The agents can be used in methods for ameliorating, preventing, delaying onset, or treating a disease or condition associated with reduced activity of amylo-alpha-1, 6-glucosidase, 4-alpha-glucanotransferase (AGL) in a subject.

20 Claims, 9 Drawing Sheets

Specification includes a Sequence Listing.

(56) References Cited

U.S. PATENT DOCUMENTS

| | | | |
|---|---|---|---|
| 10,238,754 | B2 | 3/2019 | Guild et al. |
| 10,383,952 | B2 | 8/2019 | Payne et al. |
| 10,501,512 | B2 | 12/2019 | De Fougerolles et al. |
| 10,526,284 | B2 | 1/2020 | Payne et al. |
| 10,568,972 | B2 | 2/2020 | Von Der Mulbe et al. |
| 11,377,643 | B2 * | 7/2022 | Tachikawa ........... C12N 9/1051 |
| 2005/0234327 | A1 | 10/2005 | Saracen et al. |
| 2011/0256175 | A1 | 10/2011 | Hope et al. |
| 2012/0027803 | A1 | 2/2012 | Manoharan et al. |
| 2012/0128760 | A1 | 5/2012 | Manoharan et al. |
| 2013/0259924 | A1 | 10/2013 | Bancel et al. |
| 2014/0105964 | A1 | 4/2014 | Bancel et al. |
| 2014/0105965 | A1 | 4/2014 | Bancel et al. |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2015/0064235 | A1 | 3/2015 | Bancel et al. |
| 2015/0104476 | A1 | 4/2015 | Von Der Mulbe et al. |
| 2015/0366997 | A1 * | 12/2015 | Guild .................. C07K 14/505 435/69.6 |
| 2016/0031928 | A1 | 2/2016 | DeRosa et al. |
| 2016/0089451 | A1 | 3/2016 | Armstrong |
| 2016/0130567 | A1 | 5/2016 | Chivukula et al. |
| 2016/0136301 | A1 | 5/2016 | Von Der Mulbe et al. |
| 2016/0161403 | A1 | 6/2016 | Sugimoto |
| 2016/0354493 | A1 | 12/2016 | Roy et al. |
| 2017/0056528 | A1 | 3/2017 | De Fougerolles et al. |
| 2017/0130216 | A1 | 5/2017 | Armstrong |
| 2017/0252461 | A1 | 9/2017 | Chakraborty et al. |
| 2017/0362627 | A1 | 12/2017 | Reynders, III et al. |
| 2018/0169268 | A1 | 6/2018 | Payne et al. |
| 2018/0353618 | A1 | 12/2018 | Burkhardt et al. |
| 2019/0307897 | A1 | 10/2019 | Angel et al. |
| 2020/0149017 | A1 | 5/2020 | Tachikawa et al. |

FOREIGN PATENT DOCUMENTS

| | | | |
|---|---|---|---|
| WO | WO-09/086558 | A1 | 7/2009 |
| WO | WO-09/127060 | A1 | 10/2009 |
| WO | WO-2010/005565 | A2 | 1/2010 |
| WO | WO-10/048536 | A2 | 4/2010 |
| WO | WO-10/054406 | A1 | 5/2010 |
| WO | WO-10/088537 | A2 | 8/2010 |
| WO | WO-10/129709 | A1 | 11/2010 |
| WO | WO-2011/153493 | A2 | 12/2011 |
| WO | WO-2014/130722 | A1 | 8/2014 |
| WO | WO-2014/152513 | A1 | 9/2014 |
| WO | WO-2015/051169 | A2 | 4/2015 |
| WO | WO-2015/074085 | A1 | 5/2015 |
| WO | WO-2015/192092 | A1 | 12/2015 |
| WO | WO-2016/070166 | A2 | 5/2016 |
| WO | WO-2017/054086 | A1 | 4/2017 |
| WO | WO-2018/078053 | A1 | 5/2018 |
| WO | WO 2018/222926 | A1 | 12/2018 |

OTHER PUBLICATIONS

Berge, S. M. et al. "Pharmaceutical Salts", J. Pharmaceutical Sciences; 66(1):1-19. (Jan. 1977).

Chen, Y. "Glycogen storage disease. in: Scriver CR, Beaudet al, Sly WS, Valle D, editors; Childs B, Kinzler KW, Vogelstein B, editors. The Metabolic and Molecular Bases of Inherited Disease", New York: McGraw Hill; 7(71): 1521-51. (1995).

Database GenBank [Online], "glycogen debranching enzyme isoform 1 [*Homo sapiens*]: NCBI Reference Sequence: NP_000019.2". (Jan. 13, 2020). 3 pages.

Database GenBank [Online], *Homo sapiens* amylo-alpha-1, 6-glucosidase, 4-alpha-glucanotransferase (AGL), transcript variant 4, mRNA: NCBI Reference Sequence: NM_000028.8 (Jan. 13, 2020). 6 pages.

Database GenBank [Online], "Xenopus laevis hemoglobin subunit gamma 1 L homeolog (hbg1.L), mRNA: NCBI Reference Sequence: NM_001096347.1". (Dec. 21, 2019). 2 pages.

Database GenBank [Online], *Homo sapiens* AGL gene, Virtual Transcript, partial sequence, genomic survey sequence: Genbank Accession No. DQ048148. (Jun. 2, 2005). 2 pages.

Extended European Search Report issued Feb. 3, 2021 for EP Application No. 18810235.4, 7 pages.

Goldstein, J. L. et al. "Molecular analysis of the AGL gene: Identification of 25 novel mutations and evidence of genetic heterogeneity in patients with Glycogen Storage Disease Type III", Genetics in Medicine, 12(7):424-430. (Jul. 2010).

Gould, P. L. "Salt selection for basic drugs", International Journal of Pharmaceutics, 33:201-217. (1986).

Gustafsson, C. et al. "Codon bias and heterologous protein expression". Trends Biotechnol; 22(7):346-53. (Jul. 2004).

International Preliminary Report on Patentability for International Application No. PCT/US2018/035477, mailed Dec. 12, 2019, 9 pages.

International Search Report and Written Opinion for International Application No. PCT/US2018/035477, mailed Oct. 22, 2018, 13 pages.

Invitation to Pay Additional Fees for International Application No. PCT/US2018/035477, mailed Aug. 9, 2018, 2 pages.

Jemielity, J et al. "Novel 'anti-reverse' cap analogs with superior translational properties", RNA; 9(9):1108-1122. (Sep. 2003).

Kozak, M. "Downstream secondary structure facilitates recognition of initiator codons by eukaryotic ribosomes", Proc. Natl. Acad. Sci. USA; 87:8301-8305. (Nov. 1990).

Kozak, M. "Leader Length and Secondary Structure Modulate mRNA Function under Conditions of Stress", Mol. and Cell Biol., 8(7):2737-2744. (Jul. 1988).

Kozak, M. "Structural Features in Eukaryotic mRNAs That Modulate the Initiation of Translation", J. Biol. Chem., 266(3):19867-19870. (1991).

Kozak, M. "The Scanning Model for Translation: an Update", J. Cell Biol., 108:229-241. (Feb. 1989).

Liu, K. et al. "Mouse model of glycogen storage disease type III", Mol Genet and Metabolism; 111: 467-76. (2014).

Love, K. T., et al. "Lipid-like materials for low-dose, in vivo gene silencing", PNAS, 107(5):1864-69. (Feb. 2, 2010).

Ozpolat, B. et al. "Liposomal siRNA nanocarriers for cancer therapy", Advanced Drug Delivery Reviews; 66:110-116. (2014).

Rodríguez-Gascón, A. et al. "Development of nucleic acid vaccines: use of self-amplifying RNA in lipid nanoparticles", International Journal of Nanomedicine; 9:1833-1843. (2014).

Sentner, C. P. et al. "Mutation Analysis in Glycogen Storage Disease Type III Patients in the Netherlands: Novel Genotype-Phenotype Relationships and Five Novel Mutations in the AGL Gene", JIMD Reports; 19-26. (2012).

Sercombe, L. et al. "Advances and Challenges of Liposome Assisted Drug Delivery", Frontiers in Pharmacology; 6(286):1-13. (Dec. 1, 2015).

Vidal, et al., Rescue of GSDIII Phenotype with Gene Transfer Requires Liver- and Muscle-Targeted GDE Expression, Molecular Therapy, Mar. 7, 2018, pp. 890-901, vol. 26, Issue 3.

Villalobos, A. et al. "Gene Designer: a synthetic biology tool for constructing artificial DNA segments". BMC Bioinformatics; 7(285):8 pgs. (Jun. 2006).

NCBI Reference Sequence: NP_000019.2, Glycogen Debranching Enzyme Isoform 1 [*Homo sapiens*], Nov. 29, 2015, 3 pages.

* cited by examiner

Fig. 3 AGL expression in WT mice

Fig. 4 AGL expression in WT mouse liver

SEQUENCE LISTING

<160> NUMBER OF SEQ ID NOS: 45

<210> SEQ ID NO 1
<211> LENGTH: 4599
<212> TYPE: RNA
<213> ORGANISM: Artificial Sequence
<220> FEATURE:
<223> OTHER INFORMATION: Consensus Human AGL Coding Sequence

<400> SEQUENCE: 1

```
augggacaca guaaacagau ucgaauuuua cuucugaacg aaauggagaa acuggaaaag      60
acccucuuca gacuugaaca aggguaugag cuacaguucc gauuaggccc aacuuuacag     120
ggaaaagcag uuaccgugua uacaaauuac ccauuuccug gagaaacauu uaauagagaa     180
aaauuccguu cucuggauug ggaaaaucca acagaaagag aagaugauuc ugauaaauac     240
uguaaacuua aucugcaaca aucugguuca uuucaguauu auuuccuuca aggaaaugag     300
aaaaguggug gagguuacau aguuguggac cccauuuuac guguuggugc ugauaaucau     360
gugcuacccu uggacugugu uacucuucag acauuuuuag cuaaguguuu gggaccuuuu     420
gaugaauggg aaagcagacu uaggguugca aaagaaucag gcuacaacau gauucauuuu     480
accccauugc agacucuugg acuaucuagg ucaugcuacu cccuugccaa ucaguuagaa     540
uuaaauccug acuuuucaag accuaauaga aaguauaccu ggaaugaugu uggacagcua     600
guggaaaaau uaaaaaagga auggaauguu auuuguauua cugauguugu cuacaaucau     660
acugcugcua auaguaaaug gauccaggaa cauccagaau gugccuauaa ucuugugaau     720
ucuccacacu uaaaaccugc cugggucuua gacagagcac uuuggcguuu cuccugugau     780
guugcagaag ggaaauacaa agaaaaggga auaccugcuu ugauugaaaa ugaucaccau     840
augaauucca uccgaaaaau aauuugggag gauauuuuuc caaagcuuaa acucugggaa     900
uuuuuccaag uagaugucaa caaagcgguu gagcaauuua gaagacuucu uacacaagaa     960
aauaggcgag uaaccaaguc ugauccaaac caacaccuua cgauuauuca agauccugaa    1020
uacagacggu uuggcuguac uguagauaug aacauugcac uaacgacuuu cauaccacau    1080
gacaaggggc cagcagcaau ugaagaaugc uguaauuggu uucauaaaag aauggaggaa    1140
uuaaauucag agaagcaucg acucauuaac uaucaucagg aacaggcagu uaauugccuu    1200
uugggaaaug uguuuuauga acgacuggcu ggccaugguc caaaacuagg accugucacu    1260
agaaagcauc cuuuaguuac cagguauuuu acuuucccau uugaagagau agacuucucc    1320
auggaagaau cuaugauuca ucugccaaau aaagcuuguu uucugauggc acacaaugga    1380
uggguaaugg gagaugaucc ucuucgaaac uuugcugaac cggguucaga aguuuaccua    1440
aggagagaac uuauuugcug gggagacagu guuaaauuac gcuaugggaa uaaaccagag    1500
gacuguccuu aucucugggc acacaugaaa aaauacacug aaauaacugc aacuuauuuc    1560
cagggaguac gucuugauaa cugccacuca acaccucuuc acguagcuga guacauguug    1620
gaugcugcua ggaauuugca acccaauuua uauguaguag cugaacuguu cacaggaagu    1680
gaagaucugg acaaugucuu uguuacuaga cugggcauua guuccuuaau aagagaggca    1740
augagugcau auaauaguca ugaagagggc agauuaguuu accgauaugg aggagaaccu    1800
guuggauccu uuguucagcc cuguuugagg ccuuuaaugc cagcuauugc acaugcccug    1860
uuuauggaua uuacgcauga uaaugagugu ccuauugugc auagaucagc guaugaugcu    1920
cuaccaagua cuacaauugu uucuauggca uguugugcua guggaaguac aagaggcuau    1980
gaugaauuag ugccucauca gauuucagug guuucugaag aacgguuuua cacuaagugg    2040
```

```
aauccugaag cauugccuuc aaacacaggu gaaguuaauu uccaaagcgg cauuauugca   2100
gccaggugug cuaucaguaa acuucaucag gagcuuggag ccaaggguuu uauucaggug   2160
uauguggauc aaguugauga agacauagug gcaguaacaa gacacucacc uagcauccau   2220
cagucuguug uggcuguauc uagaacugcu uucaggaauc ccaagacuuc auuuuacagc   2280
aaggaagugc cucaaaugug caucccuggc aaaauugaag aaguaguucu ugaagcuaga   2340
acuauugaga gaaacacgaa accuuauagg aaggaugaga auucaaucaa uggaacacca   2400
gauaucacag uagaaauuag agaacauauu cagcuuaaug aaaguaaaau uguuaaacaa   2460
gcuggaguug ccacaaaagg gcccaaugaa uauauucaag aaauagaauu ugaaaacuug   2520
ucuccaggaa guguuauuau auucagaguu agucuugauc cacaugcaca agucgcuguu   2580
ggaauucuuc gaaaucaucu gacacaauuc aguccucacu uuaaaucugg cagccuagcu   2640
guugacaaug cagauccuau auuaaaaauu ccuuuugcuu cucuugccuc cagauuaacu   2700
uuggcugagc uaaaucagau ccuuuaccga ugugaaucag aagaaaagga agauggugga   2760
gggugcuaug acauaccaaa cuggucagcc cuuaaauaug caggucuuca agguuuaaug   2820
ucuguauugg cagaaauaag accaaagaau gacuuggggc auccuuuuug uaauaauuug   2880
agaucuggag auuggaugau ugacuauguc aguaaccggc uuauuucacg aucaggaacu   2940
auugcugaag uugguaaaug guugcaggcu auguucuucu accugaagca gaucccacgu   3000
uaccuuaucc cauguuacuu ugaugcuaua uuaauuggug cauauaccac ucuucuggau   3060
acagcaugga agcagauguc aagcuuuguu cagaaugguu caaccuuugu gaaacaccuu   3120
ucauuggguu caguucaacu guguggagua ggaaaauucc cuucccugcc aauucuuuca   3180
ccugcccuaa uggauguacc uuauagguua aaugagauca caaaagaaaa ggagcaaugu   3240
uguguuucuc uagcugcagg cuuaccucau uuuucuucug guauuuuccg cugcugggga   3300
agggauacuu uuauugcacu uagagguaua cugcugauua cuggacgcua uguagaagcc   3360
aggaauauua uuuuagcauu ugcggguacc cugaggcaug gacucauucc uaaucuacug   3420
ggugaaggaa uuuaugccag auacaauugu cgggaugcug ugugguggug gcugcagugu   3480
auccaggauu acuguaaaau gguuccaaau ggucuagaca uucucaagug cccaguuucc   3540
agaauguauc cuacagauga uucugcuccu uugccugcug gcacacugga ucagccauug   3600
uuugaaguca uacaggaagc aaugcaaaaa cacaugcagg gcauacaguu ccgagaaagg   3660
aaugcugguc cccagauaga ucgaaacaug aaggacgaag guuuuaauau aacugcagga   3720
guugaugaag aaacaggauu uguuuaugga ggaaaucguu ucaauugugg cacauggaug   3780
gauaaaaugg gagaaaguga cagagcuaga aacagaggaa ucccagccac accaagagau   3840
gggucugcug uggaaauugu gggccugagu aaaucugcug uucgcugguu gcuggaauua   3900
uccaaaaaaa auauuuuccc uuaucaugaa gucacaguaa aaagacaugg aaaggcuaua   3960
aagguaucau augaugagug gaacagaaaa auacaagaca acuuugaaaa gcuauuucau   4020
guuuccgaag acccuucaga uuuaaaugaa aagcauccaa aucugguuca caaacguggc   4080
auauacaaag auaguuaugg agcuucaagu ccuuggugug acuaucagcu caggccuaau   4140
uuuaccauag caaugguugu ggccccugag cucuuuacua cagaaaaagc auggaaagcu   4200
uuggagauug cagaaaaaaa auugcuuggu ccccuuggca ugaaaacuuu agauccagau   4260
gauaugguuu acuguggaau uuaugacaau gcauuagaca augacaacua caaucuugcu   4320
aaagguuuca auuaucacca aggaccugag uggcuguggc cuauugggua uuuucuucgu   4380
```

-continued

```
gcaaaauuau auuuuuccag auugaugggc ccggagacua cugcaaagac uauaguuuug   4440

guuaaaaaug uucuuucccg acauuauguu caucuugaga gaucccuug gaaaggacuu   4500

ccagaacuga ccaaugagaa ugcccaguac uguccuuuca gcugugaaac acaagccugg   4560

ucaauugcua cuauucuuga gacacuuuau gauuuauag                         4599
```

<210> SEQ ID NO 2
<211> LENGTH: 1532
<212> TYPE: PRT
<213> ORGANISM: Artificial Sequence
<220> FEATURE:
<223> OTHER INFORMATION: Consensus Human AGL Amino Acid Sequence

<400> SEQUENCE: 2

```
Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270

Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Gln Val
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
```

-continued

```
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Asp Lys Gly Pro Ala Ala Ile Glu
        355                 360                 365

Glu Cys Cys Asn Trp Phe His Lys Arg Met Glu Glu Leu Asn Ser Glu
    370                 375                 380

Lys His Arg Leu Ile Asn Tyr His Gln Glu Gln Ala Val Asn Cys Leu
385                 390                 395                 400

Leu Gly Asn Val Phe Tyr Glu Arg Leu Ala Gly His Gly Pro Lys Leu
                405                 410                 415

Gly Pro Val Thr Arg Lys His Pro Leu Val Thr Arg Tyr Phe Thr Phe
            420                 425                 430

Pro Phe Glu Glu Ile Asp Phe Ser Met Glu Glu Ser Met Ile His Leu
        435                 440                 445

Pro Asn Lys Ala Cys Phe Leu Met Ala His Asn Gly Trp Val Met Gly
    450                 455                 460

Asp Asp Pro Leu Arg Asn Phe Ala Glu Pro Gly Ser Glu Val Tyr Leu
465                 470                 475                 480

Arg Arg Glu Leu Ile Cys Trp Gly Asp Ser Val Lys Leu Arg Tyr Gly
                485                 490                 495

Asn Lys Pro Glu Asp Cys Pro Tyr Leu Trp Ala His Met Lys Lys Tyr
            500                 505                 510

Thr Glu Ile Thr Ala Thr Tyr Phe Gln Gly Val Arg Leu Asp Asn Cys
        515                 520                 525

His Ser Thr Pro Leu His Val Ala Glu Tyr Met Leu Asp Ala Ala Arg
    530                 535                 540

Asn Leu Gln Pro Asn Leu Tyr Val Val Ala Glu Leu Phe Thr Gly Ser
545                 550                 555                 560

Glu Asp Leu Asp Asn Val Phe Val Thr Arg Leu Gly Ile Ser Ser Leu
                565                 570                 575

Ile Arg Glu Ala Met Ser Ala Tyr Asn Ser His Glu Glu Gly Arg Leu
            580                 585                 590

Val Tyr Arg Tyr Gly Gly Glu Pro Val Gly Ser Phe Val Gln Pro Cys
        595                 600                 605

Leu Arg Pro Leu Met Pro Ala Ile Ala His Ala Leu Phe Met Asp Ile
    610                 615                 620

Thr His Asp Asn Glu Cys Pro Ile Val His Arg Ser Ala Tyr Asp Ala
625                 630                 635                 640

Leu Pro Ser Thr Thr Ile Val Ser Met Ala Cys Cys Ala Ser Gly Ser
                645                 650                 655

Thr Arg Gly Tyr Asp Glu Leu Val Pro His Gln Ile Ser Val Val Ser
            660                 665                 670

Glu Glu Arg Phe Tyr Thr Lys Trp Asn Pro Glu Ala Leu Pro Ser Asn
        675                 680                 685

Thr Gly Glu Val Asn Phe Gln Ser Gly Ile Ile Ala Ala Arg Cys Ala
    690                 695                 700

Ile Ser Lys Leu His Gln Glu Leu Gly Ala Lys Gly Phe Ile Gln Val
705                 710                 715                 720

Tyr Val Asp Gln Val Asp Glu Asp Ile Val Ala Val Thr Arg His Ser
                725                 730                 735

Pro Ser Ile His Gln Ser Val Val Ala Val Ser Arg Thr Ala Phe Arg
            740                 745                 750
```

-continued

```
Asn Pro Lys Thr Ser Phe Tyr Ser Lys Glu Val Pro Gln Met Cys Ile
        755                 760                 765

Pro Gly Lys Ile Glu Glu Val Val Leu Glu Ala Arg Thr Ile Glu Arg
    770                 775                 780

Asn Thr Lys Pro Tyr Arg Lys Asp Glu Asn Ser Ile Asn Gly Thr Pro
785                 790                 795                 800

Asp Ile Thr Val Glu Ile Arg Glu His Ile Gln Leu Asn Glu Ser Lys
                805                 810                 815

Ile Val Lys Gln Ala Gly Val Ala Thr Lys Gly Pro Asn Glu Tyr Ile
            820                 825                 830

Gln Glu Ile Glu Phe Glu Asn Leu Ser Pro Gly Ser Val Ile Ile Phe
        835                 840                 845

Arg Val Ser Leu Asp Pro His Ala Gln Val Ala Val Gly Ile Leu Arg
    850                 855                 860

Asn His Leu Thr Gln Phe Ser Pro His Phe Lys Ser Gly Ser Leu Ala
865                 870                 875                 880

Val Asp Asn Ala Asp Pro Ile Leu Lys Ile Pro Phe Ala Ser Leu Ala
                885                 890                 895

Ser Arg Leu Thr Leu Ala Glu Leu Asn Gln Ile Leu Tyr Arg Cys Glu
            900                 905                 910

Ser Glu Glu Lys Glu Asp Gly Gly Gly Cys Tyr Asp Ile Pro Asn Trp
        915                 920                 925

Ser Ala Leu Lys Tyr Ala Gly Leu Gln Gly Leu Met Ser Val Leu Ala
    930                 935                 940

Glu Ile Arg Pro Lys Asn Asp Leu Gly His Pro Phe Cys Asn Asn Leu
945                 950                 955                 960

Arg Ser Gly Asp Trp Met Ile Asp Tyr Val Ser Asn Arg Leu Ile Ser
                965                 970                 975

Arg Ser Gly Thr Ile Ala Glu Val Gly Lys Trp Leu Gln Ala Met Phe
            980                 985                 990

Phe Tyr Leu Lys Gln Ile Pro Arg  Tyr Leu Ile Pro Cys  Tyr Phe Asp
        995                 1000                1005

Ala Ile  Leu Ile Gly Ala Tyr  Thr Thr Leu Leu Asp  Thr Ala Trp
    1010                1015                1020

Lys Gln  Met Ser Ser Phe Val  Gln Asn Gly Ser Thr  Phe Val Lys
    1025                1030                1035

His Leu  Ser Leu Gly Ser Val  Gln Leu Cys Gly Val  Gly Lys Phe
    1040                1045                1050

Pro Ser  Leu Pro Ile Leu Ser  Pro Ala Leu Met Asp  Val Pro Tyr
    1055                1060                1065

Arg Leu  Asn Glu Ile Thr Lys  Glu Lys Glu Gln Cys  Cys Val Ser
    1070                1075                1080

Leu Ala  Ala Gly Leu Pro His  Phe Ser Ser Gly Ile  Phe Arg Cys
    1085                1090                1095

Trp Gly  Arg Asp Thr Phe Ile  Ala Leu Arg Gly Ile  Leu Leu Ile
    1100                1105                1110

Thr Gly  Arg Tyr Val Glu Ala  Arg Asn Ile Ile Leu  Ala Phe Ala
    1115                1120                1125

Gly Thr  Leu Arg His Gly Leu  Ile Pro Asn Leu Leu  Gly Glu Gly
    1130                1135                1140

Ile Tyr  Ala Arg Tyr Asn Cys  Arg Asp Ala Val Trp  Trp Trp Leu
    1145                1150                1155
```

-continued

```
Gln Cys  Ile Gln Asp Tyr Cys  Lys Met Val Pro Asn  Gly Leu Asp
    1160                 1165                 1170

Ile Leu  Lys Cys Pro Val Ser  Arg Met Tyr Pro Thr  Asp Asp Ser
    1175                 1180                 1185

Ala Pro  Leu Pro Ala Gly Thr  Leu Asp Gln Pro Leu  Phe Glu Val
    1190                 1195                 1200

Ile Gln  Glu Ala Met Gln Lys  His Met Gln Gly Ile  Gln Phe Arg
    1205                 1210                 1215

Glu Arg  Asn Ala Gly Pro Gln  Ile Asp Arg Asn Met  Lys Asp Glu
    1220                 1225                 1230

Gly Phe  Asn Ile Thr Ala Gly  Val Asp Glu Glu Thr  Gly Phe Val
    1235                 1240                 1245

Tyr Gly  Gly Asn Arg Phe Asn  Cys Gly Thr Trp Met  Asp Lys Met
    1250                 1255                 1260

Gly Glu  Ser Asp Arg Ala Arg  Asn Arg Gly Ile Pro  Ala Thr Pro
    1265                 1270                 1275

Arg Asp  Gly Ser Ala Val Glu  Ile Val Gly Leu Ser  Lys Ser Ala
    1280                 1285                 1290

Val Arg  Trp Leu Leu Glu Leu  Ser Lys Lys Asn Ile  Phe Pro Tyr
    1295                 1300                 1305

His Glu  Val Thr Val Lys Arg  His Gly Lys Ala Ile  Lys Val Ser
    1310                 1315                 1320

Tyr Asp  Glu Trp Asn Arg Lys  Ile Gln Asp Asn Phe  Glu Lys Leu
    1325                 1330                 1335

Phe His  Val Ser Glu Asp Pro  Ser Asp Leu Asn Glu  Lys His Pro
    1340                 1345                 1350

Asn Leu  Val His Lys Arg Gly  Ile Tyr Lys Asp Ser  Tyr Gly Ala
    1355                 1360                 1365

Ser Ser  Pro Trp Cys Asp Tyr  Gln Leu Arg Pro Asn  Phe Thr Ile
    1370                 1375                 1380

Ala Met  Val Val Ala Pro Glu  Leu Phe Thr Thr Glu  Lys Ala Trp
    1385                 1390                 1395

Lys Ala  Leu Glu Ile Ala Glu  Lys Lys Leu Leu Gly  Pro Leu Gly
    1400                 1405                 1410

Met Lys  Thr Leu Asp Pro Asp  Asp Met Val Tyr Cys  Gly Ile Tyr
    1415                 1420                 1425

Asp Asn  Ala Leu Asp Asn Asp  Asn Tyr Asn Leu Ala  Lys Gly Phe
    1430                 1435                 1440

Asn Tyr  His Gln Gly Pro Glu  Trp Leu Trp Pro Ile  Gly Tyr Phe
    1445                 1450                 1455

Leu Arg  Ala Lys Leu Tyr Phe  Ser Arg Leu Met Gly  Pro Glu Thr
    1460                 1465                 1470

Thr Ala  Lys Thr Ile Val Leu  Val Lys Asn Val Leu  Ser Arg His
    1475                 1480                 1485

Tyr Val  His Leu Glu Arg Ser  Pro Trp Lys Gly Leu  Pro Glu Leu
    1490                 1495                 1500

Thr Asn  Glu Asn Ala Gln Tyr  Cys Pro Phe Ser Cys  Glu Thr Gln
    1505                 1510                 1515

Ala Trp  Ser Ile Ala Thr Ile  Leu Glu Thr Leu Tyr  Asp Leu
    1520                 1525                 1530
```

<210> SEQ ID NO 3
<211> LENGTH: 129
<212> TYPE: RNA

<213> ORGANISM: Tobacco Etch Virus

<400> SEQUENCE: 3
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauag 129

<210> SEQ ID NO 4
<211> LENGTH: 6
<212> TYPE: RNA
<213> ORGANISM: Unknown
<220> FEATURE:
<223> OTHER INFORMATION: Kozak Sequence

<400> SEQUENCE: 4 gccacc 6

<210> SEQ ID NO 5
<211> LENGTH: 158
<212> TYPE: RNA
<213> ORGANISM: Unknown
<220> FEATURE:
<223> OTHER INFORMATION: Xenopus sp.

<400> SEQUENCE: 5
cuagugacug acuaggaucu gguuaccacu aaaccagccu caagaacacc cgaauggagu 60
cucuaagcua cauaauacca acuuacacuu acaaaauguu gucccccaaa auguagccau 120
ucguaucugc uccuaauaaa aagaaaguuu cuucacau 158

<210> SEQ ID NO 6
<211> LENGTH: 114
<212> TYPE: RNA
<213> ORGANISM: Unknown
<220> FEATURE:
<223> OTHER INFORMATION: Poly(A) 114 Tail

<400> SEQUENCE: 6
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaa 114

<210> SEQ ID NO 7
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 7
augggacacu ccaaacagau ccggauacug cugcugaacg agauggaaaa gcuggaaaag 60
acucuauucc ggcucgagca gggauacgag cugcaguucc gccugggccc cacccuacaa 120
gggaaggccg ugaccgucua caccaacuac ccuuucccgg gcgaaacuuu caaccgggag 180
aaguuccggu cccuugacug ggaaaacccg acugagcgcg aggacgacuc ggacaaauac 240
ugcaagcuga accuccagca gucgggcucu uuccaauauu acuucuugca agggaacgag 300
aaguccggug gcggcuacau cgugguggac ccaauuuugc gcguggggc ugacaaccac 360 gugcugccac uggauugugu gacccugcaa accuuccugg ccaagugccu cggccccuuc 420
gacgaauggg agucgcgccu gagaguggcg aaagagagcg gauacaacau gauucacuuc 480
acgccgcucc aaacgcuggg ucugagccgg ucaugcuacu cacuggcgaa ccagcucgaa 540

-continued

```
cugaaccccg auuucucccg gccaaacagg aaguacaccu ggaacgacgu gggacagcug    600
gucgagaagu ugaagaagga guggaacgug aucuguauca ccgacgucgu guacaaccac    660
accgcugcaa acucgaagug gauccaggaa cauccggaau gugccuacaa ccucgugaac    720
agcccgcacc ugaagccugc cugggguguug gauagggcac uguggagguu cuccugugac    780
guggcagagg gaaaguacaa ggagaagggu auucccgcac ucaucgaaaa cgaucaccac    840
augaauucga ucagaaagau uaucugggag gauaucuucc cuaagcugaa gcugugggag    900
uucuuucaag uugaugugaa caaggcaguc gaacaguuuc ggcggcuguu aacccaagaa    960
aaccgccgcg ugaccaaguc cgauccgaau cagcaucuga ccauaaucca ggacccggaa   1020
uaccgccggu uuggcugcac cguggacaug aacauugccc ugacuaccuu uaucccgcau   1080
gauaagggcc ccgccgcuau cgaagaaugc ugcaacuggu uccacaagag gauggaggaa   1140
cugaacuccg aaaagcauag gcucauuaac uaccaccagg aacaggcagu gaacugccug   1200
cuggggaacg uguucuacga gcgacuggcu ggacacggac cgaaguuagg acccgugaca   1260
aggaagcacc cacuggucac uagauacuuc accuucccau uugaggaaau cgacuucuca   1320
auggaggagu cgaugaucca cuugccuaac aaggccugcu uucucauggc acauaacgga   1380
ugggucaugg gcgacgaucc ccuacggaau uuugcagaac caggcagcga ggucuaccuu   1440
cggcgggaac ugauuugcug gggcgacucc gucaagcugc gcuacggcaa caagccugag   1500
gacugucccu accuuugggc acacaugaag aaguacacug aaauuacugc gacauacuuc   1560
caaggagucc gcuuagauaa uugucacucc accccgcugc auguggcgga guacaugcug   1620
gaugccgcaa gaaaccucca gccgaaucuc uacgugguag cagagcuguu caccgggagc   1680
gaggaccugg acaauguguu ugucacccgg cuggggaucu ccucccugau ccgggaggcc   1740
auguccgccu acaacucaca cgaggagggg agacuggugu accgcuacgg aggagaaccc   1800
gugggcagcu uugugcagcc uugccuccgg ccgcugaugc ccgcgauugc gcaugcucug   1860
uucauggaua ucacucacga uaacgagugc cccauugugc acagauccgc cuacgacgcc   1920
cuuccuucca caaccaucgu guccauggca ugcugcgccu ccggcuccac ucgggguuac   1980
gaugagcugg ugccacacca gauuuccgug guguccgaag aacgcuucua caccaagugg   2040
aacccggaag cucugccguc aaacaccgga gaagugaacu uccaguccgg gaucaucgca   2100
gcgcgcugug cuauuagcaa gcugcaccag gagcugggag ccaaggggguu cauccagguc   2160
uauguggacc aggucgauga ggauaucguc gcugucacga gacacagccc gucuauccau   2220
caaagcgucg uggccguguc ccggacugcg uuccggaacc cuaaaaccuc auucuauucc   2280
aaagaggugc cccagaugug caucccugga aagaucgaag aagucgugcu ggaagcccgg   2340
accaucgagc ggaacaccaa gccguacagg aaggacgaaa acuccaucaa ugguaccccu   2400
gacauuaccg uggaaaucag agaacauauc cagcugaacg aguccaagau cgugaagcag   2460
gccggcgugg cgaccaaggg ucccaacgag uacauucagg aaaucgaguu ugaaaaccug   2520
uccccccggaa gcgugaucau uuuccgggug ucccuggacc cgcaugcgca agucgcuguc   2580
ggaauucugc ggaaucaccu cacccaauuc ucgccgcauu ucaagagugg uucccuggcg   2640
guggauaaug ccgauccgau ccugaagauu cccuucgcgu cccuggcauc gagacucacc   2700
cuggcggagu ugaaccagau ucuguaccgc ugcgaauccg aggaaaagga ggacggaggc   2760
gguugcuacg acaucccccaa cugguccgca cuuaaguacg cagggcugca gggucuuaug   2820
agcgugcugg cagaaauucg cccuaagaac gauuugggac accccuucug caacaaccuc   2880
```

```
cggucccggag acuggaugau cgauuacgug ucgaacagac ugauuucgag auccggcacc   2940

auugccgagg ucggaaagug gcuucaggcc auguucuucu accugaagca gaucccgaga   3000

uaccugauuc ccugcuacuu cgacgcaauc cugaucgggg cguauaccac ucuucuggac   3060

acugccugga agcagauguc cagcuucgug caaaacggau ccaccuucgu caagcaucuu   3120

agccugggcu cagugcaguu gugcggagug ggaaaauucc cuagccuccc uauucuuuca   3180

ccggcgcuga uggacgugcc uuaccgccug aacgaaauca ccaaagagaa ggagcagugu   3240

ugcgugucgc uggccgcggg ucugccgcau uucuccuccg gcaucuuccg gugcugggga   3300

agggacaccu ucaucgcucu gaggggaauc cugcugauua ccgggcgcua cguggaagcu   3360

cggaacauca uccuggccuu cgcgggaacu cugcgccacg gccugauucc aaacuugcuu   3420

ggcgaaggca ucuacgcgcg cuacaacugc cgcgacgcgg ucugguggug gcuccagugc   3480

auucaagacu acugcaagau ggugccaaac ggccuggaca uccugaagug cccggugucg   3540

agaauguacc ccaccgacga uucugcgccc cugccggccg guacucuuga ccaaccucug   3600

uucgaaguga uccaggaagc aaugcagaag cacaugcagg gcauucaguu ccgggagcgc   3660

aacgcagggc cgcaaaucga caggaacaug aaggacgaag gauucaacau caccgcggga   3720

guggacgaag agacuggcuu cgucuacggu ggaaaucggu ucaacugcgg gaccuggaug   3780

gacaagaugg gcgaaucaga ccgagcccgc aaccgcggaa ucccugccac cccccgggau   3840

gggagcgccg uggagauugu gggacugagc aagagcgcug ugcgcuggcu gcuggaguug   3900

agcaagaaga acauuuuccc cuaucacgaa gugaccguga agcggcacgg aaaagcuauc   3960

aaagugucccu acgacgagug gaacagaaag auccaggaca acuucgagaa gcuguuccac   4020

guguccgagg acccgucgga cuugaaugag aagcacccua accucgugca caagcgggga   4080

aucuacaagg acagcuacgg agcauccucg ccuuggugcg acuaucagcu gaggcccaac   4140

uucacuaucg caaugguggu ggccccagaa cuguucacua ccgaaaaggc cuggaaggca   4200

cuggagaucg cagagaaaaa gcugcugggc ccucugggca ugaaaacccu ggaccccgac   4260

gacauggugu acugcgggau cuacgauaac gcucuugaca augacaacua caaccuggcu   4320

aagggauuca acuaucacca gggccccgag uggcuguggc cgaucgguua cuuccugcgc   4380

gccaagcugu acuuuucccg gcugaugggc ccugagacua ccgcaaagac gaucgugcug   4440

gucaagaacg ugcugucacg gcacuacgug caucuggaac ggagcccgug gaaggggguug   4500

cccgaacuga ccaacgaaaa cgcgcaguac uguccguucu cgugcgaaac ucaggccugg   4560

uccaucgcca cuauccucga aacucucuac gaccuguag                        4599
```

<210> SEQ ID NO 8
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 8

```
augggacaua gcaaacaaau uaggauccuc cugcugaacg aaauggaaaa acuggaaaag     60

acgcuguuuc ggcuggaaca gggcuacgaa cuccaguuuc gccucgggcc aacgcugcaa    120

gggaaagcag ugaccgugua uacaaacuac ccauucccug gagagacauu caauagggag    180

aaguuuagaa gcuuagacug ggaaaaucca accgaacgag aagaugacag cgauaaguau    240

ugcaagcuga aucugcaaca guccggaagu uuucaguacu acuuuuugca agggaacgaa    300

aagagcggcg gagguuauau uguggugau ccaauuuuga gaguuggggc cgacaaccau    360
```

-continued

```
guacugccuc uugacugugu gacacugcaa acguuccugg ccaagugccu gggcccguuu    420
gaugaguggg aaagccguuu gcgcguggcc aaggaauccg gguacaacau gauccauuuu    480
accccacugc aaaccuuagg ccugucaagg agcuguuaca gucuggccaa ccagcuggaa    540
cugaaucccg acuucucccg gccaaauagg aaguacacgu ggaacgacgu uggccagcua    600
guggagaagu ugaagaagga guggaacguu auuugcauca cugacgucgu guauaaucac    660
acugccgcua auagcaaaug gauccaggaa cauccagagu gugccuauaa ccuggucaac    720
agcccgcauc ugaagccagc augggugcug gaccgggcgu uguggcgguu cucgugugac    780
guggccgaag gaaaguauaa ggagaagggu auuccggcuc ugauagagaa cgaccaucau    840
augaauucca ucaggaagau cauuugggag gacaucuuuc caaaguugaa gcugugggag    900
uucuuucaag uggaugugaa caaggccgua gaacaguuuc gccgccuacu aacccaggaa    960
aauaggagag ucacaaaguc cgaucccaac caacaucuga ccauaauuca ggaccccgaa   1020
uaucgucgau uuggcugcac cguggauaug aacaucgcuu ugacaacuuu cauaccacac   1080
gacaaggguc cagccgccau ugaagagugu uguaacuggu uucacaaacg aauggaggag   1140
uugaacagug aaaagcaccg ccugaucaau uaucaucagg agcaggccgu gaacuguuug   1200
cuggggaaug uguucuauga gaggcucgcu ggucauggcc cuaagcuggg uccuguaaca   1260
agaaagcauc cauuagugac gcgcuacuuu acauucccau uugaggagau cgacuuuucg   1320
auggaagagu ccaugauuca ucuccccaac aaggccuguu uucugauggc ccacaacggc   1380
uggguuaugg gggaugaucc guugagaaau uuugcggaac cagguucaga aguguaucug   1440
cgucgggagc ugauuuguug gggcgacucc gugaagcucc gcuaugggaa caagccugag   1500
gauuguccuu aucugugggc gcauaugaag aaguauacag agaucacugc cacauauuuu   1560
cagggcguca ggcuggacaa uugucauagc accccgcuuc auguggcuga guauaugcug   1620
gacgcagcaa ggaaucugca gcccaaucug uauguggugg cggaacuguu uaccgggucc   1680
gaggaccugg acaauguauu uguaacccga uugggcaucu ccagccugau uagggaagca   1740
augagugcau acaacucaca cgaggagggg cggcugguuu aucgauaugg gggggaaccu   1800
gugggcagcu uuguacagcc augucuccgg ccguugaugc cugccauugc ucaugcgcuc   1860
uuuauggaua uaacacauga caacgaaugu ccaaucguuc auaggagugc uuacgacgcc   1920
cugccgagca caacgaucgu guccauggcc uguugugcaa guggcagcac acguggcuau   1980
gacgaauugg uaccccacca aauuagcgug guuuccgagg agagguucua uacaaagugg   2040
aauccagagg cuuugcccuc gaacaccgga gaggucaacu uucaaucugg cauaauugcc   2100
gcucgcugcg ccauaucuaa guugcaucag gaacugggcg cgaagggguu uauacaaguc   2160
uacguugacc aaguggauga ggacaucguu gcugucacgc ggcacucacc uaguauucau   2220
caauccgugg uagcaguguc ucggacggcc uuuagaaacc caaagacauc auuuuacucg   2280
aaagaagugc cucaaaugug uauaccuggc aaaauugaag agguggaccu ggaagcccgc   2340
acgauagaga ggaauacuaa gccguauaga aaggaugaaa auucuaucaa cggcacuccg   2400
gauauuacag uagaaaucag agagcacauu caacuuaaug agucuaagau uguuaagcag   2460
gcugguguug caaccaaagg gccaaacgag uacauccagg agauugaauu ugaaaaucug   2520
ucaccgggcu ccgugaucau cuuuagagua ucuuuggauc cacaugcuca agucgcuguu   2580
ggaauccuga gaaaccaucu gacacaauuu uccccacauu uuaagagcgg cagccuggcc   2640
guggacaacg cagacccaau ccugaagauc ccauuugcau cccuggcuuc ccgccugacu   2700
```

-continued cuggcugagc ugaaccagau cuuguaucgc ugugaaucug aagaaaaaga ggauggcgga 2760
ggcuguuaug acaucccaaa uuggagcgcc cugaaauaug ccggacucca aggccugaug 2820
uccguucugg ccgagauuag gccaaagaau gaucugggac acccauuuug uaacaacuug 2880
cggucuggag acuggaugau cgacuauguc agcaaccgcc ugauaagcag auccgguacu 2940
aucgcugaag ucggaaaaug gcugcaggcu auguuuuucu auuugaagca gauuccgaga 3000
uauuugaucc ccuguuauuu ugaugccauu cugauuggug cuuauacuac ccugcuggau 3060
accgcuugga aacagaugag uagcuuuguc caaaauggcu ccaccuucgu aaagcaucug 3120
ucgcugggcu ccgugcaauu guguggcguc gggaaguucc cuagccugcc aauccugucc 3180
ccugcucuga uggacgugcc uuaucgccug aacgagauua cgaaggaaaa ggaacagugu 3240
ugcgugucac ucgcugcugg gcugccacac uuucuucug gaauuuuucg guguuggggg 3300
cgggacaccu uuauugcccu gaggggcauu cugcugauua ccggccgcua ugucgaggcu 3360
aggaacauua uccuggcuuu cgcgggguacc cuucggcacg gacucauacc caaccuccug 3420
ggagaaggaa ucuaugcacg guauaacugu cgggacgcag uuugguggug guugcagugu 3480
auucaagauu auugcaagau ggucccgaac ggacuggaca uacugaagug cccagugucc 3540
cggauguauc caacugacga cuccgcacca cugcccgcug ggacacuuga ccagccauug 3600
uuugaaguua uucaggaagc uaugcagaag cauaugcagg gaauucaguu uagggagaga 3660
aacgcuggac cccagauuga ccguaacaug aaggaugagg gguuuaacau uaccgcggga 3720
guggacgaag agacuggcuu cgucuauggu ggcaaucggu ucaacugcgg caccuggaug 3780
gacaaaaugg gcgaaagcga uagagcucga aauaggggca ucccagcaac accacgggau 3840
ggcucugccg uggagauugu gggccugucu aagagcgcag uucggugguu guuggaacuc 3900
agcaagaaga acauuuuucc auaccaugaa guuacaguga agcggcaugg gaaggccauc 3960
aagguuucuu acgacgaaug gaaucggaag auccaggaua acuucgagaa acuguuucau 4020
guauccgagg acccuucuga ccugaacgaa aagcauccaa auuugguaca caaaagggga 4080
aucuauaagg auaguuaugg agccagcagc ccuuggugcg acuaucagcu acgaccaaac 4140
uucacuauug ccaugguagu agcaccagaa cucuuuacua ccgaaaaggc uuggaaggca 4200
cuggagaucg ccgagaagaa gcuguuaggu ccacugggca ugaaaacccu ggaccccgac 4260
gacaugguuu acuguggcau cuaugacaac gcucuggaca augacaacua uaaucuggcc 4320
aagggcuuca acuaccacca gggcccagag uggcuauggc caauuggcua uuuucugcgg 4380
gcgaagcugu acuuuucacg auugaugggc ccagagacaa ccgcuaagac cauaguauug 4440
gucaagaacg ugcugagucg gcacuauguc caccuggaaa ggagccccug gaaggggcug 4500
cccgagcuga ccaacgaaaa ugcacaguau uguccguuuu caugcgaaac ccaggcuugg 4560
uccaucgcga cgauccugga aacccucuau gaucuguag 4599

<210> SEQ ID NO 9
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 9
augggacacu caaaacagau aaggauccug cugcugaacg aaauggagaa acuggaaaag 60
acccuguucc ggcucgaaca gggauaugaa cuccaguuua ggcugggccc aacucugcaa 120
ggaaaagcug ugaccgucua uacuaacuau ccauuucccg gggaaacguu uaaccgagag 180

-continued

```
aaguuccgau ccuuggacug ggaaaauccc acagagcggg aggaugauuc ggacaaguau    240
ugcaagcuga aucugcaaca aucgggcagc uuucaguacu auuuucuaca aggaaacgaa    300
aagagcggcg ggggauacau uguggugac ccaauccuga ggguuggggc agacaaucac    360
guacugccuu uggacugugu gacauugcaa acauuccugg caaagugccu gggccccuuc    420
gaugaauggg agucacggcu gcgaguggcu aaggaaucug gcuauaauau gauucacuuu    480
acaccauuac aaacgcuggg ccugagcaga aguugcuacu cgcuggcuaa ucaguuggag    540
uugaacccgg acuuuagccg ucccaaccgg aaguauacau ggaaugaugu uggccaacuc    600
guggagaagc ugaagaagga guggaacgug aucuguauua ccgaugucgu guauaaucau    660
acagccgcga acuccaagug gauucaggag cacccagaau gugcauauaa cuuggucaau    720
agcccccacc ugaagccggc cuggguacug gaucgggccc uguggcgguu uucuugugac    780
guggcagaag gaaaguauaa ggaaaagggg aucccagcac ugauagagaa cgaccaucau    840
augaacagca uuaggaagau cauuugggag gacauuuucc caaaguugaa gcucugggag    900
uuuuuccaag uugacgucaa caaggccgug gaacaauuuc gaaggcugcu gacacaggaa    960
aacagacgug uaacgaaguc cgaccccaau cagcauuuga cgaucauaca ggauccugag   1020
uauaggcgcu uuggcuguac ggucgacaug aauauugcuc ugaccaccuu uaucccucau   1080
gacaaggggc cagccgccau cgaagagugu uguaauuggu uccacaagcg cauggaagag   1140
uugaauuccg aaaagcauag guugaucaac uaccaccagg aacaggcagu gaacugucug   1200
cugggcaacg uguuuuauga gcggcuggcc ggucauggcc cuaagcuggg accagugacc   1260
aggaagcauc cacucguaac cagauauuuu accuucccgu uugaggagau agauuuuagc   1320
auggaagaau ccaugauuca ccuaccgaac aaggcuuguu uucugauggc ucacaacggu   1380
uggguuaugg gcgaugaucc ccugcgcaac uuugcggaac cgggcucuga gguguacuug   1440
agaagggagc ugauauguug gggggacucc gucaaacugc gcuaugggaa uaagccugaa   1500
gauugcccuu aucugugggc ccauaugaag aaguauaccg agauuaccgc gacauauuuu   1560
caaggagugc ggcuggacaa cugccacagc acgccgcugc auguggcaga guauaugcug   1620
gacgcagccc gcaaucugca gccaaaucug uauguugugg cugagcuguu uacgggcucc   1680
gaggaccucg acaacguuuu cguaacccgg cugggcauca gcagccugau ccgggaagcu   1740
augucagcgu auaauagcca ugaggagggc agacuggugu acagauaugg uggcgaacca   1800
guuggcagcu uugugcagcc cuguuugcgc ccucugaugc ccgccaucgc acaugcuuug   1860
uucauggaca ucacgcauga uaacgaaugu cccauuguac aucgcuccgc cuaugacgcu   1920
uugccaucca caacaaucgu guccauggcu uguugugcaa gcggcagcac caggggauau   1980
gacgaauugg uuccgcauca aaucagcgug guaucagagg aaagguuuua uacaaagugg   2040
aauccugaag cccugccauc caacaccggc gaagugaacu uucagucggg uaucauugcc   2100
gcgcguugcg cuauuagcaa acugcaucag gagcugggug cuaaaggcuu uauccaaguu   2160
uauguggauc aaguagacga agauauuguu gccguaacca gacauagccc cagcauucau   2220
caauccgugg uugcuguguc ccggacggcc uucaggaacc cuaaaacauc cuuuuauucc   2280
aaggaagucc cacagaugug uauuccggga aagauagagg aaguggguuuu ggaggcucgc   2340
acgauugagc ggaacaccaa gccauauagg aaggacgaga acucgaucaa cggcacgccc   2400
gacauuaccg uugaaauucg cgagcacauu cagcugaacg aaucgaaaau ugucaagcag   2460
gccggcguag cgaccaaggg uccaaacgag uauauccagg aaaucgaguu ugagaaucug   2520
```

```
ucgccugggu ccguaaucau uuuuagaguc agccuagacc cucacgcuca aguggccgua   2580
gggauccuga ggaaucaucu gacgcaguuu ucaccccauu uuaaguccgg cagccuggca   2640
guggauaacg ccgaccccau ccugaaaauu cccuuugcuu cccuggccuc gcgccugaca   2700
cuggcagaau ugaaucagau acuguaucgu ugcgagagcg aggagaagga ggacggaggg   2760
gggguguuaug auaucccgaa cugguccgcu cugaaauaug cgggauugca gggcuugaug   2820
aguguacugg ccgaaauuag acccaagaac gaucugggcc auccguucug uaacaaucug   2880
cgauccggcg auuggaugau ugauuauguc agcaaccggu ugauaagccg gagugggaca   2940
auugcagaag ucggaaagug guugcaagcc auguucuuuu accugaagca gaucccucga   3000
uaucugauac cauguuauuu cgaugccauu cugaucgggg ccuauacaac ucuguuagac   3060
acugcuugga aacagauguc uagcuucgug caaaacggcu caacauuugu uaagcacuug   3120
agccuggggu cugugcaguu guguggcgua ggaaaguuuc ccucacugcc cauccugucg   3180
cccgcccuga uggacgugcc cuaccgccuc aacgaaauua ccaaggagaa agagcagugu   3240
uguguuagcu uggcugccgg uuugccgcau uuuucaagcg gaaucuuccg augcugggga   3300
cgcgauacgu ucauagcccu gaggguauu cugcugauua cgggcagaua cguagaggcu   3360
cggaauauua uccuggccuu cgccggcacg cugcggcaug ggcugauucc gaacuugcug   3420
ggagagggca ucuacgcccg guacaacugc agggacgcug uguggugguug gcugcagugc   3480
auccaggacu auugcaaaau ggugccaaac ggccuugaca uacugaagug uccugucucu   3540
cggauguauc caacggauga cuccgcaccc cugcccgcug gaacccugga ucaaccccug   3600
uuugaaguga uacaggaagc aaugcagaag cacaugcagg gaauucaguu uagagagaga   3660
aaugcaggcc cccaaaucga cagaaacaug aaagaugaag gcuuuaacau cacggcugga   3720
guggacgaag aaacuggguu uguguauggc gggaauaggu uuaacugugg gacguggaug   3780
gacaagaugg gcgaauccga uagagcgcgg aacaggggaa ucccggcuac accccgggac   3840
gguagugcug uggagauugu cggcuuaucc aaauccgccg ugcgcuggcu gcuggagcug   3900
uccaagaaga acaucuuucc uuaccaugaa gugaccguga agcggcaugg aaaggccauc   3960
aaagucuccu acgacgaaug gaauaggaag auucaggaca auuuugagaa gcuguuucau   4020
guguccgagg aucccagcga ccugaacgag aagcacccua auuuggugca uaagcggggc   4080
aucuauaagg acuccuacgg cgcuaguucg ccuuggugcg acuaucagcu gcggccaaac   4140
uuuacgauug cgaugguggu agcccccgaa uuguuuacga cggaaaaggc uuggaaggcc   4200
cuggagaucg cagaaaagaa gcugcugggg cccuugggca ugaaaacgcu ggaccccgac   4260
gauaugguuu auuguggcau cuacgacaac gcccucgaca augacaauua caaccuggca   4320
aagggguuua acuaucauca ggguccugaa uggcuguggc caauuggcua cuuuuugcgg   4380
gccaagcugu acuuuucacg gcugauggga ccugaaacca ccgcuaagac cauuguacug   4440
gucaagaacg ugcugagcag gcauuacgug caucuggaaa gaagcccgug gaagggucug   4500
ccagaguuga cgaacgagaa cgcgcaguau uguccuuucu cuugugaaac gcaggcuugg   4560
aguauugcaa ccauucugga aacucuuuau gaccuguag                          4599
```

<210> SEQ ID NO 10
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 10

-continued

```
augggccacu caaagcagau uagaaucuua cuccugaacg agauggaaaa gcuggaaaag     60
acccuguucc gccuggaaca gggauaugag cugcaguucc ggcuuggacc aacccuccaa    120
ggaaaggccg ugaccgugua cacgaacuac ccauucccgg gcgaaaccuu caacagagag    180
aaguuccgga gccuggacug ggaaaacccg accgaaaggg aagaugauag cgacaaguac    240
ugcaagcuga acuugcaaca guccggauca uuccaguacu acuuucugca agggaacgag    300
aagucgggcg gcgguuacau cgugguggac ccuauucugc gcgugggagc cgacaaccac    360
guguugccuc uggacugugu cacccugcaa acuuuccugg ccaagugccu ggggccauuc    420
gaugaguggg aaucgcggcu gcggguggca aaagaguccg guuacaacau gauccacuuc    480
accccacucc aaacccuggg ccuguccagg ucgugcuacu cgcuggccaa ccagcuggaa    540
cugaacccgg auuucucgcg gccuaacaga aaguauaccu ggaaugacgu cggacagcuc    600
gucgaaaagc ugaagaagga auggaacgua aucuguauca ccgaugucgu guauaaccac    660
accgcugcca acuccaagug gauccaggaa caccccgagu gcgcuuacaa cuuggugaac    720
ucgccccacc ugaaaccggc uugggugcug gaccgggccc uguggcgguu cagcugcgau    780
guggcugagg gaaaguauaa ggagaagggu aucccagcgc ucauugaaaa cgaccaccau    840
augaacucga uccgcaagau cauuugggag gauauuuucc caaaguugaa acugugggag    900
uuuuuccaag uggacgugaa caaggcgguc gaacaguuca gacggcuguu gacucaggaa    960
aaucggaggg ucaccaaguc ggaucccaac cagcaccuga ccauaaucca ggauccagaa   1020
uaccggcggu ucggcugcac uguggacaug aacauugccc ugaccacuuu uaucccacac   1080
gacaagggcc cggccgccau cgaagagugc ugcaacuggu uccacaagcg gauggaggaa   1140
cugaacucgg agaagcaccg ccugaucaac uaccaccagg agcaggcggu uaacugucug   1200
uugggaaacg uguucuacga gcgguuggcc ggccacggcc cuaagcuggg cccggucacc   1260
cggaagcacc cccuggucac ccgcuacuuc accuuuccau ucgaggagau cgacuucagc   1320
auggaagaau cgaugaucca ucugccgaac aaggccugcu uccugauggc ucacaacgga   1380
ugggugaugg gcgacgaucc ucugagaaac uuugccgagc cgggcucgga gguguaccug   1440
aggagggagc ugaucuguug gggggacagc gugaagcuga gauacggaaa caagccagag   1500
gacugcccgu accugugggc ccauaugaag aaguacaccg agauuaccgc aacauacuuc   1560
caaggggucc ggcuggacaa uugccacucg acuccccugc acguggcgga guacaugcug   1620
gacgcggcca ggaaccucca gcccaaccuc uacgucgugg ccgagcuguu cacugguucc   1680
gaggaccugg auaacguguu cgugaccaga cuggggaucu ccucacugau ucgcgaagcc   1740
auguccgcgu auaacucgca ugaagagggc cgccuggugu accgcuacgg aggcgaaccu   1800
gugggcagcu ucgugcaacc gugucugcgg ccucugaugc cugccauugc gcacgcccug   1860
uucauggaca ucacccacga caacgaaugc cccaucgugc accgguccgc cuacgaugcc   1920
cucccuucga cuacuaucgu guccauggcu ugcugcgcgu ccggcucgac ccgcggcuac   1980
gaugagcucg ugccgcauca gauuagcgug guguccgagg aaagguucua caccaagugg   2040
aauccagaag cgcugccgag caacaccggg gaggucaacu uccagucggg aaucaucgcc   2100
gcccgcugug ccaucuccaa gcugcaccag gaacugggcg cgaaggguuu cauccaaguc   2160
uacgucgauc aggucgacga ggacaucgug gccgugacuc ggcauucccc gagcauucac   2220
caguccgugg uggccguguc gcgcaccgcc uuccgcaacc cuaagaccag cuucuauuca   2280
aaagaagugc cgcagaugug caucccugga aagaucgagg agguggcccu ggaagcgcgg   2340
```

-continued

```
acuaucgaaa ggaacaccaa gccauaccgc aaggacgaga acuccaucaa cgguaccccg   2400

gacaucacug uggagauccg cgagcauauu caacugaacg aguccaagau cgugaaacag   2460

gccggagugg caaccaaggg accgaacgag uauauccagg aaauugaguu cgagaaccuc   2520

uccccgggaa gcgugauuau cuuccgcgug ucccuggacc cacacgccca aguggccguc   2580

ggcaucuugc ggaaccaccu gacucaguuc uccccgcauu ucaaguccgg aagccuggcg   2640

guggacaacg cggacccaau ccugaagaua cccuucgccu cacuggccuc gcgccugacu   2700

uuggccgagu ugaaucagau ccuguaccgc ugcgaauccg aagaaaagga ggacggugga   2760

ggcuguuacg acaucccuaa cuggcuccga cugaaauacg caggacugca gggacugaug   2820

uccguccucg cugaaaucag accgaagaac gaucucggcc acccauucug caacaaccug   2880

agauccggcg auuggaugau ugauuacgug ucgaaccgac ugaucucccg cucggguacu   2940

auugcggaag ucggaaaaug gcugcaggcc auguucuucu accugaagca gaucccacga   3000

uaccuuaucc cuugcuacuu ugacgcgauu cugauuggug ccuacacgac ccugcuggac   3060

acggccugga agcaaauguc cagcuuugug cagaacggca gcaccuucgu gaaacaccug   3120

ucgcugggau cggugcagcu cugcggcgug ggaaguuuc cgucacugcc gauccugucc   3180

ccggccuuga uggaugugcc cuaccggcug aacgaaauca ccaaggagaa ggagcagugc   3240

ugcguguccgc uggccgccgg gcugccucac uucuccuccg gaauuuuucg augcuggggu   3300

agagacacuu ucauugcgcu gagggggauu cugcuuauua ccggccgcua cguggaagcc   3360

aggaacauca uccuggcauu cgccggaacc cugcggcacg ggcugauucc caaccuccuc   3420

ggagaaggaa ucuacgcucg guacaauugc cgggacgcag ugugguggug gcuccagugc   3480

auccaggacu acugcaagau ggucccuaac ggacuggaca uucugaagug cccagugucc   3540

cggauguacc ccacugacga uucggcaccg cugccggcug guacccugga ccagccgcug   3600

uucgaaguga uccaggaagc caugcaaaag cauaugcagg ggauucaguu ccgcgaaaga   3660

aaugccggac cucagaucga ccgcaacaug aaggaugaag gcuuuaacau cacugccgga   3720

guggacgaag agacuggauu cgucuacggg ggaaacagau ucaauugcgg uacauggaug   3780

gauaagaugg gagaaagcga cagagcucgg aauagaggaa uuccggccac accucgggac   3840

ggcucagccg uggagaucgu ggggcuaucc aagucugccg ugcgcuggcu guuggaacug   3900

ucgaagaaga acauuuuccc auaccacgag gucaccguga agcgccacgg aaaggccauc   3960

aaagugucau acgaugaaug gaaccgcaag auucaggaca acuucgagaa gcuguuccau   4020

gugucggagg acccuuccga ccugaacgaa aagcauccaa accuggugca caagcggggg   4080

aucuacaagg acuccuacgg agcguccucc ccuuggugcg acuaccaacu ccggccaaau   4140

uucacgaucg cgaugguggu ggccccugaa uuguuuacca ccgaaaaggc cuggaaggcc   4200

cucgagaucg cagagaagaa acugcuggga ccccugggca ugaaaacccu ggacccggac   4260

gauauggugu acugcggaau cuacgacaac gcccucgaua augacaacua uaacuuggcc   4320

aaggguuuca auuaccacca ggggccagag uggcuguggc caaucgguua cuuucugcgg   4380

gccaagcugu acuucucgag auugaugggg cccgaaacca ccgcuaagac uaucgugcuc   4440

gucaagaacg ugcugucacg gcauuacgug caccuggaac gcagcccaug gaagggccug   4500

ccggaacuga ccaacgagaa cgcacaguac uguccguucu cgugugaaac ucaggccugg   4560

agcauugcga ccauccugga aacucucuau gaucuguag                        4599
```

<210> SEQ ID NO 11
<211> LENGTH: 4599

<212> TYPE: RNA
<213> ORGANISM: Artificial Sequence
<220> FEATURE:
<223> OTHER INFORMATION: Codon-Optimized AGL Coding Sequence

<400> SEQUENCE: 11

```
augggccauu cuaagcaaau ucggauacug cugcugaacg aaauggagaa acuugaaaag     60

acccuguucc ggcuggagca gggcuaugag cugcaguuua gauugggccc gacacugcag    120

gggaaggcag ucaccguuua uaccaauuau ccuuuuccug ggaaacguu caaucgugaa     180

aaguuucgga gccucgacug ggaaaacccu accgagcgag aggaugauag cgacaaguau    240

uguaaacuca aucugcagca gucaggcuca uuccaauauu auuuucugca agggaacgag    300

aagucuggcg gaggcuacau ugucguugau ccgauacugc ggguuggcgc cgacaaccac    360

guguugccuc uggacugcgu gacacugcaa acauuucucg cgaaaugcuu aggccccuuu    420

gaugaguggg aaagccgccu gagagucgcc aaggagagcg gcuauaauau gauccauuuu    480

acgccgcugc aaacacuggg ucugucuagg ucauguuacu cauuggcuaa ccagcuggag    540

cugaacccgg acuuuaguag gccuaacagg aaguauacau ggaaugaugu ugggcaacug    600

guggagaagc ugaagaagga auggaauguc auuuguauua ccgaugucgu guacaaccac    660

acggcagcaa auucaaagug gauucaggaa cauccggaau gcgcuuauaa ccucguaaac    720

ucaccgcacc ugaagccggc cuggguacug gacagggcac uguggagauu cucuugugau    780

guagccgagg ggaaguacaa ggagaaaggc auucccgcuc uuauugaaaa ugaccaccau    840

augaauagca uuaggaagau caucugggaa gauauuuuuc caaaacugaa gcugugggaa    900

uucuuucaag uugacgugaa caaggcuguc gagcaguuca ggcggcuguu gacccaggag    960

aacagacggg uuacuaagag ugaccccaac caacaucuga cgaucaucca ggacccagag   1020

uaucggcgcu uggcugcac aguggacaug aacaucgccc ugaccacguu uaucccccau    1080

gauaagggcc cggccgcuau ugaagagugu uguaacuggu uucauaagcg cauggaagaa   1140

cucaacagcg aaaagcauag acugaucaac uaucaucaag aacaggcugu gaauugucug   1200

cugggcaacg uguuuuauga gcgguuggcu ggccauggcc ccaaguuggg ccccgugacg   1260

cgaaaacauc cccucgugac aagauauuuc accuuuccau uugaagagau cgacuucuca   1320

auggaggaaa gcaugauuca ucugccaaac aaggcuuguu uucugauggc ucauaauggc   1380

uggguuaugg gcgacgaccc ccugagaaac uuugcggaac cagggucuga aguguaucug   1440

cggagggaau ugauuugcug gggagacucu guaaagcugc gauaugggaa caagccggag   1500

gauuguccgu aucugugggc ccauaugaag aaguauacag aaauuaccgc aacguauuuu   1560

cagggcguac gccuggauaa uugucauuca acgccacugc auguggcaga guacaugcua   1620

gacgcggcua ggaaucugca gccgaaucug uaugucgugg ccgagcuguu caccggcucc   1680

gaagauuugg acaauguguu ugugacccgc cucgguauua gcucacugau uagagaagca   1740

augucggcuu acaauucgca ugaggaaggu cgccuggugu accguuacgg cggcgaaccc   1800

gugggcaguu uugugcaacc cugucugagg ccacuaaugc ccgcuauugc acaugcccug   1860

uuuauggaua uaacacauga uaacgaaugu ccaaucguac accggagugc uuaugaugcu   1920

cugcccucaa cgaccaucgu aucaauggca ugcugugccu ccggcucaac acggggcuau   1980

gaugaacugg uaccacacca gaucagcgug guuucugagg aacgguuuua cacaaagugg   2040

aauccugagg cguugccauc caacacuggc gaagugaacu uucagagcgg cauuauugcu   2100

gcccgaugug cuauuucaaa gcuacaccag gaguugggcg caaaggggu uauccagguu    2160
```

-continued

```
uauguggacc agguugacga agauaucgua gcugugacgc ggcacucucc gucuauccau   2220

caauccgugg uagccguguc uaggacggcu uuucgcaacc ccaagacaag uuucuauucc   2280

aaagaaguac cccagaugug uaucccgggg aagauugagg aaguggcccu ggaggccagg   2340

acgauagaac ggaacacgaa gccguaucgc aaggacgaaa acagcauaaa cgggacgccu   2400

gacaucacgg uggagauucg cgagcacauc caguugaacg aaucaaagau agugaaacag   2460

gcuggggugg cuaccaaggg cccaaaugag uacauucagg agaucgaguu cgaaaaccug   2520

uccccgggca gugugaucau cuuuagaguc ucuuuggauc cgcaugccca ggucgcugug   2580

ggcaucuugc gaaaucaccu gacgcaguuu ucuccacauu uuaagagugg cucccuggcu   2640

guggacaacg ccgacccaau cuugaagauu ccguucgcuu cccuggcuuc acgucugacu   2700

cucgcugaau ugaaucaaau ucuguauaga ugcgaaucag aggagaagga agauggaggc   2760

gguuguuacg acaucccgaa uuggucggca cugaaauacg ccggucugca aggcuugaug   2820

agcguacugg ccgagauaag accaaagaac gaucugggcc acccauuuug caacaacuug   2880

cgguccggcg auuggaugau ugacuauguc ucuaaccgac ucaucaguag aagcggaacc   2940

auagcugagg ucggcaaaug gcugcaagcc auguucuucu auuugaagca gaucccccga   3000

uaucugaucc ccuguuauuu ugacgcaauc cucauuggcg ccuauaccac acuccucgac   3060

accgcuugga agcagauguc cucauuugug caaaacggua gcaccuuugu gaagcaucug   3120

ucgcugggua gugugcagcu cugcggcgua gggaaguucc ccaguuugcc gauccugagu   3180

ccagcucuaa uggacgugcc auauaggcug aacgagauua ccaaggaaaa ggagcagugu   3240

ugugucuccc uugcugccgg ucugccccau uuuuccucgg gcauuuuuag auguuggggg   3300

cgggacaccu ucaucgcucu gcggggcauc cugcugauca ccggcagaua uguggaggcu   3360

cggaauauua uucuggcuuu ugcugggacg cugcgccaug gacugauucc caaucuauug   3420

ggcgaaggca uauacgcuag guauaacugu cgggacgcug uuugguggug gcugcagugu   3480

auccaagauu auugcaagau gguccccaac ggccuggaca uacugaaaug uccaguaucu   3540

aggauguacc cgacugacga cagugcuccc cugcccgcug gaacuuugga ucaaccccug   3600

uuugagguua uucaagaggc uaugcagaag cacaugcagg gcauucaguu ucgcgaaagg   3660

aacgccggcc cccaaauuga ccguaacaug aaggacgaag gcuucaauau uacggcuggc   3720

guagaugaag aaacaggcuu uguguacggc ggcaaccgcu ucaacugugg gacauggaug   3780

gacaagaugg gcgaaagcga cagggcucgg aacaggggaa uuccagccac gccccgcgau   3840

ggcagugcug uugaaauugu cggcuuguca aaaucagccg uacgcugguu auuagagcuc   3900

uccaagaaga acaucuuucc guaucaugaa gucacgguua agcggcaugg aaaagcaauc   3960

aaagugucuu acgacgaaug gaauaggaaa auucaggaca acuuugagaa gcuguuccau   4020

gugucugagg acccguccga ucuuaacgag aagcauccca auuuggugca caagaggggc   4080

aucuauaagg acucauacgg ggcuagcuca ccuuggugug acuaucagcu gcgaccgaau   4140

uucacaauag cuauggucgu ggcuccggag cuuuuuacca ccgagaaggc uuggaaggcc   4200

cuggagauug ccgagaagaa gcuguuaggc ccguugggca ugaaaacguu ggauccagac   4260

gacauggucu auuguggcau cuaugacaac gcucucgaca augacaacua uaaccuagcu   4320

aagggcuuca auuaccauca gggcccggag uggcuguggc caauuggaua uuuccugagg   4380

gcaaagcugu auuucucccg gcugaugggc cccgagacaa cggcaaaaac cauagucuug   4440

guuaagaacg ugcugucccg ccacuaugug caccuugaaa ggaguccgug gaagggccug   4500

ccggagcuga caaacgaaaa ugcccaguac ugcccauuuu cuugcgaaac ucaggcuugg   4560
```

agcaucgcca caaucuugga aacccuguau gacuuguag 4599

<210> SEQ ID NO 12
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 12
augggacacu cgaagcagau ccgcauccuc cugcugaacg aaauggaaaa acuggaaaag 60
acacucuucc ggcuggaaca gggauaugag cugcaguuua gacuggggcc caccuuacaa 120
ggaaaggccg ugacugucua uaccaacuac ccguuccccg gagaaacuuu caaccgggaa 180
aaguuccggu cacuggacug ggaaaacccg accgagcggg aggacgauag cgacaaguac 240
ugcaagcuga accuucagca guccggaucg uuccaguacu acuuccugca agggaacgag 300
aagucgggcg gaggauacau uguggucgau ccuauccugc gcgugggagc ugacaaucac 360
gugcucccuc uggacugcgu gacgcugcaa accuuccucg caaagugccu cggaccuuuc 420
gacgaauggg aauccagacu ccgcguggcc aaggagucag gauacaacau gauccacuuc 480
acgccgcugc agaccuuggg acucucucgg agcuguuacu cccuggccaa ccagcuggaa 540
cugaacccag acuucucacg cccgaauaga aaguacaccu ggaacgacgu gggacagcuu 600
guggagaagc ucaagaagga auggaacguc aucugcauaa ccgacgucgu guacaaccac 660
accgcagcca auucuaagug gauucaggaa caccccgaau gcgccuacaa ucugguuaac 720
ucaccccacc uuaagcccgc cugggucua gacagagccc ucuggcgguu cucgugugac 780
guggccgagg gaaaguacaa ggagaaggga aucccccgcuc ugauugaaaa cgaccaccac 840
augaacucca uccgcaagau uaucugggag gacaucuucc cgaagcucaa gcugugggaa 900
uucuuccaag uggacgugaa caaggcgguc gagcaguuca gacgccugcu gacccaggaa 960
aaucggagag ugaccaagag cgauccuaac cagcaccuga ccaucaucca agacccagag 1020
uaccggcggu ucggaugcac uguggauaug aacaucgccc ugaccacuuu caucccucac 1080
gacaagggac cggccgcaau ugaggaaugc ugcaacuggu uccauaagcg gauggaggaa 1140
cugaacagcg agaagcaucg acugaucaau uaucaucaag agcaggcugu gaauugccug 1200
cugggaaacg uguucuacga acggcuggcc ggacauggcc cuaagcuggg gccugugacc 1260
cggaagcacc cucuugugac ccgauacuuc accuucccgu uugaagaaau ugauuucucc 1320
auggaagaau ccaugaucca ucugccaaac aaggccugcu ucccuuauggc ccacaauggc 1380 ugggucaugg gggacgaccc ucuucggaac uucgccgaac cagggagcga gguguaccuc 1440
agaagggagc ucaucuguug gggggauucc gugaagcuca gauacggaaa caagccagaa 1500
gauugccccu accuuugggc ccacaugaag aaguacaccg aaaucaccgc cacauacuuc 1560
caaggagugc ggcuggacaa cugccauuca acuccccugc acgucgccga guacaugcug 1620
gacgcugcga gaaacuugca gcccaaccuu uacguguggg ccgagcuguu caccgggagc 1680
gaggaccugg acaacguguu ugugaccagg cucggaaucu cgucgcugau ucgcgaagcc 1740
augagcgccu acaacuccca cgaagagggu agacuggugu acagauacgg aggagagcca 1800 gugggggauccu ucguccaacc gugccugcgg ccgcucaugc cugcgaucgc acacgcgcug 1860
uucauggaca ucacccacga uaacgaaugu ccuaucgugc auaggagcgc cuaugaugcc 1920
cuucccucca ccaccaucgu guccauggcg ugcugugccu cggguagcac caggggauac 1980

-continued

```
gacgagcugg ugccgcacca gaucucggug guguccgaag aacgguuuua cacuaagugg   2040
aacccugagg cgcugccuuc caacaccgga gaagugaacu uccaguccgg uaucauugcc   2100
gcucgcugcg caaucagcaa acugcaccag gagcuuggug ccaaaggauu cauccaaguu   2160
uacgucgauc aaguggacga ggauauugug gccgucacua ggcacucucc aagcauucac   2220
caguccguag uggcagugug gaggaccgcc uuccggaacc ccaagacuuc auuuuacucg   2280
aaagaggucc cacagaugug caucccugga aagaucgaag aaguggugcu ggaagcccgg   2340
accaucgaga ggaacacaaa gcccuaccgg aaggacgaga acuccaucaa cggaaccccc   2400
gacauuaccg uggaaauuag agagcacauc caguugaacg agucgaagau cgugaagcag   2460
gccggagugg ccacuaaggg accaaacgag uacauccagg agaucgaguu ugaaaaccug   2520
uccccgggcu ccgugaucau cuuccgggug ucccuugacc cccaugccca aguggccguc   2580
ggaauccuua ggaaccaccu gacccaguuu ucgccccauu ucaaguccgg auccuuggcu   2640
gucgacaaug ccgaucccau ccugaaaauu ccguucgccu cccucgcuuc ccggcucacc   2700
cuugccgaac ucaaccagau ucuguaccgc ugcgagucag aagaaaagga agauggaggg   2760
ggaugcuacg acaucccgaa cugguccgcc cuuaaauacg ccgggcugca aggccugaug   2820
uccgugcugg cggagauuag accgaagaac gacuugggcuc acccuuuuug caacaacuug   2880
cggagcggag acuggaugau cgacuacgug ucgaaccggc ugauuagucg guccggaacc   2940
aucgccgaag ucggaaagug gcuccaagcc auguucuucu accugaagca aauuccccgc   3000
uaccugauac cgugcuacuu cgacgccauc cucauuggag ccuacaccac gcugcuggac   3060
accgccugga agcaaaugag cuccuucgug caaaacggau caaccuucgu gaagcaccug   3120
ucccugggua gcguccagcu cuguggcgug ggaaaguuuc cgucccugcc aauucugagc   3180
ccggcucuga uggaugugcc guaucgccug aacgagauca cgaaggagaa ggagcagugu   3240
ugcgugucgc uggcugcggg acugccucac uucucguccg gaaucuuccg cuguugggga   3300
cgcgacacgu uuaucgcguu gaggggguauu cuccucauua ccggacgcua cguggaagcg   3360
cggaacauua uccuggcguu cgccggaacc cugcgccacg gucugauucc uaaucugcug   3420
ggagagggaa ucuacgcgcg guacaacugc cgggaugcug uguggugug guugcagugc   3480
auccaggacu auuguaaaau ggugccgaac ggccuggaca uccugaagug cccggugucc   3540
cggauguacc cgaccgauga uucagcacca cugcccgccg ggacccugga ccagccccug   3600
uucgaaguca uucaggaagc gaugcagaag cauaugcagg gaauccaguu ccgcgaaaga   3660
aacgccggac cucagaucga ccgcaacaug aaggaugagg gcuucaacau caccgcggga   3720
guggaugagg aaaccggcuu cgucuacgga gggaaccggu ucaacugcgg aaccuggaug   3780
gacaagaugg gagaguccga ccgcgcaaga aaccgcggua uuccugccac cccgcgggac   3840
ggaagcgcgg uggagaucgu cggacugagc aagagcgcag ugcgcuggcu gcuggaguug   3900
uccaagaaga auaucuuccc cuaucacgag gucaccguga aacgccacgg gaaggccauc   3960
aaagaguccu acgaugagug gaaccgcaag auucaggaua acuucgaaaa gcuguuucau   4020
guguccgagg aucccuccga ccucaacgaa aagcacccga accucgugca uaagaggggg   4080
aucuacaagg acagcuacgg ugccuccuca ccuuggugcg auuaucagcu ccgcccgaac   4140
uucaccauug ccauggugu cgccccugaa cuguuuacua ccgagaaggc cuggaaggcg   4200
cuggagauug ccgaaaagaa gcuguuggga ccccugggca ugaaaacccu cgaccccgac   4260
gacauggugu acugcggaau cuacgacaac gcccucgaca acgacaacua caaccucgcg   4320
aagggguuca acuaccacca gggccccgaa uggcuguggc ccaucggaua cuuccuccgg   4380
```

gcgaaguugu acuucucccg ccugaugggc ccugaaacca cggccaaaac gaucgugcuc 4440
gugaagaacg ugcugucgag gcauuacgug caccucgagc ggagcccgug gaaggggcug 4500
ccggaacuga ccaacgagaa ugcacaguac ugccccuucu ccugcgaaac gcaggcuugg 4560
uccauugcca cuauuuugga aacgcuguac gaccuguag 4599

<210> SEQ ID NO 13
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 13
augggacacu cgaaacagau cagaauccug uugcucaacg aaauggagaa gcuggaaaag 60
acccucuuuc ggcucgagca gggcuacgag cugcaguucc gccugggucc gacacuacaa 120
ggaaaggcag ugacugugua caccaacuac ccauuucccg gagaaaccuu caaccgggag 180
aaguuccggu cccuggacug ggaaaaccca accgaacgag aggaugacuc cgacaaguac 240
ugcaagcuga accuccaaca guccgguuca uuccaguacu acuuucugca agggaacgag 300
aaguccggag gcggcuacau cguggucgac ccgauacuua gagugggagc cgacaaucau 360
guccugccuc uggacugcgu gacccugcaa accuucuugg ccaaaugucu gggcccguuc 420
gaugaguggg aaagccgccu cagagucgca aaggaguccg gauacaacau gauucacuuc 480
acuccgcugc aaacccucgg ucugucccgg ucgugcuauu cucuggcgaa ccagcuggag 540
cuuaaccccg acuucucgcg cccaaaccgg aaguacaccu ggaacgacgu cgggcagcuu 600
guggaaaagc ugaagaagga guggaacgug aucugcauca cugacguggu guacaaccau 660
acggccgcca acucgaagug gauccaagag caucccgagu gcgcguacaa ccucgugaac 720
agcccgcauc ugaagccugc uugggugcug gauagagccc ucuggagauu cagcugcgac 780
guggccgagg ggaaguacaa agaaaaggga auuccggccu ugauugagaa cgaccaucac 840
augaacucaa uccgcaagau caucugggag gauaucuucc cuaagcuuaa guugugggag 900
uucuuccaag uggacguaaa caaggcagug gagcaguuca gaagguugcu gacucaagaa 960
aacagacgcg ucacuaaguc cgauccuaac cagcaccuua ccaucauuca agacccugag 1020
uaccgccggu uuggcugcac cgucgacaug aacaucgccc ugaccacuuu caucccgcau 1080
gacaagggcc cggcggcaau cgaggaaugc uguaacuggu uucauaagag gauggaggaa 1140
cugaauuccg agaagcaccg gcugauuaac uaccaccagg aacaggcagu gaauugccuc 1200
cugggcaacg uguucuacga acggcuggcu ggacacggac cgaagcuggg ucccgugacu 1260
cgcaagcauc cgcucgugac ucgcuacuuc accuucccgu uugaggagau ugacuucucc 1320
auggaagaau ccaugaucca ccucccgaac aaggcuugcu uccugauggc gcacaacgga 1380
ugggucaugg gcgacgaccc acugcgcaac uucgcugagc cuggcucgga ggucuaccug 1440
agaagggaau ugauuugcug gggagacucc gucaagcugc gcuauggaaa caagcccgaa 1500
gauugccccu accugugggc ucacaugaag aaguacacgg aaaucacugc cacguacuuc 1560
cagggagucc ggcuggacaa uugccacucc acccccuccc auguggccga guacaugcuc 1620
gaugcagcga ggaaucugca gcccaaucug uacgugguug cagaacuguu cacuggcucc 1680
gaggaccucg acaacguguu cgugaccaga cuggggaucu ccucccugau ccgggaagcc 1740
augucggccu acaacuccca ugaagagggc cgccuggugu accgcuacgg cggagaaccc 1800

-continued

```
gugggaagcu ucgugcagcc uugccuccgg ccgcugaugc cugcgaucgc ccacgcccug   1860
uucauggaua ucacucacga caacgaaugc cccauugugc aucgcucggc cuacgacgca   1920
cugccuucga ccacuaucgu guccauggcc ugcugcgccu ccgggagcac ccgcggauac   1980
gaugaacucg ugccgcacca gaucagcgug guguccgaag aaagauucua uaccaagugg   2040
aaccccgaag cccugccgag caauaccggg gaagugaacu uccaguccgg uauuaucgcc   2100
gcucgcugug ccaucagcaa acuccaccaa gagcucggug ccaagggauu cauucaaguc   2160
uacguggauc aggucgacga agauauugug gccgugacca ggcacucacc uuccauccac   2220
caauccgucg ucgccguguc ccggacugcg uuucggaacc ccaagacuuc guucuacucg   2280
aaagaagugc cacagaugug uaucccggga aaaaucgaag aggucgugcu cgaagcccgg   2340
accauugaga ggaacaccaa gccuuaccgg aaagacgaga acucuaucaa cgguaccccu   2400
gauauuacug uggagauccg cgaacacauc cagcugaacg aaucaaagau cgucaagcag   2460
gcuggagugg ccaccaaggg acccaacgag uacauccagg agaucgaauu ugaaaaccuc   2520
uccccuggcu ccgugauuau cuuccgggug ucccuggacc cucacgccca aguggccgug   2580
ggaauucuca gaaaccaccu gacccaguuc ucaccccacu uuaaguccgg uucccuggcg   2640
guggacaacg ccgauccgau cuugaagauc cccuucgcau cgcuggccuc ccgccugacu   2700
cucgcggaac ugaaccagau ccuguaccgc ugugaaucag aggaaaagga ggacggcggc   2760
ggcuguuacg auauccccaa uuggucggcu uugaaauacg cgggacuuca ggggcugaug   2820
ucugugcugg cggaaauccg gccgaagaac gaccugggac acccauucug caacaacuug   2880
cggagcggag acuggaugau cgauuacguc agcaacagau ugaucagccg gagcggcacu   2940
aucgccgagg ucggaaagug gcuccaggcc auguucuucu accugaagca gauccccccga   3000
uaccucaucc ccuguuacuu cgacgccauu cugaucgggg ccuacaccac ccugcuggac   3060
accgccugga agcagaugag caguuuugug caaaacgggu ccaccuucgu gaagcaccuu   3120
ucacugggcu cagugcagcu cugcggcgug ggaaaguucc ccucgcugcc cauucugagc   3180
ccggcccuga uggacguccc uuaccggcug aacgagauca ccaaggagaa ggagcagugc   3240
uguguuuccc uggcugccgg gcugccacac uucucguccg gcaucuuccg gugcuggggc   3300
cgggauaccu ucauugcccu gcggggaauc cugcuuauca ccggucgcua cguggaggcu   3360
cggaacauua uucuggcguu cgccggcacc cuuagacacg gucugauucc gaaucuuuug   3420
ggcgaaggaa ucuacgccag auacaacugu cgggacgccg ugugguggug gcuccagugc   3480
auucaggacu auugcaagau ggugccgaac ggccuggaca uccugaagug cccagugucg   3540
aggauguauc caaccgacga cagcgcaccu cugccggccg ggacccucga ccaaccccug   3600
uucgaaguca uucaagaggc uaugcagaag cacaugcagg guauucaguu ccgggagcgg   3660
aacgcggggc cccagauuga uaggaacaug aaagacgagg gcuucaacau cacugccggc   3720
guggacgaag aaaccgguuu uguguacgga ggaaacagau ucaacugcgg uaccuggaug   3780
gacaagaugg gagaguccga ucgcgcgcgc aacagaggga ucccggcaac cccgcgggac   3840
ggauccgcgg uggaaauugu gggacugagc aagagcgccg ugcgguggcu ccuggaacug   3900
agcaaaaaga acaucuuccc cuaccacgaa gugaccguga agcggcacgg aaaggccauc   3960
aaagucucau acgaugaaug gaauaggaag auccaggaua acuucgagaa gcuguuucac   4020
guguccgagg aucccuccga ucugaacgaa aagcauccga aucucgugca caagcgcggg   4080
aucuacaagg acucguacgg agcguccucc ccuuggugcg acuaucagcu gcggccuaac   4140
uucaccauug ccauggucgu ggccccggag cuguucacaa cugagaaggc cuggaaggcc   4200
```

-continued cuugaaauug ccgagaagaa gcugcugggg ccuuugggga ugaaaacccu ggauccggac 4260
gacauggugu acugcggaau cuacgacaac gcccuggaca acgauaacua caaucuggcg 4320
aagggcuuca auuaccacca gggcccggaa uggcucuggc cuauugggua cuuccugcgc 4380
gccaagcugu acuucucacg gcugauggga ccagagacua ccgccaagac uaucguccuc 4440
gugaagaacg ugcugucccg gcacuacgug caucuggaga ggagcccuug gaagggacuu 4500
ccugagcuga cgaacgaaaa cgcgcaguac ugccccuucu ccugcgaaac ccaggcuugg 4560
uccauugcca cuauacugga aaccuuauau gaccuguag 4599

<210> SEQ ID NO 14
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 14
augggucacu ccaagcaaau cagaaucuua cuccuuaacg aaauggaaaa gcuugaaaag 60
acacucuucc gcuuggagca gggcuacgag cugcaguucc ggcugggucc gacacuucag 120
gggaaagccg ugaccgugua uaccaacuac ccccuuuccgg gagaaacauu caaucgcgag 180
aaguuccggu cgcuggacug ggagaacccu accgagaggg aggacgacuc ugauaaguac 240
ugcaagcuga aucuccagca aucagguucu uuccaauauu acuuccuuca aggaaacgaa 300
aaguccgggg gcggcuacau uguaguggac cccauccuuc gggucggcgc ggauaaccau 360
gugcuucccc ucgacugcgu gacucuccaa acuuuccucg ccaagugccu gggaccauuc 420
gaugaauggg aaucccgccu gcgcguggcc aaggagagcg gcuacaacau gauucacuuc 480
acuccgcuuc aaacccuugg gcugucccgc uccugcuauu cccuugcgaa ccagcuggaa 540
cuuaacccgg acuucucucg gccgaacaga aaguacacuu ggaacgacgu gggccagcuu 600
gucgagaagc ugaagaagga auggaacgug aucugcauca ccgacguggu guacaaccac 660
accgcggcaa acuccaagug gauccaggaa cauccugagu gcgcauacaa ccucgugaac 720
aguccgcauc ugaagccugc cugggugcug gauagagccc uguggcgcuu cuccugcgac 780
guggcugagg gaaaguacaa ggaaaagggc aucccugcgc ucauugaaaa cgaucaccac 840
augaacagca uccgcaagau uauuugggag gacaucuucc cuaagcucaa gcucugggag 900
uuuuuccaag uugacgugaa caaggccgug gagcaguuca gacggcuccu gacucaagaa 960
aacagacgcg ucaccaaguc cgacccuaac caacaccuca ccaucaucca ggaucccgaa 1020
uaccgccggu uuggcugcac uguggacaug aacauugccc ugaccaccuu cauuccgcac 1080
gacaaaggcc cggccgcgau ugaagagugc uguaacuggu uccacaagag aauggaggag 1140
cugaacuccg aaaagcauag acuuaucaac uaccaccagg aacaggccgu gaacugccug 1200
cugggaaacg uguuuuacga gagacucgcc ggacacgguc caaaguuggg uccugugacc 1260
cgcaaacacc cgcucgucac ccgcuacuuu accuucccgu ucgaggagau cgacuucagu 1320
auggaggaga gcaugaucca ucuccccaac aaggccuguu uccucauggc ccacaacggc 1380
ugggucaugg gcgacgaccc ccugcgcaac uucgcugaac ccggcucgga aguguaccuu 1440
cggagggagc uuaucuguug ggggcgacagc gugaagcuua gauacggcaa caagccagaa 1500
gauuguccgu accugugggc gcacaugaag aaguacaccg agaucaccgc gacguacuuu 1560
caaggagugc ggcucgauaa cugccacucc accccucugc acguggcaga guacaugcua 1620

-continued

```
gacgcggccc ggaaccucca gcccaaccuu uacgguggg ccgaacucuu cacugguucu   1680
gaggaucuug auaacguguu cgugacuagg cucggcauuu ccucccucau ccgggaagcc   1740
augucggccu auaacuccca cgaggagggg cggcuggugu accgcuacgg aggcgaaccg   1800
gucggcagcu ucgugcagcc gugccuccgc ccucugaugc ccgcuauugc ucacgcccuu   1860
uucauggaua ucacucacga uaaugagugc ccuaucgugc aucggagcgc cuacgacgcu   1920
cucccuucca ccaccaucgu guccauggcg ugcugcgccu ccgguucaac caggggcuac   1980
gaugaacuug ugccgcacca gaucucaguc gucagcgagg aaagguucua cacuaagugg   2040
aacccugaag cccugcccuc uaacacgggc gaagugaacu uucagagcgg uaucauugcc   2100
gcuagaugcg caaucuccaa guugcaccag gaacugggag ccaaggggguu cauccagguc   2160
uacguggacc aggucgacga ggacaucguc gccgugaccc ggcauucccc gagcauccau   2220
caguccgugg ucgccguguc acggaccgcc uuccgcaacc ccaagaccuc cuucuacucc   2280
aaggaagugc cgcaaaugug uaucccuggc aaaaucgagg aaguggugcu cgaagcgcgg   2340
acgauugaga ggaauacuaa gccguacaga aaggacgaaa acuccaucaa cggcaccccg   2400
gacaucacug uggagauccg ggagcacauc cagcucaacg agagcaaaau ugugaagcag   2460
gccggcgucg cuacuaaggg cccaaacgag uacauccagg agauugaguu cgaaaaccuu   2520
agcccugggu cugugaucau cuuucgcgug ucccucgacc cgcacgcaca ggucgcaguc   2580
gggauucucc ggaaccaucu gacucaguuc agcccccacu ucaagagcgg cagccuugcc   2640
gucgacaacg ccgaucccau ccucaaaauc ccuuucgcau cccuugcguc gaggcuuacc   2700
cuggcggaau ugaaccagau ucuguaccgc ugcgagucgg aagaaaaaga ggauggcggc   2760
ggcugcuacg acauuccgaa cuggucccgcc cugaaauacg cgggccuuca gggccuuaug   2820
agcgucuugg ccgagauccg ccccaagaac gaccuggggc accccuuuug caacaaccuc   2880
agaagcggcg auuggaugau cgacuacgug ucgaacaggc ucaucagccg auccggcacu   2940
auagccgagg ucggaaagug gcugcaggcc auguucuuuu accucaaaca gaucccgcgg   3000
uaccugaucc cgugcuacuu cgacgcuauu cucauuggcg ccuacacuac ccugcucgau   3060
accgcuugga agcagaugag cucauucgug caaaacggaa gcaccuucgu gaagcaccuc   3120
ucccugggau cagugcagcu gugcggcgug ggaaaguucc cauccuuacc aauucucucg   3180
ccugcccuga uggacguccc uuaucgccug aacgaaauca cgaaggagaa ggaacagugu   3240
ugugucucac uggcugccgg ccucccgcac uucucauccg gcaucuuccg gugcuggggu   3300
agagacacuu ucauugcgcu ccggggaauu cugcuuauca cuggccgcua cguggaagcc   3360
cgcaacauca uccuugccuu ugccgggacc cugcggcacg gccugauccc uaaccuucuc   3420
ggggagggca ucuaugcgcg auacaauugc cgggacgccg ucuggugcug gcugcagugc   3480
auucaggacu auugcaagau ggugccaaau ggucuggaca uucugaagug uccagugucc   3540
cggauguacc cuaccgacga uagcgcccca cugcccgccg gaacccucga ucagccccug   3600
uucgaaguca uucaggaagc gaugcagaag cauaugcagg guauccaauu ccgcgaaagg   3660
aaugccggcc cacaaaucga cagaaauaug aaggaugagg gcuuuaacau caccgccggc   3720
guggacgagg agacugguuu cgucuacggc ggcaaucggu ucaauugcgg gaccuggaug   3780
gacaagaugg gcgaaagcga ccgggccaga aaccggggca uuccggcuac cccccgcgau   3840
ggcucggccg uggaaaucgu gggccucucc aagucugccg ugcgguggcu uuuggagcuc   3900
uccaagaaaa acaucuuccc guaccacgaa gugaccguga agagacacgg gaaggccauc   3960
aaagugucuu acgacgaaug gaaccggaag auccaggaca acuucgaaaa gcuguuccac   4020
```

-continued

```
guguccgagg aucccuccga cuugaacgaa aagcacccca accucgugca caagcgcggc   4080

aucuacaagg auuccuacgg agcguccuca ccuuggugcg acuaucagcu gaggcccaac   4140

uucaccaucg caaugguggu ggccccugag uuguucacca cugagaaggc uuggaaggcc   4200

cuugagaucg ccgaaaagaa gcugcucggc ccgcugggga ugaaaacccu cgaccccgau   4260

gacaugguga acugcgggau auacgacaau gcacuagaca acgacaacua caaccuggcc   4320

aagggcuuca auuaccauca gggcccggag uggcuuuggc cuaucggcua cuuccugcgg   4380

gccaagcugu acuucucacg gcuuauggga ccggagacua cugcaaagac cauugugcuu   4440

gugaagaacg ugcuuucgcg ccacuacgug caucuggaac ggagccccug gaaggggcuc   4500

cccgagcuga ccaacgagaa cgcccaguac ugucccuucu ccugugaaac ccaggcuugg   4560

uccauugcca ccauucugga aacccuguac gaccucuag                          4599
```

<210> SEQ ID NO 15
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 15

```
augggacacu caaagcaaau ucggauccuc cugcucaacg agauggaaaa gcucgagaaa     60

acccucuuuc gccuggagca ggguuaugag cuccaguucc gccugggucc gacccuccaa    120

gggaaggccg ucacugugua cacuaacuau ccauuccccg gagagacuuu caaccgggaa    180

aaguuccgca gccucgauug ggagaacccu acugaacggg aggacgauuc ggacaaguac    240

uguaaacuga accuccagca gagcggcuca uuucaauacu acuuucugca agggaacgag    300

aaguccggag gggguacau cgucguggau ccuauccuuc gcgugggcgc cgacaaccau    360

gugcugccgu uggacugcgu gacccugcaa accuuccucg ccaaaugccu cggaccuuuc    420

gaugaguggg aauccaggcu gagaguggcc aaggaaucgg gguacaacau gauucacuuc    480

accccucucc aaacccuggg ccugucucgg agcugcuacu cccuggccaa ccagcuggag    540

cugaaucccg acuucucccg gcccaaccgg aaguacacuu ggaaugacgu gggccaacug    600

guggagaagc ucaagaagga guggaacgug aucugcauua ccgacguggu guacaaccau    660

accgccgcca acuccaagug gauccaggaa cacccagaau gugccuacaa ccucgucaac    720

ucaccccacc ugaaaccagc augggugcug gaucgcgccc ucuggcgguu cucgugugac    780

guggccgaag gaaaguacaa agagaagggc aucccugccc ugaucgaaaa ugaccaccac    840

augaauucca uuagaaagau cauuugggag gacauuuucc cuaaguugaa gcucugggag    900

uucuuccaag uggacgucaa caaggccgug gaacaguuuc gccggcuccu gacccaagaa    960

aaccgccgcg ugaccaaguc cgacccuaac cagcaccuga ccauaaucca ggacccugag   1020

uacagacggu ucgguugcac ugucgacaug aacaucgccu ugacuacuuu caucccgcac   1080

gacaaggguc cugccgccau ugaggagugc ugcaacuggu uccacaagcg gauggaagaa   1140

cugaacuccg aaaagcaccg ccucaucaac uaccaccagg agcaggccgu gaacugccug   1200

cuggggaacg uauucuacga gaggcuggcc ggacacggac ccaagcuggg acccgugacc   1260

agaaagcauc cucucgucac ccgcuacuuu acuuucccgu uugaagagau cgacuucuca   1320

auggaagagu cgaugaucca ucucccuaac aaggccugcu uccugauggc ccacaacggc   1380

ugggugaugg gcgacgaucc ucugagaaac uucgcugagc ccgguucgga aguguaccuu   1440
```

-continued

```
agacgggaac uuauuugcug gggcgauucc gugaaguuac gcuacggaaa caagccugag   1500
gacugcccuu accugugggc ccauaugaag aaguacaccg agauuaccgc caccuacuuc   1560
caaggggucc ggcuggacaa cugccacuca acuccucugc acguggcuga guacaugcug   1620
gaugcggccc ggaauuugca gccuaaccuu uacguggucg ccgaacucuu uaccgggucc   1680
gaggaccugg acaacguguu cgugacucgg cucggaaucu ccucacugau uagagaggcc   1740
auguccgcau acaacucgca cgaagaaggc cggcuggucu aucgauacgg cggcgaaccu   1800
gucggaagcu ucguccagcc cugccugcgg ccgcugaugc cagcgaucgc ccacgcccuc   1860
uucauggaca ucacccauga caacgaaugu cccaucgugc accgcuccgc cuacgaugcc   1920
uugccaagca ccaccaucgu guccauggcg ugcugcgcca gcgguagcac uaggggcuac   1980
gaugaacuug ugccgcacca gaucagcgug guguccgagg aaagguuuua cacgaagugg   2040
aaccccgaag cccugcccuc caacacuggg gaagugaacu uccaguccgg gaucauugcg   2100
gcccgcugcg cgaucucgaa gcuccaccag gaacucggcg cgaaaggauu cauucaaguu   2160
uacguggacc aggucgacga ggacaucguc gccgugacuc gccacucccc uucaauccau   2220
caauccgugg uggcggucuc gcggaccgcu uuccggaacc cuaagacuuc guucuacucg   2280
aaagaagugc cucagaugug uaucccccgga aagaucgagg aaguggugcu cgaggccagg   2340
acuauugaga ggaauaccaa gccuuaccgg aaggaugaga acuccauuaa cgguacuccu   2400
gacaucaccg ucgagauccg ggaacacauc cagcucaacg aaagcaaaau cgugaagcag   2460
gccggcgugg ccacuaaggg uccgaacgag uacauccagg aaaucgaauu ugagaaccug   2520
ucgcccggaa gcgugauuau uuuucgggug ucccuggacc cgcacgccca agucgccgug   2580
gguauccugc gcaaucaucu gacucaguuc agcccucacu ucaaguccgg cagccuugcc   2640
guggacaacg ccgauccgau ccugaagauc ccauucgccu cacucgccuc acggcucaca   2700
cuggccgaac ucaaucagau ccucuaucgc ugugaauccg aagagaagga ggacggcgga   2760
gguugcuacg auauuccgaa uugguccgca cugaaauacg ccggacugca gggccucaug   2820
uccguguugg ccgaaauccg cccuaagaac gaccucggcc acccguucug caacaaccuc   2880
agaucuggag acuggaugau cgauuacgug ucaaaccgcc ugaucucgag guccggcacu   2940
aucgccgaag ucggaaagug gcuccaagca auguucuucu accugaagca gaucccucgc   3000
uaccugauac cuuguuacuu cgacgccauc cucauuggcg ccuacacuac ucugcuggau   3060
acugccugga agcaaaugag cagcuucgug cagaacggaa gcacuuucgu caagcaucug   3120
ucgcucggga gcgugcagcu gugcggcguc ggaaaguuuc cuucccugcc cauucugucc   3180
ccugcccuca uggaugugcc guaccgccuu aacgagauca cuaaggagaa ggagcagugu   3240
ugcgugagcc uggcugccgg gcucccucac uucucguccg gaaucuucag augcuggggc   3300
cgcgacaccu ucauugcccu gcgagggauc cuguugauua cuggccgcua cguggaggcc   3360
aggaauauca uucucgccuu cgcgggaacc cugcggcacg gccugauccc uaaccuccug   3420
ggagaaggaa ucuaugcgag auauaacugc agggacgccg uguggugug gcuccagugc   3480
auccaggacu acugcaagau ggugcccaac gggcuggaca uccucaagug ccccguguca   3540
cggauguacc caacugauga cagugcuccu cugccggccg guacucucga ccagccacuc   3600
uuugaaguca uccaggaggc caugcagaag cacaugcagg gcauucaauu ccgggagagg   3660
aacgccggac cucagauuga ccggaacaug aaggacgagg guuucaauau cacugccggc   3720
guggacgaag aaaccggcuu cgucuacgga ggaaacagau ucaacugcgg aaccuggaug   3780
gauaagaugg gagaaagcga cagagcgcgg aacaggggua ucccugccac uccccgggac   3840
```

```
ggaucggccg uggaaauugu gggacuuucc aaguccgccg ugcgguggcu ccuggagcuu   3900

uccaagaaga acaucuuccc uuaccaugaa gugaccguga agcggcacgg gaaggccauc   3960

aaagucuccu acgaugaaug gaaccgcaag auucaggaca auuucgagaa gcuguuccau   4020

gucuccgagg acccuucuga ccugaaugag aagcauccca accuggugca caagagaggc   4080

aucuacaagg acagcuacgg agcuuccucc ccuuggugcg auuaccagcu ccggccaaac   4140

uucacuaucg ccaugguggu ggcgccugaa cuguucacca cugaaaaggc cuggaaggcg   4200

cucgaaaucg cggagaagaa gcugcucggg ccucucggga ugaaaacccu cgacccugau   4260

gauauggugu acugcggaau cuacgauaac gcccuagaca acgacaacua caaccuggcc   4320

aagggauuca acuaccauca ggggcccgag ugguuguggc cuauuggcua cuuccugaga   4380

gccaagcucu acuucucccg ccucaugggc cccgaaacca cugccaagac caucgugcuc   4440

gugaagaacg ugcucucccg gcacuaugug caccuugagc gcucgccaug gaagggacug   4500

cccgaacuga cuaacgagaa cgcccaguac ugccccuucu ccugugaaac ucaggccugg   4560

uccaucgcca caauuuugga aacccucuac gaucuguag                          4599
```

<210> SEQ ID NO 16
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 16

```
augggacauu caaagcaaau ccggauucug uuacuuaaug agauggagaa guuggagaaa     60

acauuguuua gacucgagca gggcuacgaa cugcaguuuc gccugggccc uacacuacaa    120

gggaaagccg ucaccgucua uacaaacuau cccuuccccg gcgaaacguu uaaucgggag    180

aaguucagau cucuggauug ggagaacccc accgaacggg aggaugauag cgacaaguau    240

ugcaaacuga acuugcagca gucuggcagu uuucaguauu auuuucugca agggaacgag    300

aaguccggcg gcggcuauau aguggucgac cccauccuuc gugugggagc ugacaaccau    360

guguugcccc uggacugugu uacacugcaa accuuucugg cuaagugucu cgguccuuuu    420

gaugaauggg aaucgcggcu cagggguggca aaagaauccg gcuauaacau gauucauuuu    480

acaccccugc aaacccuggg ccucucaagg aguuguuaca gccuugccaa ucagcuggag    540

cugaaccccg acuuuucccg ucccaaccgg aaguauacuu ggaacgacgu gggccagcuc    600

guagaaaagc ugaaaaagga guggaacgug aucuguauaa ccgauguggu cuauaaccac    660

accgccgcca auucgaagug gauccaggag caucccgagu gugcuuacaa ccucgugaac    720

agcccccauc uuaagcccgc uuggguacuu gaccgcgcac uuuggagguu uuccugugac    780

guggcugagg ggaaguauaa ggaaaagggc auccccgccc ugaucgaaaa cgaccaucac    840

augaacagua uacggaagau cauuugggag gauauuuuuc ccaaacugaa gcugugggag    900

uuuuuucaag uggaugugaa caaggcuguc gaacaguuua ggaggcugcu gacccaagaa    960

aauagacgcg ugacuaagag cgacccaaau cagcauuuga caauuauaca ggaccccgaa   1020

uaucgccgau ucggcuguac cguggauaug aauaucgcau ugacuacuuu caucccccac   1080

gacaagggcc ccgccgcuau ugaggaaugc uguaauuggu uucauaagcg aauggaggag   1140

cugaacucug agaagcacag gcugauuaac uaucaucagg aacaggccgu uaacuguuug   1200

cugggcaacg uguuuuauga acggcuugcc ggccauggcc cgaaguuggg cccgguuaca   1260
```

-continued

```
agaaagcauc cacuugugac ccgcuacuuc accuuuccgu ucgaagaaau ugacuuuagc   1320
auggaggagu caaugaucca ccuccccaac aaggcuugcu uucuuauggc ucacaacggc   1380
ugggugaugg gcgacgaccc ccugcggaac uuugcggaac cgggcucaga ggucuaucua   1440
agaagggaac ugauuugcug gggcgacucc gugaagcuga gauacgggaa caagccugag   1500
gauugccccu accucugggc ucacaugaaa aaguauacag aaauuacugc uacguauuuc   1560
caaggcguac ggcuugacaa cugucacucc accccacugc augucgccga guauauguua   1620
gaugcugcuc gaaacuugca gcccaauuug uaugugcucg cugaacuguu uacggggagu   1680
gaagaucucg acaacgucuu uguaacccga cugggcauca gcucgcuaau ucgggaggcc   1740
auguccgcuu acaacuccca ugaggaaggc cgccuuguau aucguuaugg cggcgaaccc   1800
guggggagcu uuguucaacc gugucuacgc cccugaugc ccgccaucgc ucaugcccua   1860
uucauggaua ucacucauga caaugagugu ccuauugugc auaggagugc uuaugacgcc   1920
cucccaagca caacgaucgu guccauggcu uguugugcua guggcuccac aagaggcuau   1980
gacgaacugg ugccccauca aaucuccgua gugucugaag agagauuuua caccaagugg   2040
aaccccgagg cucucccuuc aaacacugga gagguuaacu uucaauccgg gauuauugcu   2100
gcuagaugug cuaucagcaa gcuccaucag gaacugggcg caaagggcuu cauucaaguu   2160
uauguagacc agguugacga ggacauaguu gcaguaacuc ggcauucccc uucgauacau   2220
cagucugucg uggccguguc caggacagca uuucgcaauc ccaagacuag cuuuuacucc   2280
aaagaaguac cacaaaugug uauccccggg aagaucgagg aaguggguacu ggaagcccgg   2340
acuauugaga gaaacaccaa gccguaucgg aaggacgaga auucuaucaa cggcacaccu   2400
gauauaacag uggaaauacg cgaacacauu caguugaaug aguccaagau cgugaagcag   2460
gccggcgucg ccaccaaggg ccccaacgag uauauccagg agaucgaauu ugaaaaccug   2520
agccccggcu cuguuauuau auuucggguu ucauuagauc cucaugcuca aguggcugua   2580
ggcauccucc ggaaucaucu gacucaguuc ucuccccacu ucaagagcgg cagccuggcu   2640
gucgauaaug ccgaccccau acuuaagauu cccuuugcuu cccuggcuuc aaggcugacc   2700
cuggcugaac uuaaucaaau ccuauaccga ugcgaaagcg aagagaagga agauggcggc   2760
ggcuguuacg auaucccgaa cuggagcgca cugaaauaug cuggcuuaca aggccucaug   2820
aguguguugg cugagauuag acccaagaau gacuugggcc auccauuuug uaacaaccug   2880
agaagcggcg acuggaugau cgauuacgug ucuaaccgac ucaucucccg aagcggcacc   2940
auugcugagg uuggcaaaug gcugcaggcu auguucuuuu aucugaaaca gauuccucgg   3000
uaccugauuc ccuguuauuu cgacgcuauu cugauuggcg cauauaccac gcucuuggac   3060
acugcaugga agcaaaugag cucuuuuguc caaaauggcu ccacuuuugu uaaacaucug   3120
aguuugggca gcgugcaguu auguggcguu ggcaaauuuc caagccugcc cauacugucc   3180
cccgcucuga uggacguccc cuaccgacug aacgagauca ccaaggaaaa ggaacagugc   3240
ugugugucuu uagcugccgg cuugccgcau uuuucaagcg gcauuuuccg guguuggggu   3300
cgggacaccu ucaucgcacu gagaggcauu cugcugauca cuggccgcua uguggaagcu   3360
aggaauauca uuuuagccuu ugcggguacc cuucggcacg ggcugauccc caaucuuuug   3420
ggcgaaggca ucuacgcacg uuacaauugc cgggaugccg uauggugug gcuccaaugu   3480
auccaggacu auugcaagau gguucccaac ggccucgaua uccugaagug ccccguguca   3540
aggauguauc cuaccgauga cagugcuccc cuuccugcug gcacccugga ucagccgcuc   3600
uuugaaguua uucaggaagc aaugcaaaag cauaugcagg gcauccaguu ucgggaaaga   3660
```

aacgcuggcc cgcaaauaga caggaacaug aaggaugaag gcuucaauau uacugcuggc 3720
guagacgaag agacaggguu cgucuacggc ggcaauaggu uuaacugugg cacuuggaug 3780
gacaagaugg gcgaaucuga ccgcgcgagg aacagaggca ucccagcaac accgagggac 3840
ggcagcgcug uggagauugu gggccugucu aagucugccg ugcgcuggcu acucgaacug 3900
uccaagaaga auaucuuucc cuaucaugaa gucaccguaa agcggcaugg caaagcuauu 3960
aagguuuccu augacgagug gaacaggaag auucaggaca auuuugagaa gcuguuccau 4020
gugucggagg acccuagcga ucucaacgag aagcacccca acuuaguaca uaagaggggc 4080
aucuauaagg auagcuaugg cgcuagcagc ccuuggugug acuaucagcu ccgucccaac 4140
uuuaccauug cuaugguagu ggcgcccgag uuguuuacca cugagaaggc uuggaaggcu 4200
cuugaaauag ccgagaagaa auugcugggc ccccugggca ugaaaacucu ggaucccgau 4260
gacaugguau acuguggcau cuaugacaau gcccuggaca augacaauua caaucuggcc 4320
aaggguuuua acuaucacca gggcccugaa uggcuguggc cuauuggcua uuuucuucgc 4380
gccaagcuau auuuuaguag gcugaugggu ccagaaacaa cugcaaagac aauugugcuc 4440
gugaagaacg ugcuuucccg gcacuaugug caucuggaaa ggaguccaug gaagggcuug 4500
ccggaauuga cuaacgagaa cgcccaguau ugucccuuuu cuugugaaac ucaggccugg 4560
uccauugcua cuauucugga gacucuauau gacuuguag 4599

<210> SEQ ID NO 17
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 17
augggccauu ccaagcaaau ucgaauucug cugcugaacg aaauggaaaa guuggaaaag 60
acauuguucc gucuggagca gggcuaugag cugcaguuua ggcuuggccc gacguugcag 120
ggcaaagccg ugaccguaua uacuaacuau cccuucccug gcgaaacguu uaaccgggag 180
aaguuucgcu cacuggacug ggagaauccc acggaaaggg aggacgauag cgauaaguac 240
uguaaacuga aucugcaaca gucuggcucu uuccaauauu auuuucugca agggaacgag 300
aaguccgggg gcggcuauau uguaguggac cccaucuuga gagugggcgc ugacaaccau 360
guauuacccc uugauugcgu gacgcugcag accuuucugg cuaaguguuu gggcccuuuc 420
gaugaguggg aaagccggcu gagggguggcc aaggagagcg gcuauaaauau gauucauuuu 480 accccuuugc aaacucuggg gcucucuagg agcuguuauu ccuuggcuaa ucagcuggaa 540
cugaaccccg auuuuagccg gcccaaccga aaguauacau ggaaugacgu ugggcaauug 600
guugagaagc ugaagaagga auggaauguu auauguauaa cagacguggu guauaaccau 660
accgcugcua auucgaaaug gauucaggaa cauccugagu gcgccuacaa ccucguaaau 720
aguccucauc ugaagccggc uugggugcug gacagggcuc ucuggagguu uagcugugau 780
guggccgaag ggaaguauaa ggagaagggu aucccggcuc ugauugagaa cgaccaccau 840
augaacagua uaaggaagau aaucugggag gacauuuuuc ccaaacugaa gcugugggaa 900
uucuuucaag uggacgugaa caaggccguu gagcaguuua gacgcuugcu gacacaagag 960
aaccgaaggg ucaccaagag ugacccuaac cagcaucuua caauuaucca agaccccgag 1020
uaucgucggu uuggcuguac uguggacaug aacauugcuc ugaccaccuu uauaccccac 1080

-continued

```
gauaagggcc ccgcugcuau cgaagagugu uguaacuggu uccacaagag gauggaagag   1140

uugaacucug aaaagcaucg gcugauuaac uaucaucagg aacaggcugu gaacugccug   1200

cucggcaacg uauucuacga gagauuggcu ggccauggac cuaagcuggg cccgguuacg   1260

agaaagcauc cccugguuac gcgguauuuc accuucccgu uugaggagau ugauuuuagc   1320

auggaagaau ccaugaucca ccuccccaac aaggcuugcu uccugauggc acauaacgga   1380

uggguuaugg gcgacgaccc ccugaggaau uuugcugaac ccggcuccga agucuaucug   1440

agaagggaac ugaucuguug ggcgacuccc gucaaguugc gcuauggcaa uaagccugag   1500

gacuguccau aucugugggc ucacaugaag aaguacacag agaucaccgc uacauacuuu   1560

cagggcguca ggcucgacaa uugucacucc acaccccugc acguggcuga guauaugcug   1620

gaugccgcua ggaaucucca gccuaaccua uauguggucg cugaacuguu caccggcucu   1680

gaggaucugg auaauguguu ugugacacgc cugggcauca gcucccugau ccgcgaggcu   1740

augagugccu acaauaguca cgaggaaggc cggcuugugu accgcuaugg cggcgaaccc   1800

gugggcagcu uuguacaacc uugucugcgg ccucugaugc ccgcuauugc ucacgcuuug   1860

uuuauggaca ucacccauga caacgaaugu cccauuguac accggucugc uuacgacgcu   1920

cugcccucca caacuauugu caguauggcu uguugugcau cuggcucaac ucggggcuac   1980

gacgaauuag uuccgcauca aaucucugua guguccgaag aacgguuuua uacaaaaugg   2040

aaccccgaag cgcugcccuc caauaccggc gaagugaacu uucagucugg gaucaucgcc   2100

gcuagaugug cuauuucuaa acugcaucag gaacugggcg cuaagggcuu uauucaagua   2160

uauguggacc aggucgacga ggacaucgua gcuguaaccc ggcacagccc cagcauacau   2220

cagagugucg uggcuguguc uagaacagcu uuuaggaacc caaagaccuc uuuuuacucc   2280

aaagagguuc cacagaugug uaucccgggc aaaauugagg aaguggucuu ggaggccagg   2340

acaauugagc guaauacgaa gcccuauaga aaggaugaga auagcaucaa cggcacuccu   2400

gauaucacug uggaaauccg ggagcauaua caguugaacg agucuaagau cguuaagcag   2460

gcugguguag cuaccaaggg ucccaaugag uauauucagg aaauugaguu ugaaaaccug   2520

uccccgggca gcguaauuau cuuuagaguc agucucgacc cccaugcuca aguggcagug   2580

gggauccugc ggaaccauuu gacucaguuc uccccccauu uuaagucugg cagucuggcc   2640

guugacaacg cugaccccau auugaagauu cccuuugcuu cccuggcuuc acgguugacc   2700

cuggccgaac ugaaccagau uuuauaucgc ugcgaguccg aggaaaagga ggauggcggc   2760

ggcuguuaug acauucccaa cuggucugcu cuaaaauacg cugggcugca gggucugaug   2820

agugugcugg cugaaauucg ccccaagaac gaccugggcc auccauuuug caacaaucug   2880

cgcaguggcg acuggaugau ugauuaugug uccaaccggc ugauuagucg gagcggcacg   2940

aucgcagaag ucggcaaaug gcuccaggcu auguuuuuuu accuaaagca gauacccaga   3000

uaccugaucc cuuguuauuu ugacgcuaua cugauuggcg cuuacacaac cuugcuggac   3060

accgccugga agcagaugag cagcuuuguc caaaauggca gcacauucgu gaagcauuug   3120

ucucugggca gugugcagcu guguggcgug ggcaaauuuc caaguuugcc gauccugucu   3180

cccgcuuuga uggaugugcc auaucgacug aacgagauaa ccaaggaaaa ggaacagugu   3240

uguguuucac ucgcugcugg cuugccccau uuuuccucug gcauuuuccg auguuggggg   3300

agggacacau ucauugcccu gcgugggauc cugcugauua ccggccgcua cguugaggcu   3360

agaaacauua uuuuggcuuu cgccggcaca uugagacaug gucugauacc caaucugcug   3420

ggcgaaggca uauaugcuag guauaacugu cgcgacgcag ugugguggug gcugcaaugc   3480
```

```
auccaggauu auugcaagau gguuccuaac ggccuagaca uccugaagug cccagugucc   3540
cggauguauc caaccgauga uucagcuccc cugcccgccg guacacugga ccaaccccug   3600
uucgaaguua uucaagaagc caugcagaag cacaugcagg guauccaguu ucgagagagg   3660
aaugcaggcc cccaaauuga ccggaacaug aaggaugaag gcuucaacau uacugcuggc   3720
gucgacgaag aaacaggguu uguguacggc ggcaaccggu uuaacugcgg cacauggaug   3780
gacaagaugg gcgaaagcga ucgcgcacgg aaccggggca uccccgccac gccgcgugau   3840
ggcucugcug uggagaucgu cggccucagc aaauccgcug uccgauggcu guuagagcug   3900
ucgaagaaga acaucuuucc cuaccaugag guuaccguua agagacacgg caaagcuauc   3960
aaagugucuu augacgaaug gaauagaaag auucaagaca acuucgagaa acuguuucau   4020
guguccgagg aucccagcga ccucaacgaa aagcauccca aucucguaca uaagaggggc   4080
aucuauaagg acucauaugg cgcaucaagu ccuuggugcg acuaucagcu ucggcccaau   4140
uucacgaucg caauggucgu ggcacccgag cuguuuacua cggagaaggc uuggaaggcu   4200
cuggaaaucg cugagaagaa gcugcugggc ccuuugggca ugaaaacccu ggaucccgac   4260
gacaugguau acuguggcau auaugacaac gcucuggaua acgauaacua uaauuuggcu   4320
aaaggcuuua auuaucacca gggcccagaa uggcuauggc ccauuggcua cuuucugcga   4380
gcuaagcuau auuuuucucg ccugaugggc ccugaaacca ccgcuaagac uaucgugcuc   4440
gucaagaacg uacugaguag gcauuacgug cacuuggagc gcagcccaug gaagggcuug   4500
ccggaacuga cgaacgaaaa cgcucaguau uguccguuuu cuugugaaac acaggcuugg   4560
aguauugcua cuauccugga aacucuguac gaucuguag                          4599
```

<210> SEQ ID NO 18
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 18

```
augggucauu ccaaacaaau uaggauccug cuguugaacg aaauggaaaa gcucgaaaag     60
accuuauuuc gccuggagca gggcuaugag uugcaguuuc ggcugggacc aacucugcaa    120
ggaaaggcug uaaccgugua cacaaauuau ccuuuucccg gcgaaacguu uaacagggag    180
aaguuucgau cucuggauug ggagaacccc acugaaaggg aggacgauag cgacaaguau    240
ugcaaacuga aucugcaaca guccggcagc uuucaauauu auuuucugca agggaacgaa    300
aagagcggcg ggggcuauau uguaguagac ccuauacuga gagucggagc ugacaaccau    360
guucugcccu uggacugcgu gacacugcag accuuuuugg cuaagugucu gggccccuuu    420
gaugaauggg agagucggcu ccguguggcu aaggagagcg gguacaauau gauucacuuu    480
acccccugc aaacuuuggg acuuucccgg agcuguuaua gccuggcaaa ccagcuggag    540
uugaauccug acuuuucccg cccaaauagg aaguauaccu ggaacgacgu gggccaacug    600
guggagaagc ugaagaagga guggaacgug aucugcauua ccgacgucgu guauaaucau    660
accgccgcca acuccaagug gauacaggaa cauccugagu gugcuuacaa ccucguaaac    720
ucccccgcauc ugaagccagc uuggguucug gauagagcuu uguggcgguu cagcugugac    780
gucgcugagg gaaaguacaa ggaaaaaggg auuccugcuc ucaucgagaa ugaccaccac    840
augaacagua uuaggaagau uaucugggag gacaucuucc cgaagcuaaa gcugugggaa    900
```

-continued

```
uucuuccaag uggacgugaa caaggccgug gagcaguucc gacggcuguu aacucaagag    960
aaccguaggg ucacaaaauc ggauccuaac cagcaccuga ccauuaucca agacccggaa   1020
uaucggcggu ucggcuguac uguggacaug aacauugcuu ugacaacuuu cauuccccac   1080
gacaaggguc cagcagcuau cgaggaaugu uguaauuggu uucauaagcg gauggaggaa   1140
cucaacuccg agaagcauag gcugauuaau uaucaucagg aacaggcugu gaauugucug   1200
uugggcaaug uuuucuacga acggcuggcu ggccauggcc ccaaacucgg accuguuaca   1260
aggaagcauc cacugguuac ccgauacuuu accuuuccau uugaagaaau ugauuuuagc   1320
auggaagaau ccaugaucca ucuaccuaac aaggccuguu uucugauggc ccauaacggc   1380
uggguuaugg gagaugaucc cuugcggaac uuugcugaac ccggaucuga aguauaucug   1440
cggagagagu ugauuuguug gggcgacucc guaaagcugc gcuauggcaa caagccagag   1500
gacugucccu auuugugggc ucauaugaag aaguauaccg agaucaccgc uacguauuuu   1560
caaggcguca ggcucgauaa uugucauucc acuccgcugc auguugcuga guauauguug   1620
gacgcugcuc gaaaucugca gcccaauuug uauguugugg ccgagcuguu uaccggcucc   1680
gaggaccucg auaacguguu cgucacgcga cuaggcauca gcagcuugau ccgggaagcc   1740
auguccgcuu auaacuccca cgaggagggc cgacuggucu accgcuaugg cggcgaacca   1800
gugggcaguu uuguacagcc uugucugagg ccccucaugc ccgcuauugc ucaugcucug   1860
uucauggaca uuacucauga uaacgagugc ccuauagugc aucgguccgc cuacgacgcc   1920
cugccgagca cuacaauagu guccauggcu uguugugcaa gcgggagcac ccgcggcuau   1980
gacgagcugg ugccgcauca aauaucugua gucagcgaag aaagguuuua uaccaagugg   2040
aacccggaag cuuuaccuuc caauacuggg gaagugaacu uucagagcgg cauuaucgcu   2100
gcgagaugug cuauauccaa guugcaucag gaacuggggg caaagggguu uauucaagua   2160
uauguagacc agguugacga agauauagug gcugugacac gccacagccc aagcauccac   2220
caguccgugg uggcugucag ccggacugcu uuucgcaacc caaagacaag cuuuuauagc   2280
aaagaagugc cgcagaugug cauucccggc aaaauugagg aggucgugcu ggaggcuagg   2340
acuaucgaaa ggaacaccaa gccguacagg aaggacgaga auuccaucaa cgggacucca   2400
gauauuacag uugagauccg ggaacauauu caguugaaug agucgaagau uguuaagcag   2460
gcuggcguag cuacaaaggg gccaaacgag uauauucaag agauagaauu cgaaaaccug   2520
agccccgguu ccgugaucau uuuucgagug ucccuggauc cucaugcuca aguggccguu   2580
ggcauucuga gaaaccaucu cacacaauuu uccccucacu uuaaaagugg cagccuggcu   2640
guggacaacg ccgauccgau ccugaagauu ccauucgcuu cccuggcuag ucgccugaca   2700
cuggcugaac uaaaccagau ucuuuaccgc ugugaaucug aagagaagga ggacggcggc   2760
gguugcuaug acaucccaaa uuggagcgcu cugaaauacg cugggcugca gggccucaug   2820
agcguacugg cagaaaucag acccaagaac gaccugggcc accccuucug uaacaaccug   2880
agguccggcg auuggaugau cgacuaugug ucgaacagac ucaucucaag aagcggcacu   2940
auagcugagg ucggcaaaug guugcaggcu auguucuuuu aucugaagca aauuccgcgg   3000
uaucugaucc cgugcuauuu ugacgcuaua uugaucggcg cuuauacgac uuugcuggac   3060
acagccugga agcagauguc cagcuucgug cagaacggca gcacuuuugu gaagcaccug   3120
agucugggcu caguacagcu guguggcgug ggcaaauucc ccagccuacc aauucugucc   3180
cccgcucuga uggauguucc cuaucggcug aacgagauua ccaaggaaaa ggagcaaugu   3240
ugcgugagcc uggcagccgg ccugccccac uuuucuuccg gcauuuuucg cuguuggggu   3300
```

cgggacaccu ucauugcacu gcggggcauc cuguuaauca ccggccgcua uguggaagcu 3360
agaaauauua ucuuggcuuu ugcuggcacu cugcgacacg gccugauccc caaccuucug 3420
ggcgaaggca ucuaugcucg cuacaauugu cgcgacgccg ucugguggug gcugcagugu 3480
auacaggacu auugcaagau ggugccaaau ggccuggaca uccuuaaaug uccaguuucc 3540
cggauguacc caacugacga cagcgcuccu uugccugccg gcacacugga ucagccgcug 3600
uuugaaguga uccaggaagc uaugcagaag cauaugcagg gcauucaguu ucgggaacga 3660
aaugcuggcc cacaaauuga cagaaacaug aaggaugagg guuuuaacau uacugcuggc 3720
gucgaugaag agacaggguu uguguacggc ggcaacaggu ucaacugcgg cacauggaug 3780
gacaagaugg gcgaaucuga ccgugcuagg aacaggggaa uccccgcuac cccccgggac 3840
ggcagcgcug uggaaaucgu aggccugucc aaguccgccg uucgcuggcu ucuggagcug 3900
agcaagaaaa acaucuuucc cuaucacgag gucacaguga agagacaugg caaagcuauc 3960
aaagucucuu acgaugagug gaauagaaag auucaagaua acuuugaaaa guuguuccac 4020
guuucggagg accccagcga ucugaaugag aagcauccca acuuggugca caagaggggc 4080
auauacaagg acucuuaugg ugcuagcagc ccuuggugcg acuaucagcu gaggcccaac 4140
uuuacuaucg ccauggugu ggcaccggaa cuguuuacaa cggagaaggc uuggaaggcu 4200
cuggaaauug cugagaagaa guugcugggg ccccugggga ugaaaacgcu ggauccagac 4260
gacauggucu acuguggcau auaugauaau gcucuggaua acgauaauua caaucuggcu 4320
aaggguuuca acuaucauca ggggccagag uggcucuggc cuauuggcua uuuccuccgu 4380
gcuaagcugu acuuuucucg ccugaugggg ccagaaacua ccgcaaagac cauuguauug 4440
gucaagaacg ugcugagccg gcauuaugua cauuuggaac gguccccuug gaaaggccug 4500
cccgaacuca cuaacgagaa cgcucaguau uguccguuuu ccugcgaaac ccaggcuugg 4560
uccaucgcaa cuauuuugga aacccuguac gaccuguag 4599

<210> SEQ ID NO 19
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 19
augggccaca gcaagcaaau cagaauccuc cugcucaacg agauggaaaa gcucgaaaag 60
acccuguuca gacuggagca gggauacgag cugcaguucc gccucggacc aacccuccaa 120
gggaaggccg ugaccgugua caccaacuac ccauucccgg gagaaaccuu caaccgggaa 180
aaguucagga gccuggacug ggaaaacccc accgagagag aggacgacag cgacaaauac 240
ugcaagcuga accuccaaca gagcggcagc uuccaguacu acuuccucca aggaaacgaa 300
aagagcgggg gcggcuacau cgugguggac ccaauccugc gggucggggc agacaaccac 360
gugcugccac uggacugcgu gacacugcag accuuccugg ccaagugccu gggaccguuc 420
gacgaauggg agagccggcu gcggguggcc aaggagagcg gcuacaacau gauccacuuc 480
acaccgcucc aaacccucgg ccugagcaga agcugcuaca gccuagccaa ccagcuggag 540
cucaacccgg acuucagcag gcccaacaga aaguacaccu ggaacgacgu gggacagcuc 600
guggaaaagc ugaaaaagga auggaacgug aucugcauca ccgacguggu guacaaccac 660
accgccgcca acagcaaaug gauccaggaa cacccggaau gcgcguacaa ccucgugaac 720

-continued

```
agcccccacc ugaagccggc cuggguacug gacagggcac uguggcgcuu cagcugcgac    780
guggccgaag gaaaguacaa ggagaagggc auccccgccc ugaucgagaa cgaccaccac    840
augaacagca uccggaagau caucugggag gacaucuucc caaagcugaa gcugugggag    900
uucuuccaag ucgacgugaa caaggccgug gaacaguuca gacgccugcu gacgcaggag    960
aaccggaggg ucaccaagag cgaccccaac cagcaccuga ccaucaucca agacccggaa   1020
uaccggagau ucggaugcac cguggacaug aacaucgccc ugaccaccuu caucccacac   1080
gacaaggggc ccgcagccau cgaggagugc ugcaacuggu uccacaagag aauggaggaa   1140
cugaacagcg aaaagcaccg ccucaucaac uaccaccagg aacaggccgu gaacugccuc   1200
cucggaaacg uguucuacga gcggcuggcc ggccacgggc ccaagcuggg ccccgugacc   1260
cgcaagcacc cgcucgugac gcgguacuuc accuucccgu ucgaagaaau cgacuucagc   1320
auggaggaga gcaugaucca ccucccgaac aaggccugcu uccucauggc ccacaacggc   1380
ugggucaugg gcgacgaccc gcugcggaac uucgcagagc ccggaagcga aguguaccuc   1440
agaagggagc ugaucugcug ggagacagc gugaagcugc gcuacggaaa caagcccgag    1500
gacugcccgu accugugggc gcacaugaag aaguacaccg agaucaccgc caccuacuuc   1560
caaggagugc ggcuggacaa cugccacagc accccgcugc acguggccga guacaugcug   1620
gacgccgcca gaaaccucca gcccaaccuc uacguggugg cagagcuguu caccgggagc   1680
gaggaccucg acaacguguu cgugacccga cucggcauca gcagccugau ccgggaagca   1740
augagcgccu acaacagcca cgaggaaggg aggcuggugu acagauacgg aggagaaccc   1800
gugggcagcu ucgugcagcc gugccugagg ccccugaugc cagccaucgc gcacgcgcug   1860
uucauggaca ucacccacga caacgaaugc ccgaucgugc accggagcgc auacgacgcc   1920
cugccgagca ccacgaucgu cagcauggcc ugcugcgcca gcggcagcac ccgaggauac   1980
gacgagcugg ugccccacca aaucagcguc gucagcgaag aacgcuucua caccaagugg   2040
aacccggaag cacugccgag caacaccgga gaagugaacu uccagagcgg aaucaucgcc   2100
gcgcgcugcg cgaucagcaa acugcaccag gaacugggag ccaaggggguu cauccagguc   2160
uacgucgacc aaguggacga ggacaucgug gcagugaccc gccacagccc cagcauccac   2220
caaagcgugg uggccgugag ccggacagcg uuccggaacc ccaagacgag cuucuacagc   2280
aaagaggugc cccagaugug caucccggga aagaucgagg aaguggugcu cgaagcgcgc   2340
accaucgaac gcaacaccaa accguaccgc aaggacgaaa acagcauaaa cgggaccccc   2400
gacaucaccg uggagaucag ggaacacauc cagcugaacg agagcaagau cgugaagcag   2460
gccggggucg ccaccaaggg cccgaacgag uacauccagg agaucgaguu cgagaaccuc   2520
agccccggga gcgugaucau cuucagaguc agccuggacc cacacgccca aguggccgug   2580
ggcauccucc ggaaccaccu gacccaguuc agcccgcacu ucaagagcgg gagccucgcc   2640
guggacaacg ccgacccgau ccugaagauc ccguucgcga gccuggccag ccggcucacc   2700
cuggccgaac ugaaccagau ccuguaccgc ugcgagagcg aagaaaagga ggacggagga   2760
gggugcuacg acaucccaaa cuggagcgcg cugaaauacg cgggccugca gggccugaug   2820
agcgugcugg ccgaaauccg ccccaagaac gaccugggac acccauucug caacaaccug   2880
aggagcggag acuggaugau cgacuacguc agcaacagac ugaucagccg cagcggcacc   2940
aucgccgaag ucggaaaaug gcuccaggcc auguucuucu accugaagca gaucccgcgg   3000
uaccugaucc cgugcuacuu cgacgccauc cugaucggcg ccuacaccac ccugcucgac   3060
accgccugga agcagaugag cagcuucguc caaaacggga gcaccuucgu gaagcaccuc   3120
```

```
agccugggca gcgugcagcu gugcggggUC ggaaaauucc cgagccugcc cauccugagc   3180

ccggcgcuga uggacgugcc guacagacug aacgagauca ccaaggaaaa ggaacagugc   3240

ugcgugagcc uggccgccgg acugccgcac uucagcagcg gcaucuuccg gugcuggggg   3300

cgcgacaccu ucaucgcccu gcggggaauc cugcugauca cgggccgcua cguggaggcc   3360

cggaacauca uccuggccuu cgccggcacc cugcggcacg gacugauccc gaaccuccug   3420

ggagagggga ucuacgcccg guacaacugc cgggacgccg uguggguggug gcugcagugc   3480

auccaggacu acugcaagau ggugcccaac ggccuggaca uccugaagug ccccgucagc   3540

cggauguacc cgaccgacga cagcgccccg cuccccgccg gaacccucga ccagccacug   3600

uucgaaguga uccaggaggc caugcaaaag cacaugcagg gaauccaguu cagagaacgg   3660

aacgccggac cccagaucga ccggaacaug aaggacgagg gauucaacau caccgccgga   3720

gucgacgagg aaaccggcuu cgucuacgga gggaaccggu ucaacugcgg aacauggaug   3780

gacaagaugg gagagagcga ccgcgccagg aaccgcggaa ucccagcaac cccgcgggac   3840

gggagcgcag uggaaaucgu ggggcugagc aaaagcgccg ugcgguggcu gcucgaacuc   3900

agcaagaaga acaucuuccc cuaccacgaa gucaccguga agagacacgg aaaggccauc   3960

aaagucagcu acgacgaaug gaacaggaag auacaggaca acuucgagaa gcuguuccac   4020

gucagcgagg acccgagcga ccugaacgag aagcacccca accuggugca caagcgcggg   4080

aucuacaagg acagcuacgg cgcgagcagc ccguggugcg acuaccaacu gcgccccaac   4140

uucaccaucg ccauggucgu ggcccccgaa cucuucacga ccgagaaagc guggaaggcg   4200

cuggagaucg cggaaaagaa gcuccucgga ccccugggga ugaaaacccu ggaccccgac   4260

gacauggugu acugcggcau cuacgacaac gcgcuggaca acgacaacua caaccuggcc   4320

aagggcuuca acuaccacca gggccccgaa uggcuauggc cgaucggcua cuuccugcgg   4380

gccaagcugu acuucagccg ccucaugggc ccagaaacca ccgcaaagac caucgugcug   4440

gucaagaacg uccugagccg ccacuacgug caccucgaga gaagcccaug gaagggacug   4500

cccgagcuga ccaacgaaaa cgcgcaguac ugcccguuca gcugcgaaac ccaggccugg   4560

agcaucgcca ccauccugga aacacuguac gaccucuag                          4599
```

```
<210> SEQ ID NO 20
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 20

augggccaca gcaaacagau ccggauccuc cuacucaacg aaauggaaaa gcucgaaaag     60

acucuguucc ggcuggagca aggauacgag cuucaguucc gguugggccc gacgcugcag    120

gggaaggccg ugacagucua cacuaacuac ccauuccccg gcgaaaccuu caacagagag    180

aaguucaggu cccuggacug ggagaacccc acugaacggg aagaugauuc cgacaaguac    240

ugcaagcuga accuccagca auccgguuca uuccaguacu auuuccugca aggaaacgaa    300

aagagcggag gaggcuacau ugugguugau ccaauccuuc gcgugggagc cgauaaucau    360

gugcugccgc uggauugcgu cacccugcaa accuuccugg cgaagugccu gggcccguuc    420

gacgaauggg aaucccgccu gcgggucgcc aaagaguccg gguauaacau gauccacuuc    480

accccacucc aaacucuugg ccuguccaga uccugcuacu cguuggccaa ccaguuggag    540
```

-continued

```
cugaacccgg acuucucacg gccuaaccgg aaguacacuu ggaacgacgu cggacaacuc    600
guggagaagc ugaagaagga auggaauguc aucugcauua cugaugucgu guacaaccac    660
acggcggcga auucaaagug gauccaggag cacccagaau gcgccuacaa ccuggucaau    720
uccccucacc ugaagccggc cugggugcuc gaccgggccc uguggcgguu uucgugcgau    780
guggcggagg gaaaguacaa ggagaagggg auuccggcuc ucaucgaaaa cgaccaccac    840
augaacucca uccggaaaau uaucugggag gacaucuucc cgaaacuuaa gcugugggaa    900
uucuuccaag uggacgucaa caaggcugug gagcaguucc ggagauugcu gacacaagaa    960
aaccgccgcg ugaccaaauc cgauccgaac cagcaccuga cuaucauuca agacccggaa   1020
uaccggaggu uuggcugcac uguggacaug aauaucgcgc ugaccaccuu caucccgcac   1080
gacaagggac cggcagccau cgaagagugc uguaacuggu uccauaagag gauggaagaa   1140
uugaacucug aaaagcaccg gcugauuaac uaccaucagg aacaggccgu gaacugucuc   1200
cugggaaacg uguucuacga gcggcuggcg ggacacggac ccaagcucgg ccccgugacc   1260
cgcaagcauc cucucgugac uagauacuuu acuuucccau ucgaggagau cgacuucucc   1320
auggaagaau caaugaucca ccucccuaac aaggcuugcu uucugauggc acacaacggc   1380
ugggugaugg gcgaugaccc ccugaggaac uuugccgagc ccggcuccga aguguaccug   1440
aggagagagc ugauuugcug gggggacagc gucaagcugc gcuauggaaa caagccggaa   1500
gauugcccuu accucugggc ccacaugaag aaguacacug agauuacugc caccuacuuu   1560
caaggagugc gccuggauaa cugccacuca accccgcugc augucgcuga guacauguug   1620
gacgcagccc ggaaucugca accgaaccuc uacguggugg cggagcuguu caccggcucg   1680
gaggaucucg acaacguguu cgugacucgc cugggcaucu caucgcugau ccgggaagca   1740
auguccgccu acaacuccca ugaggagggu cggcuggugu accgcuacgg cggagaaccc   1800
guggggaccu ucgugcaacc gugccugcga ccccugaugc ccgccaucgc ccaugcccuc   1860
uuuauggaua uuacccacga uaacgaaugc ccuaucgugc accgcucagc cuaugaugcc   1920
cuccccucca ccaccaucgu guccauggcc ugcugcgccu cggggagcac ccgggguuau   1980
gacgagcugg ugccgcacca gauuucggug guguccgagg agagauucua caccaagugg   2040
aacccagaag cucugccguc aaacacugga gagguuaacu uucaguccgg uauuaucgcc   2100
gcuagaugug cuauuagcaa acugcaccaa gagcugggcg ccaaggguuu cauccaaguc   2160
uacgucgauc aggucgacga ggacaucgug gcugucacua ggcacucacc uagcauccac   2220
cagagcgugg uggccgugag ccgcacugcc uuccgcaacc caaagaccag cuuuuacucc   2280
aaggaggucc cucagaugug cauuccugga aagaucgaag aagugguccu ggaagcccgg   2340
accaucgaac gcaacaccaa gccuuaccgg aaggacgaaa acucgaucaa cgguaccccg   2400
gauauuacug uggagauucg cgaacacauc cagcucaaug aguccaagau cgugaagcag   2460
gccggaguggg caaccaaggg gccgaacgag uacauccagg agaucgaauu cgagaaucuc   2520
agcccuggca gcgugaucau cuuccgagug ucguuggacc cacaugcuca ggucgccgug   2580
ggcauccuga ggaaccaccu gacccaguuu uccccgcauu ucaaguccgg uucgcuggcc   2640
guggacaacg cagauccgau ccugaagauc ccuucgccu ccuuggcuuc gcgccucacg   2700
cuggccgagc ugaaccagau ccuguauaga ugcgaauccg aagaaaagga agauggaggc   2760
gguuguuacg acaucccgaa cugguccgcc uugaaauacg ccggacugca gggauugaug   2820
uccgugcugg ccgaaauuag accgaagaac gaccuggggc acccguucug caacaaccuc   2880
cggucggggg acuggaugau ugauuacgug ucgaaccgcc ucaucucccg guccgguacu   2940
```

-continued

```
auugcggagg ucggcaaaug gcuccaggcc auguucuucu acuugaagca aaucccccgc   3000
uaccugaucc ccugcuacuu cgacgccauc cugaucggag ccuacaccac ccugcuggac   3060
accgcgugga agcagauguc uagcuucguc cagaacggcu ccaccuucgu gaagcaccug   3120
ucacugggcu cagugcagcu gugcggaguu ggaaaguucc ccagccugcc uauccugucc   3180
ccggccuuga uggacgugcc guacagacug aacgaaauca cuaaggagaa ggagcagugu   3240
ugcguguccgu uggcggccgg gcugccccac uuuucaagcg ggauuuuccg gugcugggga   3300
agggacaccu ucaucgcgcu gcggggaauc cugcugauua ccggacgcua cguggaggcu   3360
cggaacauca uucucgcguu cgccggcacc cugcgccaug gacugauccc uaaucugcuu   3420
ggagagggca ucuacgcucg guacaacugc agagaugccg uguggugug gcuccaaugc   3480
auccaggauu acugcaagau ggugccuaac ggucuggaca uucugaagug cccuguguce   3540
cgcauguacc ccaccgacga cuccgccccc cugccugccg gaacccucga ccagccucug   3600
uucgaaguca uccaagaggc caugcagaag cauaugcagg gcauucaguu ccgcgaacgg   3660
aacgcagggc cccagaucga ccggaacaug aaggaugaag gguucaacau caccgccgga   3720
guggaugaag agacuggauu ugucuacgga ggaaaccgcu uuaacugcgg gaccuggaug   3780
gacaagaugg gagagucaga cagggccaga aauagaggaa uccccgcgac cccgcgcgac   3840
ggauccgccg uggagauugu gggccuguca aagagcgccg uccgcuggcu gcuggaacuu   3900
agcaagaaga acaucuuccc uuaccacgaa gugaccguga aaagacaugg caaagccauc   3960
aaagucuccu acgacgagug gaaccgcaag auucaggaca acuucgaaaa gcuguuccac   4020
guguccgaag aucccuccga ucugaacgag aagcauccga accuggucca uaagcgggga   4080
aucuacaagg auagcuacgg ugccagcucg ccguggugug acuaccagcu gcggccaaau   4140
uucacgauug cgauggucgu cgccccugag uuguucacca cugagaaggc cuggaaagcc   4200
cuggaaauag ccgagaagaa auuacugggg ccacugggca ugaaaacucu cgacccugac   4260
gacauggugu acuguggaau cuacgacaac gcacuggaca acgauaacua caauuuggcc   4320
aagggauuca acuaccacca ggggcccgaa uggcuguggc cuaucggaua cuuccuucgg   4380
gcaaagcuuu acuucucccg ccugauggga ccugaaacua cugccaagac cauugugcuu   4440
gugaagaacg ugcucucacg gcacuacgug caccuggaga gauccccgug gaaggggcuc   4500
ccggagcuga ccaacgagaa cgcccaguac ugcccuuucu ccugcgaaac ccaagccugg   4560
uccaucgcca ccauacuuga aacucuguac gaccuguag                          4599
```

<210> SEQ ID NO 21
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 21

```
augggacacu ccaagcagau ccgcauucuc cuccugaacg aaauggaaaa gcuggaaaag     60
accuuauuuc gccuugaaca aggauacgag cugcaguucc ggcuuggacc gacccuccaa    120
gggaaagcug ucaccgucua caccaacuac cccuucccgg gggagacuuu caacagagag    180
aaguucagau ccuuggacug ggaaaauccc acggaacggg aggacgacuc cgauaaguac    240
uguaaacuga accuccagca gucgggaucg uuccaguacu acuuccuaca agggaacgaa    300
aaguccggug gugguuacau cgugguggac ccgauccugc gcguggggggc cgacaaccac    360
```

-continued

```
gugcugccgc uggacugcgu gacucugcaa accuuccugg ccaagugccu cggcccguuc    420
gaugaauggg agucgagacu gcggguggcc aaggaaagcg gauacaauau gauucacuuu    480
acuccgcugc aaacccuggg gcugucgcgc uccugcuacu cgcucgcuaa ccagcuggaa    540
cugaauccgg auuuuagccg gccgaaccgg aaguauacgu ggaacgacgu cggucagcug    600
gucgagaagc ucaagaagga guggaacguc auuugcauca ccgacguggu cuacaaccac    660
accgcggcca auuccaagug gauccaggaa cacccggagu gcgccuauaa cuuggugaac    720
uccccucauu ugaaacccgc augggugcuc gaccgggccc uguggcgcuu uucaugcgac    780
guggcggaag ggaaguacaa ggaaaagggg auucccgccc ugaucgagaa cgaucaccac    840
augaacucaa uucgcaaaau caucugggag gauaucuucc cuaagcucaa gcugugggaa    900
uucuuccaag ucgacgucaa caaggccgug gaacaauuca gaaggcugcu gacccaagag    960
aaccgcagag ugaccaaguc ggacccgaac cagcaccuga cuauaaucca ggacccggaa   1020
uaccggaggu ucgguugcac cguggacaug aacauugcac ucaccaccuu caucccgcac   1080
gauaaggguc cggcggcgau ugaggagugc ugcaacuggu uccacaagcg gauggaggaa   1140
cugaacuccg agaagcaccg gcugauuaac uaccaccagg aacaggcugu gaauugccug   1200
cuggggaacg uguucuacga acggcucgcc ggccacggcc ccaagcuggg gcccgucacc   1260
cgcaagcacc cgcucgugac ucgauauuuc accuucccgu ucgaggaaau ugauuucucc   1320
auggaggaau caaugaucca ucugccgaac aaggccuguu ucuugauggc ccacaacggc   1380
ugggugaugg gagaugaccc gcugagaaau uucgccgagc cggggguccga gguguaccug   1440
aggagagaac ucaucugcug gggggauucc gugaaacugc gcuacgggaa caagcccgag   1500
gacugccccu accugugggc acauaugaag aaguacaccg aaaucaccgc caccuacuuc   1560
caaggggucc ggcuggauaa cugccauuca acuccgcucc auguggccga auacaugcug   1620
gacgccgcac ggaacuugca gcccaaccuc uacguggugg ccgaacucuu cacugggagc   1680
gaagaucucg auaacguguu cgugacccgg cucggaauuu cgagccugau ccgggaagcg   1740
augucugcuu acaacucgca cgaagaggga aggcuggugu acagauacgg gggggagccc   1800
gugggauccu ucgugcaacc gugccugagg ccgcuuaugc ccgcgaucgc ccacgcucug   1860
uucauggaca ucacccacga caacgaaugu ccgauugucc accggagugc cuacgaugcc   1920
cuuccgagca cuaccaucgu gucgauggcg ugcugugcgu ccgggucuac ccgcggcuac   1980
gacgaacucg ucccgcacca aaucagcgug guguccgaag aacgguuuua cacuaagugg   2040
aacccggagg ccuugcccuc gaacaccggg gaggucaacu uccagucggg aaucauugcc   2100
gcccgaugug ccaucucaaa guugcaccaa gaacucgggg caaaggggguu cauccaagug   2160
uacguggacc aaguggacga ggauauugug gccgugacca ggcacucccc gucgauccac   2220
caguccgugg uggcagucuc aagaacugcc uuccggaacc ccaagaccuc cuuuuacucg   2280
aaggaagugc cccagaugug caucccgggc aaaaucgaag aagucgugcu ggaagccaga   2340
acuaucgagc ggaacaccaa gcccuaccgg aaggaugaga acagcaucaa cggcacgccc   2400
gacaucaccg ucgagaucag agagcacauc cagcugaacg aauccaagau ugucaagcag   2460
gccggcguag cgacuaaggg acccaacgaa uacauccagg agaucgaauu cgaaaaccug   2520
ucgccgggau ccgugauuau cuucccgggug ucccuggacc cgcacgccca aguggccgug   2580
ggaauccugc ggaaccaccu gacccaguuc uccccgcauu ucaaguccgg cucccuggcg   2640
guggacaaug cagacccgau ucucaagauc ccguucgccu ccuuggccuc ccgccugacc   2700
cucgccgaac ucaaccagau ccuguaccgc ugcgagucug aggaaaagga ggacggggga   2760
```

```
ggaugcuacg auauuccgaa cugguccugcc cuuaaauacg cgggacugca gggucugaug   2820

ucggugcucg ccgagaucag accgaagaac gaccuggggc acccguuuug caacaaccug   2880

agaucggggg auuggaugau cgacuacgug ucgaaccggc uuaucucucg cuccggcacc   2940

aucgccgagg ucgggaagug gcugcaggcc auguucuucu accugaagca aauuccgcgc   3000

uaccugaucc cgugcuacuu ugaugccauc cugaucggcg ccuacacgac cuugcuggac   3060

accgccugga agcagaugag cagcuucgug cagaacggcu ccacguucgu gaagcaucug   3120

ucccugggau ccgugcagcu uugcggguguc ggaaaguucc cuucgcugcc uauucugucc   3180

ccggcgcuga uggacgugcc guaccggcug aacgagauca cuaaggagaa ggaacaaugc   3240

ugcguguccac uggcggcggg acucccccac uucuccuccg ggauuuuccg guguuggggga   3300

agagauaccu ucauugcccu gagggggaua cugcugauca ccggaagaua cguggaggcu   3360

agaaacauca uccucgccuu cgccggcacu cuccgccacg ggcugauccc caaccucuug   3420

ggcgaaggaa ucuacgcccg guauaacugc cgcgacgcgg ucugguggug gcuucagugc   3480

auccaggauu acugcaaaau ggugccgaau ggacuggaua uucugaagug ccccguuagc   3540

cgcauguacc ccaccgauga cuccgcaccc uugccggcgg gcaccuugga ccagccgcuc   3600

uuugaaguga uccaggaggc caugcagaag cacaugcagg guauccaguu cagagagcgg   3660

aacgcugggc cgcagauuga ccggaacaug aaggacgaag guuucaacau uacugccggg   3720

guggacgaag agacuggguu uguguacggg gggaaccgcu ucaacugugg gaccuggaug   3780

gauaagaugg gggagucgga ucgggcucgg aacaggggga uccccgcuac cccccgggac   3840

gggucggcug uggagauugu cgggcugagc aagagcgcag ugcgcuggcu gcuggagcuc   3900

agcaaaaaga acaucuuccc cuaccacgaa gucacuguga agagacacgg aaaggccauc   3960

aaggugucccu acgaugagug gaacagaaag auccaagaca acuucgagaa gcuguuccau   4020

guguccgagg auccgagcga ucugaacgaa aagcauccga accucgugca caagcgcggg   4080

aucuacaagg acucguacgg cgcauccucg ccgugggugcg acuaccagcu gcgccccaau   4140

uucaccauug ccaugguggu ggcgcccgag cuguucacua ccgagaaggc cuggaaggcc   4200

cuggagauug cugagaagaa gcugcuggga ccgcucggga ugaaaacuuu ggacccugac   4260

gacaugguguu acuguggaau cuacgacaau gcgcucgaca acgacaacua caaucuugcg   4320

aagggauuca acuaccauca ggggcccgaa uggcuguggc cgaucgggua cuuccugcgc   4380

gccaagcugu acuucucccg gcugaugggg cccgagacaa ccgccaagac cauugugcuc   4440

gucaagaacg uucucucccg gcacuacgug caccucgaaa gaucccccgug gaaggggcug   4500

cccgagcuca ccaacgagaa cgcacaguac ugcccguucu ccugugaaac ccaggccugg   4560

agcaucgcca ccauauugga aacucuguau gaccucuag                          4599
```

<210> SEQ ID NO 22
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 22

```
augggacacu cgaaacagau cagaauccug uugcugaacg aaauggagaa gcuggaaaag     60

acccucuuuc ggcucgaaca gggcuacgag cugcaguucc gccugggucc gacucuacaa    120

ggaaaggcag ugacugugua caccaacuac ccauuucccg gagaaaccuu caaccgggag    180
```

-continued

```
aaguuccggu cccuggacug ggaaaaccca accgaacgag aggaugauuc cgacaaguac    240
ugcaagcuga accuccaaca guccggauca uuccaguacu acuuuuugca aggaaacgag    300
aaguccggag gaggcuacau cgugguccgac ccgauucuga gagugggagc ugacaaucau    360
guccugccuc uggacugcgu aacccugcaa accuucuugg ccaaaugccu gggcccguuc    420
gaugaguggg aaagccgccu ccgggucgca aaggaaagcg gcuacaauau gauucacuuc    480
acuccucugc aaacccucgg ucugucccgg uccuguuauu cccuggcgaa ccagcuggag    540
cuuaaccccg acuucucgcg cccaaaccgg aaguacaccu ggaacgacgu cgggcagcuu    600
guggaaaagc ugaagaagga guggaacgug aucugcauca cugacguggu guacaaccac    660
accgcggcca acuccaagug gauccaagaa caucccgaau gcgcguacaa ccucgugaac    720
agcccgcauc ugaagccugc cugggugcug gauagggccc ucuggagauu cagcugcgac    780
guggccgagg ggaaguacaa agaaaaggga auucccgccc ugauugagaa cgaccaucac    840
augaacucaa uccgcaagau caucugggag gauaucuucc cuaagcuuaa guuguggggag    900
uucuuccaag uggacgugaa caaggcagug gagcaguuca gaaggcugcu gacucaagaa    960
aacagacggg ucacuaaguc cgacccuaac cagcaccuua ccaucauuca agacccggag   1020
uaccgccggu uuggcugcac ugucgacaug aacaucgccc ugaccacuuu caucccgcau   1080
gacaagggcc cggcggcaau cgaggaaugc uguaacuggu uucauaagag gauggaggaa   1140
cugaauuccg agaagcaccg gcugauuaac uaccaccagg aacaggcagu gaauugccuc   1200
cugggaaacg uguucuacga acggcuggcu ggacacggac cgaagcuggg ucccgugacu   1260
cgcaagcauc cgcucgugac ucgcuacuuc accuucccgu uugaggagau ugacuuuucc   1320
auggaagaau ccaugaucca ccucccgaac aaggcuugcu uccugauggc gcacaacgga   1380
ugggucaugg gcgacgaccc acugcgcaac uucgcugagc cuggcagcga ggucuaccug   1440
agaagggaac ugauuugcug gggagacucc gucaagcugc gcuauggaaa caagcccgaa   1500
gauugccccu accugugggc ucacaugaag aaguacacug aaaucacugc cacguacuuc   1560
cagggagucc ggcuggacaa uugccacucc acccccucc auguggccga guacaugcuc   1620
gaugcagcga ggaaucugca gcccaaucug uacgugguug ccgaacuguu caccggcucc   1680
gaggaccucg acaacguguu cgugaccaga cuugggauuu ccagccugau ccgggaagcc   1740
augucggccu acaacuccca ugaagagggc cgccuggugu accgcuacgg cggagaaccc   1800
gugggaagcu ucgugcagcc uugccucgg ccgcugaugc cugcgaucgc ccacgcccug   1860
uucauggaua uuacccacga caacgaaugc cccaucgugc aucgcucggc cuacgacgca   1920
cugccuucga ccaccaucgu guccauggcc ugcugcgccu ccgguagcac ccgcggauac   1980
gaugaacucg ugccgcacca gaucagcgug guguccgaag aaagauucua caccaagugg   2040
aacccugagg cacugccgag caacaccgga gaagugaacu uccagucggg uauuaucgcc   2100
gcucgcugug ccaucuccaa acuccaccaa gagcucggug ccaagggauu cauucaaguc   2160
uacguggauc aggucgacga agauauugug gccgugacca ggcacucacc uuccauccac   2220
caauccgucg ucgccguguc acggacugcc uuccggaacc ccaagacuuc guucuacucg   2280
aaagaggugc cacagaugug uaucccccgga aagaucgaag aggucguccu ggaagcccgg   2340
accauugaga ggaacaccaa gccuuaccgg aaggacgaga acagcaucaa cgguaccccu   2400
gauauuacug uggagauccg cgaacacauc cagcucaacg aaucaaagau ugucaagcag   2460
gccggagugg ccaccaaggg acccaacgag uacauccagg agaucgaauu ugaaaaccuc   2520
uccccuggcu ccgugauuau cuuccgggug ucccuggacc cucacgccca aguggccguc   2580
```

```
ggcauccuca gaaaccaccu gacccaguuc ucaccccauu ucaaguccgg uucccuggcg   2640

guggacaacg ccgauccgau cuugaagauc cccuuugcau cccuggccuc ccgccugacu   2700

cucgcggaac ugaaccagau ccuguaccgc ugcgaaucag aggaaaagga ggacggcggc   2760

ggcuguuacg auaucccgaa uugguccgcu cugaaauaug cgggacuuca ggggcugaug   2820

agcgugcugg cggagauccg gccgaagaau gaccugggac acccauucug caacaacuug   2880

cggagcggag acuggaugau cgauuacguc agcaacagau ugaucucccg gagcggcacu   2940

aucgcggagg ucggaaagug gcuccaggcc auguucuucu accugaagca gaucccccga   3000

uaccucaucc cguguuacuu cgacgccauu cugaucgggg ccuacaccac ccugcuggac   3060

accgccugga agcagaugag cuccuuugug caaaacgggu ccaccuucgu gaagcaccuu   3120

ucacugggau cagugcagcu cugcggcgug ggaaaauucc ccucgcugcc cauucugagc   3180

ccggcccuca uggacguccc uuaccggcug aacgagauca ccaaggagaa ggagcagugc   3240

uguguuuccc uggcugccgg acuuccacac uucucguccg gcaucuuccg gugcuggggc   3300

cgggauaccu ucauugcccu gcggggcauc uuguugauca ccggucgcua cguggaggcu   3360

cggaacauua uucuggcauu cgccggcacu cugagacacg gucugauucc gaaucuuuug   3420

ggcgaaggaa ucuacgcccg cuacaacugu cgggacgccg ugugguggug gcuccagugc   3480

auucaggacu auugcaagau ggugccgaac ggccuggaca uccugaagug cccagugucg   3540

aggauguauc caaccgacga cagcgcgccu cugccggccg ggacccucga ccaaccccug   3600

uucgaaguca uucaagaggc uaugcagaag cacaugcagg guauucaguu ccgggagaga   3660

aacgcggggc cccagauuga uaggaacaug aaagacgagg gcuucaacau cacugccggc   3720

guggacgaag aaaccgguuu uguguacgga ggaaaccggu ucaacugcgg uaccuggaug   3780

gacaagaugg gagaguccga ucgcgcgcgc aacagaggga ucccggcaac cccgcgggac   3840

ggaucagcgg uggaaauugu gggacugagc aagagcgccg ugcgcuggcu ccuggaacug   3900

agcaaaaaga acaucuuccc cuaccacgaa gugaccguga agcggcacgg aaaggccauc   3960

aaagucucau acgaugaaug gaauaggaag auccaggaua acuucgagaa gcuguuucac   4020

guguccgagg aucccuccga ucugaacgaa aagcauccga aucucgugca caagcgcggc   4080

aucuacaagg acucguacgg agccuccucc ccuuggugcg auuaucagcu gcggccuaac   4140

uucaccauug ccauggucgu ggcuccggag cuguucacua cugagaaggc cuggaaggca   4200

cuugaaauug ccgagaagaa gcugcuuggg ccuuugggga ugaaaacccu ggauccggac   4260

gacauggugu acugcggaau cuacgacaac gcccuggaca acgacaacua caaucuggcg   4320

aagggcuuca auuaccacca gggcccggaa uggcuguggc cuauugggua cuuccugcgc   4380

gccaagcugu acuucucacg gcugauggga ccagagacua ccgccaagac uaucguccuc   4440

gugaagaacg ugcugucccg gcacuacgug caucuggaga ggagcccuug gaagggccuu   4500

ccugagcuga ccaacgaaaa cgcccaguac ugccccuucu ccugcgaaac ccaggcuugg   4560

uccauugcca cuauacugga aaccuuauau gaccuguag                        4599
```

<210> SEQ ID NO 23
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 23

-continued

```
augggacacu caaagcagau ccggauccuc cugcugaacg aaauggaaaa gcucgaaaag     60
acucuguucc ggcuggaaca gggcuaugag cugcaguucc ggcucggacc gacgcugcaa    120
ggaaaggccg ugacugugua caccaacuac cccuucccgg gagaaacuuu uaacagagaa    180
aaguuuaggu cccuggacug ggagaacccg accgagcggg aagaugacuc cgauaaguac    240
ugcaagcuga accuccagca gucgggaucg uuccaguacu acuuccuuca aggaaaugag    300
aagucuggug gaggauacau cgugguggac cccauccuga gagugggagc cgacaaucac    360
guccugccgc uugacugcgu gacucugcaa accuuccugg cuaagugucu cgggccguuc    420
gacgaauggg aguccaggcu gcgcguggcu aaggagagcg gcuacaauau gauccacuuc    480
accccgcucc aaacucucgg acucucgcgc uccuguuacu cccucgccaa ccaacuggag    540
cugaacccgg acuucucccg cccgaaccgg aaguacaccu ggaacgacgu cggucagcuc    600
guggagaaau ugaagaagga guggaacgug aucugcauua cggacgucgu guacaaccau    660
acugcggcca acuccaagug gauucaagag cacccggaau gcgcuuacaa ccuugucaac    720
uccccgcacc ugaagccggc cugggugcug gacagagccc uguggcgguu cucgugcgac    780
guggcagagg gaaaguacaa ggagaagggc auccccgccc uuauugagaa ugaccaucac    840
augaacucca uccggaagau caucugggag gauaucuucc cgaagcucaa gcugugggaa    900
uucuuccaag uggacgugaa caaggccgug gaacaguucc ggagacuccu gacccaagaa    960
aaccggagag ugaccaagag cgacccgaac cagcaucuga cuaucauuca ggauccggag   1020
uaucggcggu uuggcugcac uguggacaug aacaucgccc ucaccaccuu caucccgcac   1080
gacaagggcc ccgccgcgau cgaggaaugc ugcaacuggu uccacaagcg cauggaggag   1140
cugaauuccg aaaagcaccg ccugaucaac uaccaucagg agcaggcagu gaacugucuc   1200
cugggaaacg uguuuuacga acggcuggcc ggacacggcc cgaagcuggg ucccgugacc   1260
cgcaagcauc cccucgugac gcgguacuuc accuucccgu ucgaggagau cgacuucagc   1320
auggaagagu ccaugaucca ucugccgaac aaggccugcu uccucauggc gcauaauggu   1380
ugggucaugg gagaugaucc ccuccgaaac uuugcggagc cggguucgga aguguaucug   1440
aggagggagc ucaucugcug ggagagauagc gugaaacuga gauacgggaa caagccggaa   1500
gauuguccgu accugugggc acacaugaag aaguacaccg aaaucacugc cacuuacuuc   1560
caaggaguuc gccuggauaa cugccauuca accccucugc augucgccga guacaugcug   1620
gacgccgcuc gcaaccuuca gccgaaucuc uacgugguucg ccgagcuguu caccgguucc   1680
gaagaucugg acaacguguu cgugacuaga cugggaauca gcagccugau ccgggaagcg   1740
augagcgccu acaacuccca cgaagagggc cggcucgugu auagauacgg cggagagccg   1800
gucgggagcu ucgugcaacc cugccugcgg ccgcugaugc ccgccauugc ccacgccuug   1860
uucauggaua ucacccacga caacgagugu ccgaucgugc accggagcgc guacgacgcg   1920
uuaccgucca ccacgauugu gucgauggcc ugcugcgccu ccggaucgac ccgcggcuac   1980
gaugagcugg ucccgcauca aaucagcguc gucagcgaag aacgguucua cacuaagugg   2040
aaccccgagg cgcuccccuc caacaccgga gaagugaacu uccaauccgg cauuaucgcu   2100
gcacgcugcg cgauuagcaa gcugcaucag gagcuuggcg cuaaggggguu cauacagguc   2160
uacguggauc aggucgacga ggacauugug gccgugacuc gccacucacc guccauucac   2220
caaagcgugg uggcuguguc ccggaccgcu uuccggaauc ccaagaccuc auucuacucc   2280
aaggagguuc cgcagaugug uaucccggga aagauugagg aaguggucu agaggcucgc   2340
acuauugaac gcaacaccaa gccguacaga aaggacgaga auuccauuaa cgggaccccg   2400
```

```
gauauuaccg uagaaauuag agaacauauu cagcugaacg agucgaagau cgugaagcag   2460
gccggggugg cuaccaaggg cccgaacgaa uacauccagg agauugaguu cgaaaaccuc   2520
ucccccggcu cggugaucau cuuccgggug ucccucgauc cccacgccca aguggccgug   2580
ggaaucuuga gaaaccaccu gacucaguuc agcccgcauu ucaaguccgg aucacucgcc   2640
guggacaacg ccgacccgau ccuuaagauc ccuucgcau cacuggccag ccgccugacc   2700
cuugccgaac ugaaccaaau ccucuaucgg ugcgaauccg aggagaagga agaugggggu   2760
ggaugcuaug acauuccuaa cuggucugcc cugaaauacg caggccugca gggacugaug   2820
uccguccugg ccgaaauccg cccgaagaau gaccuggggc accccuuuug caacaaucug   2880
agguccggag auuggaugau ugauuacgug uccaaccgcc ugauuucgcg gagcggcacc   2940
aucgcggaag ugggaaagug gcugcaagcc auguuuuucu accugaaaca gauccccgg   3000
uaccucaucc cgugcuauuu cgaugcgauu uugauuggcg cguacaccac ccuccucgac   3060
acugccugga agcaaaugag cuccuucgug caaaacgguu caaccuucgu caagcacuug   3120
ucgcuggggu cgguccaacu guguggaguc ggaaaguucc cgagccugcc cauccugucg   3180
ccugcccuga uggacgugcc cuaccggcug aacgagauca ccaaagaaaa ggagcagugc   3240
ugcgaguccc uggcggccgg acucccccau uucucguccg ggaucuuuag auguuggga   3300
cgggauacuu ucauugcgcu gcgcggcauc uuguugauua ccggacgcua cguggaagcg   3360
cggaacauca uacucgccuu cgccggcacc cucagacacg gccugauccc gaaccuccug   3420
ggagaaggca ucuacgcacg auacaacugu cgggacgccg ucugguggug gcugcagugc   3480
auucaggacu acugcaagau ggugccgaac ggucuggaca uccugaagug ccccguguca   3540
aggauguacc cgaccgacga uagcgcaccg cugcccgcgg ggacccugga ucagccgcug   3600
uucgaaguga uccaagaagc caugcaaaag cacaugcagg gaauucaguu cagagaaagg   3660
aacgcaggcc cccagauuga ccggaacaug aaggacgagg guuucaacau caccgccggc   3720
gucgacgaag aaacgggguu uguguacggg ggcaaccgcu ucaacugcgg uacuuggaug   3780
gacaagaugg gggaaucaga ccgcgcccgc aaccgcggaa uuccggcgac ccgcgcgau   3840
ggauccgcag uggaaaucgu gggacugucc aagucggcug ugcgguggcu gcuggagcug   3900
uccaagaaga acaucuuccc guaccacgag gucaccguga agagacacgg gaaggccauc   3960
aaggugucu acgacgaaug gaaccggaaa auccaggaua acuucgaaaa acuguuucac   4020
guguccgagg acccgucuga ccugaacgaa aaacacccga acuuggugca uaagcgggga   4080
aucuacaagg acaguuacgg agccucaagc ccguggugcg acuaccagcu gcggcccaac   4140
uucacaaucg cgaugguggu ggcgcccgag cuuuucacca cggagaaagc cuggaaggca   4200
cuggagaucg cugaaaagaa gcugcucggu ccccucggca ugaaaacccu ggacccggac   4260
gauauggugu acugcggaau cuacgacaac gcccuggaca augauaacua caaccuggcc   4320
aagggauuca auuaccacca ggggccggaa uggcuguggc cgaucggcua cuuucugcgg   4380
gcuaagcucu acuucucgcg gcugauggga ccggaaacca cagccaagac cauuguccuc   4440
gucaagaacg ugcuguccg ccacuacgug caucuggagc ggucaccuug gaagggccug   4500
cccgagcuga ccaacgaaaa cgcccaguac ugccccuucu ccugugaaac ucaagccugg   4560
ucaaucgcca cuauucucga aacucuguac gaucuguag                          4599
```

<210> SEQ ID NO 24
<211> LENGTH: 4599
<212> TYPE: RNA

-continued

```
<213> ORGANISM: Artificial Sequence
<220> FEATURE:
<223> OTHER INFORMATION: Codon-Optimized AGL Coding Sequence

<400> SEQUENCE: 24

augggucaca gcaaacaaau ccggauccug cugcucaacg aaauggaaaa gcuggaaaag     60
acucuguuuc gccuggagca gggcuacgaa cuccaauucc ggcugggacc aacgcugcaa    120
gggaaggccg ucaccgugua caccaacuac cccuuucccg gagagacuuu uaaccgcgaa    180
aaguucagaa gccuggacug ggaaaacccc accgaacggg aagaugauuc ggacaaguac    240
ugcaagcuga accuccagca guccggcagc uuccaguacu acuuccucca agggaacgaa    300
aagagcggag gaggcuacau cgugguggau ccgauccuuc ggguuggagc ggacaaccau    360
gugcugccuc uggacugcgu gacucugcaa accuuccuag ccaagugccu cggcccguuc    420
gaugaguggg aaucccggcu gcgaguggcg aaggagucag guuacaacau gauccacuuc    480
acaccgcugc agacccuggg acucucccgg uccugcuacu cauuggccaa ccagcucgaa    540
cugaacccgg acuucucaag gccgaaccgc aaguacacuu ggaaugacgu gggacaguug    600
guggagaagc ugaagaaaga guggaacgug aucugcauua ccgacguggu guacaaccac    660
acugcggcga auucgaagug gauucaggaa cauccggaau gcgccuacaa cuuggugaac    720
ucaccucacc ugaagccugc cugggugcug gacagagccc uguggcgcuu uagcugugac    780
gucgcggagg ggaaguacaa ggaaaaggga aucccgccc ugaucgagaa cgaccaccau    840
augaauagca uucgcaagau caucugggag gacauuuucc cgaagcugaa gcugugggag    900
uucuuccaag ucgacgucaa caaggccguc gaacaguucc ggcgguugcu gacccaagaa    960
aaccggagag ugacgaaaag cgacccuaac cagcaccuga caaucauuca ggacccugaa   1020
uaccggagau ucggcuguac cgucgauaug aacaucgccc ugaccaccuu uauuccccac   1080
gauaagggcc cggcggccau cgaggagugu ugcaacuggu uccacaagag aauggaggaa   1140
cucaacuccg aaaaacaccg guugauuaau uaccaccagg agcaggcggu caacugccug   1200
cugggcaacg uguucuacga aaggcucgcu gggcacggcc cuaagcuggg accugucacu   1260
cggaaacacc cccuggugac ccgguacuuu acuuucccgu ucgaagagau cgacuucucc   1320
auggaggaaa gcaugaucca ccucccuaac aaggccugcu uccugauggc ccacaacgga   1380
ugggucaugg gcgacgaccc uuugcggaac uuugccgagc cgggcucaga gguguaccuu   1440
agacgcgaac ugaucugcug gggagacucc gugaagcugc gcuacgggaa caagcccgaa   1500
gauuguccuu accugugggc acacaugaag aaguacaccg aaaucacugc caccuacuuc   1560
caaggagugc gcuuggauaa cugucauagc acuccucugc acgucgccga guacaugcug   1620
gacgcagcca ggaaucucca gccuaaucug uacgguggug ccgaacuguu caccgggagc   1680
gaggaccugg acaacguguu cgugacccgg cugggcauca gcucccuuau ccgggaggcc   1740
auguccgcau acaacucgca cgaggagggu cgccuggugu accgcuacgg aggagagccg   1800
gucggaucau uuguccaacc augccuccgg ccccugaugc cagcgaucgc gcacgcucuc   1860
uucauggaca ucacccacga uaacgaaugc ccuaucgugc accggagcgc uuacgacgcc   1920
cucccuucga ccaccauugu guccauggcc ugcugcgccu ccgguuccac ucggggcuac   1980
gaugaacugg ugccacacca gauuuccgug gugucagagg agcgguucua caccaagugg   2040
aacccagagg cgcugccgag caacacuggg gaagugaacu uccaguccgg aaucauagcg   2100
gcuagaugug caauuuccaa gcuucaucag gagcugggcg ccaaaggauu cauccagguc   2160
uacguggacc aaguggauga ggacauugug gccgugacua gacauucacc gucaauccac   2220
```

-continued

```
caaucggucg uggcugugucc cagaaccgca uuccgcaacc ccaagacuuc cuucuacucc   2280
```

caaucggucg uggcuguguc cagaaccgca uuccgcaacc ccaagacuuc cuucuacucc 2280
aaggaggucc cucagaugug caucccggga aagaucgagg agguggugcu ggaggccagg 2340
accaucgaaa gaaacacuaa gccuuaccgg aaagacgaaa acuccaucaa ugggacuccc 2400
gauauuaccg uggagauuag ggagcacauu cagcugaacg aaucaaagau ugugaaacag 2460
gccggggucg caacuaaagg gccuaaugag uacauccaag agaucgaguu cgaaaaccug 2520
ucgccggguu ccgugaucau uuuccgcgug uccuuggacc cucacgccca aguggccgug 2580
ggcauccuga ggaaccaccu gacccaguuc agcccacacu ucaaguccgg auccuuggcu 2640
guggacaacg ccgauccaau ccucaagauc ccuuuugcgu cgcuggccuc acggcuuacc 2700
cuggccgagc ugaaccagau ccuguaccgc ugcgagagcg aagaaaagga ggacggugga 2760
gguugcuacg acauuccaaa cugguccgcg cuuaaguacg ccggacucca gggucugaug 2820
uccgugcuug ccgagaucag accgaaaaac gaccuggggc accccuuuug caacaaccug 2880
agaagcggag acuggaugau cgacuaugug uccaaccggc ugauuucgag aagcgguacu 2940
auugccgagg ucggaaagug gcuccaagca auguuuuucu accugaagca aauuccccgc 3000
uaccugaucc cgugcuacuu ugacgccauu cugaucggug cauacacuac ccugcuggac 3060
accgcgugga agcagauguc cagcuucgug cagaauggcu ccaccuucgu caagcaucug 3120
ucccucggaa gcgugcagcu gugcggagug ggaaaguuuc cgucgcugcc aauccugucc 3180
cccgcgcuga uggauguccc guaccggcug aacgaaauca cgaaggaaaa agaacagugc 3240 ugcgIguccc uugccgccgg acugccgcac uucuccuccg gcauuuuccg gugcuggga 3300 cgggauaccu ucaucgcgcu gagagguauu cugcugauua ccggcagaua uguggaagcc 3360
cgcaacauca uccuggccuu ugccggcacu cugcggcacg ggcucauccc uaaccucuug 3420
ggagaaggca ucuacgcgcg cuacaacugc cgggaugcug ugugguggug gcugcagugc 3480
auccaggacu acuguaaaau ggugcccaau ggccuugaca uccucaagug cccagugucc 3540
cggauguacc cgaccgauga cuccgcgccc cugcccgccg gcacccuuga ucaaccucug 3600
uucgaaguca uccaagaggc caugcagaag cacaugcagg gaauccaguu cagggaaaga 3660
aacgccgggc cucagaucga ccggaacaug aaggacgagg gauucaacau uaccgccgga 3720
guggacgagg aaacuggcuu cgugua cggu ggaaaccgcu ucaacugcgg caccuggaug 3780
gauaagaugg gcgaauccga ucgcgcccgc aaccggggaa ucccagcaac uccuagggac 3840
ggaagcgcag ucgagaucgu ggggcugucc aaguccgccg ugcgguggcu cuuagaacug 3900
uccaagaaga auauuuuccc cuaccacgag gucaccguga agcgccaugg aaaggccauc 3960
aaaguguccu augacgaaug gaaccgcaag auccaggaca acuucgaaaa guuguuccac 4020
guguccgagg accccagcga ucugaacgaa aagcacccca accucgugca caagaggggc 4080
aucuacaagg acuccuacgg agcuagcucc ccuuggugcg auuaccaacu gcggccuaau 4140
uucaccaucg ccaugggucgu cgcacccgaa cucuucacca ccgagaaggc cuggaaggcu 4200
cuggaaaucg ccgaaaagaa gcuucugggc ccgcugggca ugaaaacucu cgauccugac 4260
gauauggucu acuguggcau cuacgacaac gcccuugaca acgacaacua caaccuggcc 4320
aagggcuuua acuaccacca gggcccagag uggcucuggc ccaucggaua uuuccugcgg 4380
gccaaacugu acuucucgcg guugaugggu ccggaaacca cagcuaagac caucgugcuc 4440
gugaagaaug ugcugucgcg gcacuauguc caucuggagc gcucccccug gaagggacuc 4500
ccugagcuga cuaaugagaa cgcccaguac ugcccuuucu ccugcgaaac ccaggccugg 4560
agcaucgcua ccauucucga aacgcucuac gaucuguag 4599

<210> SEQ ID NO 25
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 25
augggacauu cuaaacagau ucggauccuc cugcucaacg aaauggagaa gcucgaaaag 60
acccuguucc ggcucgaaca gggauacgaa cugcaauucc ggcugggucc caccuuacaa 120
ggaaaggccg ugacugucua caccaacuac ccguuccccg gcgaaaccuu caauagggag 180
aaguuccggu cccucgauug ggagaacccu acagagcgcg aagaugauuc agacaaguau 240
ugcaagcuga auuugcagca gagcggcuca uuccaauacu acuuccugca aggaaacgaa 300
aagucgggcg gcggcuacau cgugguggac ccuauucuga gagugggcgc cgacaaccau 360
guccugccgc uggacugcgu cacccugcaa acuuuccugg ccaagugccu ggguccuuuc 420
gaugaguggg aaucgagacu ucgcguggca aaggaaucgg guuauaauau gauucacuuc 480
accccgcugc aaacccuggg ccugucgcgg ucuugcuacu cacuggccaa ccagcuggaa 540
cugaacccag auuucucacg ccccaaccgg aaguacaccu ggaacgaugu gggccagcuu 600
guggaaaagc ucaaaaagga guggaacgug aucugcauua cugacguggu guacaaccau 660
acugcugcua auuccaagug gauccaggaa cauccugagu gugcuuacaa ccuggucaac 720
uccccacacc ugaagcccgc cugggugcug gaucgggcuc ucuggcgguu cuccugcgau 780
gucgccgaag gaaaguacaa ggagaagggg aucccugcgc ugaucgaaaa cgaccaucac 840
augaauucca ucaggaaaau caucugggag gacaucuucc cuaagcucaa gcugugggag 900
uucuuucaag ucgacgugaa caaggccgug gagcaguuca gacggcugcu gacacaagag 960
aaccgccgcg ucaccaagag cgacccgaau cagcaccuga cgauuaucca ggacccugag 1020
uacagaagau ucggcugcac cguggauaug aacauugcuc ugaccaccuu caucccccac 1080
gauaaggguc ccgcagccau ugaggagugc ugcaacuggu uccacaagag gauggaagaa 1140
cugaauuccg agaagcaccg gcugaucaau uaucaccaag aacaagccgu gaacugccuu 1200
cugggaaacg ucuuuuacga gcgccuggcg ggacaugggc caaagcucgg gcccgugacc 1260
agaaagcacc cacuggucac ccgcuacuuc accuuccccgu ucgaggaaau cgacuucagc 1320
auggaagagu cgaugaucca cuugccgaac aaggccugcu uccucauggc ccauaacggu 1380
ugggucaugg gcgaugaccc ucuucgcaac uucgcggagc ccgguucuga agucuaucuu 1440
cggcgggaac ugauuugcug ggggagacucc gucaagcugc gcuacggaaa caagcccgag 1500
gauugcccgu acuugugggc ccauaugaag aaguacacug agaucacugc cacuuacuuc 1560
caaggagugc gccucgacaa uugucacagc acuccgcugc acguggcgga guacaugcug 1620
gacgccgcuc gcaacuugca gccuaaucug uaugucgugg ccgaguuguu caccggcucg 1680
gaagaucugg acaacguguu cgucacucgc cugggaaucu ccucccugau ccgggaagcg 1740
augagcgccu acaacuccca cgaagagggg cgguuggugu accgcuacgg cggagagccu 1800
gucggaaguu ucgugcagcc cugucugagg ccccugaugc ccgcuaucgc ccaugcgcug 1860
uuuauggaca ucacccacga caacgaaugc ccuauugugc accgcuccgc cuaugaugcc 1920
cugcccucca ccacuauugu cagcauggcc ugcugcgccu cggggucccac ccggggauac 1980 gacgaacugg ugccccacca aauuuccgug guguccgagg aacgguucua caccaagugg 2040

-continued

```
aacccugaag cgcugccauc gaacacugga gaagugaacu uucagucggg aauuaucgca   2100
gcccgaugcg ccaucagcaa gcugcaccag gaacucggcg caaaggguuu uauccaaguc   2160
uacguggacc aggucgacga ggacauuguc gccgugaccc ggcacucccc auccauccac   2220
cagucugugg uggcuguguc aaggacggcu uuccggaacc caaagaccag cuucuacagc   2280
aaggaagugc cucagaugug caucccgggg aagaucgaag aaguggugcu ggaggccaga   2340
accaucgaaa gaaacaccaa gcccuaucgg aaggacgaga acucgaucaa cgguacuccg   2400
gacauuaccg ucgagauacg cgagcacauu cagcugaacg aguccaaaau cgugaagcag   2460
gccggggugg ccacgaaggg ucccaacgag uacauucagg agaucgaguu cgagaaccug   2520
agccccgggu ccgugaucau cuuccgcgug ucccuggacc cccacgccca aguggccgug   2580
ggcauccugc ggaaccaucu gacccaguuc uccccgcacu ucaagagcgg cucgcucgcc   2640
guggacaacg cggacccgau ccucaagauc ccuuucgcau cgcuggccuc ccgccugacc   2700
cuggccgaac ugaaucagau cuuguaccga ugcgaaucag aagagaagga ggacgggggg   2760
ggcugcuacg auaucccaa cuggagcgcg uugaaguacg caggauugca gggauugaug   2820
uccguccucg cugaaauccg cccgaagaac gaccugggac acccguuuug caacaaccug   2880
agaucagggg auuggaugau cgauuacgug ucgaacagac ugaucucgcg cagcggcacu   2940
auugccgaag uggggaagug gcuccaggcc auguucuucu accugaagca gaucccucgg   3000
uacuugaucc cuuguuacuu cgacgccauc cugaucggag ccuacaccac ccugcuugac   3060
acugcaugga agcagauguc cagcuucgug caaaacggaa gcaccuucgu gaagcaccug   3120
ucccugggau ccgugcagcu cugcggcgug ggaaaguuuc cgucccuccc cauccugagc   3180
ccugcccuua uggacgugcc guacaggcug aacgaaauua ccaaagagaa ggagcaaugc   3240
ugugugucu uggcggccgg auugccgcau uucuccuccg ggauuuuccg gugcugggga   3300
cgggacaccu uuaucgcacu gaggggguauu cuccugauca ccggucgcua cguggaggcu   3360
cgcaacauua uucuggccuu cgcgggcacg cuuagacaug gauugauccc uaaccuucug   3420
ggagaaggga ucuacgcgcg guacaacugc cgcgaugccg ugugguggug gcugcagugc   3480
auccaggacu acugcaaaau ggugccgaau ggucuggaua uccugaagug uccgguuucg   3540
cggauguacc cuaccgacga cagcgccccu cucccggccg gcacucucga ccagccccua   3600
uuugaaguaa uccaggaggc caugcaaaag cacaugcagg gcauacaguu cagagagagg   3660
aacgccggac cgcagauuga ccggaacaug aaggacgagg gauucaacau uaccgcggga   3720
guggaugagg aaacugguuu cguguacggc ggaaaccggu uuaacugcgg cacuuggaug   3780
gacaagaugg gagaauccga ccgcgcccga aaccgcggaa uucccgccac uccccgcgac   3840
ggcuccgccg uggaaauugu gggacuguca aaguccgcag uccgcuggcu gcuggaacuc   3900
ucaaagaaga acaucuuccc guaccacgag gucaccguga agcggcacgg caaagcgauc   3960
aaagugucgu acgacgagug gaaccggaag auucaggaua acuucgagaa gcuguuucac   4020
guguccgaag auccaagcga ccugaacgag aagcauccca acuuggugca caagcgcggc   4080
aucuacaagg auuccuacgg agccagcagc ccguggugcg acuaccaacu ccgccccaac   4140
uucaccaucg ccaugguggu ggcgccggag cuguucacga cggagaaagc uuggaaggcu   4200
cucgaaaucg cggagaagaa gcugcugggu ccucuggga ugaaaacccu ggacccggac   4260
gauauggugu acugugggau cuacgacaac gcccuggaca acgacaacua caaccucgcc   4320
aaggggguuca acuaccacca gggacccgaa uggcucuggc caaucggaua cuuccugaga   4380
```

gcgaagcuuu acuucucgcg gcugaugggu ccugaaacca cggccaagac caucgugcuc 4440
gugaaaaaug ugcugucaag gcacuacgug caucuggaga ggucgccaug gaagggucug 4500
ccggaacuga ccaacgaaaa cgcacaguac ugccccuuuu cgugcgagac ucaggccugg 4560
uccaucgcca ccauucucga aacucucuac gaccuguag 4599

<210> SEQ ID NO 26
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 26
augggacacu cgaaacagau cagaauccug uugcucaacg aaauggagaa gcuggaaaag 60
acccucuuuc ggcucgaaca gggcuacgag cugcaguucc gccugggucc gacacuacaa 120
ggaaaggcag ucacugugua caccaacuac ccauuucccg gagaaaccuu caaccgggag 180
aaguuccggu cccuggacug ggaaaaccca accgaacgag aggaugacuc cgacaaguac 240
ugcaagcuga accuccaaca guccggauca uuccaguacu acuuucugca agggaacgag 300
aaguccggag gcggcuacau cguggucgac ccaauacuua gagugggagc cgacaaucau 360
guccugccuc uggacugcgu gacccugcaa accuucuugg cgaaaugucu gggcccguuc 420
gaugaguggg aaagccgccu cagagucgca aaggaguccg gauacaacau gauucacuuc 480
acuccgcugc aaacccucgg ucugucccgg ucgugcuauu cucuggcgaa ccagcuggag 540
cuuaaccccg acuucucgcg cccaaaccgg aaguacaccu ggaacgacgu cgggcagcuu 600
guggaaaagc ugaagaagga guggaacgug aucugcauca cugacguggu guacaaccau 660
acggccgcca acucgaagug gauccaagag caucccgagu gcgcguacaa ccucgugaau 720
agcccgcauc ugaagccugc uugggugcug gauagagccc ucuggagauu cagcugcgac 780
guggccgagg ggaaguacaa agaaaaggga auuccggccu ugauugagaa cgaccaucac 840
augaacucaa uccgcaagau caucugggag gauaucuucc cuaagcuuaa guugugggag 900
uucuuccaag uggacguaaa caaggcagug gagcaguuca gaagguugcu gacucaagaa 960
aacagacggg ucacuaaguc cgauccuaac cagcaccuua ccaucauuca agacccugag 1020
uaccgccggu uuggcugcac cgucgacaug aacaucgccc ugaccacuuu caucccgcau 1080
gacaagggcc cggcggcaau cgaggaaugc uguaacuggu uucauaagag gauggaggaa 1140
cugaauuccg agaagcaccg gcugauuaac uaccaccagg aacaggcagu caacugccuc 1200
cugggcaacg uguucuacga acggcuggcu ggacacggac cgaagcuggg ucccgugacu 1260
cgcaagcauc cgcucgugac ucgcuacuuc accuucccgu uugaggagau ugacuucucc 1320
auggaagaau ccaugaucca ccucccgaac aaggcuugcu uccugauggc gcacaacgga 1380
ugggucaugg gcgacgaccc acugcgcaau uucgcugagc cuggcucgga ggucuaccug 1440
agaagggaau ugauuugcug ggagacuccc gugaagcugc gcuauggcaa caagccugaa 1500
gauugccccu accugugggc ucacaugaag aaguacacgg aaaucacugc cacguacuuc 1560
cagggagucc ggcuggacaa uugccacucg accccgcucc auguggccga guacaugcug 1620
gaugcagcga ggaaucugca gcccaaucug uacgugguug cagaacuguu cacuggcucc 1680
gaggaccucg acaacguguu cgugaccaga cuggggauuu ccucacugau ccgggaagcc 1740
augucggccu acaacuccca ugaagagggc cgccuggugu accgcuaugg gggagaaccc 1800 guggggaagcu ucgugcagcc uugccuccgg ccgcugaugc cugcgaucgc ccacgcccug 1860

-continued

```
uucauggaua ucacucacga caacgaaugc cccauugugc aucgcucggc cuacgacgca   1920
cugccuucga ccacuaucgu guccauggcc ugcugcgccu ccgggagcac ccgcggauac   1980
gaugaacucg ugccgcacca gaucagcgug guguccgaag aacgguucua caccaagugg   2040
aaccccgaag cccugccuag caauaccggg gaagugaacu uccaguccgg uauuaucgcc   2100
gcucgcugcg ccaucuccaa acuccaccaa gagcucggug ccaagggauu cauucaaguc   2160
uacgguggauc aggucgacga agauauugug gccgugacca ggcacucacc uuccauccac   2220
caauccgucg ucgccguguc ccggacugcg uuucggaacc ccaagacuuc guucuacucg   2280
aaagaagugc cacagaugug uaucccggga aaaaucgagg aggucgugcu cgaagcccgg   2340
accauugaga ggaacaccaa gccuuaccgg aaagacgaga acucuaucaa cgguacccu   2400
gauauuacug uggagauccg cgaacacauc cagcugaacg aaucaaagau cgucaagcag   2460
gcuggagugg ccaccaaggg acccaacgag uacauccagg agaucgaauu ugaaaaccuc   2520
uccccuggcu ccgugauuau cuuccgggug ucccuggacc cucacgccca aguggccgug   2580
ggaauucuca gaaaccaccu gacccaguuc ucaccacacu uuaaguccgg uucccuggcg   2640
guggacaacg ccgauccgau cuugaagauc cccuucgcau cgcucgccuc ccgccugacu   2700
cucgcggaac ugaaccagau ccuguaccgc ugugaauccg aggaaaagga ggacggcggc   2760
ggcuguuacg auaucccaa uuggucggcu uugaaauacg cgggacuuca ggggcugaug   2820
ucugugcugg cggaaauccg gccgaagaac gaccugggac acccauucug caacaacuug   2880
cggagcggag acuggaugau cgauuacguc agcaacagau ugaucagccg gagcggcacu   2940
aucgccgagg ucggaaagug gcuccaggcc auguucuucu accugaagca gauccccga   3000
uaccucaucc ccuguuacuu cgacgccauu cugaucgggg ccuacaccac ccugcuggac   3060
accgccugga agcagaugag caguuuugug caaaacgggu ccaccuucgu gaagcaccuu   3120
ucacugggcu cagugcagcu cugcggcgug ggaaaguucc ccucgcugcc cauucugagc   3180
cccgcccuga uggacguccc uuaccggcug aacgagauca ccaaggagaa ggagcagugc   3240
uguguuuccc uggcugccgg gcugccacac uucucguccg gcaucuuccg guguuggggc   3300
cgggauaccu ucauugcccu gcggggaauc cugcuuauca ccggucgcua cguggaggcu   3360
cggaacauua uucucgcguu cgccggcacc cugagacacg gucugauucc gaaucuguug   3420
ggcgaaggaa ucuacgccag auacaacugu cgggacgccg uguggugug gcuccagugc   3480
auucaggacu auugcaagau ggugccgaac ggccuggaca uccugaagug cccagugucg   3540
aggauguauc caacugacga cagcgcaccu cugccggccg ggacccucga ccaaccccug   3600
uucgaaguca uucaagaggc uaugcagaag cacaugcagg guauucaguu ccgggagcgg   3660
aacgcggggc cccagauuga uaggaacaug aaagacgagg gcuucaacau cacugccggc   3720
guggacgaag aaaccgguuu uguguacgga ggaaaccgcu ucaacugcgg uaccuggaug   3780
gacaagaugg gagaauccga ucgcgcgcgc aacagaggga ucccggcaac cccucgggac   3840
ggauccgcgg uggaaauugu gggacugagc aagagcgccg ugcgguggcu ccuggaacug   3900
uccaaaaaga acaucuuccc cuaccacgaa gugaccguga agagacacgg aaaggccauc   3960
aaagucucau acgaugaaug gaacaggaag auccaggaua acuucgagaa gcuguuucac   4020
guguccgagg aucccuccga ucugaacgag aagcauccga aucuggugca caagcgcggg   4080
aucuacaagg acucguacgg agcguccucc ccuuggugcg acuaucagcu gcggccuaac   4140
uucaccauug ccauggucgu ggccccggag cuguucacaa cugagaaggc cuggaaggcc   4200
```

-continued

```
cuugaaauug ccgagaagaa gcugcugggg ccuuugggga ugaaaacccu ggauccggac   4260

gacauggugu acugcggaau cuacgacaac gcccuggaca acgauaacua caaucucgcg   4320

aagggcuuca auuaccacca aggccccgaa uggcucuggc cuauugggua cuuccugcgc   4380

gccaagcugu acuucucacg gcugauggga ccagagacua ccgccaagac uaucguccuc   4440

gugaagaacg ugcugucccg gcacuacgug caucuggaga ggagcccuug gaagggacuu   4500

ccugagcuga cgaacgaaaa cgcgcaguac ugccccuucu ccugcgaaac ccaggcuugg   4560

uccauugcca cuauacugga aaccuuauau gaccuguag                          4599
```

<210> SEQ ID NO 27
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 27

```
augggacacu cgaaacagau ccggauccug uugcugaacg aaauggagaa gcuugaaaag     60

acccuguuuc ggcuggagca gggcuacgag cugcaguucc gccugggucc gacacuacaa    120

ggaaaggccg ugacugugua caccaacuac ccauuucccg gagaaacuuu caaccgggag    180

aaguuccggu cccuggacug ggaaaaccca accgaacgag aggacgacuc ggacaaguac    240

ugcaagcuga accuccaaca guccggauca uuccaguacu acuuucugca agggaacgag    300

aaguccggag gcggcuacau cgugguucgac ccgauacuua gagugggcgc cgacaaucau    360

guccugccuc uggauugcgu gacccugcaa accuucuugg ccaaaugucu gggcccguuc    420

gaugaguggg aaagccgccu cagagucgca aaggaguccg gauacaacau gauucauuuc    480

accccgcugc aaacccuggg ucugucccgg ucgugcuauu cucuggcgaa ccagcuggag    540

cuuaaccccg acuucucgcg cccaaaccgg aaguacaccu ggaacgacgu cgggcagcuu    600

guggaaaagc ugaagaagga guggaacgug aucugcauca cugacguggu guacaaccau    660

acggccgcca acucgaagug gauccaggag caucccgagu gcgcauacaa ccucgugaac    720

agcccgcacc uuaagccugc uugggugcug gacagagccc ucuggagauu caguugcgac    780

guggccgagg ggaaguacaa ggaaaaggga auuccggccu ugaucgagaa cgaccaucac    840

augaacucaa ucaggaagau caucugggag gacaucuucc cuaagcuuaa guuguggggag   900

uucuuccaag uggacguaaa caaggcagug gagcaguuca gaagguugcu gacccaagaa    960

aacagacgcg ucacuaaguc cgauccuaac caacaccuua ccaucauuca agacccugaa   1020

uaccgccggu uuggcugcac cgucgauaug aacaucgccc ugaccacuuu caucccgcau   1080

gacaagggcc cggcggcaau cgaggaaugc uguaacuggu uucauaagag aauggaagaa   1140

cugaauuccg agaagcaccg gcugauuaac uaccaccagg aacaggcagu gaacugccug   1200

cugggcaaug uguucuacga acggcuggcu ggacacggac cgaagcuggg ucccgugacu   1260

aggaagcauc cgcucgugac ucgcuacuuc accuucccgu uugaggagau ugacuucucg   1320

auggaagaau ccaugaucca ucugccuaac aaggcuugcu uccugauggc gcacaacgga   1380

ugggucaugg gcgacgaccc ccugcgcaac uucgccgagc cuggcucgga ggucuaccug   1440

agaagggaac uuaucuguug gggagacucc gucaagcugc gcuacggaaa caagcccgaa   1500

gauugccccu accugugggc ucacaugaag aaguacacgg aaaucacugc aacguacuuc   1560

cagggagucc ggcuggacaa uugccacucc acccccccuuc auguggccga guacaugcuc  1620

gaugcagcga ggaaucugca gccgaaucug uacgugguug ccgaacuguu cacuggcucc   1680
```

-continued

```
gaggacuugg acaacguguu cgugaccaga cuggggaucu ccucccugau ccgggaagcc   1740
augucggccu acaacuccca ugaagagggc cgccuggugu accgcuacgg gggagaaccc   1800
gugggaagcu ucgugcaacc uugccugcgg ccgcugaugc cugcgaucgc ccacgcccug   1860
uucauggaca ucacucacga uaacgaaugc ccgauugugc aucgcucggc cuacgacgca   1920
cugccgagca ccacuaucgu guccauggcc ugcugcgccu ccgggagcac ucgcggauac   1980
gaugaacucg ugccgcacca gaucagcgug guguccgaag aacgcuucua uaccaagugg   2040
aaccccgaag cgcugccauc gaauacuggc gaagugaacu uccaguccgg uauuaucgcc   2100
gcucgcugug ccaucagcaa acugcaccaa gagcuuggug ccaagggauu cauucaaguc   2160
uacguggauc aggucgacga agauauugug gccgugacca ggcacucacc uuccauccac   2220
caaucagucg uggccguguc ccggaccgcg uuccggaacc ccaagaccag cuucuacucg   2280
aaagaagugc cucagaugug uaucccggga aaaaucgaag aggucgugcu ggaagcccgg   2340
accauugaga ggaacaccaa gccuuaccgg aaagacgaga acucuaucaa cgguaccccu   2400
gauauuacug uggagauccg cgaacacauc cagcugaacg aaucaaagau cgucaagcag   2460
gcuggagugg ccaccaaggg acccaacgag uacauccagg agaucgaauu ugaaaaccuc   2520
uccccuggcu ccgugauuau cuuucgggug ucccuggacc cucacgccca aguggccgug   2580
ggaauucuca gaaaccaccu gacccaguuc ucaccccacu ucaaguccgg uucccuggcg   2640
guggauaacg ccgacccgau uuugaagauc cccuucgccu cgcuggccuc ccgccugacu   2700
cucgcggaac ugaaccagau ccuguaccgc ugugaaucag aggaaaaaga ggacggcggc   2760
ggcuguuacg auauucccaa uuggucggcu uugaaauacg cgggacuuca ggggcugaug   2820
ucugugcugg cggaaauccg gccgaagaac gaccugggac acccauucug caacaacuug   2880
cgguccggag acuggaugau cgauuacguc agcaacagau ugaucagccg gagcggcacu   2940
aucgcugagg ucggaaagug gcugcaggcc auguucuucu aucugaagca gaucccccga   3000
uaccucaucc ccuguuacuu cgacgccauu cugaucgggg ccuacaccac ccugcuggac   3060
accgccugga agcagaugag caguuuugug caaaacgggu ccaccuucgu gaagcaccuu   3120
ucacugggcu cagugcagcu cugcggcgug ggaaaguucc ccucucugcc cauucugagc   3180
ccggcccuga uggacguccc uuaccggcug aacgagauca ccaaggagaa ggagcagugc   3240
ugcguuuccc uggcugccgg gcugccacac uucucguccg gcaucuuccg gugcuggggc   3300
cgggauaccu ucaucgcccu gcgggguauc cugcuuauca ccggucgcua cguggaggcu   3360
cggaacauua uucuggcguu cgccggcacc cuuagacacg gacugauucc gaaccuuuug   3420
ggcgaaggaa ucuacgccag auacaacugu cgggacgccg uguggugugg gcuucagugc   3480
auucaggacu auugcaagau ggugccgaac ggccuggaca uccugaagug cccagugucg   3540
aggauguauc caaccgacga cagcgcaccu cugccggccg ggacccucga ccaaccccug   3600
uucgaaguca uucaggaggc uaugcagaag cacaugcagg guauucaguu ccgggagcgg   3660
aacgcggggc cgcagauuga uaggaacaug aaagacgagg gcuucaacau cacugccggc   3720
guggacgaag aaaccgguuu uguguacgga ggaaacagau ucaacugcgg uaccuggaug   3780
gacaagaugg gagaguccga ucgcgcgcgc aacagaggga ucccggcaac cccgcgggac   3840
ggauccgcgg uggaaauugu gggacugagc aagagcgccg ugcgguggcu gcuggaacug   3900
agcaaaaaga acaucuuccc cuaccacgaa gugaccguga agcggcacgg aaaggccauc   3960
aaagucucau acgaugaaug gaauaggaag auccaggaua acuucgagaa gcuguuucac   4020
```

```
guguccgagg aucccuccga ucugaacgaa aagcacccga aucucgugca caagcgcggg   4080
aucuauaagg acucguacgg agcguccucc ccuuggugcg acuaucagcu gcggccuaac   4140
uucaccauug ccaugggucgu ggccccggag cuguucacaa cugagaaggc cuggaaggcc   4200
cuugaaauug ccgagaagaa gcugcugggg ccuuugggga ugaaaacccu ggauccggac   4260
gacauggugu acugcggaau cuacgacaac gcccuggaca acgauaacua caaucuggcc   4320
aagggcuuca auuaccacca gggcccggaa uggcuguggc ccauugggua cuuccugcgc   4380
gccaagcugu acuucucacg gcugauggga ccagagacua ccgccaagac uaucguccuc   4440
gugaagaacg ugcugucccg gcacuacgug caucuggaga ggagcccuug gaagggacuu   4500
ccugaacuga cuaacgagaa cgcgcaguac ugccccuucu ccugcgaaac ccaggcuugg   4560
uccauugcca ccauacugga aacccuuuau gaccuguag                          4599
```

<210> SEQ ID NO 28
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 28

```
augggacacu cgaaacagau uagaauccug uugcucaacg aaauggagaa gcuggaaaag     60
acccucuuuc ggcuggagca gggcuacgag cuccaguucc gccugggucc gacacuacaa    120
gggaaggcag ugaccgugua caccaacuac ccauuucccg gagaaaccuu caaccgggag    180
aaguuccggu cccuggacug ggaaaaccca accgaacgag aggaugacag cgacaaguac    240
ugcaagcuga accuccaaca gucgggaucg uuccaguacu acuuucugca agggaacgag    300
aaguccggag gaggcuacau cgguggucgac ccgauacuua gagugggagc cgacaaccau    360
guccugccuc uggacugcgu gacccugcaa accuucuugg ccaaaugucu gggcccguuc    420
gaugaguggg aaagccgccu cagaguggcc aaggaguccg gguacaacau gauucacuuc    480
acuccgcugc aaacccucgg ucugucccgg ucgugcuauu cucuggcgaa ccagcuggag    540
cugaaccccg acuucucccg cccaaaccgg aaguacaccu ggaacgacgu cgggcagcuu    600
guggaaaagc ugaagaagga guggaacgug aucugcauua cugacguggu guacaaccac    660
accgccgcca acucgaagug gauccaagaa caucccgagu gcgcguacaa ccucgugaac    720
agcccgcauc ugaagccggc uugggugcuc gauagagccc ucuggagauu cuccugugac    780
gucgccgagg ggaaguacaa agagaagggu auuccggccc ucauugagaa cgaccaucac    840
augaacucaa uccggaagau caucugggag gauaucuucc cuaagcuuaa guugugggag    900
uucuuccaag uggacguaaa caaggccgug gaacaguuca gaaggcugcu gacucaagaa    960
aaccgccgcg ucacuaaguc cgauccuaac cagcaucuua ccaucaucca agacccugag   1020
uaucgccggu uugggugcac cgucgacaug aacaucgcac ugaccacuuu caucccgcau   1080
gacaaggggc cggcggccau cgaggaaugc uguaacuggu uucauaagag gauggaggaa   1140
cugaauuccg agaagcaccg gcugauuaac uaccaccagg aacaggcagu gaauugccuc   1200
cuggggaacg uguucuacga aaggcuggcu ggacacggac cgaagcuggg gcccgugacu   1260
cgcaagcauc cgcucgugac ucgcuacuuc accuucccgu uugaggagau ugacuucuca   1320
auggaagaau ccaugaucca ccucccgaac aaggcuugcu ucuugauggc gcacaaugga   1380
ugggucaugg gcgacgaccc acugcgcaac uucgcugagc cuggcucgga ggucuaccug   1440
agaagggaau ugauuugcug gggggacucc gucaagcugc gcuauggaaa caagccggaa   1500
```

-continued

```
gauugcccu accugugggc ucacaugaag aaguacacgg aaauuacugc cacguacuuc   1560
cagggcgucc ggcuggacaa cugccacucc acuccccucc auguggccga guacaugcuc   1620
gacgcagcga ggaaucugca gcccaaucug uacgugguug cagaacuguu cacugggucc   1680
gaggaccucg acaauguguu cgugaccaga cuggggaucu ccucccugau ccgggaagcc   1740
augucggccu acaacuccca ugaagagggc cgccuggugu accgcuacgg gggagaaccc   1800
guggggagcu ucgugcagcc uugccuccgc ccgcugaugc cugccaucgc ccacgcccug   1860
uucauggaua ucacucauga caacgaaugu cccauugugc aucgcucggc cuacgacgca   1920
cugccuucga ccacuaucgu guccauggcc ugcugcgccu ccgggagcac caggggauac   1980
gacgaacucg ugccgcacca gaucagcgug guguccgaag agagauucua uaccaagugg   2040
aaccccgaag cgcugcccag caauaccggg gaagugaacu uccaguccgg uauuaucgcc   2100
gcucgcugug cgaucagcaa gcuccaccag gagcucggug ccaagggauu cauucaaguc   2160
uacguggacc aggucgacga agauaucgug gccgugacca ggcacucacc uuccauucac   2220
caauccgugg ucgccguguc ccggacugcu uuucggaacc ccaagacuuc guucuacucg   2280
aaagaagugc cacagaugug uaucccgggg aaaaucgaag aggucguccu cgaagcccgg   2340
accauugaga ggaacaccaa gccuuaccgg aaagacgaga acucuaucaa cgggaccccu   2400
gauauuacug uggagauccg cgaacacauc cagcugaacg aaucaaagau cgucaagcag   2460
gcuggagugg cgaccaaggg acccaacgag uacauccagg agaucgaauu ugaaaaccuc   2520
uccccuggcu ccgugauuau cuuccgggug ucccuggacc cucacgccca aguggccgug   2580
ggaauucuca gaaaccaccu gacucaguuc ucaccccacu uuaagucugg gucccuggcg   2640
guggacaacg ccgauccgau cuugaaaauc ccuuucgcaa gccuggccuc ccgccugacu   2700
uuggccgagc ugaaccagau ccuguaccgc ugugaaucag aggaaaagga ggacggggu    2760
ggcuguuacg auauccccaa cugguccgcu uugaaauacg cgggacugca ggggcugaug   2820
uccgugcugg cggaaaucag accgaagaac gaucuggggc accccuucug caacaacuug   2880
cgguccggag acuggaugau cgauuacguc agcaaccggu ugaucagcag aagcgguacu   2940
aucgccgagg ucggaaagug gcugcaggcc auguucuucu accugaagca gaucccucga   3000
uaccucaucc ccuguuacuu cgacgccauu uugaucgggg ccuacaccac ccugcuggac   3060
acugccugga agcagaugag caguuuugug caaaaugggu cgaccuucgu gaagcaccuu   3120
uccuugggcu cagugcagcu cugcggcgug gggaaguucc ccucgcugcc cauucugucc   3180
ccggcccuga uggacguccc uuaccggcug aacgagauua ccaaggagaa ggagcagugc   3240
uguguuuccc uggcugccgg gcugccacac uucucguccg ggaucuuccg gugcuggggc   3300
cgcgauaccu ucauugcgcu gcgggguauc cugcuuauca ccggucgcua cguggaggcu   3360
cggaacauua uccuugcauu cgccgguacc cugagacacg gucugauccc gaaucuucuc   3420
ggggaaggaa ucuacgcaag auacaacugc cgggacgccg ugugguggug gcuccagugc   3480
auucaggacu auugcaagau ggugccgaac ggacuugaca uccugaagug cccagugucg   3540
aggauguacc cuaccgacga cagcgcuccu cugccggccg ggacccugga ccaaccccug   3600
uucgaaguca uccaagaggc uaugcagaag cacaugcagg guauucaguu ccgggaacgg   3660
aacgcggggc cccagauuga uaggaacaug aaggacgagg guuucaacau cacugccggc   3720
guggacgaag aaacuggguu uguguacgga ggaaacagau ucaacugcgg uaccuggaug   3780
gacaagaugg gagaauccga ucgcgcgcgc aacagaggga ucccggcaac cccgcgggac   3840
```

-continued

```
ggauccgcgg uggaaauugu gggacugagc aagagcgccg ugcgguggcu ccuggaacug   3900
uccaaaaaga acaucuuccc cuaccacgaa gugaccguga agcggcacgg aaaggccauc   3960
aaagucucau acgaugaaug gaaucggaag auccaggaua acuucgagaa gcuguuucac   4020
guguccgagg aucccuccga ucucaacgaa aagcauccga aucucgugca caagcgcggg   4080
aucuacaagg acucguacgg ggcguccuca ccuuggugcg acuaucagcu gcggccuaac   4140
uucacuauug cgauggucgu ggccccggag uuauucacaa cggagaaggc cuggaaggcc   4200
cuugaaauug cggagaagaa gcugcugggg ccucucggga ugaaaacccu ggauccggac   4260
gacauggugu acugcggaau cuacgacaac gcccuugaca acgauaacua caaucuggcc   4320
aagggguuca auuaccacca ggggccggaa uggcucuggc ccauugggua cuuccugcgc   4380
gccaagcugu acuucucacg gcugaugggg ccagagacua ccgccaagac uaucguccuc   4440
gugaaaaacg ugcugucccg gcacuacgug caucuggaga ggagcccuug gaagggacug   4500
ccagagcuga cgaacgagaa cgcgcaguac ugccccuucu ccugcgaaac ccaggcuugg   4560
ucgauugcca cuauacugga aaccuuauau gaccuguag                          4599
```

<210> SEQ ID NO 29
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 29

```
augggacacu caaagcaaau ccgcauucug cugcugaacg agauggaaaa gcuggaaaag     60
acucuguucc ggcuggaaca ggguuacgag cugcaguuuc ggcucggccc aaccuugcaa    120
gggaaggccg ucacugucua caccaacuac ccuuuuccgg gggagacuuu caaccgcgaa    180
aaguuccgcu cccuggauug ggaaaacccc acugaacggg aggaugacag cgacaaguac    240
ugcaaacuga accuucagca guccggcagc uuccaauacu acuuccugca aggaaacgaa    300
aaguccggcg gcgguuacau cguggucgac cccauucuga gagugggagc cgauaaucau    360
gugcugcccc uggacugcgu cacccugcaa acuuuccugg cuaagugccu gggaccguuc    420
gaugaguggg aauccaggcu ccgcguggcg aaggagucgg gcuacaacau gauucauuuc    480
acuccccuuc aaacucuggg gcugagucgc agcuguuacu cccuggccaa ccagcuugaa    540
cugaacccag acuuuucccg gccaaacaga aaguacaccu ggaacgacgu gggacaauug    600
guggagaagc uuaagaagga auggaacgug aucugcauca ccgauguggu guauaaccac    660
acugccgcga auuccaagug gauccaggaa caccccgagu gugcuuacaa ccuugugaac    720
agcccucacc uuaagccggc cugggugcug gaucgggcgc uguggagauu cuccugcgac    780
guggccgaag ggaaguacaa agaaaaggga aucccccgccc ugauugaaaa ugaccaccau    840
augaacucca uucggaaaau cauuugggaa gauaucuuuc ccaagcugaa gcucugggag    900
uucuuucaag uggaugugaa caaggcugug gagcaguucc ggcggcugcu gacccaggag    960
aaccgccgcg ugaccaaguc cgacccuaac cagcacuuga ccaucauaca ggacccggaa   1020
uaccggagau ucggcugcac ugucgacaug aacauugccc ucacuaccuu caucccgcau   1080
gacaagggac ccgcugccau cgaagagugc ugcaacuggu uccacaagcg gauggaagaa   1140
cugaacucug aaaagcacag gcugaucaac uaccaccagg aacaggcugu gaacugccug   1200
cugggcaacg uguucuacga gagacucgca ggacacggac cgaagcuggg cccugugacc   1260
cggaagcauc cucuggucac ccgcuacuuc accuucccgu ucgaagagau cgacuuuucg   1320
```

-continued

```
auggaagaau cgaugaucca ccucccuaac aaggccugcu uccucauggc gcacaacggc   1380
ugggucaugg gcgacgaccc gcugagaaac uucgccgagc ccgggagcga aguguaccuc   1440
cggcgggaac uuauuugcug ggagauagc gugaagcuua gauauggcaa caagccugag   1500
gacugcccau accugugggc gcacaugaag aaguacacug aaauuaccgc gaccuacuuc   1560
caaggagucc gacucgacaa cugccacagc accccacuuc acgucgcgga guacauguug   1620
gaugccgcac ggaaucucca gcccaaucug uaugucgugg cugaacuguu cacuggaucc   1680
gaggaccuug acaauguguu cgugacuaga cuggggaucu ccagccugau ccgggaagcu   1740
auguccgcgu acaacuccca cgaagaggga cggcuggugu accgcuacgg cggagagccc   1800
gugggaagcu ucgugcagcc cugccugcgg ccucugaugc cggccaucgc ucacgcccug   1860
uucauggaua ucacucacga caaugagugu ccuaucgugc acaggagcgc guacgacgcc   1920
cugcccucca cuacuaucgu gucgauggcc ugcugcgcaa gcgguucuac ccgcgguuac   1980
gacgagcuug ucccgcacca aauauccgug gugucagagg aacgguucua caccaagugg   2040
aacccggagg cccugccuuc aaacaccggc gaagugaacu uccaguccgg aaucauugcc   2100
gcccgcugug ccauuucaaa guugcaccag gagcugggcg ccaagggauu cauucagguc   2160
uacguugacc aggucgacga agauaucgug gccguuacua gacauucacc gagcauccau   2220
cagagcgugg ucgcagucag caggacugcc uuccgcaacc cgaaaaccuc guucuacucc   2280
aaggaagugc cccagaugug uaucccggga aaaauugagg aaguggugcu ggaggcccgg   2340
accaucgagc ggaacacuaa gcccuaccgg aaggacgaga auucaaucaa cggaaccccu   2400
gacaucaccg uggagauccg cgagcauauc caacugaacg agucgaagau cgucaagcag   2460
gcugggggugg caacuaaggg cccuaacgag uacauucagg agauugaauu cgagaaccug   2520
ucccccgggu ccgugaucau uuuccgcgug ucccuggacc cacaugcuca aguagcagug   2580
gggauccuga gaaaccaccu gacccaguuu agcccgcacu ucaaguccgg aucccuggcc   2640
guggauaacg ccgacccgau ccugaagauc cccuuugcau cccuggcuuc ccggcugacc   2700
uuggccgaac ugaaccagau ucuguaccgc ugcgaaucag aggaaaagga ggacggaggc   2760
ggaugcuacg auauccccaa uuggucggcg cugaaguacg ccggccuuca aggacugaug   2820
uccgugcugg ccgagaucag gccgaagaau gaccugggac acccguucug caacaacuug   2880
agaagcgggg acuggaugau ugauuacgug ucgaaccggc ugaucucccg gagcggcacc   2940
aucgcggaag ucggaaagug gcuccaggcc auguucuucu accugaagca gauccccgc   3000
uaccugaucc ccugcuacuu cgacgcgauc uugauugggg cauacaccac ucugcuugac   3060
accgcuugga agcagauguc cuccuucgug caaaacggau ccaccuucgu gaagcaccug   3120
ucccuuggau cagugcagcu gugcggcgug ggaaaguucc cuucccuucc cauccugucc   3180
ccugcgcuga uggacgugcc guaccggcuc aacgagauca ccaaggaaaa ggaacagugc   3240
ugcgugucac uggcagccgg ccuuccgcau uuuucgagcg gaauuuucag auguugggc   3300
agagacaccu ucauugcgcu gcgcgguauc cugcugauua ccggcagaua cguggaagcc   3360
agaaacauua uccuggcguu ugcugguacu cugcggcacg gacugauucc uaaccuguug   3420
ggagagggga ucuacgcccg guacaauugc agagaugccg uguggugug gcugcagugc   3480
auccaggacu acugcaagau ggugcccaac ggacuugaca uucugaagug cccggugucg   3540
cgcauguacc ccaccgacga cucugcgccc cugccggccg guacccugga ucagccgcug   3600
uucgaaguga uccaggaagc caugcaaaag cacaugcagg gaauucaguu cagggaacgg   3660
```

-continued

```
aacgcaggcc cgcaaaucga ccggaacaug aaggacgaag gcuucaacau uaccgccggc   3720

guggacgagg aaaccggcuu cguguacggc ggcaaccggu ucaauugcgg uacuuggaug   3780

gacaagaugg gagaaagcga ccgcgccagg aaucggggca uuccugccac cccgcgggac   3840

gguagcgcgg uggagaucgu gggccuuucg aaguccgcgg uccgcuggcu ucuggagcug   3900

ucuaagaaaa acaucuuccc uuaccacgag gucaccguga aacgccacgg aaaggccauc   3960

aaggugucu acgacgaaug gaacaggaag auccaggaca acuuugagaa gcuguuucac   4020

gugucggaag auccguccga ccugaacgaa aagcacccca accuugucca uaagcgcggu   4080

aucuacaaag auucguaugg ugcauccucc ccuuggugcg acuaccaacu ccggccgaac   4140

uucaccaucg caaugguggu ggccccggag cuguucacca cugaaaaggc cuggaaggcc   4200

cuggaaaucg ccgaaaagaa gcugcuggga ccgcuggga ugaaaacccu ggaccccgau   4260

gauauggugu acugcgggau cuacgacaac gcccuggaua acgacaacua caaccuggcc   4320

aagggcuuca acuaccauca ggguccggag uggcuguggc caaucggaua cuuccugagg   4380

gccaagcugu acuucucccg cuugaugggc cccgaaacua ccgcaaagac uaucgugcuc   4440

gugaagaacg uccugucccg gcacuacgug caucuggaac ggucgccgug gaaaggccug   4500

ccagaguuga ccaacgagaa ugcccaguau ugcccguucu caugcgaaac ccaagccugg   4560

agcauugcca cuauucugga aacccucuac gaccuguag                         4599
```

<210> SEQ ID NO 30
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 30

```
augggacacu cgaaacagau cagaauccug uugcucaacg aaauggagaa gcucgaaaag     60

acccuguucc ggcuggagca ggguuacgag cugcaguucc gccugggucc gacucuacaa    120

gggaaagcag ugacggucua caccaacuac ccguuucccg gagaaaccuu caaccgggag    180

aaguuccggu cccuggacug ggagaacccg accgaacgag aggaugacuc agauaaguac    240

ugcaagcuga acuugcaaca guccggguca uuccaguacu acuuucugca agggaacgag    300

aagucaggag ggggcuacau cguggucgac ccgauacugc gcgugggagc cgacaaucac    360

guccugccgc uggacugcgu gacccugcaa accuuccucg ccaaaugucu ggggccguuc    420

gaugaguggg aaagccgccu cagagucgca aaggaguccg gauacaacau gauucacuuc    480

acuccgcugc aaacacucgg ucugucccgg ucgugcuauu cucuggcgaa ccagcuggag    540

cuuaaucccg acuuuucccg cccgaaccgg aaguacaccu ggaacgacgu cgggcagcuu    600

guggaaaagc ugaagaagga guggaacgug aucugcauca cugauguggu guacaaccac    660

acggcugcca acucgaagug gauccaagag caucccgagu gcgcguacaa cuuggugaac    720

agcccgcauc ugaagccugc uugggugcug gacagagccc ucuggagauu cagcugcgac    780

guggccgagg ggaaguacaa agaaaagggg auuccggccu ugauugagaa cgaccaucac    840

augaacucaa uccgcaagau cauuugggag gauaucuucc cuaagcuuaa guugugggag    900

uucuuccaag uggacguaaa caaggcagug gagcaguuca gaaggcugcu gacucaagaa    960

aacagacgcg ucacuaaguc cgacccgaac cagcaccuua ccaucaucca agacccggag   1020

uaccgccggu ucggcugcac cgucgauaug aacauagccc ugaccacuuu caucccccau   1080

gacaaggggc cggcggcaau cgaggaaugc uguaacuggu uucauaagcg gauggaggaa   1140
```

-continued

```
cugaauuccg agaagcaccg gcugauuaac uaccaccagg aacaggcagu gaacugccug   1200
cugggcaacg uguucuacga acggcuggcu ggacacggac cgaagcuggg ucccgugacu   1260
agaaagcauc cgcucgucac ucgcuacuuc accuucccgu uugaggagau ugacuucucc   1320
auggaagaau ccaugaucca cuugccgaac aaggcuugcu uccugauggc gcacaacgga   1380
ugggucaugg gcgacgaccc gcugaggaau uucgcggagc cgggucgga aguguaccug   1440
agaagggaac ucauuugcug gggagacucc gucaagcugc gcuaugggaa caagcccgag   1500
gauugcccu accugugggc ucacaugaag aaguacacgg aaaucaccgc cacguacuuc   1560
cagggagucc ggcuggacaa uugccacucc acccccccucc auguggccga guacaugcug   1620
gaugcagcgc gcaaucugca gccgaaucug uacgugguug cagagcuguu cacugggucc   1680
gaggaccucg acaacguguu cgugacuaga uuggggaucu ccucccucau ccgggaagcc   1740
augucggccu acaacuccca ugaggagggg aggcuggugu acagauacgg cggcgaaccc   1800
gugggaagcu ucgugcagcc gugccuccgg ccgcugaugc cggccaucgc ccacgcccug   1860
uucauggaua ucacucacga caacgaaugc ccgaucgugc aucgcucggc cuacgacgca   1920
cugccgucca ccacuaucgu guccauggca ugcugcgccu ccgggagcac ccgcggauac   1980
gaugagcucg ugccgcacca gauuagcgug guguccgaag aacgcuucua uaccaagugg   2040
aaccccgaag cccugccguc caauaccggg gaagugaacu uccaguccgg uauuaucgcc   2100
gcucgcugug cgaucucgaa acuccaccaa gagcucggug ccaaggggu cauucagguc   2160
uacgugaguc aggucgacga ggauauugug gcagugacca ggcacucacc uagcauccac   2220
caauccgugg ucgccguguc acgcacugcg uuucggaacc ccaagaccuc guucuacucg   2280
aaagaagugc cgcagaugug uaucccggga aagaucgaag aggucgugcu ggaagcacgg   2340
accauugaga ggaacaccaa gccuuaccgg aaagacgaga acucuaucaa cgggaccccg   2400
gauaucacug uggagauucg cgaacacauc cagcugaacg aaucaaagau cgucaagcag   2460
gcuggagugg ccaccaaggg acccaacgag uacauccagg agaucgaauu ugaaaaccuc   2520
uccccggggu ccgugaucau cuuccgggug ucccuggacc cccacgccca aguggccgug   2580
ggaauucuca gaaaccaccu gacccaguuc ucaccccacu uuaagucggg uucccuggcc   2640
guggacaacg ccgauccgau ccucaagauc ccguucgcgu cgcuggccuc ccgccucacu   2700
cucgcggaac ugaaccagau ccuguaccgc ugugaaucag aggaaaagga ggacggcggc   2760
ggcuguuacg auauuccgaa uuggucggcu uugaaauacg cgggacuuca ggggcugaug   2820
ucuguccugg cggaaauccg gccgaagaac gaccuggggc acccguucug caacaacuug   2880
cggagcggag auuggaugau cgacuacguc agcaacagac ugaucagccg gagcggcacu   2940
aucgccgagg ucggaaagug guugcaggcc auguucuucu accugaagca gauccccccga   3000
uaccucaucc cguguuacuu cgacgccauc cugaucgggg ccuacaccac ccuccuggac   3060
accgccugga agcagaugag caguuuugug caaaacgggu ccaccuucgu gaagcaccuu   3120
ucccugggcu cagugcagcu gugcggcgug ggaaaguucc ccucgcugcc cauucugagc   3180
ccggcccuga uggacguccc cuaccggcug aacgagauca ccaaggagaa ggagcagugc   3240
uguguguccc uggcugccgg gcugccgcac uuuucguccg gcaucuuccg gugcuggggg   3300
cgggauaccu ucauugcccu gcggggaauc cuucuuauca ccggucgcua uguggaggcu   3360
cggaacauua uucuggcguu cgccggaacc cugagacacg ggcugauucc gaaccucuug   3420
ggggaaggga ucuacgcccg cuacaacugu cgggacgccg uguggugug gcuccagugc   3480
```

```
auucaggacu auugcaagau ggugcccaac gggcuggaca uccugaagug cccggugucg   3540
aggauguauc cgaccgacga cagcgcaccc cugccggccg ggacccucga ccaaccccug   3600
uucgaaguca uucaagaggc uaugcagaag cacaugcagg guauucaguu ccgggaacgg   3660
aacgcggggc cccagauuga uaggaacaug aaagacgagg guuucaacau cacugccggc   3720
guggacgaag aaaccgguuu uguguacgga ggaaaccggu ucaacugcgg uaccuggaug   3780
gauaagaugg gagaaucaga ucgcgcgcgc aacagaggga ucccggcaac cccgcgggac   3840
ggaucggcug uggaaauugu gggacugagc aagagcgccg ugcgguggcu gcuggaacug   3900
agcaaaaaga acaucuuccc cuaccacgaa gugaccguga agcggcacgg aaaggccauc   3960
aaagucuccu acgaugaaug gaauaggaag auccaggaua acuucgagaa gcuuuuucac   4020
guguccgagg aucccuccga ucugaacgag aagcauccga aucucgugca uaagaggggg   4080
aucuacaagg acuccuacgg agcguccucc ccuuggugcg acuaucagcu gcggccuaac   4140
uucaccauug ccauggucgu ggccccggag cucuuuacaa ccgagaaggc cuggaaggcc   4200
cucgaaauug ccgaaaagaa gcugcugggg cccuugggga ugaaaacccu ggauccggac   4260
gacauggugu acugcggaau cuacgacaac gcccuggaca acgacaacua caaucuggcg   4320
aagggcuuca auuaccacca ggggccggaa uggcucuggc cgauugggua cuuccugcgc   4380
gccaagcugu acuucucacg gcugauggga ccggagacua ccgccaagac caucguccuc   4440
gugaagaacg ugcugucgcg gcacuacgug caccuggaga ggagccccug gaaggggcuu   4500
cccgagcuga cgaacgagaa cgcgcaguac ugucccuucu ccugcgaaac ccaagccugg   4560
uccauugcca cuauacugga aaccuuauau gaccuguag                          4599
```

<210> SEQ ID NO 31
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 31

```
augggccaca gcaagcagau ccggaucuug cugcugaacg agauggagaa gcuggagaag     60
acccuguuca ggcuggagca gggcuacgag cugcaguucc gguugggccc caccuugcag    120
ggcaaggccg ugaccgugua caccaacuac cccuuccccg gcgaaaccuu caacagggag    180
aaguuccggu cccuggacug ggagaacccc accgagaggg aggacgacuc cgacaaguac    240
ugcaagcuga accugcagca guccggcucc uuccaguacu acuuccugca gggcaacgag    300
aaaagcggcg gcggcuacau cgugguggac cccaucuugc gggugggcgc cgacaaccac    360
gugcugcccu uggacugcgu gacccugcag accuucuugg ccaagugcuu gggccccuuc    420
gacgaguggg agagcaggcu gagggugccc aaggaguccg gcuacaacau gauccacuuc    480
acccccuugc agacccuggg ccuguccagg uccugcuacu cccuggccaa ccaguuggag    540
uugaaccccg acuucuccag gcccaacagg aaguacaccu ggaacgacgu gggccagcug    600
guggagaagu ugaagaagga guggaacgug aucugcauca ccgacguggu guacaaccac    660
accgccgcca acagcaagug gauccaggag caccccgagu gcgccuacaa ccuggugaac    720
ucccccccacu ugaagcccgc cuggguguug gacagggccc uguggcgguu cuccugcgac    780
guggccgagg gcaaguacaa ggagaagggc auccccgccu ugaucgagaa cgaccaccac    840
augaacucca uccggaagau caucugggag gacaucuucc ccaagcugaa gcugugggag    900
uucuuccagg uggacgugaa caaggccgug gagcaguuca ggaggcugcu gacccaggag    960
```

-continued

```
aacaggcggg ugaccaaguc cgaccccaac cagcaccuga ccaucaucca ggaccccgag   1020
uacaggcggu ucggcugcac cguggacaug aacaucgccc ugaccaccuu caucccccac   1080
gacaagggcc ccgccgccau cgaggagugc ugcaacuggu uccacaagag gauggaggag   1140
uugaacuccg agaagcaccg gcugaucaac uaccaccagg agcaggccgu gaacugccug   1200
uugggcaacg uguucuacga gcggcuggcc ggccacggcc ccaagcuggg ccccgugacc   1260
aggaagcacc ccuuggugac cagguacuuc accuuccccu ucgaggagau cgacuucucc   1320
auggaggagu ccaugaucca ccugcccaac aaggccugcu uccugauggc ccacaacggc   1380
ugggugaugg gcgacgaccc ccugcggaac uucgccgagc ccggcuccga gguguaccug   1440
aggagggagc ugaucugcug gggcgacagc gugaaguugc gguacggcaa caagcccgag   1500
gacugccccu accugugggc ccacaugaag aaguacaccg agaucaccgc caccuacuuc   1560
cagggcgugc ggcuggacaa cugccacucc accccccugc acguggccga guacauguug   1620
gacgccgcca ggaacuugca gcccaacuug uacgugugg ccgagcuguu caccggcagc   1680
gaggaccugg acaacguguu cgugaccagg cugggcauca gcuccuugau cagggaggcc   1740
augagcgccu acaacagcca cgaggagggc agguuggugu accgguacgg cggcgagccc   1800
gugggcuccu ucgugcagcc cugcuugagg cccuugaugc ccgccaucgc ccacgcccug   1860
uucauggaca ucacccacga caacgagugc cccaucgugc acagguccgc cuacgacgcc   1920
cugcccagca ccaccaucgu guccauggcc ugcugcgcca gcggcagcac caggggcuac   1980
gacgaguugg ugccccacca gaucuccgug guguccgagg agcgguucua caccaagugg   2040
aaccccgagg ccuugcccuc caacaccggc gaggugaacu uccagagcgg caucaucgcc   2100
gccaggugcg ccaucagcaa gcugcaccag gagcugggcg ccaagggcuu cauccaggug   2160
uacguggacc agguggacga ggacaucgug gccgugacca ggcacucccc cagcauccac   2220
caguccgugg uggccguguc caggaccgcc uucaggaacc ccaagaccuc cuucuacagc   2280
aaggaggugc cccagaugug cauccccggc aagaucgagg agguggugcu ggaggccagg   2340
accaucgaga ggaacaccaa gcccuacagg aaggacgaga acuccaucaa cggcaccccc   2400
gacaucaccg uggagaucag ggagcacauc cagcugaacg agagcaagau cgugaagcag   2460
gccggcgugg ccaccaaggg ccccaacgag uacauccagg agaucgaguu cgagaacuug   2520
ucccccggca gcgugaucau cuucagggug agccuggacc cccacgccca gguggccgug   2580
ggcauccugc ggaaccaccu gacccaguuc agcccccacu ucaaguccgg cagccuggcc   2640
guggacaacg ccgaccccau cuugaagauc cccuucgccu cccuggccuc cagguugacc   2700
uuggccgagc ugaaccagau ccuguaccgg ugcgaguccg aggagaagga ggacggcggc   2760
ggcugcuacg acauccccaa cugguccgcc cugaaguacg ccggccugca gggcuugaug   2820
uccguguugg ccgagaucag gcccaagaac gacuugggcc accccuucug caacaacuug   2880
agguccggcg acuggaugau cgacuacgug agcaaccggc ugaucucccg guccggcacc   2940
aucgccgagg ugggcaagug guugcaggcc auguucuucu accugaagca gauccccccgg  3000
uaccugaucc ccugcuacuu cgacgccauc uugaucggcg ccuacaccac ccugcuggac   3060
accgccugga agcagauguc cagcuucgug cagaacggcu ccaccuucgu gaagcaccug   3120
uccuugggcu ccgugcagcu gugcggcgug ggcaaguucc ccucccugcc cauccugucc   3180
cccgcccuga uggacgugcc cuacagguug aacgagauca ccaaggagaa ggagcagugc   3240
ugcgugucce uggccgccgg cuugccccac uucuccuccg gcaucuuccg gugcuggggc   3300
```

-continued

```
agggacaccu ucaucgcccu gaggggcauc cugcugauca ccggccggua cguggaggcc   3360

aggaacauca ucuuggccuu cgccggcacc cugaggcacg gccugauccc caaccugcug   3420

ggcgagggca ucuacgccag guacaacugc cgggacgccg uguggugug gcugcagugc   3480

auccaggacu acugcaagau ggugcccaac ggccuggaca uccugaagug ccccgugucc   3540

aggauguacc ccaccgacga cuccgccccc uugcccgccg gcacccugga ccagcccuug   3600

uucgagguga uccaggaggc caugcagaag cacaugcagg gcauccaguu ccgggagagg   3660

aacgccggcc cccagaucga ccggaacaug aaggacgagg gcuucaacau caccgccggc   3720

guggacgagg aaaccggcuu cguguacggc ggcaaccggu ucaacugcgg caccuggaug   3780

gacaagaugg gcgagagcga cagggccagg aacaggggca uccccgccac ccccagggac   3840

ggcuccgccg uggagaucgu gggccugagc aaguccgccg ugcggugguu gcuggaguug   3900

uccaagaaga acaucuuccc cuaccacgag gugaccguga agaggcacgg caaggccauc   3960

aaggugucc u acgacgagug gaacaggaag auccaggaca acuucgagaa gcuguuccac   4020

guguccgagg accccuccga cuugaacgag aagcacccca accuggugca caagcggggc   4080

aucuacaagg acagcuacgg cgccuccagc cccugguggcg acuaccagcu gaggcccaac   4140

uucaccaucg ccaugguggu ggcccccgag cuguucacca ccgagaaggc cuggaaggcc   4200

uuggagaucg ccgagaagaa guugcugggc ccccugggca ugaagaccuu ggaccccgac   4260

gacauggugu acugcggcau cuacgacaac gccuuggaca acgacaacua caaccuggcc   4320

aagggcuuca acuaccacca gggccccgag uggcuguggc ccaucggcua cuuccugcgg   4380

gccaaguugu acuucuccag guugaugggc cccgaaacca ccgccaagac caucguguug   4440

gugaagaacg ugcugucccg gcacuacgug caccuggaga gguccccug gaagggccug   4500

cccgagcuga ccaacgagaa cgcccaguac ugccccuuca gcugcgaaac ccaggccugg   4560

uccaucgcca ccauccugga aacccuguac gacuuguag                          4599
```

<210> SEQ ID NO 32
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 32

```
augggacaua gcaagcagau ccggaucuug cugcugaaug aaauggaaaa gcuggaaaag     60

acccuguuca gacuggaaca gggauacgaa cugcaguucc gguugggacc uaccuugcag    120

ggaaaggcug ugaccgugua caccaauuac ccuuucccug gagaaaccuu caauagagaa    180

aaguucagau cucuagauug ggaaaauccu accgaaagag aagaugauuc ugauaaguac    240

ugcaagcuga aucugcagca gucuggaucu uuccaguacu acuuccugca gggaaaugaa    300

aagagcggag gaggauacau cgugguggau ccuaucuugc gggugggagc ugauaaucau    360

gugcugccuu uggauugcgu gacccugcag accuucuugg cuaagugcuu gggaccuuuc    420

gaugaauggg aaagcagacu gagaguggcu aaggaaucug gauacaauau gauccauuuc    480

accccuuugc agacccuggg acugucuaga ucuugcuacu cucuggcuaa ucaguuggaa    540

uugaauccug auuucucuag accuaauaga aaguacaccu ggaaugaugu gggacagcug    600

guggaaaagu ugaagaagga auggaaugug aucugcauca ccgauguggu guacaaucau    660

accgcugcua auagcaagug gauccaggaa cauccugaau gcgcuuacaa ucuggugaau    720

ucuccucauu ugaagccugc uuggguguug gauagagcuc uguggcgguu cucuugcgau    780
```

```
guggcugaag gaaaguacaa ggaaaaggga aucccugcuu ugaucgaaaa ugaucaucau    840
augaauucua uccggaagau caucugggaa gauaucuucc cuaagcugaa gcugugggaa    900
uucuuccagg uggaugugaa uaaggcugug gaacaguuca gaagacugcu gacccaggaa    960
aauagacggg ugaccaaguc ugauccuaau cagcaucuga ccaucaucca ggauccugaa   1020
uacagacggu ucggaugcac cguggauaug aauaucgcuc ugaccaccuu caucccucau   1080
gauaagggac cugcugcuau cgaagaaugc ugcaauuggu uccauaagag aauggaagaa   1140
uugaauucug aaaagcaucg gcugaucaau uaccaucagg aacaggcugu gaauugccug   1200
uugggaaaug uguucuacga acggcuggcu ggacauggac cuaagcuggg accugugacc   1260
agaaagcauc cuuuggugac cagauacuuc accuucccuu ucgaagaaau cgauuucucu   1320
auggaagaau cuaugaucca ucugccuaau aaggcuugcu ucccugauggc ucauaaugga   1380
ugggugaugg gagaugaucc ucugcggaau uucgcugaac cuggaucuga aguguaccug   1440
agaagagaac ugaucugcug ggagagauagc gugaaguugc gguacggaaa uaagccugaa   1500
gauugcccuu accugugggc ucauaugaag aaguacaccg aaaucaccgc uaccuacuuc   1560
cagggagugc ggcuggauaa uugccauucu accccucugc auguggcuga auacauguug   1620
gaugcugcua gaaauuugca gccuaauuug uacguggugg cugaacuguu caccggaagc   1680
gaagaucugg auaaauguuu cgugaccaga cugggaauca gcucuuugau cagagaagcu   1740
augagcgcuu acaauagcca ugaagaagga agauuggugu accgguacgg aggagaaccu   1800
gugggaucuu ucgugcagcc uugcuugagg ccuuugaugc cugcuaucgc ucaugcucug   1860
uucauggaua ucacccauga uaaugaaugc ccuaucgugc auagaucugc uuacgaugcu   1920
cugccuagca ccaccaucgu gucuauggcu ugcugcgcua gcggaagcac cagaggauac   1980
gaugaauugg ugccucauca gaucucugug gugucugaag aacgguucua caccaagugg   2040
aauccugaag cuuugccuuc uaauaccgga gaagugaauu uccagagcgg aaucaucgcu   2100
gcuagaugcg cuaucagcaa gcugcaucag gaacugggag cuaagggauu cauccaggug   2160
uacgugggauc agguggauga agauaucgug gcugugacca gacauuucuc uagcauccau   2220
cagucugugg uggcugugc uagaaccgcu uucagaaauc cuaagaccuc uuucuacagc   2280
aaggaagugc cucagaugug caucccugga aagaucgaag aaguggugcu ggaagcuaga   2340
accaucgaaa gaaauaccaa gccuuacaga aaggaugaaa auucuaucaa uggaaccccu   2400
gauaucaccg uggaaaucag agaacauauc cagcugaaug aaagcaagau cgugaagcag   2460
gcuggagugg cuaccaaggg accuaaugaa uacauccagg aaaucgaauu cgaaaauuug   2520
ucuccuggaa gcgugaucau cuucagagug agccuggauc cucaugcuca gguggcugug   2580
ggaauccugc ggaaucaucu gacccaguuc agcccucauu ucaagucugg aagccuggcu   2640
guggauaaug cugauccuau cuugaagauc ccuuucgcuu cucuggcuuc uagauugacc   2700
uuggcugaac ugaaucagau ccuguaccgg ugcgaaucug aagaaaagga agauggagga   2760
ggaugcuacg auaucccuaa uuggucugcu cugaaguacg cuggacugca gggauugaug   2820
ucuguguugg cugaaaucag accuaagaau gauuugggac auccuuucug caauaauuug   2880
agaucuggag auuggaugau cgauuacgug agcaaucggc ugaucucucg gucuggaacc   2940
aucgcugaag ugggaaagug guugcaggcu auguucuucu accugaagca gaucccucgg   3000
uaccugaucc cuugcuacuu cgaugcuauc uugaucggag cuuacaccac ccugcuggau   3060
accgcuugga agcagauguc uagcuucgug cagaauggau cuaccuucgu gaagcaucug   3120
```

-continued

```
ucuuugggau cugugcagcu gugcggagug ggaaaguucc cuucucugcc uauccugucu   3180

ccugcucuga uggaugugcc uuacagauug aaugaaauca ccaaggaaaa ggaacagugc   3240

ugcgugucuc uggcugcugg auugccucau uucucuucug gaaucuuccg gugcugggga   3300

agagauaccu ucaucgcucu gagaggaauc cugcugauca ccggacggua cguggaagcu   3360

agaaauauca ucuuggcuuu cgcuggaacc cugagacaug gacugauccc uaaucugcug   3420

ggagaaggaa ucuacgcuag auacaauugc cgggaugcug uguggugug gcugcagugc    3480

auccaggauu acugcaagau ggugccuaau ggacuggaua uccugaagug cccugugucu   3540

agaauguacc cuaccgauga uucugcuccu uugccugcug gaacccugga ucagccuuug   3600

uucgaaguga uccaggaagc uaugcagaag cauaugcagg gaauccaguu ccgggaaaga   3660

aaugcuggac cucagaucga ucggaauaug aaggaugaag gauucaauau caccgcugga   3720

guggaugaag aaaccggauu cguguacgga ggaaaucggu ucaauugcgg aaccuggaug   3780

gauaagaugg gagaaagcga uagagcuaga aauagaggaa ucccugcuac cccuagagau   3840

ggaucugcug uggaaaucgu gggacugagc aagucugcug ugcggugguu gcuggaauug   3900

ucuaagaaga auaucuuccc uuaccaugaa gugaccguga agagacaugg aaaggcuauc   3960

aaggugucuu acgaugaaug gaauagaaag auccaggaua auuucgaaaa gcuguuccau   4020

gugucugaag auccuucuga uuugaaugaa aagcauccua aucuggugca uaagcgggga   4080

aucuacaagg auagcuacgg agcuucuagc ccuuggugcg auuaccagcu gaggccuaau   4140

uucaccaucg cuauggugu ggcuccugaa cuguucacca ccgaaaaggc uuggaaggcu    4200

uuggaaaucg cugaaaagaa guugcuggga ccucugggaa ugaagaccuu ggauccugau   4260

gauauggugu acugcggaau cuacgauaau gcuuuggaua augauaauua caaucuggcu   4320

aagggauuca auuaccauca gggaccugaa uggcuguggc cuaucggaua cuuccugcgg   4380

gcuaaguugu acuucucuag auugauggga ccugaaacca ccgcuaagac caucguguug   4440

gugaagaaug ugcugucucg gcauuacgug caucuggaaa gaucuccuug gaagggacug   4500

ccugaacuga ccaaugaaaa ugcucaguac ugcccuuuca gcugcgaaac ccaggcuugg   4560

ucuaucgcua ccauccugga aacccuguac gauuuguag                          4599
```

<210> SEQ ID NO 33
<211> LENGTH: 158
<212> TYPE: RNA
<213> ORGANISM: Artificial Sequence
<220> FEATURE:
<223> OTHER INFORMATION: Modified Xenopus beta-globin 3'UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 33

```
cnagugacug acuaggaucu gguuaccacu aaaccagccu caagaacacc cgaauggagu     60

cucuaagcua cauaauacca acuuacacuu acaaaauguu gucccccaaa auguagccau    120

ucguaucugc uccuaauaaa aagaaaguuu cuucacnu                            158
```

<210> SEQ ID NO 34
<211> LENGTH: 158
<212> TYPE: RNA
<213> ORGANISM: Artificial Sequence
<220> FEATURE:
<223> OTHER INFORMATION: Modified Xenopus beta-globin 3'UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (3)..(3)
<223> OTHER INFORMATION: n is unlocked nucleomonomer UNA-A
<220> FEATURE:
<221> NAME/KEY: misc_feature
<222> LOCATION: (4)..(4)
<223> OTHER INFORMATION: n is unlocked nucleomonomer UNA-G
<220> FEATURE:
<221> NAME/KEY: misc_feature
<222> LOCATION: (155)..(155)
<223> OTHER INFORMATION: n is unlocked nucleomonomer UNA-A
<220> FEATURE:
<221> NAME/KEY: misc_feature
<222> LOCATION: (156)..(156)
<223> OTHER INFORMATION: n is unlocked nucleomonomer UNA-C
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 34
cnnnugacug acuaggaucu gguuaccacu aaaccagccu caagaacacc cgaauggagu 60
cucuaagcua cauaauacca acuuacacuu acaaaauguu gucccccaaa auguagccau 120
ucguaucugc uccuaauaaa aagaaaguuu cuucnnnu 158

<210> SEQ ID NO 35
<211> LENGTH: 158
<212> TYPE: RNA
<213> ORGANISM: Artificial Sequence
<220> FEATURE:
<223> OTHER INFORMATION: Modified Xenopus beta-globin 3'UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (8)..(8)
<223> OTHER INFORMATION: n is unlocked nucleomonomer UNA-C
<220> FEATURE:
<221> NAME/KEY: misc_feature
<222> LOCATION: (14)..(14)
<223> OTHER INFORMATION: n is unlocked nucleomonomer UNA-A
<220> FEATURE:
<221> NAME/KEY: misc_feature
<222> LOCATION: (20)..(20)
<223> OTHER INFORMATION: n is unlocked nucleomonomer UNA-U
<220> FEATURE:
<221> NAME/KEY: misc_feature
<222> LOCATION: (26)..(26)
<223> OTHER INFORMATION: n is unlocked nucleomonomer UNA-C
<220> FEATURE:
<221> NAME/KEY: misc_feature
<222> LOCATION: (32)..(32)
<223> OTHER INFORMATION: n is unlocked nucleomonomer UNA-A
<220> FEATURE:
<221> NAME/KEY: misc_feature
<222> LOCATION: (38)..(38)
<223> OTHER INFORMATION: n is unlocked nucleomonomer UNA-C
<220> FEATURE:
<221> NAME/KEY: misc_feature
<222> LOCATION: (44)..(44)
<223> OTHER INFORMATION: n is unlocked nucleomonomer UNA-G
<220> FEATURE:
<221> NAME/KEY: misc_feature
<222> LOCATION: (50)..(50)
<223> OTHER INFORMATION: n is unlocked nucleomonomer UNA-C
<220> FEATURE:

<221> NAME/KEY: misc_feature
<222> LOCATION: (56)..(56)
<223> OTHER INFORMATION: n is unlocked nucleomonomer UNA-G
<220> FEATURE:
<221> NAME/KEY: misc_feature
<222> LOCATION: (62)..(62)
<223> OTHER INFORMATION: n is unlocked nucleomonomer UNA-U
<220> FEATURE:
<221> NAME/KEY: misc_feature
<222> LOCATION: (68)..(68)
<223> OTHER INFORMATION: n is unlocked nucleomonomer UNA-C
<220> FEATURE:
<221> NAME/KEY: misc_feature
<222> LOCATION: (74)..(74)
<223> OTHER INFORMATION: n is unlocked nucleomonomer UNA-A
<220> FEATURE:
<221> NAME/KEY: misc_feature
<222> LOCATION: (80)..(80)
<223> OTHER INFORMATION: n is unlocked nucleomonomer UNA-A
<220> FEATURE:
<221> NAME/KEY: misc_feature
<222> LOCATION: (86)..(86)
<223> OTHER INFORMATION: n is unlocked nucleomonomer UNA-C
<220> FEATURE:
<221> NAME/KEY: misc_feature
<222> LOCATION: (92)..(92)
<223> OTHER INFORMATION: n is unlocked nucleomonomer UNA-C
<220> FEATURE:
<221> NAME/KEY: misc_feature
<222> LOCATION: (98)..(98)
<223> OTHER INFORMATION: n is unlocked nucleomonomer UNA-G
<220> FEATURE:
<221> NAME/KEY: misc_feature
<222> LOCATION: (104)..(104)
<223> OTHER INFORMATION: n is unlocked nucleomonomer UNA-C
<220> FEATURE:
<221> NAME/KEY: misc_feature
<222> LOCATION: (110)..(110)
<223> OTHER INFORMATION: n is unlocked nucleomonomer UNA-A
<220> FEATURE:
<221> NAME/KEY: misc_feature
<222> LOCATION: (116)..(116)
<223> OTHER INFORMATION: n is unlocked nucleomonomer UNA-G
<220> FEATURE:
<221> NAME/KEY: misc_feature
<222> LOCATION: (122)..(122)
<223> OTHER INFORMATION: n is unlocked nucleomonomer UNA-C
<220> FEATURE:
<221> NAME/KEY: misc_feature
<222> LOCATION: (128)..(128)
<223> OTHER INFORMATION: n is unlocked nucleomonomer UNA-U
<220> FEATURE:
<221> NAME/KEY: misc_feature
<222> LOCATION: (134)..(134)
<223> OTHER INFORMATION: n is unlocked nucleomonomer UNA-U
<220> FEATURE:
<221> NAME/KEY: misc_feature
<222> LOCATION: (140)..(140)
<223> OTHER INFORMATION: n is unlocked nucleomonomer UNA-A
<220> FEATURE:
<221> NAME/KEY: misc_feature
<222> LOCATION: (146)..(146)
<223> OTHER INFORMATION: n is unlocked nucleomonomer UNA-A
<220> FEATURE:
<221> NAME/KEY: misc_feature
<222> LOCATION: (152)..(152)
<223> OTHER INFORMATION: n is unlocked nucleomonomer UNA-U
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 35
cnaguganug acunggaucn gguuancacu anaccagncu caanaacacn cgaaungagu 60
cncuaagnua caunauaccn acuuanacuu anaaaaunuu gucncccaan auguanccau 120
unguaucngc uccnaauaan aagaanguuu cnucacnu 158

<210> SEQ ID NO 36
<211> LENGTH: 158
<212> TYPE: RNA
<213> ORGANISM: Artificial Sequence
<220> FEATURE:
<223> OTHER INFORMATION: Modified Xenopus beta-globin 3'UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (3)..(3)
<223> OTHER INFORMATION: n is unlocked nucleomonomer UNA-A
<220> FEATURE:
<221> NAME/KEY: misc_feature
<222> LOCATION: (8)..(8)
<223> OTHER INFORMATION: n is unlocked nucleomonomer UNA-C
<220> FEATURE:
<221> NAME/KEY: misc_feature
<222> LOCATION: (9)..(9)
<223> OTHER INFORMATION: n is unlocked nucleomonomer UNA-U
<220> FEATURE:
<221> NAME/KEY: misc_feature
<222> LOCATION: (14)..(14)
<223> OTHER INFORMATION: n is unlocked nucleomonomer UNA-A
<220> FEATURE:
<221> NAME/KEY: misc_feature
<222> LOCATION: (15)..(15)
<223> OTHER INFORMATION: n is unlocked nucleomonomer UNA-G
<220> FEATURE:
<221> NAME/KEY: misc_feature
<222> LOCATION: (20)..(20)
<223> OTHER INFORMATION: n is unlocked nucleomonomer UNA-U
<220> FEATURE:
<221> NAME/KEY: misc_feature
<222> LOCATION: (21)..(21)
<223> OTHER INFORMATION: n is unlocked nucleomonomer UNA-G
<220> FEATURE:
<221> NAME/KEY: misc_feature
<222> LOCATION: (26)..(27)
<223> OTHER INFORMATION: n is unlocked nucleomonomer UNA-C
<220> FEATURE:
<221> NAME/KEY: misc_feature
<222> LOCATION: (32)..(33)
<223> OTHER INFORMATION: n is unlocked nucleomonomer UNA-A
<220> FEATURE:
<221> NAME/KEY: misc_feature
<222> LOCATION: (38)..(39)
<223> OTHER INFORMATION: n is unlocked nucleomonomer UNA-C
<220> FEATURE:
<221> NAME/KEY: misc_feature
<222> LOCATION: (44)..(44)
<223> OTHER INFORMATION: n is unlocked nucleomonomer UNA-G
<220> FEATURE:
<221> NAME/KEY: misc_feature
<222> LOCATION: (45)..(45)
<223> OTHER INFORMATION: n is unlocked nucleomonomer UNA-A
<220> FEATURE:
<221> NAME/KEY: misc_feature
<222> LOCATION: (50)..(51)
<223> OTHER INFORMATION: n is unlocked nucleomonomer UNA-C
<220> FEATURE:
<221> NAME/KEY: misc_feature
<222> LOCATION: (56)..(57)
<223> OTHER INFORMATION: n is unlocked nucleomonomer UNA-G
<220> FEATURE:
<221> NAME/KEY: misc_feature
<222> LOCATION: (62)..(62)
<223> OTHER INFORMATION: n is unlocked nucleomonomer UNA-U
<220> FEATURE:
<221> NAME/KEY: misc_feature
<222> LOCATION: (63)..(63)
<223> OTHER INFORMATION: n is unlocked nucleomonomer UNA-C
<220> FEATURE:
<221> NAME/KEY: misc_feature
<222> LOCATION: (68)..(68)

<223> OTHER INFORMATION: n is unlocked nucleomonomer UNA-C
<220> FEATURE:
<221> NAME/KEY: misc_feature
<222> LOCATION: (69)..(69)
<223> OTHER INFORMATION: n is unlocked nucleomonomer UNA-U
<220> FEATURE:
<221> NAME/KEY: misc_feature
<222> LOCATION: (74)..(75)
<223> OTHER INFORMATION: n is unlocked nucleomonomer UNA-A
<220> FEATURE:
<221> NAME/KEY: misc_feature
<222> LOCATION: (80)..(81)
<223> OTHER INFORMATION: n is unlocked nucleomonomer UNA-A
<220> FEATURE:
<221> NAME/KEY: misc_feature
<222> LOCATION: (86)..(86)
<223> OTHER INFORMATION: n is unlocked nucleomonomer UNA-C
<220> FEATURE:
<221> NAME/KEY: misc_feature
<222> LOCATION: (87)..(87)
<223> OTHER INFORMATION: n is unlocked nucleomonomer UNA-A
<220> FEATURE:
<221> NAME/KEY: misc_feature
<222> LOCATION: (92)..(92)
<223> OTHER INFORMATION: n is unlocked nucleomonomer UNA-C
<220> FEATURE:
<221> NAME/KEY: misc_feature
<222> LOCATION: (93)..(93)
<223> OTHER INFORMATION: n is unlocked nucleomonomer UNA-A
<220> FEATURE:
<221> NAME/KEY: misc_feature
<222> LOCATION: (98)..(98)
<223> OTHER INFORMATION: n is unlocked nucleomonomer UNA-G
<220> FEATURE:
<221> NAME/KEY: misc_feature
<222> LOCATION: (99)..(99)
<223> OTHER INFORMATION: n is unlocked nucleomonomer UNA-U
<220> FEATURE:
<221> NAME/KEY: misc_feature
<222> LOCATION: (104)..(105)
<223> OTHER INFORMATION: n is unlocked nucleomonomer UNA-C
<220> FEATURE:
<221> NAME/KEY: misc_feature
<222> LOCATION: (110)..(111)
<223> OTHER INFORMATION: n is unlocked nucleomonomer UNA-A
<220> FEATURE:
<221> NAME/KEY: misc_feature
<222> LOCATION: (116)..(116)
<223> OTHER INFORMATION: n is unlocked nucleomonomer UNA-G
<220> FEATURE:
<221> NAME/KEY: misc_feature
<222> LOCATION: (117)..(117)
<223> OTHER INFORMATION: n is unlocked nucleomonomer UNA-C
<220> FEATURE:
<221> NAME/KEY: misc_feature
<222> LOCATION: (122)..(122)
<223> OTHER INFORMATION: n is unlocked nucleomonomer UNA-C
<220> FEATURE:
<221> NAME/KEY: misc_feature
<222> LOCATION: (123)..(123)
<223> OTHER INFORMATION: n is unlocked nucleomonomer UNA-G
<220> FEATURE:
<221> NAME/KEY: misc_feature
<222> LOCATION: (128)..(128)
<223> OTHER INFORMATION: n is unlocked nucleomonomer UNA-U
<220> FEATURE:
<221> NAME/KEY: misc_feature
<222> LOCATION: (129)..(129)
<223> OTHER INFORMATION: n is unlocked nucleomonomer UNA-G
<220> FEATURE:
<221> NAME/KEY: misc_feature
<222> LOCATION: (134)..(134)
<223> OTHER INFORMATION: n is unlocked nucleomonomer UNA-U
<220> FEATURE:
<221> NAME/KEY: misc_feature
<222> LOCATION: (135)..(135)
<223> OTHER INFORMATION: n is unlocked nucleomonomer UNA-A
<220> FEATURE:
<221> NAME/KEY: misc_feature
<222> LOCATION: (140)..(141)
<223> OTHER INFORMATION: n is unlocked nucleomonomer UNA-A
<220> FEATURE:
<221> NAME/KEY: misc_feature
<222> LOCATION: (146)..(146)
<223> OTHER INFORMATION: n is unlocked nucleomonomer UNA-A
<220> FEATURE:
<221> NAME/KEY: misc_feature
<222> LOCATION: (147)..(147)
<223> OTHER INFORMATION: n is unlocked nucleomonomer UNA-G
<220> FEATURE:
<221> NAME/KEY: misc_feature
<222> LOCATION: (152)..(153)
<223> OTHER INFORMATION: n is unlocked nucleomonomer UNA-U
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 36
cnnguganng acunngaucn nguuannacu annccagnnu caannacacn ngaaunnagu 60
cnnuaagnna caunnuaccn ncuuanncuu annaaaunnu gucnnccaan nuguanncau 120
unnuaucnnc uccnnauaan nagaannuuu cnncacnu 158

<210> SEQ ID NO 37
<211> LENGTH: 158
<212> TYPE: RNA
<213> ORGANISM: Artificial Sequence
<220> FEATURE:
<223> OTHER INFORMATION: Modified Xenopus beta-globin 3'UTR
<220> FEATURE:
<221> NAME/KEY: misc_feature
<222> LOCATION: (1)..(1)
<223> OTHER INFORMATION: n is unlocked nucleomonomer UNA-C
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (3)..(3)
<223> OTHER INFORMATION: n is unlocked nucleomonomer UNA-A
<220> FEATURE:
<221> NAME/KEY: misc_feature
<222> LOCATION: (4)..(4)
<223> OTHER INFORMATION: n is unlocked nucleomonomer UNA-G
<220> FEATURE:
<221> NAME/KEY: misc_feature
<222> LOCATION: (5)..(5)
<223> OTHER INFORMATION: n is unlocked nucleomonomer UNA-U
<220> FEATURE:
<221> NAME/KEY: misc_feature
<222> LOCATION: (6)..(6)
<223> OTHER INFORMATION: n is unlocked nucleomonomer UNA-G
<220> FEATURE:
<221> NAME/KEY: misc_feature
<222> LOCATION: (7)..(7)
<223> OTHER INFORMATION: n is unlocked nucleomonomer UNA-A
<220> FEATURE:
<221> NAME/KEY: misc_feature
<222> LOCATION: (8)..(8)
<223> OTHER INFORMATION: n is unlocked nucleomonomer UNA-C
<220> FEATURE:
<221> NAME/KEY: misc_feature
<222> LOCATION: (9)..(9)
<223> OTHER INFORMATION: n is unlocked nucleomonomer UNA-U
<220> FEATURE:
<221> NAME/KEY: misc_feature
<222> LOCATION: (10)..(10)
<223> OTHER INFORMATION: n is unlocked nucleomonomer UNA-G
<220> FEATURE:
<221> NAME/KEY: misc_feature
<222> LOCATION: (11)..(11)
<223> OTHER INFORMATION: n is unlocked nucleomonomer UNA-A
<220> FEATURE:

<221> NAME/KEY: misc_feature
<222> LOCATION: (12)..(12)
<223> OTHER INFORMATION: n is unlocked nucleomonomer UNA-C
<220> FEATURE:
<221> NAME/KEY: misc_feature
<222> LOCATION: (13)..(13)
<223> OTHER INFORMATION: n is unlocked nucleomonomer UNA-U
<220> FEATURE:
<221> NAME/KEY: misc_feature
<222> LOCATION: (14)..(14)
<223> OTHER INFORMATION: n is unlocked nucleomonomer UNA-A
<220> FEATURE:
<221> NAME/KEY: misc_feature
<222> LOCATION: (15)..(16)
<223> OTHER INFORMATION: n is unlocked nucleomonomer UNA-G
<220> FEATURE:
<221> NAME/KEY: misc_feature
<222> LOCATION: (17)..(17)
<223> OTHER INFORMATION: n is unlocked nucleomonomer UNA-A
<220> FEATURE:
<221> NAME/KEY: misc_feature
<222> LOCATION: (18)..(18)
<223> OTHER INFORMATION: n is unlocked nucleomonomer UNA-U
<220> FEATURE:
<221> NAME/KEY: misc_feature
<222> LOCATION: (19)..(19)
<223> OTHER INFORMATION: n is unlocked nucleomonomer UNA-C
<220> FEATURE:
<221> NAME/KEY: misc_feature
<222> LOCATION: (20)..(20)
<223> OTHER INFORMATION: n is unlocked nucleomonomer UNA-U
<220> FEATURE:
<221> NAME/KEY: misc_feature
<222> LOCATION: (21)..(22)
<223> OTHER INFORMATION: n is unlocked nucleomonomer UNA-G
<220> FEATURE:
<221> NAME/KEY: misc_feature
<222> LOCATION: (23)..(24)
<223> OTHER INFORMATION: n is unlocked nucleomonomer UNA-U
<220> FEATURE:
<221> NAME/KEY: misc_feature
<222> LOCATION: (25)..(25)
<223> OTHER INFORMATION: n is unlocked nucleomonomer UNA-A
<220> FEATURE:
<221> NAME/KEY: misc_feature
<222> LOCATION: (26)..(27)
<223> OTHER INFORMATION: n is unlocked nucleomonomer UNA-C
<220> FEATURE:
<221> NAME/KEY: misc_feature
<222> LOCATION: (28)..(28)
<223> OTHER INFORMATION: n is unlocked nucleomonomer UNA-A
<220> FEATURE:
<221> NAME/KEY: misc_feature
<222> LOCATION: (29)..(29)
<223> OTHER INFORMATION: n is unlocked nucleomonomer UNA-C
<220> FEATURE:
<221> NAME/KEY: misc_feature
<222> LOCATION: (30)..(30)
<223> OTHER INFORMATION: n is unlocked nucleomonomer UNA-U
<220> FEATURE:
<221> NAME/KEY: misc_feature
<222> LOCATION: (31)..(33)
<223> OTHER INFORMATION: n is unlocked nucleomonomer UNA-A
<220> FEATURE:
<221> NAME/KEY: misc_feature
<222> LOCATION: (34)..(35)
<223> OTHER INFORMATION: n is unlocked nucleomonomer UNA-C
<220> FEATURE:
<221> NAME/KEY: misc_feature
<222> LOCATION: (36)..(36)
<223> OTHER INFORMATION: n is unlocked nucleomonomer UNA-A
<220> FEATURE:
<221> NAME/KEY: misc_feature
<222> LOCATION: (37)..(37)
<223> OTHER INFORMATION: n is unlocked nucleomonomer UNA-G
<220> FEATURE:
<221> NAME/KEY: misc_feature
<222> LOCATION: (38)..(39)
<223> OTHER INFORMATION: n is unlocked nucleomonomer UNA-C
<220> FEATURE:
<221> NAME/KEY: misc_feature
<222> LOCATION: (40)..(40)
<223> OTHER INFORMATION: n is unlocked nucleomonomer UNA-U
<220> FEATURE:
<221> NAME/KEY: misc_feature
<222> LOCATION: (41)..(41)
<223> OTHER INFORMATION: n is unlocked nucleomonomer UNA-C
<220> FEATURE:
<221> NAME/KEY: misc_feature
<222> LOCATION: (42)..(43)
<223> OTHER INFORMATION: n is unlocked nucleomonomer UNA-A
<220> FEATURE:
<221> NAME/KEY: misc_feature
<222> LOCATION: (44)..(44)
<223> OTHER INFORMATION: n is unlocked nucleomonomer UNA-G
<220> FEATURE:
<221> NAME/KEY: misc_feature
<222> LOCATION: (45)..(46)
<223> OTHER INFORMATION: n is unlocked nucleomonomer UNA-A
<220> FEATURE:
<221> NAME/KEY: misc_feature
<222> LOCATION: (47)..(47)
<223> OTHER INFORMATION: n is unlocked nucleomonomer UNA-C
<220> FEATURE:
<221> NAME/KEY: misc_feature
<222> LOCATION: (48)..(48)
<223> OTHER INFORMATION: n is unlocked nucleomonomer UNA-A
<220> FEATURE:
<221> NAME/KEY: misc_feature
<222> LOCATION: (49)..(51)
<223> OTHER INFORMATION: n is unlocked nucleomonomer UNA-C
<220> FEATURE:
<221> NAME/KEY: misc_feature
<222> LOCATION: (52)..(52)
<223> OTHER INFORMATION: n is unlocked nucleomonomer UNA-G
<220> FEATURE:
<221> NAME/KEY: misc_feature
<222> LOCATION: (53)..(54)
<223> OTHER INFORMATION: n is unlocked nucleomonomer UNA-A
<220> FEATURE:
<221> NAME/KEY: misc_feature
<222> LOCATION: (55)..(55)
<223> OTHER INFORMATION: n is unlocked nucleomonomer UNA-U
<220> FEATURE:
<221> NAME/KEY: misc_feature
<222> LOCATION: (56)..(57)
<223> OTHER INFORMATION: n is unlocked nucleomonomer UNA-G
<220> FEATURE:
<221> NAME/KEY: misc_feature
<222> LOCATION: (58)..(58)
<223> OTHER INFORMATION: n is unlocked nucleomonomer UNA-A
<220> FEATURE:
<221> NAME/KEY: misc_feature
<222> LOCATION: (59)..(59)
<223> OTHER INFORMATION: n is unlocked nucleomonomer UNA-G
<220> FEATURE:
<221> NAME/KEY: misc_feature
<222> LOCATION: (60)..(60)
<223> OTHER INFORMATION: n is unlocked nucleomonomer UNA-U
<220> FEATURE:
<221> NAME/KEY: misc_feature
<222> LOCATION: (61)..(61)
<223> OTHER INFORMATION: n is unlocked nucleomonomer UNA-C
<220> FEATURE:
<221> NAME/KEY: misc_feature
<222> LOCATION: (62)..(62)
<223> OTHER INFORMATION: n is unlocked nucleomonomer UNA-U
<220> FEATURE:
<221> NAME/KEY: misc_feature
<222> LOCATION: (63)..(63)
<223> OTHER INFORMATION: n is unlocked nucleomonomer UNA-C
<220> FEATURE:
<221> NAME/KEY: misc_feature
<222> LOCATION: (64)..(64)
<223> OTHER INFORMATION: n is unlocked nucleomonomer UNA-U
<220> FEATURE:
<221> NAME/KEY: misc_feature
<222> LOCATION: (65)..(66)

<223> OTHER INFORMATION: n is unlocked nucleomonomer UNA-A
<220> FEATURE:
<221> NAME/KEY: misc_feature
<222> LOCATION: (67)..(67)
<223> OTHER INFORMATION: n is unlocked nucleomonomer UNA-G
<220> FEATURE:
<221> NAME/KEY: misc_feature
<222> LOCATION: (68)..(68)
<223> OTHER INFORMATION: n is unlocked nucleomonomer UNA-C
<220> FEATURE:
<221> NAME/KEY: misc_feature
<222> LOCATION: (69)..(69)
<223> OTHER INFORMATION: n is unlocked nucleomonomer UNA-U
<220> FEATURE:
<221> NAME/KEY: misc_feature
<222> LOCATION: (70)..(70)
<223> OTHER INFORMATION: n is unlocked nucleomonomer UNA-A
<220> FEATURE:
<221> NAME/KEY: misc_feature
<222> LOCATION: (71)..(71)
<223> OTHER INFORMATION: n is unlocked nucleomonomer UNA-C
<220> FEATURE:
<221> NAME/KEY: misc_feature
<222> LOCATION: (72)..(72)
<223> OTHER INFORMATION: n is unlocked nucleomonomer UNA-A
<220> FEATURE:
<221> NAME/KEY: misc_feature
<222> LOCATION: (73)..(73)
<223> OTHER INFORMATION: n is unlocked nucleomonomer UNA-U
<220> FEATURE:
<221> NAME/KEY: misc_feature
<222> LOCATION: (74)..(75)
<223> OTHER INFORMATION: n is unlocked nucleomonomer UNA-A
<220> FEATURE:
<221> NAME/KEY: misc_feature
<222> LOCATION: (76)..(76)
<223> OTHER INFORMATION: n is unlocked nucleomonomer UNA-U
<220> FEATURE:
<221> NAME/KEY: misc_feature
<222> LOCATION: (77)..(77)
<223> OTHER INFORMATION: n is unlocked nucleomonomer UNA-A
<220> FEATURE:
<221> NAME/KEY: misc_feature
<222> LOCATION: (78)..(79)
<223> OTHER INFORMATION: n is unlocked nucleomonomer UNA-C
<220> FEATURE:
<221> NAME/KEY: misc_feature
<222> LOCATION: (80)..(81)
<223> OTHER INFORMATION: n is unlocked nucleomonomer UNA-A
<220> FEATURE:
<221> NAME/KEY: misc_feature
<222> LOCATION: (82)..(82)
<223> OTHER INFORMATION: n is unlocked nucleomonomer UNA-C
<220> FEATURE:
<221> NAME/KEY: misc_feature
<222> LOCATION: (83)..(84)
<223> OTHER INFORMATION: n is unlocked nucleomonomer UNA-U
<220> FEATURE:
<221> NAME/KEY: misc_feature
<222> LOCATION: (85)..(85)
<223> OTHER INFORMATION: n is unlocked nucleomonomer UNA-A
<220> FEATURE:
<221> NAME/KEY: misc_feature
<222> LOCATION: (86)..(86)
<223> OTHER INFORMATION: n is unlocked nucleomonomer UNA-C
<220> FEATURE:
<221> NAME/KEY: misc_feature
<222> LOCATION: (87)..(87)
<223> OTHER INFORMATION: n is unlocked nucleomonomer UNA-A
<220> FEATURE:
<221> NAME/KEY: misc_feature
<222> LOCATION: (88)..(88)
<223> OTHER INFORMATION: n is unlocked nucleomonomer UNA-C
<220> FEATURE:
<221> NAME/KEY: misc_feature
<222> LOCATION: (89)..(90)
<223> OTHER INFORMATION: n is unlocked nucleomonomer UNA-U
<220> FEATURE:
<221> NAME/KEY: misc_feature
<222> LOCATION: (91)..(91)
<223> OTHER INFORMATION: n is unlocked nucleomonomer UNA-A
<220> FEATURE:
<221> NAME/KEY: misc_feature
<222> LOCATION: (92)..(92)
<223> OTHER INFORMATION: n is unlocked nucleomonomer UNA-C
<220> FEATURE:
<221> NAME/KEY: misc_feature
<222> LOCATION: (93)..(96)
<223> OTHER INFORMATION: n is unlocked nucleomonomer UNA-A
<220> FEATURE:
<221> NAME/KEY: misc_feature
<222> LOCATION: (97)..(97)
<223> OTHER INFORMATION: n is unlocked nucleomonomer UNA-U
<220> FEATURE:
<221> NAME/KEY: misc_feature
<222> LOCATION: (98)..(98)
<223> OTHER INFORMATION: n is unlocked nucleomonomer UNA-G
<220> FEATURE:
<221> NAME/KEY: misc_feature
<222> LOCATION: (99)..(100)
<223> OTHER INFORMATION: n is unlocked nucleomonomer UNA-U
<220> FEATURE:
<221> NAME/KEY: misc_feature
<222> LOCATION: (101)..(101)
<223> OTHER INFORMATION: n is unlocked nucleomonomer UNA-G
<220> FEATURE:
<221> NAME/KEY: misc_feature
<222> LOCATION: (102)..(102)
<223> OTHER INFORMATION: n is unlocked nucleomonomer UNA-U
<220> FEATURE:
<221> NAME/KEY: misc_feature
<222> LOCATION: (103)..(107)
<223> OTHER INFORMATION: n is unlocked nucleomonomer UNA-C
<220> FEATURE:
<221> NAME/KEY: misc_feature
<222> LOCATION: (108)..(111)
<223> OTHER INFORMATION: n is unlocked nucleomonomer UNA-A
<220> FEATURE:
<221> NAME/KEY: misc_feature
<222> LOCATION: (112)..(112)
<223> OTHER INFORMATION: n is unlocked nucleomonomer UNA-U
<220> FEATURE:
<221> NAME/KEY: misc_feature
<222> LOCATION: (113)..(113)
<223> OTHER INFORMATION: n is unlocked nucleomonomer UNA-G
<220> FEATURE:
<221> NAME/KEY: misc_feature
<222> LOCATION: (114)..(114)
<223> OTHER INFORMATION: n is unlocked nucleomonomer UNA-U
<220> FEATURE:
<221> NAME/KEY: misc_feature
<222> LOCATION: (115)..(115)
<223> OTHER INFORMATION: n is unlocked nucleomonomer UNA-A
<220> FEATURE:
<221> NAME/KEY: misc_feature
<222> LOCATION: (116)..(116)
<223> OTHER INFORMATION: n is unlocked nucleomonomer UNA-G
<220> FEATURE:
<221> NAME/KEY: misc_feature
<222> LOCATION: (117)..(118)
<223> OTHER INFORMATION: n is unlocked nucleomonomer UNA-C
<220> FEATURE:
<221> NAME/KEY: misc_feature
<222> LOCATION: (119)..(119)
<223> OTHER INFORMATION: n is unlocked nucleomonomer UNA-A
<220> FEATURE:
<221> NAME/KEY: misc_feature
<222> LOCATION: (120)..(121)
<223> OTHER INFORMATION: n is unlocked nucleomonomer UNA-U
<220> FEATURE:
<221> NAME/KEY: misc_feature
<222> LOCATION: (122)..(122)
<223> OTHER INFORMATION: n is unlocked nucleomonomer UNA-C
<220> FEATURE:
<221> NAME/KEY: misc_feature
<222> LOCATION: (123)..(123)
<223> OTHER INFORMATION: n is unlocked nucleomonomer UNA-G
<220> FEATURE:

<221> NAME/KEY: misc_feature
<222> LOCATION: (124)..(124)
<223> OTHER INFORMATION: n is unlocked nucleomonomer UNA-U
<220> FEATURE:
<221> NAME/KEY: misc_feature
<222> LOCATION: (125)..(125)
<223> OTHER INFORMATION: n is unlocked nucleomonomer UNA-A
<220> FEATURE:
<221> NAME/KEY: misc_feature
<222> LOCATION: (126)..(126)
<223> OTHER INFORMATION: n is unlocked nucleomonomer UNA-U
<220> FEATURE:
<221> NAME/KEY: misc_feature
<222> LOCATION: (127)..(127)
<223> OTHER INFORMATION: n is unlocked nucleomonomer UNA-C
<220> FEATURE:
<221> NAME/KEY: misc_feature
<222> LOCATION: (128)..(128)
<223> OTHER INFORMATION: n is unlocked nucleomonomer UNA-U
<220> FEATURE:
<221> NAME/KEY: misc_feature
<222> LOCATION: (129)..(129)
<223> OTHER INFORMATION: n is unlocked nucleomonomer UNA-G
<220> FEATURE:
<221> NAME/KEY: misc_feature
<222> LOCATION: (130)..(130)
<223> OTHER INFORMATION: n is unlocked nucleomonomer UNA-C
<220> FEATURE:
<221> NAME/KEY: misc_feature
<222> LOCATION: (131)..(131)
<223> OTHER INFORMATION: n is unlocked nucleomonomer UNA-U
<220> FEATURE:
<221> NAME/KEY: misc_feature
<222> LOCATION: (132)..(133)
<223> OTHER INFORMATION: n is unlocked nucleomonomer UNA-C
<220> FEATURE:
<221> NAME/KEY: misc_feature
<222> LOCATION: (134)..(134)
<223> OTHER INFORMATION: n is unlocked nucleomonomer UNA-U
<220> FEATURE:
<221> NAME/KEY: misc_feature
<222> LOCATION: (135)..(136)
<223> OTHER INFORMATION: n is unlocked nucleomonomer UNA-A
<220> FEATURE:
<221> NAME/KEY: misc_feature
<222> LOCATION: (137)..(137)
<223> OTHER INFORMATION: n is unlocked nucleomonomer UNA-U
<220> FEATURE:
<221> NAME/KEY: misc_feature
<222> LOCATION: (138)..(142)
<223> OTHER INFORMATION: n is unlocked nucleomonomer UNA-A
<220> FEATURE:
<221> NAME/KEY: misc_feature
<222> LOCATION: (143)..(143)
<223> OTHER INFORMATION: n is unlocked nucleomonomer UNA-G
<220> FEATURE:
<221> NAME/KEY: misc_feature
<222> LOCATION: (144)..(146)
<223> OTHER INFORMATION: n is unlocked nucleomonomer UNA-A
<220> FEATURE:
<221> NAME/KEY: misc_feature
<222> LOCATION: (147)..(147)
<223> OTHER INFORMATION: n is unlocked nucleomonomer UNA-G
<220> FEATURE:
<221> NAME/KEY: misc_feature
<222> LOCATION: (148)..(149)
<223> OTHER INFORMATION: n is unlocked nucleomonomer UNA-U
<220> FEATURE:
<221> NAME/KEY: misc_feature
<222> LOCATION: (150)..(150)
<223> OTHER INFORMATION: n is unlocked nucleomonomer UNA-U
<220> FEATURE:
<221> NAME/KEY: misc_feature
<222> LOCATION: (151)..(151)
<223> OTHER INFORMATION: n is unlocked nucleomonomer UNA-C
<220> FEATURE:
<221> NAME/KEY: misc_feature
<222> LOCATION: (152)..(153)
<223> OTHER INFORMATION: n is unlocked nucleomonomer UNA-U
<220> FEATURE:
<221> NAME/KEY: misc_feature
<222> LOCATION: (154)..(154)
<223> OTHER INFORMATION: n is unlocked nucleomonomer UNA-C
<220> FEATURE:
<221> NAME/KEY: misc_feature
<222> LOCATION: (155)..(155)
<223> OTHER INFORMATION: n is unlocked nucleomonomer UNA-A
<220> FEATURE:
<221> NAME/KEY: misc_feature
<222> LOCATION: (156)..(156)
<223> OTHER INFORMATION: n is unlocked nucleomonomer UNA-C
<220> FEATURE:
<221> NAME/KEY: misc_feature
<222> LOCATION: (157)..(157)
<223> OTHER INFORMATION: n is unlocked nucleomonomer UNA-A
<220> FEATURE:
<221> NAME/KEY: misc_feature
<222> LOCATION: (158)..(158)
<223> OTHER INFORMATION: n is unlocked nucleomonomer UNA-U

<400> SEQUENCE: 37
nnnnnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnn 158

<210> SEQ ID NO 38
<211> LENGTH: 100
<212> TYPE: RNA
<213> ORGANISM: Unknown
<220> FEATURE:
<223> OTHER INFORMATION: Poly(A) 100 Tail

<400> SEQUENCE: 38
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa 100

<210> SEQ ID NO 39
<211> LENGTH: 110
<212> TYPE: RNA
<213> ORGANISM: Unknown
<220> FEATURE:
<223> OTHER INFORMATION: Poly(A) 110 Tail

<400> SEQUENCE: 39
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa 110

<210> SEQ ID NO 40
<211> LENGTH: 9
<212> TYPE: RNA
<213> ORGANISM: Unknown
<220> FEATURE:
<223> OTHER INFORMATION: Triple Stop Codon

<400> SEQUENCE: 40 auaagugaa 9

<210> SEQ ID NO 41
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 41

-continued

```
augggccaca gcaagcagau ccggauccug cugcugaacg agauggagaa gcuggagaag     60
acccuguucc ggcuggagca gggcuacgag cugcaguucc ggcugggccc cacccugcag    120
ggcaaggccg ugaccgugua caccaacuac ccuuccccg gcgagaccuu caaccgggag    180
aaguuccgga gccuggacug ggagaacccc accgagcggg aggacgacag cgacaaguac    240
ugcaagcuga accugcagca gagcggcagc uuccaguacu acuuccugca gggcaacgag    300
aagagcggcg gcggcuacau cguggugac cccauccugc gggugggcgc cgacaaccac    360
gugcugcccc uggacugcgu gacccugcag accuuccugg ccaagugccu gggccccuuc    420
gacgaguggg agagccggcu gcggguggcc aaggagagcg gcuacaacau gauccacuuc    480
accccccugc agacccuggg ccugagccgg agcugcuaca gccuggccaa ccagcuggag    540
cugaaccccg acuucagccg gcccaaccgg aaguacaccu ggaacgacgu gggccagcug    600
guggagaagc ugaagaagga guggaacgug aucugcauca ccgacguggu guacaaccac    660
accgccgcca acagcaagug gauccaggag caccccgagu gcgccuacaa ccuggugaac    720
agcccccacc ugaagcccgc cugggugcug gaccgggccc uguggcgguu cagcugcgac    780
guggccgagg gcaaguacaa ggagaagggc auccccgccc ugaucgagaa cgaccaccac    840
augaacagca uccggaagau caucugggag gacaucuucc ccaagcugaa gcugugggag    900
uucuuccagg uggacgugaa caaggccgug gagcaguucc ggcggcugcu gacccaggag    960
aaccggcggg ugaccaagag cgaccccaac cagcaccuga ccaucaucca ggaccccgag   1020
uaccggcggu ucggcugcac cguggacaug aacaucgccc ugaccaccuu cauccccac   1080
gacaagggcc ccgccgccau cgaggagugc ugcaacuggu uccacaagcg gauggaggag   1140
cugaacagcg agaagcaccg gcugaucaac uaccaccagg agcaggccgu gaacugccug   1200
cugggcaacg uguucuacga gcggcuggcc ggccacggcc ccaagcuggg ccccgugacc   1260
cggaagcacc cccuggugac ccgguacuuc accuuccccu ucgaggagau cgacuucagc   1320
auggaggaga gcaugaucca ccugcccaac aaggccugcu uccugauggc ccacaacggc   1380
ugggugaugg gcgacgaccc ccugcggaac uucgccgagc ccggcagcga gguguaccug   1440
cggcgggagc ugaucugcug gggcgacagc gugaagcugc gguacggcaa caagcccgag   1500
gacugccccu accugugggc ccacaugaag aaguacaccg agaucaccgc caccuacuuc   1560
cagggcgugc ggcuggacaa cugccacagc accccccugc acguggccga guacaugcug   1620
gacgccgccc ggaaccugca gcccaaccug uacgugugg ccgagcuguu caccggcagc   1680
gaggaccugg acaacguguu cgugacccgg cugggcauca gcagccugau ccgggaggcc   1740
augagcgccu acaacagcca cgaggagggc cggcuggugu accgguacgg cggcgagccc   1800
gugggcagcu ucgugcagcc cugccugcgg ccccugaugc ccgccaucgc ccacgcccug   1860
uucauggaca ucacccacga caacgagugc cccaucgugc accggagcgc cuacgacgcc   1920
cugcccagca ccaccaucgu gagcauggcc ugcugcgcca gcggcagcac ccggggcuac   1980
gacgagcugg ugccccacca gaucagcgug gugagcgagg agcgguucua caccaagugg   2040
aaccccgagg cccugcccag caacaccggc gaggugaacu uccagagcgg caucaucgcc   2100
gcccggugcg ccaucagcaa gcugcaccag gagcugggcg ccaagggcuu cauccaggug   2160
uacguggacc agguggacga ggacaucgug gccgugaccc ggcacagccc cagcauccac   2220
cagagcgugg uggccgugag ccggaccgcc uuccggaacc ccaagaccag cuucuacagc   2280
aaggaggugc cccagaugug cauccccggc aagaucgagg agguggugcu ggaggcccgg   2340
accaucgagc ggaacaccaa gcccuaccgg aaggacgaga acagcaucaa cggcaccccc   2400
```

```
gacaucaccg uggagauccg ggagcacauc cagcugaacg agagcaagau cgugaagcag   2460
gccggcgugg ccaccaaggg ccccaacgag uacauccagg agaucgaguu cgagaaccug   2520
agccccggca gcgugaucau cuuccgggug agccuggacc cccacgccca gguggccgug   2580
ggcauccugc ggaaccaccu gacccaguuc agcccccacu ucaagagcgg cagccuggcc   2640
guggacaacg ccgaccccau ccugaagauc cccuucgcca gccuggccag ccggcugacc   2700
cuggccgagc ugaaccagau ccuguaccgg ugcgagagcg aggagaagga ggacggcggc   2760
ggcugcuacg acauccccaa cuggagcgcc cugaaguacg ccggccugca gggccugaug   2820
agcgugcugg ccgagauccg gcccaagaac gaccugggcc accccuucug caacaaccug   2880
cggagcggcg acuggaugau cgacuacgug agcaaccggc ugaucagccg gagcggcacc   2940
aucgccgagg ugggcaagug gcugcaggcc auguucuucu accugaagca gaucccccgg   3000
uaccugaucc ccugcuacuu cgacgccauc cugaucggcg ccuacaccac ccugcuggac   3060
accgccugga agcagaugag cagcuucgug cagaacggca gcaccuucgu gaagcaccug   3120
agccugggca gcgugcagcu gugcggcgug ggcaaguucc ccagccugcc cauccugagc   3180
cccgcccuga uggacgugcc cuaccggcug aacgagauca ccaaggagaa ggagcagugc   3240
ugcgugagcc uggccgccgg ccugccccac uucagcagcg gcaucuuccg gugcuggggc   3300
cgggacaccu ucaucgcccu gcggggcauc cugcugauca ccggccggua cguggaggcc   3360
cggaacauca uccuggccuu cgccggcacc cugcggcacg gccugauccc caaccugcug   3420
ggcgagggca ucuacgcccg guacaacugc cgggacgccg ugugguggug gcugcagugc   3480
auccaggacu acugcaagau ggugcccaac ggccuggaca uccugaagug ccccgugagc   3540
cggauguacc ccaccgacga cagcgccccc cugcccgccg gcacccugga ccagccccug   3600
uucgagguga uccaggaggc caugcagaag cacaugcagg gcauccaguu ccgggagcgg   3660
aacgccggcc cccagaucga ccggaacaug aaggacgagg gcuucaacau caccgccggc   3720
guggacgagg agaccggcuu cguguacggc ggcaaccggu ucaacugcgg caccuggaug   3780
gacaagaugg gcgagagcga ccgggcccgg aaccggggca ucccccgcac cccccgggac   3840
ggcagcgccg uggagaucgu gggccugagc aagagcgccg ugcgguggcu gcuggagcug   3900
agcaagaaga acaucuuccc cuaccacgag gugaccguga agcggcacgg caaggccauc   3960
aaggugagcu acgacgagug gaaccggaag auccaggaca acuucgagaa gcuguuccac   4020
gugagcgagg accccagcga ccugaacgag aagcacccca accuggugca caagcggggc   4080
aucuacaagg acagcuacgg cgccagcagc cccugguccg acuaccagcu gcggcccaac   4140
uucaccaucg ccaugguggu ggcccccgag cuguucacca ccgagaaggc cuggaaggcc   4200
cuggagaucg ccgagaagaa gcugcugggc ccccugggca ugaagacccu ggaccccgac   4260
gacaugguu acugcggcau cuacgacaac gcccuggaca acgacaacua caaccuggcc   4320
aagggcuuca acuaccacca gggcccgag uggcuguggc ccaucggcua cuuccugcgg   4380
gccaagcugu acuucagccg gcugaugggc cccgagacca ccgccaagac caucgugcug   4440
gugaagaacg ugcugagccg gcacuacgug caccuggagc ggagccccug gaagggccug   4500
cccgagcuga ccaacgagaa cgcccaguac ugccccuuca gcugcgagac ccaggccugg   4560
agcaucgcca ccauccugga gacccuguac gaccuguag                          4599
```

<210> SEQ ID NO 42
<211> LENGTH: 4599
<212> TYPE: RNA

<213> ORGANISM: Artificial Sequence
<220> FEATURE:
<223> OTHER INFORMATION: Codon-Optimized AGL Coding Sequence

<400> SEQUENCE: 42
augggccaua gcaagcagau ccggauccuc cugcucaaug agauggaaaa gcucgagaaa 60
acccucuuua ggcuggagca aggcuacgaa cuccaguuuc ggcucgggcc cacucuccag 120
ggcaaggccg ugaccgucua caccaacuau cccuucccug gcgagaccuu caacagggag 180
aaguuucggu cccucgacug ggagaacccc accgagaggg aggacgacuc cgacaaguau 240
ugcaagcuga accuccaaca auccgggucc uuccaguacu acuuucugca aggcaacgaa 300
aagagcgggg gcggguauau uguggucgau cccauccucc gggugggggc ugacaaccac 360
guccuccccc uggauugcgu gacucugcag accuuccucg cuaaaugccu gggcccuuuc 420
gacgaguggg agagcaggcu gcggguggcc aaggaguccg gguauaauau gauccacuuc 480
accccccugc agacucuggg ccucucccgg uccuguuaua gccuggccaa ccagcucgag 540
cucaacccug auuucuccag gccuaacagg aaauacaccu ggaacgacgu gggccagcuc 600
gucgagaagc ucaagaaaga guggaacgug aucugcauca cugacguggu cuauaaccac 660
acugcugcua acagcaagug gauucaggag caccccgagu gcgccuacaa ccuggucaac 720
uccccccauc ucaagccugc cugggucuc gauagggccc uguggcgguu uagcugcgac 780
guggccgagg gcaaguauaa ggagaaaggc auuccugcuc ugaucgagaa cgaccaucac 840
augaacagca uucggaagau uaucugggaa gacaucuucc ccaaacugaa gcucugggag 900
uucuuucaag ucgacgucaa uaaggcugug gaacaauuca ggaggcugcu gacccaagag 960
aaccggcggg ucaccaaauc cgaccccaau caacaucuga cuaucaucca agacccugag 1020
uauaggcggu ucgggugcac ugucgacaug aauaucgccc ucacuacuuu uauuccccac 1080
gauaaaggcc ccgccgccau cgaggagugu ugcaacuggu uccacaagag gauggaagag 1140
cucaacuccg aaaaacaccg gcucaucaau uaccaccagg agcaggccgu gaacugucug 1200
cugggcaacg ucuucuacga gcggcucgcu gggcacgggc ccaagcucgg cccugucacu 1260
aggaaacacc cucucgugac ccgguacuuc acuuucccu ucgaggaaau ugauuuuagc 1320
auggaggagu ccaugaucca ccuccccaac aaggcuugcu uccucauggc ccauaacggc 1380
ugggucaugg gcgacgaccc ucugcggaau uucgcugagc ccgggucga gguguaucuc 1440 cggagggagc ugaucuguug gggcgauagc gugaagcucc gguacggcaa caagcccgaa 1500
gauugcccuu accucugggc ccauaugaag aaguauacug agauuacugc cacuuacuuu 1560
cagggcgucc ggcuggacaa uugucauucc accccucugc augucgcuga auauaugcug 1620
gacgcugcuc ggaaccugca acccaaccuc uacgucgucg cugagcucuu uaccggcagc 1680
gaggaccucg auaacgucuu cgugacuagg cucgggauca gcagccucau uagggaagcc 1740
augagcgccu acaacagcca cgaggaaggg aggcucgugu aucgguacgg cggcgagccu 1800
gugggcagcu ucgugcagcc cugccugcgg ccucucaugc ccgcuaucgc ccacgcccuc 1860
uucauggaca ucacucacga caacgaaugc ccuaucgucc acagguccgc uuacgacgcu 1920
cugcccagca cuaccaucgu guccauggcc ugcugcgcua gcggcagcac caggggguac 1980
gacgagcucg ucccucacca gaucuccguc guguccgagg agcgguucua uacuaaaugg 2040
aacccugagg cccugccuuc caauaccggg gaggugaacu uucaaagcgg gaucaucgcc 2100
gcccggugcg cuauuagcaa gcugcaccag gaacugggcg ccaaaggguu cauccagguc 2160
uacgucgacc aaguggacga ggauauuguc gccgucacca ggcauucccc uagcauucac 2220

-continued

```
caguccgugg ucgcugucuc caggacugcu uuucggaacc ccaaaacuuc cuucuauagc   2280
aaagaggucc cucaaaugug uauuccuggg aagaucgagg aggucgugcu ggaggcuagg   2340
acuaucgaaa ggaauacuaa gccuuaccgg aaagacgaaa acuccauuaa cggcaccccc   2400
gacauuaccg ucgagaucag ggagcacauc cagcugaacg agagcaagau cgugaagcaa   2460
gcuggcgugg ccaccaaggg ccccaacgag uacauccaag agauugaguu cgagaaucug   2520
ucccccggca gcgugaucau uuuuagggug agccuggacc cccacgccca agucgcugug   2580
ggcauccugc ggaaccaccu cacccaauuu agcccucauu ucaaguccgg gagccucgcu   2640
guggauaacg ccgacccuau ucucaagauc ccuuucgcuu cccuggccag caggcucacu   2700
cuggcugaac ucaaccagau ucuguaucgg ugcgaguccg aggagaaaga ggacgggggc   2760
ggcuguuacg auauucccaa uugguccgcc cugaaguacg ccgggcugca agggcucaug   2820
uccguccugg ccgagauuag gcccaaaaac gaucugggcc acccuuucug caacaaccug   2880
agguccggcg acuggaugau cgauuacguc agcaaucggc ugaucucccg guccggcacu   2940
aucgcugagg uggggaagug gcugcaggcu auguuuuuuu aucucaaaca gauuccccgg   3000
uaucugauuc ccugcuauuu cgacgcuauu cucaucgggg ccuacaccac ucugcucgac   3060
accgccugga aacagauguc cagcuucgug cagaacgggu ccaccuucgu caagcaucug   3120
ucccuggggu ccgugcaacu cugcggcguc ggcaaguuuc cuagccuccc cauccugucc   3180
ccugcccuca uggacguccc uuaccggcuc aacgaaauua ccaaggagaa agaacaaugc   3240
ugcguguccc ucgcugccgg gcucccucac uucuccuccg ggaucuuucg guguuggggc   3300
cgggacacuu ucaucgcccu gagggggauu cuccucauca cuggccggua cgucgaggcc   3360
cggaacauca uccucgccuu cgcugggacc cuccggcacg ggcucauccc uaaccuccuc   3420
ggggagggca ucuacgccag guauaacugc cgggacgcug ucugguggug gcuccagugc   3480
auucaggacu auugcaagau ggugcccaac gggcucgaua uccucaaaug ucccgugagc   3540
aggauguacc cuaccgacga cuccgcuccu cugccugcug ggacccucga ccagccccug   3600
uucgagguca uucaggaggc caugcaaaag cauaugcagg ggauucaguu ucgggagcgg   3660
aacgcugggc cccagauuga ccggaauaug aaagaugagg gguucaacau uacugccggc   3720
guggacgagg agaccggcuu cguguacggc ggcaaccggu uuaacugcgg gaccuggaug   3780
gacaagaugg gcgagagcga uagggcuagg aauaggggca uucccgccac ccccagggac   3840
ggcuccgcug ucgagaucgu cgggcucagc aaguccgcug ugcgguggcu gcucgagcuc   3900
agcaagaaga acaucuuucc uuaccacgag gucaccguca agaggcacgg caaagcuauu   3960
aaagucuccu acgacgaaug gaauaggaag auucaagaua auuucgagaa acucuuccac   4020
gugagcgagg auccuuccga ccucaacgag aaacacccca accucgugca uaagcggggg   4080
auuuauaagg acagcuacgg cgcuuccagc ccuuggugcg auuaccagcu ccggccuaac   4140
uucaccauug ccauggugga cgccccugaa cucuucacua ccgagaaggc cuggaaggcu   4200
cuggaaaucg ccgagaagaa gcugcugggg ccccuggggga ugaagacucu cgaccccgac   4260
gacauggugu auugcggcau cuacgauaac gcccucgaua acgauaauua uaaccuggcu   4320
aagggguuua acuaccauca aggcccugaa uggcucuggc cuaucggcua cuuccugcgg   4380
gccaagcucu acuucagcag gcugaugggg cccgaaacua cugccaaaac uauugugcug   4440
gugaagaacg ugcugagccg gcacuacgug caccuggaaa ggagcccuug gaagggccug   4500
cccgagcuca ccaacgaaaa cgcccaguau ugcccuuuua gcugcgagac ccaagccugg   4560
```

uccaucgcua cuauccugga aacccuguac gaccucuag 4599

<210> SEQ ID NO 43
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 43
auggggcaca gcaaacaaau caggauccuc cuccucaacg aaauggaaaa acucgaaaaa 60
acccucuuca ggcucgaaca aggguacgaa cuccaauuca ggcucgggcc gacgcuccaa 120
gggaaagcgg ugacggugua cacgaacuac ccguucccgg gggaaacguu caacagggaa 180
aaauucagga gccucgacug ggaaaacccg acggaaaggg aagacgacag cgacaaauac 240
ugcaaacuca accuccaaca aagcgggagc uuccaauacu acuuccucca agggaacgaa 300
aaaagcgggg gggguacau cgugguggac ccgauccuca gggugggggc ggacaaccac 360
gugcucccgc ucgacugcgu gacgcuccaa acguuccucg cgaaaugccu cgggccguuc 420
gacgaauggg aaagcaggcu cagggugggcg aaagaaagcg gguacaacau gauccacuuc 480
acgccgcucc aaacgcucgg gcucagcagg agcugcuaca gccucgcgaa ccaacucgaa 540
cucaacccgg acuucagcag gccgaacagg aaauacacgu ggaacgacgu ggggcaacuc 600
guggaaaaac ucaaaaaaga auggaacgug aucugcauca cggacguggu guacaaccac 660
acggcggcga acagcaaaug gauccaagaa cacccggaau gcgcguacaa ccucgugaac 720
agcccgcacc ucaaaccggc gugggugcuc gacagggcgc ucuggagguu cagcugcgac 780
guggcggaag ggaaauacaa agaaaaaggg aucccggcgc ucaucgaaaa cgaccaccac 840
augaacagca ucaggaaaau caucugggaa gacaucuucc cgaaacucaa acucugggaa 900
uucuuccaag uggacgugaa caaagcggug gaacaauuca ggaggcuccu cacgcaagaa 960
aacaggaggg ugacgaaaag cgacccgaac caacaccuca cgaucaucca agacccggaa 1020
uacaggaggu ucgggugcac gguggacaug aacaucgcgc ucacgacguu caucccgcac 1080
gacaaagggc cggcggcgau cgaagaaugc ugcaacuggu uccacaaaag gauggaagaa 1140
cucaacagcg aaaaacacag gcucaucaac uaccaccaag aacaagcggu gaacugccuc 1200
cucgggaacg uguucuacga aaggcucgcg gggcacgggc cgaaacucgg gccggugacg 1260
aggaaacacc cgcucgugac gagguacuuc acguucccgu ucgaagaaau cgacuucagc 1320
auggaagaaa gcaugaucca ccucccgaac aaagcgugcu uccucauggc gcacaacggg 1380
ugggugaugg gggacgaccc gcucaggaac uucgcggaac cggggagcga aguguaccuc 1440
aggagggaac ucaucugcug gggggacagc gugaaacuca gguacgggaa caaaccggaa 1500
gacugcccgu accucugggc gcacaugaaa aaauacacgg aaaucacggc gacguacuuc 1560 caaggggga ggcucgacaa cugccacagc acgccgcucc acguggcgga auacaugcuc 1620
gacgcggcga ggaaccucca accgaaccuc uacgugugg cggaacucuu cacggggagc 1680
gaagaccucg acaacguguu cgugacgagg cucgggauca gcagccucau cagggaagcg 1740
augagcgcgu acaacagcca cgaagaaggg aggcucgugu acagguacgg gggggaaccg 1800
guggggagcu ucgugcaacc gugccucagg ccgcucaugc cggcgaucgc gcacgcgcug 1860
uucauggaca ucacgcacga caacgaaugc ccgaucgugc acaggagcgc guacgacgcg 1920
cucccgagca cgacgaucgu gagcauggcg ugcugcgcga gcgggagcac gagggggguac 1980 gacgaacucg ugccgcacca aaucagcgug gugagcgaag aaagguucua cacgaaaugg 2040

-continued

```
aacccggaag cgcucccgag caacacgggg gaagugaacu uccaaagcgg gaucaucgcg   2100
gcgaggugcg cgaucagcaa acuccaccaa gaacucgggg cgaaaggguu cauccaagug   2160
uacguggacc aaguggacga agacaucgug gcggugacga ggcacagccc gagcauccac   2220
caaagcgugg uggcggugag caggacggcg uucaggaacc cgaaaacgag cuucuacagc   2280
aaagaagugc cgcaaaugug caucccgggg aaaaucgaag aaguggugcu cgaagcgagg   2340
acgaucgaaa ggaacacgaa accguacagg aaagacgaaa acagcaucaa cgggacgccg   2400
gacaucacgg uggaaaucag ggaacacauc caacucaacg aaagcaaaau cgugaaacaa   2460
gcgggggugg cgacgaaagg gccgaacgaa uacauccaag aaaucgaauu cgaaaaccuc   2520
agcccgggga gcgugaucau cuucagggug agccucgacc cgcacgcgca aguggcggug   2580
gggauccuca ggaaccaccu cacgcaauuc agcccgcacu ucaaaagcgg gagccucgcg   2640
guggacaacg cggacccgau ccucaaaauc ccguucgcga gccucgcgag caggcucacg   2700
cucgcggaac ucaaccaaau ccucuacagg ugcgaaagcg aagaaaaaga agacgggggg   2760
gggugcuacg acaucccgaa cuggagcgcg cucaaauacg cggggcucca agggcucaug   2820
agcgugcucg cggaaaucag gccgaaaaac gaccucgggc acccguucug caacaaccuc   2880
aggagcgggg acuggaugau cgacuacgug agcaacaggc ucaucagcag gagcgggacg   2940
aucgcggaag uggggaaaug gcuccaagcg auguucuucu accucaaaca aaucccgagg   3000
uaccucaucc cgugcuacuu cgacgcgauc cucaucgggg cguacacgac gcuccucgac   3060
acggcgugga aacaaaugag cagcuucgug caaaacggga gcacguucgu gaaacaccuc   3120
agccucggga gcgugcaacu cugcggggug ggaaauuccc cgagccuccc gauccucagc   3180
ccggcgcuca uggacgugcc guacaggcuc aacgaaauca cgaaagaaaa agaacaaugc   3240
ugcgugagcc ucgcggcggg gcucccgcac uucagcagcg ggaucuucag gugcuggggg   3300
agggacacgu ucaucgcgcu caggggggauc cuccucauca cggggaggua cguggaagcg   3360
aggaacauca uccucgcguu cgcggggacg cucaggcacg ggcucauccc gaaccuccuc   3420
ggggaaggga ucuacgcgag guacaacugc agggacgcgg ugugguggug gcuccaaugc   3480
auccaagacu acugcaaaau ggugccgaac gggcucgaca uccucaaaug cccggugagc   3540
aggauguacc cgacggacga cagcgcgccg cucccggcgg ggacgcucga ccaaccgcug   3600
uucgaaguga uccaagaagc gaugcaaaaa cacaugcaag ggauccaauu cagggaaagg   3660
aacgcggggc cgcaaaucga caggaacaug aaagacgaag gguucaacau cacggcgggg   3720
guggacgaag aaacgggguu cguguacggg gggaacaggu ucaacugcgg gacguggaug   3780
gacaaaaugg gggaaagcga cagggcgagg aacaggggga ucccggcgac gccgagggac   3840
gggagcgcgg uggaaaucgu ggggcucagc aaaagcgcgg ugagguggcu ccucgaacuc   3900
agcaaaaaaa acaucuuccc guaccacgaa gugacgguga aaaggcacgg gaaagcgauc   3960
aaagugagcu acgacgaaug gaacaggaaa auccaagaca acuucgaaaa acucuuccac   4020
gugagcgaag acccgagcga ccucaacgaa aaacacccga accucgugca caaaaggggg   4080
aucuacaaag acagcuacgg ggcgagcagc ccguggugcg acuaccaacu caggccgaac   4140
uucacgaucg cgauggugu ggcgccggaa cucuucacga cggaaaaagc guggaaagcg   4200
cucgaaaucg cggaaaaaaa acuccucggg ccgcucggga ugaaaacgcu cgacccggac   4260
gacauggugu acugcgggau cuacgacaac gcgcucgaca acgacaacua caaccucgcg   4320
aaagggguuca acuaccacca agggccggaa uggcucuggc cgaucgggua cuuccucagg   4380
```

```
gcgaaacucu acuucagcag gcucaugggg ccggaaacga cggcgaaaac gaucgugcuc   4440

gugaaaaacg ugcucagcag gcacuacgug caccucgaaa ggagcccgug gaaagggcuc   4500

ccggaacuca cgaacgaaaa cgcgcaauac ugcccguuca gcugcgaaac gcaagcgugg   4560

agcaucgcga cgauccucga aacgcucuac gaccucuga                          4599
```

<210> SEQ ID NO 44
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 44

```
augggccaca gcaagcagau caggauccuc cuccucaacg aaauggaaaa gcucgaaaag     60

acacucuuca ggcucgaaca gggcuacgaa cuccaguuca ggcucggccc aacacuccag    120

ggcaaggccg ugacagugua cacaaacuac ccauucccag gcgaaacauu caacagggaa    180

aaguucagga gccucgacug ggaaaaccca acagaaaggg aagacgacag cgacaaguac    240

ugcaagcuca accuccagca gagcggcagc uuccaguacu acuuccucca gggcaacgaa    300

aagagcggcg gcggcuacau cguggugac ccaauccuca gggugggcgc cgacaaccac    360

gugcucccac ucgacugcgu gacacuccag acauuccucg ccaagugccu cggcccauuc    420

gacgaauggg aaagcaggcu cagggugcc aaggaaagcg gcuacaacau gauccacuuc    480

acaccacucc agacacucgg ccucagcagg agcugcuaca gccucgccaa ccagcucgaa    540

cucaacccag acuucagcag gccaaacagg aaguacacau ggaacgacgu gggccagcuc    600

guggaaaagc ucaagaagga auggaacgug aucugcauca cagacguggu guacaaccac    660

acagccgcca acagcaagug gauccaggaa cacccagaau gcgccuacaa ccucgugaac    720

agcccacacc ucaagccagc cugggugcuc gacagggccc ucuggagguu cagcugcgac    780

guggccgaag gcaaguacaa ggaaaagggc aucccagccc ucaucgaaaa cgaccaccac    840

augaacagca ucaggaagau caucugggaa gacaucuucc caaagcucaa gcucugggaa    900

uucuuccagg uggacgugaa caaggccgug gaacaguuca ggaggcuccu cacacaggaa    960

aacaggaggg ugacaaagag cgacccaaac cagcaccuca caaucaucca ggacccagaa   1020

uacaggaggu ucggcugcac aguggacaug aacaucgccc ucacaacauu caucccacac   1080

gacaagggcc agccgccau cgaagaaugc ugcaacuggu uccacaagag gauggaagaa   1140

cucaacagcg aaaagcacag gcucaucaac uaccaccagg aacaggccgu gaacugccuc   1200

cucggcaacg uguucuacga aaggcucgcc ggccacggcc caaagcucgg cccagugaca   1260

aggaagcacc cacucgugac aagguacuuc acauucccau ucgaagaaau cgacuucagc   1320

auggaagaaa gcaugaucca ccucccaaac aaggccugcu uccucauggc ccacaacggc   1380

ugggugaugg gcgacgaccc acucaggaac uucgccgaac caggcagcga aguguaccuc   1440

aggagggaac ucaucugcug ggcgacagc gugaagcuca gguacggcaa caagccagaa   1500

gacugcccau accucugggc ccacaugaag aaguacacag aaaucacagc cacauacuuc   1560

cagggcguga ggcucgacaa cugccacagc acaccacucc acguggccga auacaugcuc   1620

gacgccgcca ggaaccucca gccaaaccuc uacgugguggg ccgaacucuu cacaggcagc   1680

gaagaccucg acaacguguu cgugacaagg cucggcauca gcagccucau cagggaagcc   1740

augagcgccu acaacagcca cgaagaaggc aggcucgugu acagguacgg cggcgaacca   1800

gugggcagcu ucgugcagcc augccucagg ccacucaugc cagccaucgc ccacgcccuc   1860
```

-continued

```
uucauggaca ucacacacga caacgaaugc ccaaucgugc acaggagcgc cuacgacgcc   1920
cucccaagca caacaaucgu gagcauggcc ugcugcgcca gcggcagcac aaggggcuac   1980
gacgaacucg ugccacacca gaucagcgug gugagcgaag aaagguucua cacaaagugg   2040
aacccagaag cccucccaag caacacaggc gaagugaacu uccagagcgg caucaucgcc   2100
gccaggugcg ccaucagcaa gcuccaccag gaacucggcg ccaagggcuu cauccaggug   2160
uacguggacc agguggacga agacaucgug gccgugacaa ggcacagccc aagcauccac   2220
cagagcgugg uggccgugag caggacagcc uucaggaacc caaagacaag cuucuacagc   2280
aaggaagugc cacagaugug caucccaggc aagaucgaag aaguggugcu cgaagccagg   2340
acaaucgaaa ggaacacaaa gccauacagg aaggacgaaa acagcaucaa cggcacacca   2400
gacaucacag uggaaaucag ggaacacauc cagcucaacg aaagcaagau cgugaagcag   2460
gccggcgugg ccacaaaggg cccaaacgaa uacauccagg aaaucgaauu cgaaaaccuc   2520
agcccaggca gcgugaucau cuucagggug agccucgacc cacacgccca gguggccgug   2580
ggcauccuca ggaaccaccu cacacaguuc agcccacacu ucaagagcgg cagccucgcc   2640
guggacaacg ccgacccaau ccucaagauc ccauucgcca gccucgccag caggcucaca   2700
cucgccgaac ucaaccagau ccucuacagg ugcgaaagcg aagaaaagga agacggcggc   2760
ggcugcuacg acaucccaaa cuggagcgcc cucaaguacg ccggccucca gggccucaug   2820
agcgugcucg ccgaaaucag gccaaagaac gaccucggcc acccauucug caacaaccuc   2880
aggagcggcg acuggaugau cgacuacgug agcaacaggc ucaucagcag gagcggcaca   2940
aucgccgaag ugggcaagug gcuccaggcc auguucuucu accucaagca gaucccaagg   3000
uaccucaucc caugcuacuu cgacgccauc cucaucggcg ccuacacaac acuccucgac   3060
acagccugga agcagaugag cagcuucgug cagaacggca gcacauucgu gaagcaccuc   3120
agccucggca gcgugcagcu cugcggcgug ggcaaguucc caagccuccc aauccucagc   3180
ccagcccuca uggacgugcc auacaggcuc aacgaaauca caaaggaaaa ggaacagugc   3240
ugcgugagcc ucgccgccgg ccucccacac uucagcagcg gcaucuucag gugcuggggc   3300
agggacacau ucaucgcccu caggggcauc cuccucauca caggcaggua cguggaagcc   3360
aggaacauca uccucgccuu cgccggcaca cucaggcacg gccucauccc aaaccuccuc   3420
ggcgaaggca ucuacgccag guacaacugc agggacgccg ugugguggug gcuccagugc   3480
auccaggacu acugcaagau ggugccaaac ggccucgaca uccucaagug cccagugagc   3540
aggauguacc caacagacga cagcgcccca cucccagccg gcacacucga ccagccacuc   3600
uucgaaguga uccaggaagc caugcagaag cacaugcagg gcauccaguu cagggaaagg   3660
aacgccggcc cacagaucga caggaacaug aaggacgaag gcuucaacau cacagccggc   3720
guggacgaag aaacaggcuu cguguacggc ggcaacaggu ucaacugcgg cacauggaug   3780
gacaagaugg gcgaaagcga cagggccagg aacaggggca ucccagccac accaagggac   3840
ggcagcgccg uggaaaucgu gggccucagc aagagcgccg ugagguggcu ccucgaacuc   3900
agcaagaaga acaucuuccc auaccacgaa gugacaguga agaggcacgg caaggccauc   3960
aaggugagcu acgacgaaug gaacaggaag auccaggaca acuucgaaaa gcuguuccac   4020
gugagcgaag acccaagcga ccucaacgaa aagcacccaa accucgugca caagaggggc   4080
aucuacaagg acagcuacgg cgccagcagc ccauggugcg acuaccagcu caggccaaac   4140
uucacaaucg ccauggugu ggccccagaa cucuucacaa cagaaaaggc cuggaaggcc   4200
```

```
cucgaaaucg ccgaaaagaa gcuccucggc ccacucggca ugaagacacu cgacccagac   4260

gacauggugu acugcggcau cuacgacaac gcccucgaca acgacaacua caaccucgcc   4320

aagggcuuca acuaccacca gggcccagaa uggcucuggc caaucggcua cuuccucagg   4380

gccaagcucu acuucagcag gcucaugggc ccagaaacaa cagccaagac aaucgugcuc   4440

gugaagaacg ugcucagcag gcacuacgug caccucgaaa ggagcccaug gaagggccuc   4500

ccagaacuca caaacgaaaa cgcccaguac ugcccauuca gcugcgaaac acaggccugg   4560

agcaucgcca caauccucga aacacucuac gaccucuga                          4599
```

<210> SEQ ID NO 45
<211> LENGTH: 4599
<212> TYPE: RNA
<213> ORGANISM: Artificial Sequence
<220> FEATURE:
<223> OTHER INFORMATION: Codon-Optimized AGL Coding Sequence

<400> SEQUENCE: 45

```
augggccaca gcaagcagau ccggaucuug cugcugaacg agauggagaa gcuggagaag     60

acccuguuca ggcuggagca gggcuacgag cugcaguucc gguugggccc caccuugcag    120

ggcaaggccg ugaccgugua caccaacuac cccuuccccg gcgagacguu caacagggag    180

aaguuccggu cccuggacug ggagaacccc accgagaggg aggacgacuc cgacaaguac    240

ugcaagcuga accugcagca guccggcucc uuccaguacu acuuccugca gggcaacgag    300

aagaguggcg gcggcuacau cgugguggac cccaucuugc gggugggcgc cgacaaccac    360

gugcugcccu uggacugcgu gacccugcag accuucuugg ccaagugcuu gggccccuuc    420

gacgaguggg agagcaggcu gagggugggcc aaggaguccg gcuacaacau gauccacuuc    480

acccccuugc agacccuggg ccuguccagg uccugcuacu cccuggccaa ccaguuggag    540

uugaaccccg acuucuccag gcccaacagg aaguacaccu ggaacgacgu gggccagcug    600

guggagaagu ugaagaagga guggaacgug aucugcauca ccgacguggu guacaaccac    660

accgccgcca acagcaagug gauccaggag caccccgagu gcgccuacaa ccuggugaac    720

ucccccacu ugaagcccgc cugggguguug gacagggccc uguggcgguu cuccugcgac    780

guggccgagg gcaaguacaa ggagaagggc auccccgccu ugaucgagaa cgaccaccac    840

augaacucca uccggaagau caucugggag gacaucuucc ccaagcugaa gcugugggag    900

uucuuccagg uggacgugaa caaggccgug gagcaguuca ggaggcugcu gacccaggag    960

aacaggcggg ugaccaaguc cgaccccaac cagcaccuga ccaucaucca ggaccccgag   1020

uacaggcggu ucggcugcac cguggacaug aacaucgccc ugaccaccuu cauccccac   1080

gacaagggcc ccgccgccau cgaggagugc ugcaacuggu uccacaagag gauggaggag   1140

uugaacuccg agaagcaccg gcugaucaac uaccaccagg agcaggccgu gaacugccug   1200

uugggcaacg uguucuacga gcggcuggcc ggccacggcc ccaagcuggg ccccgugacc   1260

aggaagcacc ccuuggugac cagguacuuc accuuccccu ucgaggagau cgacuucucc   1320

auggaggagu ccaugaucca ccugcccaac aaggccugcu uccugauggc ccacaacggc   1380

ugggugaugg gcgacgaccc ccugcggaac uucgccgagc ccggcuccga gguguaccug   1440

aggagggagc ugaucugcug ggggcgacagc gugaaguugc gguacggcaa caagcccgag   1500

gacugccccu accugugggc ccacaugaag aaguacaccg agaucaccgc caccuacuuc   1560

cagggcgugc ggcuggacaa cugccacucc acccccugc acguggccga guacauguug   1620

gacgccgcca ggaacuugca gcccaacuug uacguggugg ccgagcuguu caccggcagc   1680
```

-continued

```
gaggaccugg acaacguguu cgugaccagg cugggcauca gcuccuugau cagggaggcc   1740
augagcgccu acaacagcca cgaggagggc agguuggugu accgguacgg cggcgagccc   1800
gugggcuccu ucgugcagcc cugcuugagg cccuugaugc ccgccaucgc ccacgcccug   1860
uucauggaca ucacccacga caacgagugc cccaucgugc acagguccgc cuacgacgcc   1920
cugcccagca ccaccaucgu guccauggcc ugcugcgcca gcggcagcac caggggcuac   1980
gacgaguugg ugccccacca gaucuccgug guguccgagg agcgguucua caccaagugg   2040
aaccccgagg ccuugcccuc caacaccggc gaggugaacu uccagagcgg caucaucgcc   2100
gccaggugcg ccaucagcaa gcugcaccag gagcugggcg ccaagggcuu cauccaggug   2160
uacguggacc agguggacga ggacaucgug gccgugacca ggcacucccc cagcauccac   2220
caguccgugg uggccguguc caggaccgcc uucaggaacc ccaagaccuc cuucuacagc   2280
aaggaggugc cccagaugug caucccccggc aagaucgagg agguggugcu ggaggccagg   2340
accaucgaga ggaacaccaa gcccuacagg aaggacgaga acuccaucaa cggcaccccc   2400
gacaucaccg uggagaucag ggagcacauc cagcugaacg agagcaagau cgugaagcag   2460
gccggcgugg ccaccaaggg ccccaacgag uacauccagg agaucgaguu cgagaacuug   2520
ucccccggca gcgugaucau cuucagggug agccuggacc cccacgccca gguggccgug   2580
ggcauccugc ggaaccaccu gacccaguuc agcccccacu ucaaguccgg cagccuggcc   2640
guggacaacg ccgaccccau cuugaagauc cccuucgccu cccuggccuc cagguugacc   2700
uuggccgagc ugaaccagau ccuguaccgg ugcgaguccg aggagaagga ggacggcggc   2760
ggcugcuacg acauccccaa cugguccgcc cugaaguacg ccggccugca gggcuugaug   2820
uccguguugg ccgagaucag gcccaagaac gacuugggcc accccuucug caacaacuug   2880
agguccggcg acuggaugau cgacuacgug agcaaccggc ugaucucccg guccggcacc   2940
aucgccgagg ugggcaagug guugcaggcc auguucuucu accugaagca gaucccccgg   3000
uaccugaucc ccugcuacuu cgacgccauc uugaucggcg ccuacaccac ccugcuggac   3060
accgccugga agcagaaguc cagcuucgug cagaacggcu ccaccuucgu gaagcaccug   3120
uccuugggcu ccgugcagcu gugcggcgug ggcaaguucc ccucccugcc cauccugucc   3180
cccgcccuga uggacgugcc cuacagguug aacgagauca ccaaggagaa ggagcagugc   3240
ugcgugucccc uggccgccgg cuugccccac uucuccuccg gcaucuuccg gugcuggggc   3300
agggacaccu ucaucgcccu gaggggcauc cugcugauca ccggccggua cguggaggcc   3360
aggaacauca ucuuggccuu cgccggcacc cugaggcacg gccugauccc caaccugcug   3420
ggcgagggca ucuacgccag guacaacugc cgggacgccg ugugguggug gcugcagugc   3480
auccaggacu acugcaagau ggugcccaac ggccuggaca uccugaagug ccccgugucc   3540
aggauguacc ccaccgacga cuccgccccc uugcccgccg gcacccugga ccagcccuug   3600
uucgagguga uccaggaggc caugcagaag cacaugcagg gcauccaguu ccgggagagg   3660
aacgccggcc cccagaucga ccggaacaug aaggacgagg gcuucaacau caccgccggc   3720
guggacgagg agacuggcuu cguguacggc ggcaaccggu ucaacugcgg caccuggaug   3780
gacaagaugg gcgagagcga cagggccagg aacaggggca uccccgccac ccccagggac   3840
ggcuccgccg uggagaucgu gggccugagc aaguccgccg ugcgguggu gcuggaguug   3900
uccaagaaga acaucuuccc cuaccacgag gugaccguga agaggcacgg caaggccauc   3960
aagguguccu acgacgagug gaacaggaag auccaggaca acuucgagaa gcuguuccac   4020
```

-continued

```
guguccgagg accccuccga cuugaacgag aagcacccca accuggugca caagcggggc   4080

aucuacaagg acagcuacgg cgccuccagc cccuggugcg acuaccagcu gaggcccaac   4140

uucaccaucg ccauggugu ggcccccgag cuguucacca ccgagaaggc cuggaaggcc   4200

uuggagaucg ccgagaagaa guugcugggc ccccugggca ugaagaccuu ggaccccgac   4260

gacauggugu acugcggcau cuacgacaac gccuuggaca acgacaacua caaccuggcc   4320

aagggcuuca acuaccacca gggccccgag uggcuguggc ccaucggcua cuuccugcgg   4380

gccaaguugu acuucuccag guugaugggc cccgagacga ccgccaagac caucguguug   4440

gugaagaacg ugcuguccg gcacuacgug caccuggaga ggucccccug gaagggccug   4500

cccgagcuga ccaacgagaa cgcccaguac ugccccuuca gcugcgagac gcaggccugg   4560

uccaucgcca ccauccugga gacgcuguac gacuuguag                           4599
```

THERAPEUTICS FOR GLYCOGEN STORAGE DISEASE TYPE III

CROSS-REFERENCE TO RELATED APPLICATIONS

This application is a continuation of U.S. patent application Ser. No. 16/617,431, filed Nov. 26, 2019, which is a U.S. National Stage Application under 35 U.S.C. § 371 of International Application No. PCT/US2018/035477, filed on May 31, 2018, which claims priority to U.S. Provisional Application Ser. No. 62/513,350, filed May 31, 2017, each of which is herein incorporated by reference in its entirety for all purposes.

TECHNICAL FIELD OF THE INVENTION

This invention relates to the fields of molecular biology and genetics, as well as to biopharmaceuticals and therapeutics generated from translatable molecules. More particularly, this invention relates to methods, structures and compositions for molecules having the ability to be translated into active polypeptides or proteins, for use in vivo and as therapeutics.

DESCRIPTION OF TEXT FILE SUBMITTED ELECTRONICALLY

The contents of the text file submitted electronically herewith are incorporated herein by reference in their entirety: A computer readable format copy of the Sequence Listing (filename: ULPI_041_02US_SeqList_ST25.txt, date recorded: May 4, 2022, file size: 225 kilobytes).

BACKGROUND OF THE INVENTION

Glycogen storage disease type III (also known as GSD III or Cori disease) is a rare (incidence 1:100,000) inborn error of glycogen metabolism caused by the deficiency of a glycogen debranching enzyme known as amylo-alpha-1, 6-glucosidase, 4-alpha-glucanotransferase (AGL). This autosomal recessive metabolic disorder is characterized by variable liver, cardiac muscle, and skeletal muscle involvement.

There are four subtypes GSD III, based on differences in tissue expression of the deficient enzyme, AGL. GSD IIIa accounts for approximately 85% of all GSD III and presents with liver and muscle involvement, resulting from enzyme deficiency in both liver and muscle. GSDIIIb accounts for approximately 15% and generally presents with only liver involvement, resulting from enzyme deficiency in the liver only. Meanwhile, GSDIIIc and GSDIIId are both extremely rate, with GSDIIIc believed to result from a deficiency of glucosidase debranching activity and GSDIIId believed to result from a deficiency of the transferase debranching activity.

In infancy and early childhood, liver involvement presents as ketotic hypoglycemia, hepatomegaly, hyperlipidemia, and elevated hepatic transaminases. In adolescence and adulthood, liver disease becomes less prominent. Hypertrophic cardiomyopathy develops in the majority of those with GSD IIIa, usually during childhood. Its clinical significance ranges from asymptomatic in the majority to severe cardiac dysfunction, congestive heart failure, and, rarely, sudden death. Skeletal myopathy manifesting as weakness is not usually evident in childhood, but slowly progresses, typically becoming prominent in adults.

In agreement with the organs affected, enhanced alanine transaminase (ALT), aspartate transaminase (AST), alkaline phosphatase (ALP), and/or creatine phosphokinase (CPK) activities are frequently present in the serum of GSD III patients.

As noted above, GSD III is caused by a deficiency in AGL. This deficiency is generally attributed to inherited mutation(s) of the AGL gene, which results in partial or total abolishment of AGL enzyme activity in a subject afflicted with GSD III. Molecular analyses of the AGL protein in GSD III patients have been performed in several ethnic populations, and over 100 different AGL mutations have been described. See Goldstein et al., 2010*, Genet. Med.* 12: 424-430. See also Sentner et al., 2013*, JIMD Rep.* 7: 19-26.

There is presently no effective treatment of GSD III. Attempts have been made to control hypoglycemia with frequent meals high in carbohydrates, often via the use of nocturnal gastric drip feedings or cornstarch supplements. Meanwhile, patients with myopathy have been treated with diets high in protein during the daytime plus overnight enteral infusions. Transient improvement in symptoms has been documented in a few patients but there is no long-term data demonstrating that the high protein diet prevents or treats the progressive myopathy. See Chen Y T, Burchell A, Glycogen storage disease. In: Scriver C R, Beaudet A L, Sly W S, Valle D, The metabolic and molecular basis of inherited disease. New York: McGraw Hill, 1995: 935-65. The progressive myopathy and/or cardiomyopathy is a major cause of morbidity in adults, and patients presenting with progressive liver cirrhosis and hepatic carcinoma have been reported. Thus, there is an urgent need for therapy which can address the underlying cause of this disease, i.e., the deficiency of AGL enzyme activity.

To date, enzyme replacement has not been explored in diseases in which the defective enzyme is present in the cytosol, such as AGL in GSD III, presumably due to the lack of an efficient and specific cellular uptake mechanism that delivers exogenous enzyme across the plasma membrane into the cytoplasm.

The present invention addresses the above-mentioned needs by providing molecules, structures, and compositions that have the ability to be translated in the cytoplasm to provide active AGL, which can ameliorate, prevent or treat a disease or condition associated with AGL deficiency, such as GSD III.

SUMMARY OF THE INVENTION

This invention provides compositions comprising novel molecules having the ability to be translated, which can be used to provide one or more active polypeptides and proteins, or fragments thereof. The invention further provides methods of using these compositions comprising novel molecules for the prevention or treatment of various disorders. More specifically, embodiments of this invention provide compositions comprising translatable molecules to provide active amylo-alpha-1, 6-glucosidase, 4-alpha-glucanotransferase (AGL) and methods of using the compositions for the treatment of GSD III.

The translatable molecules of this invention can have functional cytoplasmic activity for producing AGL polypeptides or proteins. The peptides and proteins may be active for therapeutic modalities.

The translatable molecules of this invention can have long half-life, particularly in the cytoplasm of a cell. The translatable molecules can be expressible to provide a product that is active for ameliorating, preventing or treating a disease or condition associated with an AGL deficiency.

This disclosure provides a range of structures for translatable molecules for producing AGL polypeptides or proteins. In some embodiments, the translatable molecules can have an increased ability to be translated and/or an extended half-life over a native mRNA.

The translatable molecules of this invention can be used in medicines, and for methods and compositions for producing and delivering active polypeptides and proteins. The translatable molecules of this invention can be used to provide polypeptides or proteins in vitro, ex vivo, or in vivo.

Embodiments of this disclosure provide a range of novel polynucleotides for expressing a human amylo-alpha-1, 6-glucosidase, 4-alpha-glucanotransferase (AGL), or a fragment thereof having AGL activity. The polynucleotides can include natural nucleotides and chemically modified nucleotides. The polynucleotides can be expressible to provide a human AGL or a fragment thereof having AGL activity.

In further aspects, this invention provides a range of novel translatable oligomers comprising one or more unlocked nucleic acid (UNA) monomers for expressing a human amylo-alpha-1, 6-glucosidase, 4-alpha-glucanotransferase (AGL), or a fragment thereof having AGL activity. A translatable oligomer can contain one or more UNA monomers, along with natural nucleotides and chemically modified nucleotides. A translatable oligomer comprising one or more UNA monomers can be expressible to provide the human amylo-alpha-1, 6-glucosidase, 4-alpha-glucanotransferase (AGL), or a fragment thereof having AGL activity.

In certain aspects, the translatable molecules of this invention can provide high-efficiency expression of a polypeptide or protein, or a fragment thereof. The expression can be in vitro, ex vivo, or in vivo.

In some embodiments, a molecule of this invention can have increased cytoplasmic half-life over a native, mature mRNA that encodes the same polypeptide or protein. The inventive molecules and compositions can provide increased functional cellular activity with respect to a native, mature mRNA.

In further aspects, a translatable molecule of this invention can provide increased activity as a drug agent providing a peptide or protein product, as compared to a native, mature mRNA. A translatable molecule of this invention may reduce the dose level required for efficacious therapy.

Embodiments of this invention include the following.

BRIEF DESCRIPTION OF THE DRAWINGS

FIG. 1 shows the relative expression of AGL in AML12 and C2C12 cells normalized to reference molecule 534. The vertical axis reflects the fold-increase relative to the reference, e.g., 10 being a 10-fold increase over the reference. The molecules, including the reference molecule, comprise a tobacco etch virus (TEV) 5' UTR and XenopusXenopus beta-globin (XBG) 3' UTR. The molecules were capped during transcription and synthesized with $N^1$-methylpseudouridine, so that 100% of uridines were replaced with $N^1$-methylpseudouridine. The translatable molecules encoding AGL were transfected in two cell lines (AML12, C2C12). Cells were lysed and harvested at 6 h post-transfection. Quantitative Western Blot was performed to detect AGL by using an antibody specific for AGL (ab133720, rabbit).

FIG. 2 shows the relative expression of AGL in AML12 and C2C12 cells normalized to reference molecule 534. The vertical axis reflects the fold-increase relative to the reference, e.g., 10 being a 10-fold increase over the reference. The molecules, including the reference molecule, comprise a tobacco etch virus (TEV) 5' UTR and *Xenopus* beta-globin (XBG) 3' UTR. The molecules were capped during transcription and synthesized with $N^1$-methylpseudouridine, so that 100% of uridines were replaced with $N^1$-methylpseudouridine. The translatable molecules encoding AGL were transfected in two cell lines (AML12, C2C12). Cells were lysed and harvested at 24 h post-transfection. Quantitative Western Blot was performed to detect AGL by using an antibody specific for AGL (ab133720, rabbit).

FIG. 3 shows the relative expression of AGL in WT mice for translatable molecules 528 and 534 (reference) at timepoints 24 h and 48 h. The molecules comprise a tobacco etch virus (TEV) 5' UTR and *Xenopus* beta-globin (XBG) 3' UTR. The molecules were capped during transcription and synthesized with $N^1$-methylpseudouridine, so that 100% of uridines were replaced with $N^1$-methylpseudouridine. The translatable molecules encoding AGL were each prepared in a lipid nanonparticle formulation and intravenously injected into WT mice at 10 mg/kg. Mice livers were harvested at 24 h and 48 h, and Quantitative Western Blot was performed to detect AGL by using an antibody specific for AGL (ab133720, rabbit).

FIG. 4 shows the relative liver expression of AGL in WT mice post-dose of translatable molecules 525, 527, 528, 529, and 546, as compared to baseline PBS (100). The synthesized translatable molecules 525, 527, 528, 529, and 546 encoding AGL were prepared in a lipid nanoparticle formulation and injected via IP in WT mice. Dose injected was 10 mpk, and livers were collected at 6 h for further analysis. Quantitative Western Blot was performed to detect AGL by using an antibody specific for AGL (ab133720, rabbit).

DETAILED DESCRIPTION OF THE INVENTION

Figure 1:
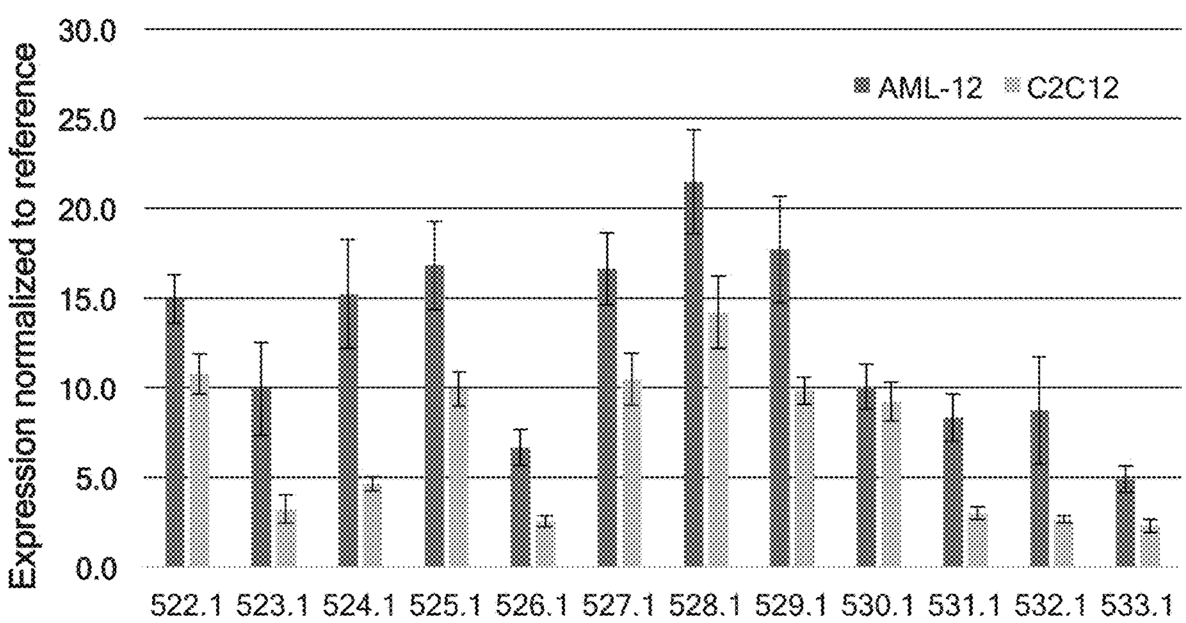
FIG. 1 shows the results of expressing human amylo-alpha-1, 6-glucosidase, 4-alpha-glucanotransferase (AGL, NM_000028) in vitro using translatable molecules of this invention.
Figure 2:
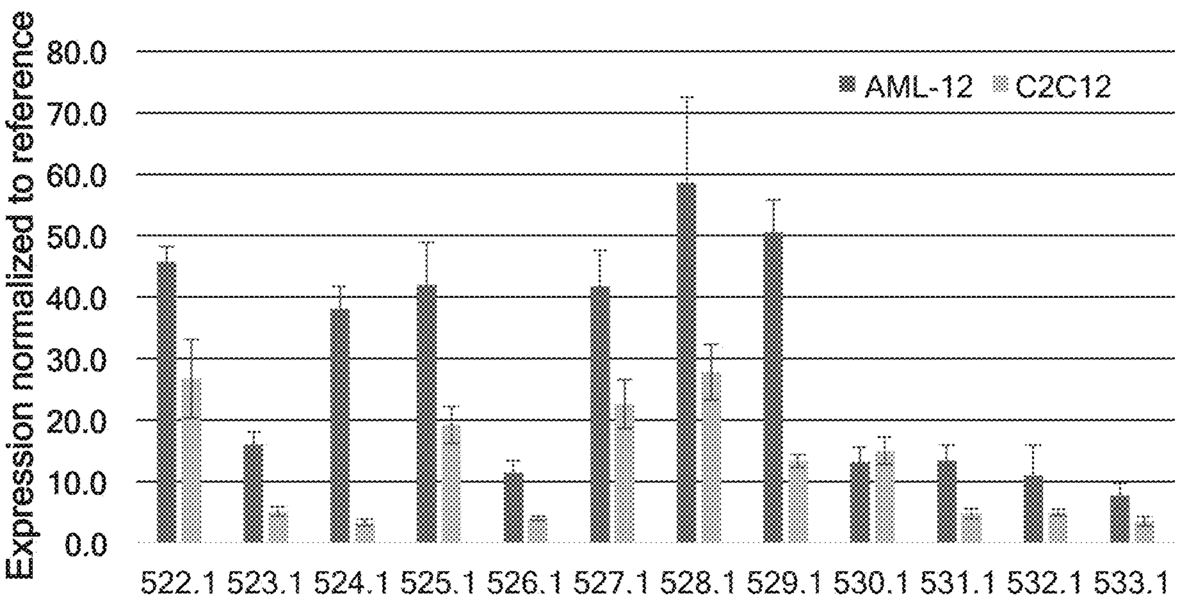
FIG. 2 shows the results of expressing human amylo-alpha-1, 6-glucosidase, 4-alpha-glucanotransferase (AGL, NM_000028) in vitro using translatable molecules of this invention.
Figure 3:
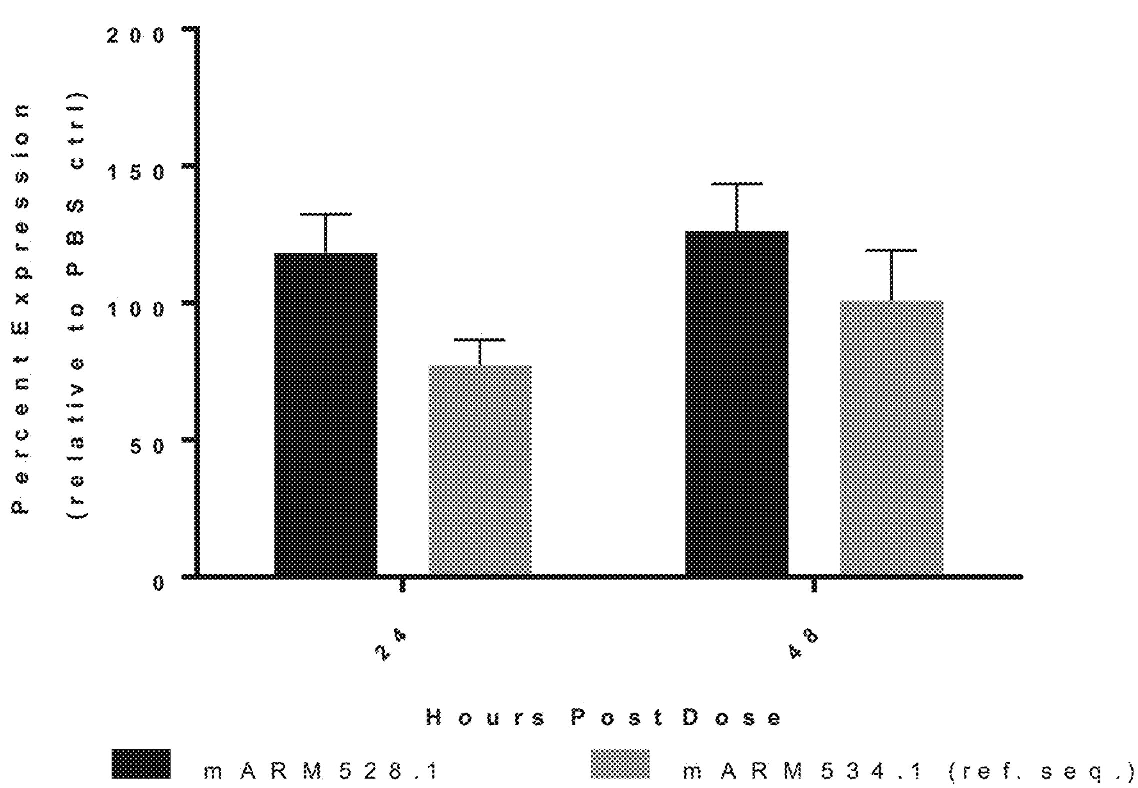
FIG. 3 shows the results of expressing human amylo-alpha-1, 6-glucosidase, 4-alpha-glucanotransferase (AGL, NM_000028) in vivo using translatable molecules of this invention.
Figure 4:
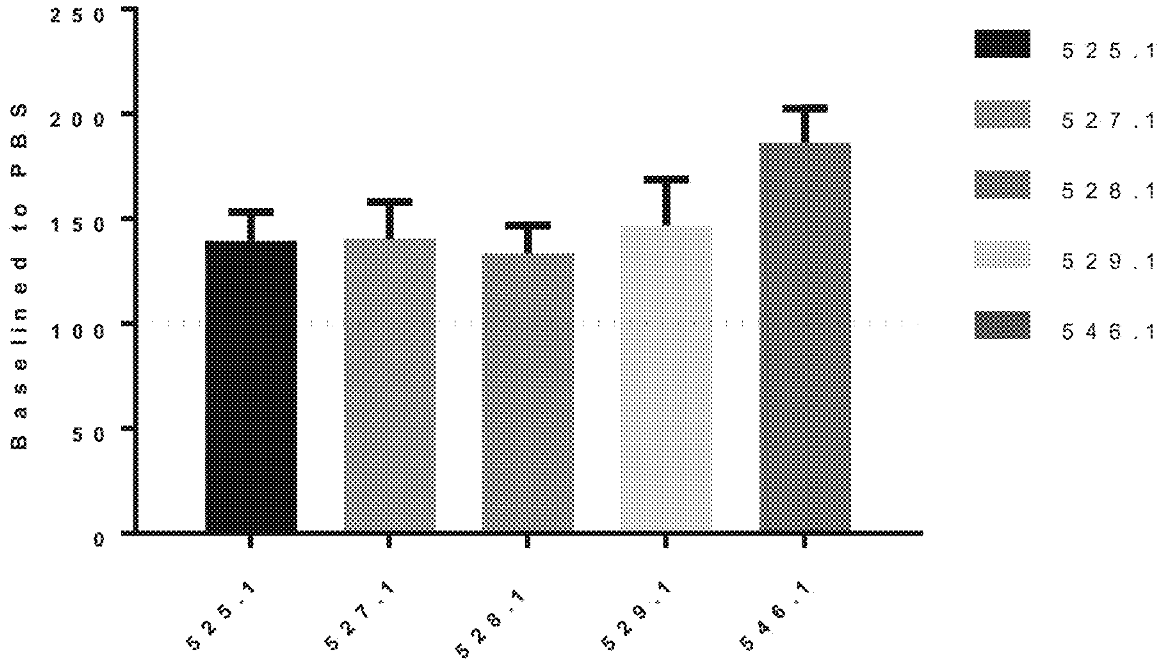
FIG. 4 shows the results of expressing human amylo-alpha-1, 6-glucosidase, 4-alpha-glucanotransferase (AGL, NM_000028) in vivo using translatable molecules of this invention.

This invention provides a range of novel agents and compositions to be used for therapeutic applications. The molecules and compositions of this invention can be used for ameliorating, preventing or treating GSD III and/or a disease associated reduced presence or function of amylo-alpha-1, 6-glucosidase, 4-alpha-glucanotransferase (AGL) in a subject.

In some embodiments, this invention encompasses synthetic, purified, translatable polynucleotide molecules for expressing a human amylo-alpha-1, 6-glucosidase, 4-alpha-glucanotransferase. The molecules may contain natural and chemically modified nucleotides, and encode the human amylo-alpha-1, 6-glucosidase, 4-alpha-glucanotransferase (AGL), or a fragment thereof having AGL activity.

In certain embodiments, this disclosure includes synthetic, purified, translatable oligomer molecules comprising one or more UNA monomers for expressing a human amylo-alpha-1, 6-glucosidase, 4-alpha-glucanotransferase (AGL), or a fragment thereof having AGL activity. A translatable oligomer may contain one or more UNA monomers, as well as natural and chemically-modified nucleotides. A translatable oligomer comprising one or more UNA monomers can be expressible to provide the human amylo-alpha-1, 6-glucosidase, 4-alpha-glucanotransferase (AGL), or a fragment thereof having AGL activity.

As used herein, the term "translatable" may be used interchangeably with the term "expressible" and refers to the ability of polynucleotide, or a portion thereof, to be converted to a polypeptide by a host cell. As is understood in the art, translation is the process in which ribosomes in a cell's cytoplasm create polypeptides. In translation, messenger RNA (mRNA) is decoded by tRNAs in a ribosome complex to produce a specific amino acid chain, or polypeptide. Furthermore, the term "translatable" when used in this specification in reference to an oligomer, means that at least a portion of the oligomer, e.g., the coding region of an oligomer sequence (also known as the coding sequence or CDS), is capable of being converted to a protein or a fragment thereof.

As used herein, the term "monomer" refers to a single unit, e.g., a single nucleic acid, which may be joined with another molecule of the same or different type to form an oligomer. In some embodiments, a monomer may be an unlocked nucleic acid, i.e., a UNA monomer.

Meanwhile, the term "oligomer" may be used interchangeably with "polynucleotide" and refers to a molecule comprising at least two monomers and includes oligonucleotides such as DNAs and RNAs. In the case of oligomers containing RNA monomers and/or unlocked nucleic acid (UNA) monomers, the oligomers of the present invention may contain sequences in addition to the coding sequence (CDS). These additional sequences may be untranslated sequences, i.e., sequences which are not converted to protein by a host cell. These untranslated sequences can include a 5' cap, a 5' untranslated region (5' UTR), a 3' untranslated region (3' UTR), and a tail region, e.g., a polyA tail region. As described in further detail herein, any of these untranslated sequences may contain one or more UNA monomers—these UNA monomers are not capable of being translated by a host cell's machinery. In the context of the present invention, a "translatable oligomer", a "translatable molecule", "translatable polynucleotide", or "translatable compound" refers to a sequence that comprises a region, e.g., the coding region of an RNA (e.g., the coding sequence of human AGL or a codon-optimized version thereof), that is capable of being converted to a protein or a fragment thereof, e.g., the human AGL protein or a fragment thereof.

As used herein, the term "codon-optimized" means a natural (or purposefully designed variant of a natural) coding sequence which has been redesigned by choosing different codons without altering the encoded protein amino acid sequence increasing the protein expression levels (Gustafsson et al., *Codon bias and heterologous protein expression.* 2004, Trends Biotechnol 22: 346-53). Variables such as high codon adaptation index (CAI), LowU method, mRNA secondary structures, cis-regulatory sequences, GC content and many other similar variables have been shown to somewhat correlate with protein expression levels (Villalobos et al., *Gene Designer: a synthetic biology tool for constructing artificial DNA segments.* 2006, BMC Bioinformatics 7:285). High CAI (codon adaptation index) method picks a most frequently used synonymous codon for an entire protein coding sequence. The most frequently used codon for each amino acid is deduced from 74218 protein-coding genes from a human genome. The LowU method targets only U-containing codons that can be replaced with a synonymous codon with fewer U moieties. If there are a few choices for the replacement, the more frequently used codon will be selected. The remaining codons in the sequence are not changed by the LowU method. This method may be used in conjunction with the disclosed mRNAs to design coding sequences that are to be synthesized with 5-methoxyuridine.

As will be appreciated by the skilled artisan equipped with the present disclosure, the translatable molecules of the present invention may be used to ameliorate, prevent, or treat any disease or disorder associated with reduced activity (e.g., resulting from reduced concentration, presence, and/or function) of amylo-alpha-1, 6-glucosidase, 4-alpha-glucanotransferase (AGL) in a subject. In some embodiments, the translatable molecules of this invention can be used in methods for ameliorating, preventing or treating one or more of GSD IIIa, GSD IIIb, GSDIIIc, and GSDIIId (collectively or individually referred to herein as "GSD III" or "glycogen storage disease type III"). The disease or disorder to be treated herein (e.g., GSD IIIa, GSD IIIb, GSDIIIc, or GSDIIId) may be associated with low blood sugar (hypoglycemia), enlargement of the liver (hepatomegaly), excessive amounts of fat in the blood (hyperlipidemia), elevated blood levels of liver enzymes, chronic liver disease (cirrhosis), liver failure, slow growth, short stature, benign tumors (adenomas), hypertrophic cardiomyopathy, cardiac dysfunction, congestive heart failure, skeletal myopathy, and/or poor muscle tone (hypotonia). In some embodiments, the translatable molecules of the present invention may be used to ameliorate, prevent, or treat any or all of these aforementioned symptoms.

As is understood by the skilled artisan, GSD III may be referred to by any number of alternative names in the art, including, but not limited to, AGL deficiency, Cori disease, Con's disease, debrancher deficiency, Forbes disease, glycogen debrancher deficiency, GSD3, or limit dextrinosis (due to the limit dextrin-like structures in the cytosol). Accordingly, GSD III may be used interchangeably with any of these alternative names in the specification, the examples, the drawings, and the claims.

A translatable molecule of this invention encoding a functional AGL moiety can be delivered to the liver, in particular to hepatocytes, of a patient in need (e.g., a GSD III patient), and can elevate active AGL levels of the patient. The translatable molecule can be used for preventing, treating, ameliorating or reversing any symptoms of GSD III in the patient.

In further aspects, a translatable molecule of this invention can also be used for reducing the dependence of a GSD III patient on a particular diet to control the disease. For instance, a translatable molecule of this invention can be used to reduce a GSD III patient's dependence on frequent high carbohydrate meals and/or diets abnormally high in protein.

Embodiments of this invention further encompass processes for making a translatable molecule for expressing a human amylo-alpha-1, 6-glucosidase, 4-alpha-glucanotransferase (AGL). The processes include transcribing in vitro an AGL DNA template in the presence of natural and chemically-modified nucleoside triphosphates to form a product mixture, and purifying the product mixture to isolate the translatable molecule. A translatable molecule may also be made by methods as are known in the art.

The molecules of this invention can be translatable molecules containing RNA and/or UNA monomers. These translatable molecules can have long half-life, particularly in the cytoplasm. The long duration translatable molecules can be used for ameliorating, preventing, or treating disease or disorder associated with reduced activity (e.g., resulting from reduced concentration, presence, and/or function) of amylo-alpha-1, 6-glucosidase, 4-alpha-glucanotransferase (AGL) in a subject.

The properties of the translatable molecules of this invention arise according to their molecular structure, and the structure of the molecule in its entirety, as a whole, can provide significant benefits based on those properties. Embodiments of this invention can provide translatable molecules having one or more properties that advantageously provide enhanced protein concentration or increased protein activity. The molecules and compositions of this invention can provide formulations comprising therapeutic agents for ameliorating, preventing, or treating any disease or disorder associated with reduced activity (e.g., resulting from reduced concentration, presence, and/or function) of amylo-alpha-1, 6-glucosidase, 4-alpha-glucanotransferase (AGL) in a subject.

This invention provides a range of translatable molecules that are surprisingly translatable to provide active polypeptide or protein, in vitro, ex vivo, and in vivo.

A translatable molecule of this invention is expressible to provide one or more active polypeptides or proteins, or fragments thereof.

The translatable structures and compositions can have increased translational activity or cytoplasmic half-life. In these embodiments, the translatable structures and compositions can provide increased functional half-life in the cytoplasm of mammalian cells, as compared to a native mRNA.

As used herein, the term "half-life" is the time required for a quantity such as nucleic acid or protein concentration or activity to fall to half of its value as measured at the beginning of a time period.

A range of structures for translatable molecules of this invention are provided herein, including oligomers containing one or more UNA monomers. An oligomer containing one or more UNA monomers can incorporate specialized linker groups. The linker groups can be attached in a chain in the translatable molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain, or at any position in the chain.

In further aspects, the linker groups of a chain molecule can each be attached to a nucleobase. The presence of nucleobases in the chain molecule can provide a sequence of nucleobases in the chain molecule.

In certain embodiments, this invention provides translatable oligomer molecules having chain structures that incorporate novel combinations of the linker group monomers, along with certain natural nucleotides, or non-natural nucleotides, or modified nucleotides, or chemically modified nucleotides.

The oligomer molecules of this invention can display a sequence of nucleobases, and can be designed to express a polypeptide or protein, in vitro, ex vivo, or in vivo. The expressed polypeptide or protein can have activity in various forms, including activity corresponding to a protein expressed from a natural, native or wild type mRNA, or activity corresponding to a negative or dominant negative protein.

In some aspects, this invention can provide active, translatable oligomer molecules having a base sequence that is identical to at least a fragment of a native nucleic acid molecule of a cell.

In some embodiments, the cell can be a eukaryotic cell, a mammalian cell, or a human cell.

This invention provides structures, methods and compositions for translatable oligomeric agents that incorporate the linker group monomers. The oligomeric molecules of this invention can be used as active agents in formulations for therapeutics.

This invention provides a range of translatable molecules that are useful for providing therapeutic effects because of their ability to be expressed as polypeptide or protein in a cell in a subject.

In certain embodiments, a translatable molecule can be structured as an oligomer composed of monomers. The oligomeric structures of this invention may contain one or more linker group monomers, along with certain nucleotides.

In certain embodiments, a translatable molecule may contain a sequence of nucleobases, and can be designed to express a peptide or protein of any isoform, in part by having sufficient homology with a native polynucleotide sequence.

In some embodiments, a translatable molecule can be from about 200 to about 12,000 monomers in length, or more. In certain embodiments, a translatable molecule can be from 1,000 to 9,000 monomers in length, from 3,000 to 7,000 monomers in length, or from 4,000 to 6,000 monomers in length. In an exemplary embodiment, the translatable molecule is from 4,500 to 5,500 monomers in length. In a further exemplary embodiment, the translatable molecule is about 5,000 monomers in length.

In some embodiments, a translatable molecule can contain from 1 to about 800 UNA monomers. In certain embodiments, a translatable molecule can contain from 1 to 600 UNA monomers, or 1 to 100 UNA monomers, or 1 to 12 UNA monomers.

In some embodiments, a translatable molecule can contain from 1 to about 800 locked nucleic acid (LNA) monomers. In certain embodiments, a translatable molecule can contain from 1 to 600 LNA monomers, or 1 to 100 LNA monomers, or 1 to 12 LNA monomers.

A translatable molecule of this invention may comprise a 5' cap, a 5' untranslated region of monomers, a coding region of monomers, a 3' untranslated region of monomers, and a tail region of monomers.

A translatable molecule of this invention may comprise a 3' untranslated region of monomers containing one or more UNA monomers.

A translatable molecule of this invention may comprise a tail region of monomers containing one or more UNA monomers.

A translatable molecule of this invention may comprise regions of sequences or structures that are operable for translation in a cell, or which have the functionality of regions of an mRNA including, for example, a 5' cap, a 5' untranslated region, a coding region, a 3' untranslated region, and a polyA tail.

This invention further contemplates methods for delivering one or more vectors comprising one or more translatable molecules to a cell. In further embodiments, the invention also contemplates delivering or one or more translatable molecules to a cell.

In some embodiments, one or more translatable molecules can be delivered to a cell, in vitro, ex vivo, or in vivo. Viral and non-viral transfer methods as are known in the art can be used to introduce translatable molecules in mammalian cells. Translatable molecules can be delivered with a pharmaceutically acceptable vehicle, or for example, with nanoparticles or liposomes.

In some embodiments, translatable structures and compositions of this invention can reduce the number and frequency of transfections required for cell-fate manipulation in culture as compared to utilizing native compositions.

In further aspects, this invention provides increased activity for translatable molecules as active agent, as compared to utilizing a native mRNA.

In some aspects, this invention can provide translatable molecules that may reduce the cellular innate immune response, as compared to that induced by a native nucleic acid, polypeptide or protein.

This invention can provide synthetic translatable molecules that are refractory to deadenylation as compared to native molecules.

In certain embodiments, this invention can provide synthetic translatable molecules with increased specific activity and longer functional half-life as compared to native molecules. The synthetic translatable molecules of this invention can provide increased levels of ectopic protein expression. When expressing a translatable molecule using a vector, cellular-delivery can be at increased levels, and cytotoxic innate immune responses can be restrained so that higher levels of ectopic protein expression can be achieved. The translatable molecules of this invention can have increased specific activity and longer functional half-life than native mRNAs.

In certain aspects, a translatable molecule may have a number of mutations relative to a native mRNA.

In further embodiments, this invention can provide translatable molecules having cleavable delivery and targeting moieties attached at a 3' end and/or a 5' end.

In general, the specific activity for a synthetic translatable molecule delivered by transfection can be viewed as the number of molecules of protein expressed per delivered transcript per unit time.

As used herein, translation efficiency refers to a measure of the production of a protein or polypeptide by translation of a translatable molecule in vitro or in vivo.

This invention provides a range of translatable oligomer molecules, which can contain one or more UNA monomers, and a number of nucleic acid monomers, wherein the translatable molecule can be expressible to provide a polypeptide or protein.

In some embodiments, this invention includes a range of translatable oligomer molecules, which can contain one or more UNA monomers in one or more untranslated regions, and a number of nucleic acid monomers, wherein the translatable molecule can be expressible to provide a polypeptide or protein.

In some embodiments, this invention includes a range of translatable molecules, which contain one or more UNA monomers in a tail region, and a number of nucleic acid monomers, wherein the translatable molecule can be expressible to provide a polypeptide or protein.

In some embodiments, a translatable molecule can contain a modified 5' cap.

In further embodiments, a translatable molecule can contain a translation enhancing 5' untranslated region of monomers.

In additional embodiments, a translatable molecule can contain a translation enhancing 3' untranslated region of monomers.

In additional embodiments, a translatable molecule can contain one or more UNA monomers in a 3' untranslated region of monomers.

In further embodiments, a translatable molecule can contain one or more UNA monomers in a tail region of monomers.

In further embodiments, a translatable molecule can contain one or more UNA monomers in a polyA tail.

In some embodiments, a translatable molecule can contain one or more LNA monomers in a 3' untranslated region of monomers or in a tail region of monomers, e.g., in a polyA tail.

In another aspect, a translatable molecule of this invention can exhibit at least 2-fold, 3-fold, 5-fold, or 10-fold increased translation efficiency in vivo as compared to a native mRNA that encodes the same translation product.

In a further aspect, a translatable molecule can produce at least a 2-fold, 3-fold, 5-fold, or 10-fold increased polypeptide or protein level in vivo as compared to a native mRNA that encodes the same polypeptide or protein.

In certain embodiments, a translatable molecule can provide increased levels of a polypeptide or protein in vivo as compared to a native mRNA that encodes the same polypeptide or protein. For example, the level of a polypeptide or protein can be increased by 10%, or 20%, or 30%, or 40%, or 50%, or more.

In additional embodiments, this invention provides methods for treating a disease or condition in a subject by administering to the subject a composition containing a translatable molecule of the invention.

A translatable molecule of this invention may be used for ameliorating, preventing or treating a disease or disorder, e.g., a disease or disorder associated with reduced activity (e.g., resulting from reduced concentration, presence, and/or function) of amylo-alpha-1, 6-glucosidase, 4-alpha-glucanotransferase (AGL) in a subject. In these embodiments, a composition comprising a translatable molecule of this invention can be administered to regulate, modulate, or increase the concentration or effectiveness of the AGL enzyme in a subject. In some aspects, the enzyme can be an unmodified, natural enzyme for which the patient has an abnormal quantity (e.g., a patient with a mutated version of AGL which partially or totally abolishes AGL activity). In some aspects, the enzyme can be an unmodified, natural AGL enzyme which can be used to treat a patient harboring a mutated version of AGL. In exemplary embodiments, a translatable molecule of this invention may be used for ameliorating, preventing or treating GSD III.

In some embodiments, a translatable molecule may be delivered to cells or subjects, and translated to increase AGL levels in the cell or subject.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

In an exemplary embodiment, a subject of the present invention is a subject with reduced activity (e.g., resulting from reduced concentration, presence, and/or function) of amylo-alpha-1, 6-glucosidase, 4-alpha-glucanotransferase (AGL). In a further exemplary embodiment, the subject is a human.

In some embodiments, administering a composition comprising a translatable molecule of the invention can result in increased liver AGL protein levels in a treated subject. In some embodiments, administering a composition comprising a translatable molecule of the invention results in about a 5%, 10%, 20%, 30%, 40%, 50%, 60%, 70%, 80%, 90%, or 95% increase in liver AGL protein levels relative to a baseline AGL protein level in the subject prior to treatment. In an exemplary embodiment, administering a composition comprising a translatable molecule of the invention results in an increase in liver AGL levels relative to baseline liver AGL levels in the subject prior to treatment. In some embodiments, the increase in liver AGL levels can be at least about 5%, 10%, 20%, 30%, 40%, 50%, 100%, 200%, or more.

In some embodiments, the AGL protein which is expressed from a translatable molecule of the invention is detectable in the liver, serum, plasma, kidney, heart, muscle, brain, cerebrospinal fluid, or lymph nodes. In exemplary embodiments, the AGL protein is expressed in the liver cells, e.g., hepatocytes of a treated subject.

In some embodiments, administering a composition comprising a translatable molecule of the invention results in the expression of a natural, non-mutated human AGL (i.e., normal or wild-type AGL as opposed to abnormal or mutated AGL) protein level at or above about 10 ng/mg, about 20 ng/mg, about 50 ng/mg, about 100 ng/mg, about 150 ng/mg, about 200 ng/mg, about 250 ng/mg, about 300 ng/mg, about 350 ng/mg, about 400 ng/mg, about 450 ng/mg, about 500 ng/mg, about 600 ng/mg, about 700 ng/mg, about 800 ng/mg, about 900 ng/mg, about 1000 ng/mg, about 1200 ng/mg or about 1500 ng/mg of the total protein in the liver of a treated subject.

As used herein, the term "about" or "approximately" as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

In some embodiments, the expression of the natural, non-mutated human AGL protein is detectable 6, 12, 18, 24, 30, 36, 48, 60, and/or 72 hours after administration of a composition comprising a translatable molecule of the invention. In some embodiments, the expression of the natural, non-mutated human AGL protein is detectable 1 day, 2 days, 3 days, 4 days, 5 days, 6 days, and/or 7 days after administration of a composition comprising a translatable molecule of the invention. In some embodiments, the expression of the natural, non-mutated human AGL protein is detectable 1 week, 2 weeks, 3 weeks, and/or 4 weeks after the administration. In some embodiments, the expression of the natural, non-mutated human AGL protein is detectable after administration of a composition comprising a translatable molecule of the invention. In some embodiments, expression of natural, non-mutated human AGL protein is detectable in the liver, e.g., hepatocytes, after administration of a composition comprising a translatable molecule of the invention.

Variant Templates for Making Translatable Molecules

In various embodiments described herein, the translatable oligomer may comprise a mRNA encoding AGL, wherein the mRNA encoding AGL is codon-optimized. In some embodiments, the AGL is human AGL (i.e., hAGL). In some embodiments, the human AGL comprises an amino acid sequence of SEQ ID NO: 2. In some embodiments, the human AGL consists of an amino acid sequence of SEQ ID NO: 2.

In some embodiments, a variant DNA template may be utilized to make a translatable molecule capable of encoding AGL. A variant DNA template of this disclosure may exhibit advantages in processes for making a translatable molecule, and the efficiency of the translatable molecule. Variation of the template can be utilized to enhance incorporation of modified nucleotides or monomers in a translatable molecule of this invention. In certain aspects, variation of the template can be utilized to enhance the structural features of the translatable molecule. The enhanced structural features of the translatable molecule can provide unexpectedly advantageous properties, including translation efficiency to provide a polypeptide or protein product.

In some aspects of this invention, variation of the template may include reducing the occurrence or frequency of appearance of certain nucleotides in the template strand. Reducing the occurrence of a certain nucleotide can alter the structures and processes of this disclosure to provide non-native forms, which achieve surprisingly improved properties of a translatable RNA product encoding AGL.

Aspects of this invention may require a variant DNA template in processes for making a translatable molecule. A DNA molecule can have a non-coding template strand of nucleotides that can be transcribed to provide a target translatable molecule encoding AGL.

A target translatable molecule can be any RNA, whether native or modified, synthetic or derived from a natural source.

In some embodiments, a variant DNA template can be used for which an open reading frame of the template strand is transformed to an alternative form, while preserving codon assignment.

In certain embodiments, a DNA template can be used for which alternative nucleotides are used based on alternative codon optimization and/or sequence degeneracy.

In additional embodiments, a DNA template may have certain nucleotides replaced with alternative nucleotides, while preserving codon assignment.

Embodiments of this invention advantageously utilize alternative codons in a DNA template of this invention to be used in processes for making a translatable molecule encoding AGL. The variations that can be achieved in a DNA template of this invention can be far greater in scope than for cells and organisms, which may require preferred codons in many processes. In this invention, a wide range of alternative codons and positions can be used in a DNA template for transcribing a translatable molecule.

In further aspects of this invention, variation of the template may include reducing the occurrence or frequency of appearance of certain nucleotides in the template strand. For example, the occurrence of a nucleotide in a template may be reduced to a level below 25% of nucleotides in the template. In further examples, the occurrence of a nucleotide in a template may be reduced to a level below 20% of nucleotides in the template. In some examples, the occurrence of a nucleotide in a template may be reduced to a level below 16% of nucleotides in the template. In certain examples, the occurrence of a nucleotide in a template may be reduced to a level below 12% of nucleotides in the template.

Human AGL

The human AGL gene encodes a 1532 amino acid protein with a molecular mass of approximately 174.8 kDa. AGL is a multifunctional enzyme acting as a 1,4-alpha-D-glucan:1,4-alpha-D-glucan-4-alpha-D-glycosyltransferase and an amylo-1,6-glucosidase in glycogen degradation. As noted above, genetic deficiency of normal AGL activity causes glycogen storage disease III.

The consensus human AGL coding sequence has an RNA sequence of 4,599 nucleobases, shown in SEQ ID NO: 1.

The consensus human AGL coding sequence—found at NCBI Accession No. NP_000019.2—translates into SEQ ID NO: 2.

In some embodiments, a translatable molecule can be made and used for expressing human amylo-alpha-1, 6-glucosidase, 4-alpha-glucanotransferase (hAGL) with advantageously increased efficiency of translation, as compared to a native mRNA of hAGL. The translatable molecule expressing hAGL may exhibit activity suitable for use in methods for ameliorating, preventing or treating disease. In some embodiments, the translatable molecule may comprise one or more UNA monomers.

In some embodiments, a translatable molecule may include a 5' cap, a 5' UTR, a translation initiation sequence, e.g., a Kozak sequence, a human AGL CDS, a 3'UTR, and/or a tail region. In an exemplary embodiment, a translatable molecule may include a 5' cap (m7GpppGm), a 5' UTR of tobacco etch virus (TEV), a Kozak sequence, a human AGL CDS, a 3' UTR of *Xenopus* beta-globin, and a tail region. In further exemplary embodiments, the human AGL CDS may comprise a codon-optimized sequence of SEQ ID NOs: 7-32 or SEQ ID NOs: 41-45, described in further detail below. In any of these and other embodiments described herein, the translatable molecule may comprise one or more UNA monomers. In any of these and other embodiments described herein, the translatable molecule may comprise one or more LNA monomers.

The translation efficiency of the molecule can be increased as compared to a native mRNA of AGL. In particular, after 48 hours, the translation efficiency of the molecule may be more than doubled as compared to the native mRNA of AGL.

In some embodiments, a suitable mRNA sequence for the present invention comprises an mRNA sequence encoding the human AGL protein. The sequence of the naturally occurring human AGL protein is shown in SEQ ID NO: 2.

In some embodiments, a suitable mRNA sequence may be an mRNA sequence that encodes a homolog or variant of human AGL. As used herein, a homolog or a variant of human AGL protein may be a modified human AGL protein containing one or more amino acid substitutions, deletions, and/or insertions as compared to a wild-type or naturally-occurring human AGL protein while retaining substantial AGL protein activity. In some embodiments, an mRNA suitable for the present invention encodes a protein substantially identical to human AGL protein. In some embodiments, an mRNA suitable for the present invention encodes an amino acid sequence at least 80%, 85%, 90%, 91%, 92%, 93%, 94%, 95%, 96%, 97%, 98%, 99% or more identical to SEQ ID NO: 2. In some embodiments, an mRNA suitable for the present invention encodes a fragment or a portion of human AGL protein.

In some embodiments, an mRNA suitable for the present invention encodes a fragment or a portion of human AGL protein, wherein the fragment or portion of the protein still maintains AGL activity similar to that of the wild-type protein.

In some embodiments, an mRNA suitable for the present invention comprises a sequence that is at least 80%, 85%, 90%, 91%, 92%, 93%, 94%, 95%, 96%, 97%, 98%, 99% or more identical to SEQ ID NOs: 7-32 or SEQ ID NOs: 41-45.

In some embodiments, a translatable oligomeric molecule of the present invention comprises a coding sequence that is at least 80%, 85%, 90%, 91%, 92%, 93%, 94%, 95%, 96%, 97%, 98%, 99% or more identical to SEQ ID NOs: 7-32 or SEQ ID NOs: 41-45. In some embodiments, a translatable oligomeric molecule comprising a coding sequence that is at least 80%, 85%, 90%, 91%, 92%, 93%, 94%, 95%, 96%, 97%, 98%, 99% or more identical to SEQ ID NOs: 7-32 or SEQ ID NOs: 41-45 further comprises one or more sequences selected from a 5' cap, a 5' UTR, a translation initiation sequence, a 3' UTR, and a tail region.

In some embodiments, a translatable oligomeric molecule of the present invention comprises a coding sequence that is less than 80%, 85%, 90%, 91%, 92%, 93%, 94%, 95%, 96%, 97%, 98%, or 99% identical to the wild-type human AGL coding sequence over the full length human AGL coding sequence of SEQ ID NO: 1, and expresses a functional human AGL protein. In an exemplary embodiment, a translatable oligomeric molecule of the present invention comprises a coding sequence that is less than 80% identical to the wild-type human AGL coding sequence over the full length human AGL coding sequence of SEQ ID NO: 1, and expresses a functional human AGL protein. In another exemplary embodiment, a translatable oligomeric molecule of the present invention comprises a coding sequence that is less than 80% identical to the wild-type human AGL coding sequence over the full length human AGL coding sequence of SEQ ID NO: 1, and expresses a functional human AGL protein, wherein the coding sequence is at least 80%, 85%, 90%, 91%, 92%, 93%, 94%, 95%, 96%, 97%, 98%, 99% or more identical to a sequence selected from SEQ ID NOs: 7-32 or SEQ ID NOs: 41-45. In yet another exemplary embodiment, a translatable oligomeric molecule of the present invention comprises a coding sequence that is less than 80% identical to the wild-type human AGL coding sequence over the full length human AGL coding sequence of SEQ ID NO: 1, and expresses a functional human AGL protein, wherein the coding sequence is at least 95% identical to a sequence selected from SEQ ID NOs: 7-32 or SEQ ID NOs: 41-45. In yet another exemplary embodiment, a translatable oligomeric molecule of the present invention comprises a coding sequence that is less than 80% identical to the wild-type human AGL coding sequence over the full length human AGL coding sequence of SEQ ID NO: 1, and expresses a functional human AGL protein, wherein the coding sequence is at least 95% identical to a sequence selected from SEQ ID NO: 19, SEQ ID NO: 31, or SEQ ID NO: 45. Accordingly, in some embodiments, the present application provides a polynucleotide comprising of or consisting of a nucleobase sequence that is less than 80% identical to the wild-type human AGL coding sequence over the full length human AGL coding sequence of SEQ ID NO: 1, and wherein the human AGL coding sequence is at least 80%, 85%, 90%, 91%, 92%, 93%, 94%, 95%, 96%, 97%, 98%, 99% or more identical to a sequence selected from SEQ ID NOs: 7-32 or SEQ ID NOs: 41-45. In an exemplary embodiment, the present application provides a polynucleotide comprising of or consisting of a nucleobase sequence that is less than 80% identical to the wild-type human AGL coding sequence over the full length human AGL coding sequence of SEQ ID NO: 1, and wherein the human AGL coding sequence is at least 95% identical to a sequence selected from SEQ ID NO: 19, SEQ ID NO: 31, or SEQ ID NO: 45. In a specific embodiment, the present application provides a polynucleotide comprising of a nucleobase sequence that is less than 80% identical to the wild-type human AGL coding sequence over the full length human AGL coding sequence of SEQ ID NO: 1, and wherein the human AGL coding sequence is at least 95% identical to SEQ ID NO: 19. In another specific embodiment, the present application provides a polynucleotide comprising of a nucleobase sequence that is less than 80% identical to the wild-type human AGL coding sequence over the full length human AGL coding sequence of SEQ ID NO: 1, and wherein the human AGL coding sequence is at least 95% identical to SEQ ID NO: 31. In another specific embodiment, the present application provides a polynucleotide comprising of a nucleobase sequence that is less than 80% identical to the wild-type human AGL coding sequence over the full length human AGL coding sequence of SEQ ID NO: 1, and wherein the human AGL coding sequence is at least 95% identical to SEQ ID NO: 45.

In some embodiments, a translatable oligomeric molecule of the invention encodes a fusion protein comprising a full length, fragment or portion of a AGL protein fused to another sequence (e.g., an N or C terminal fusion). In some embodiments, the N or C terminal sequence is a signal sequence or a cellular targeting sequence.

UNA Monomers and Oligomers

In some embodiments, linker group monomers can be unlocked nucleomonomers (UNA monomers), which are small organic molecules based on a propane-1,2,3-tri-yl-trisoxy structure as shown below:

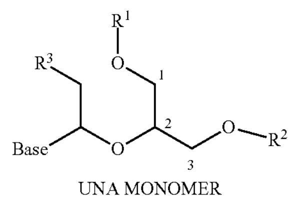

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

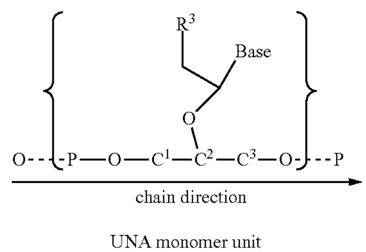

UNA monomer unit where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

Examples of a nucleobase include pseudouracil, 1-methylpseudouracil (m1Ψ), i.e., $N^1$-methylpseudouracil, and 5-methoxyuracil.

In general, a UNA monomer, which is not a nucleotide, can be an internal linker monomer in an oligomer. An internal UNA monomer in an oligomer is flanked by other monomers on both sides.

A UNA monomer can participate in base pairing when the oligomer forms a complex or duplex, for example, and there are other monomers with nucleobases in the complex or duplex.

Examples of UNA monomer as internal monomers flanked at both the propane-1-yl position and the propane-3-yl position, where $R^3$ is —OH, are shown below.

UNA-A

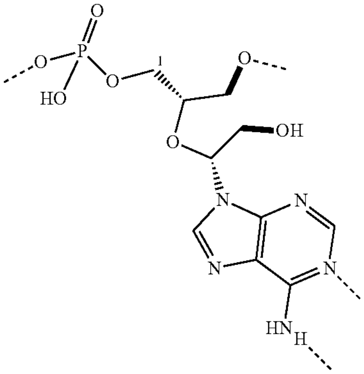

UNA-U

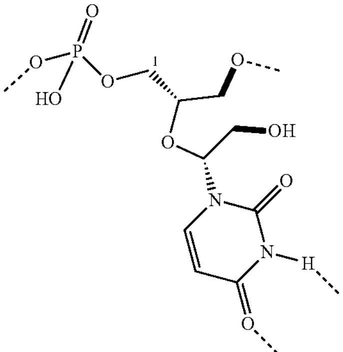

UNA-C

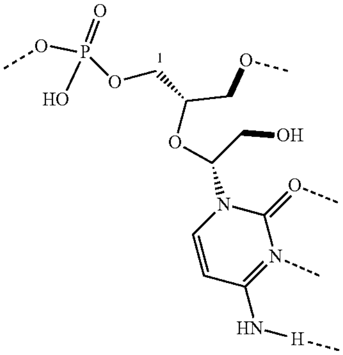

UNA-G

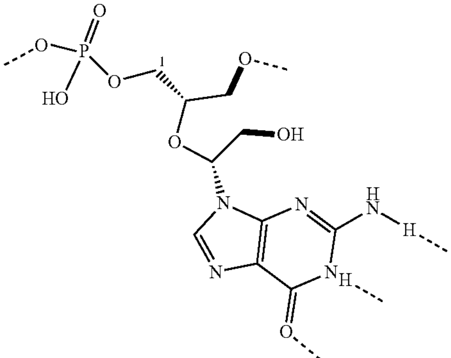

A UNA monomer can be a terminal monomer of an oligomer, where the UNA monomer is attached to only one monomer at either the propane-1-yl position or the propane-3-yl position. Because the UNA monomers are flexible organic structures, unlike nucleotides, the terminal UNA monomer can be a flexible terminator for the oligomer.

Examples of a UNA monomer as a terminal monomer attached at the propane-3-yl position are shown below.

terminal UNA-A

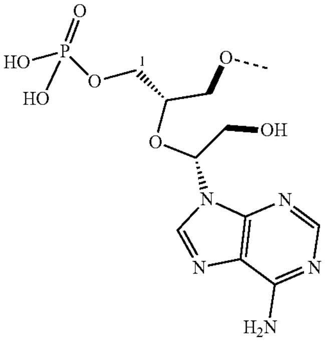

terminal UNA-U

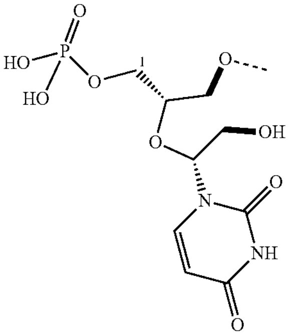

terminal UNA-C

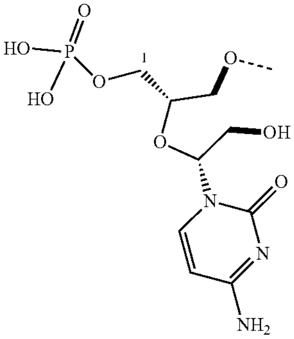

terminal UNA-G

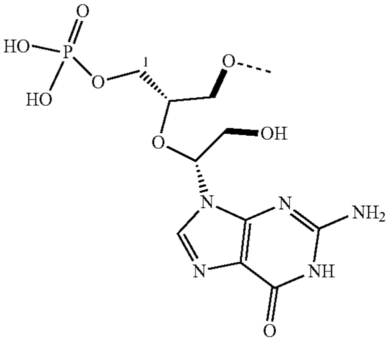

Because a UNA monomer can be a flexible molecule, a UNA monomer as a terminal monomer can assume widely differing conformations. An example of an energy minimized UNA monomer conformation as a terminal monomer attached at the propane-3-yl

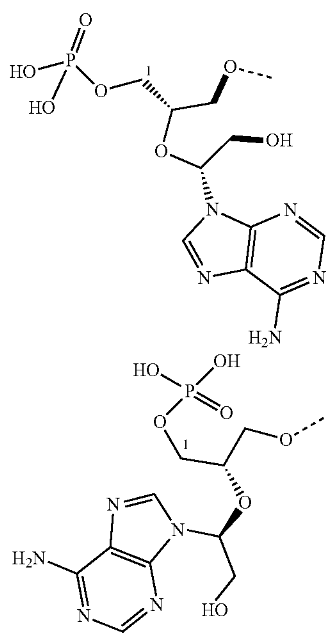

UNA-A terminal forms: the dashed bond shows the propane-3-yl attachment

Among other things, the structure of the UNA monomer allows it to be attached to naturally-occurring nucleotides.

A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4_2$, —NH(C═O)$R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule.

In some embodiments, as shown above, a UNA monomer can be UNA-A (designated Ã), UNA-U (designated Ũ), UNA-C (designated Č), and UNA-G (designated Ğ).

Designations that may be used herein include mA, mG, mC, and mU, which refer to the 2'-O-Methyl modified ribonucleotides.

Designations that may be used herein include dT, which refers to a 2'-deoxy T nucleotide.

As used herein, in the context of oligomer sequences, the symbol N can represent any natural nucleotide monomer, or any modified nucleotide monomer.

As used herein, in the context of oligomer sequences, the symbol Q represents a non-natural, modified, or chemically-modified nucleotide monomer.

As used herein, in the context of oligomer sequences, the symbol X may be used to represent a UNA monomer.

Modified and Chemically-Modified Nucleotides

In the examples of modified or chemically-modified nucleotides herein, an alkyl, cycloalkyl, or phenyl substituent may be unsubstituted, or further substituted with one or more alkyl, halo, haloalkyl, amino, or nitro substituents.

Examples of nucleic acid monomers include non-natural, modified, and chemically-modified nucleotides, including any such nucleotides known in the art.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4$,$N^4$-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4$,$N^4$-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine, 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyladenosine, $N^6$,$N^6$-dimethyladenosine, N6-hydroxynorvalylcarbamoyladenosine, 2-methylthio-$N^6$-hydroxynorvalylcarbamoyl-adenosine, $N^6$-acetyladenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6$,$N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include $N^1$-alkylguanosines, $N^2$-alkylguanosines, thienoguanosines, 7-deazaguanosines, 8-oxoguanosines, 8-bromoguanosines, $O^6$-alkylguanosines, xanthosines, inosines, and $N^1$-alkylinosines.

Examples of modified or chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Examples of modified or chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include $N^1$-methylpseudouridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-0,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include $N^6$-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Some examples of modified nucleotides are given in Saenger, Principles of Nucleic Acid Structure, Springer-Verlag, 1984.

Example of base modifications described above can be combined with additional modifications of nucleoside or nucleotide structure, including sugar modifications and linkage modifications.

Certain modified or chemically-modified nucleotide monomers may be found in nature.

Translatable Molecules Containing One or More UNA Monomers

Aspects of this invention provide structures and compositions for translatable molecules that are oligomeric compounds containing one or more UNA monomers. The translatable oligomers can be active agents for pharmaceutical compositions. In some embodiments, the translatable oligomers encode human AGL or a variant thereof.

An oligomeric, translatable molecule of this invention may contain one or more UNA monomers. Oligomeric molecules of this invention can be used as active agents in formulations for supplying peptide and protein therapeutics. In some embodiments, the translatable oligomers encode human AGL or a variant thereof.

In some embodiments, this invention provides oligomeric, translatable compounds having a structure that incorporates novel combinations of UNA monomers with certain natural nucleotides, non-natural nucleotides, modified nucleotides, or chemically-modified nucleotides.

Translatable oligomeric compounds of this invention can have a length of from about 200 to about 12,000 bases in length. Translatable oligomeric compounds of this invention can have a length of about 1000, 2000, 3000, 4000, 5000, 6000, 7000, 8000, or about 9000 bases. In some embodiments, translatable oligomeric compounds of this invention can have a length of about 4000, 4100, 4200, 4300, 4400, 4500, 4600, 4700, 4800, 4900, 5000, 5100, 5200, 5300, 5400, or about 5500 bases. In an exemplary embodiment, the translatable oligomeric compound of the invention has a length of about 5000 bases.

In further aspects, the oligomeric, translatable compounds of this invention which comprise one or more UNA monomers can be pharmacologically active molecules. A translatable oligomeric molecule can be used as an active pharmaceutical ingredient for generating a peptide or protein active agent in vitro, in vivo, or ex vivo. In an exemplary embodiment, the translatable oligomeric compound of this invention encodes human AGL or a variant thereof.

A translatable oligomeric molecule of this invention can have the structure of Formula I.

Formula I

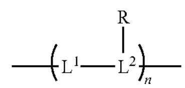

wherein $L^1$ is a linkage, n is from 200 to 12,000, and for each occurrence $L^2$ is a UNA linker group having the formula —$C^1$—$C^2$—$C^3$—, where R is attached to $C^2$ and has the formula —$OCH(CH_2R^3)R^5$, where $R^3$ is —$OR^4$, —$SR^4$, —$NR^4_2$, —$NH(C{=}O)R^4$, morpholino, morpholin-1-yl, piperazin-1-yl, or 4-alkanoyl-piperazin-1-yl, where $R^4$ is the same or different for each occurrence and is H, alkyl, a cholesterol, a lipid molecule, a polyamine, an amino acid, or a polypeptide, and where $R^5$ is a nucleobase, or $L^2(R)$ is a sugar such as a ribose and R is a nucleobase, or $L^2$ is a modified sugar such as a modified ribose and R is a nucleobase. In certain embodiments, a nucleobase can be a modified nucleobase. $L^1$ can be a phosphodiester linkage.

The base sequence of a translatable oligomeric molecule can be any sequence of nucleobases.

In some aspects, a translatable oligomeric molecule of this invention can have any number of phosphorothioate intermonomer linkages in any intermonomer location.

In some embodiments, any one or more of the intermonomer linkages of a translatable oligomeric molecule can be a phosphodiester, a phosphorothioate including dithioates, a chiral phosphorothioate, and other chemically modified forms.

When a translatable oligomeric molecule terminates in a UNA monomer, the terminal position has a 1-end, or the terminal position has a 3-end, according to the positional numbering shown above.

Enhanced Translation

A translatable molecule of this invention can incorporate a region that enhances the translational efficiency of the molecule.

In general, translational enhancer regions as known in the art can be incorporated into the structure of a translatable molecule to increase peptide or protein yields.

A translatable molecule containing a translation enhancer region can provide increased production of peptide or protein.

In some embodiments, a translation enhancer region can comprise, or be located in a 5' or 3' untranslated region of a translatable molecule.

Examples of translation enhancer regions include naturally-occurring enhancer regions from TEV 5'UTR and *Xenopus* beta-globin 3'UTR.

Molecular Structures and Sequences

A translatable molecule can be designed to express a target peptide or protein. In some embodiments, the target peptide or protein can be associated with a condition or disease in a subject.

In some aspects, the base sequence of a translatable molecule can include a portion that is identical to at least an effective portion or domain of a base sequence of an mRNA, where an effective portion is sufficient to impart a therapeutic activity to a translation product of the translatable molecule.

In some aspects, this invention provides active translatable molecules having a base sequence identical to at least a fragment of a native nucleic acid molecule of a cell.

In certain embodiments, the base sequence of a translatable molecule can include a portion that is identical to a base sequence of an mRNA, except for one or more base mutations. The number of mutations for the translatable molecule should not exceed an amount that would produce a translation product of the translatable molecule having substantially less activity than the mRNA.

The oligomeric, translatable UNA molecules of this invention can display a sequence of nucleobases, and can be designed to express a peptide or protein, in vitro, ex vivo, or in vivo. The expressed peptide or protein can have activity in various forms, including activity corresponding to protein expressed from a native or natural mRNA.

In some embodiments, a translatable molecule of this invention may have a chain length of about 400 to 15,000 monomers, where any monomer that is not a UNA monomer can be an N or Q monomer.

Molecular Cap Structure

A translatable molecule of this invention may have a 5'-end capped with various groups and their analogues as are known in the art. In an exemplary embodiment, the 5' cap may be a m7GpppGm cap. In further embodiments, the 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m72'dGpppG, m7,3'OmeGpppG, m7,3'dGpppG and their tetraphosphate derivatives) (see, e.g., Jemielity, J. et al., RNA 9: 1108-1122 (2003). In other embodiments, the 5' cap may be an ARCA cap (3'-OMe-m7G(5')pppG). The 5' cap may be an mCAP (m7G(5')ppp(5')G, $N^7$-Methyl-Guanosine-5'-Triphosphate-5'-Guanosine). The 5' cap may be resistant to hydrolysis.

Some examples of 5' cap structures are given in WO2015/051169A2, WO/2015/061491, and U.S. Pat. Nos. 8,093,367 and 8,304,529.

Tail Region

In some embodiments, the translatable oligomer encoding AGL comprises a tail region, which can serve to protect the mRNA from exonuclease degradation. In some embodiments, the tail region can be a polyA tail.

PolyA tails can be added using a variety of methods known in the art, e.g., using poly A polymerase to add tails to synthetic or in vitro transcribed RNA. Other methods include the use of a transcription vector to encode poly A tails or the use of a ligase (e.g., via splint ligation using a T4 RNA ligase and/or T4 DNA ligase), wherein polyA may be ligated to the 3' end of a sense RNA. In some embodiments, a combination of any of the above methods is utilized.

In some embodiments, a translatable oligomer comprises a 3' polyA tail structure. In some embodiments, the length of the polyA tail can be at least about 5, 10, 15, 20, 25, 30, 35, 40, 45, 50, 100, 200, or 300 nucleotides. In some embodiments, a 3' polyA tail contains about 5 to 300 adenosine nucleotides (e.g., about 30 to 250 adenosine nucleotides, about 60 to 220 adenosine nucleotides, about 80 to 200 adenosine nucleotides, about 90 to about 150 adenosine nucleotides, or about 100 to about 120 adenosine nucleotides). In an exemplary embodiment, the 3' polyA tail is about 100 nucleotides in length. In another exemplary embodiment, the 3' polyA tail is about 115 nucleotides in length. In another exemplary embodiment, the 3' polyA tail is about 250 nucleotides in length.

In some embodiments, the 3' polyA tail comprises one or more UNA monomers. In some embodiments, the 3' polyA tail contains 2, 3, 4, 5, 10, 15, 20, or more UNA monomers. In an exemplary embodiment, the 3' polyA tail contains 2 UNA monomers. In a further exemplary embodiment, the 3' polyA tail contains 2 UNA monomers which are found consecutively, i.e., contiguous to each other in the 3' polyA tail.

In an exemplary embodiment, the 3' polyA tail comprises or consists of a sequence shown in SEQ ID NO: 6. In another exemplary embodiment, the 3' polyA tail comprises or consists of a sequence shown in SEQ ID NO: 38. In yet another exemplary embodiment, the 3' polyA tail comprises or consists of a sequence shown in SEQ ID NO: 39.

In some embodiments, the translatable oligomer comprises a 3' polyC tail structure. In some embodiments, the length of the polyC tail can be at least about 5, 10, 15, 20, 25, 30, 35, 40, 45, 50, 100, 200, or 300 nucleotides. In some embodiments, a 3' polyC tail contains about 5 to 300 cytosine nucleotides (e.g., about 30 to 250 cytosine nucleotides, about 60 to 220 cytosine nucleotides, about 80 to about 200 cytosine nucleotides, about 90 to 150 cytosine nucleotides, or about 100 to about 120 cytosine nucleotides). In an exemplary embodiment, the 3' polyC tail is about 100 nucleotides in length. In another exemplary embodiment, the 3' polyC tail is about 115 nucleotides in length. The polyC tail may be added to the polyA tail or may substitute the polyA tail. The polyC tail may be added to the 5' end of the polyA tail or the 3' end of the polyA tail.

In some embodiments, the length of the poly A and/or poly C tail is adjusted to control the stability of a modified translatable oligomeric molecule of the invention and, thus, the transcription of protein. For example, since the length of the polyA tail can influence the half-life of a translatable molecule, the length of the polyA tail can be adjusted to modify the level of resistance of the mRNA to nucleases and thereby control the time course of polynucleotide expression and/or polypeptide production in a target cell.

5' and 3' Untranslated Regions (UTRs)

In some embodiments, the translatable oligomer encoding AGL may comprise a 5' untranslated region and/or a 3' untranslated region. As is understood in the art, the 5' and/or 3' UTR may affect an mRNA's stability or efficiency of translation. In an exemplary embodiment, the translatable oligomer comprises a 5' UTR and a 3' UTR.

In some embodiments, the translatable oligomer may comprise a 5' UTR that is at least about 25, 50, 75, 100, 125, 150, 175, 200, 300, 400, or 500 nucleotides. In some embodiments, a 5' UTR contains about 50 to 300 nucleotides (e.g., about 75 to 250 nucleotides, about 100 to 200 nucleotides, about 120 to 150 nucleotides, or about 135 nucleotides). In an exemplary embodiment, the 5' UTR is about 135 nucleotides in length.

In some embodiments, the 5' UTR is derived from an mRNA molecule known in the art to be relatively stable (e.g., histone, tubulin, globin, GAPDH, actin, or citric acid cycle enzymes) to increase the stability of the translatable oligomer. In other embodiments, a 5' UTR sequence may include a partial sequence of a CMV immediate-early 1 (IE1) gene. Examples of 5' UTR sequences may be found in U.S. Pat. No. 9,149,506. In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK, AT1G58420, mouse beta globin, mouse albumin, and a tobacco etch virus, or fragments of any of the foregoing. In an exemplary embodiment, the 5' UTR is derived from a tobacco etch virus (TEV). In a further exemplary embodiment, the 5' UTR comprises or consists of a sequence set forth in SEQ ID NO: 3. In yet another exemplary embodiment, the 5' UTR is a fragment of a sequence set forth in SEQ ID NO: 3, such as a fragment of at least 10, 20, 30, 40, 50, 60, 70, 80, 90, 100, 110, 120, or 125 contiguous nucleotides of SEQ ID NO: 3.

In some embodiments, the translatable oligomeric molecule comprises an internal ribosome entry site (IRES). As is understood in the art, an IRES is an RNA element that allows for translation initiation in an end-independent manner. In exemplary embodiments, the IRES is in the 5' UTR. In other embodiments, the IRES may be outside the 5' UTR.

In some embodiments, the translatable oligomer may comprise a 3' UTR that is at least about 25, 50, 75, 100, 125, 150, 175, 200, 300, 400, or 500 nucleotides. In some embodiments, a 3' UTR contains about 50 to 300 nucleotides (e.g., about 75 to 250 nucleotides, about 100 to 200 nucleotides, about 140 to 175 nucleotides, or about 160 nucleotides). In an exemplary embodiment, the 3' UTR is about 160 nucleotides in length.

In some embodiments, the 3' UTR comprises one or more UNA monomers. In some embodiments, the 3' UTR contains 2, 3, 4, 5, 10, 15, 20, or more UNA monomers.

Examples of 3' UTR sequences may be found in U.S. Pat. No. 9,149,506. In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *Xenopus* beta globin, or fragments of any of the foregoing In an exemplary embodiment, the 3' UTR is derived from *Xenopus* beta globin. In another exemplary embodiment, the 3' UTR is derived from *Xenopus* beta globin and contains one or more UNA monomers. In a further exemplary embodiment, the 3' UTR comprises or consists of a sequence set forth in SEQ ID NOs: 5 and 33-37. In yet another exemplary embodiment, the 3' UTR is a fragment of a sequence set forth in SEQ ID NOs: 5 and 33-37, such as a fragment of at least 10, 20, 30, 40, 50, 60, 70, 80, 90, 100, 110, 120, 130, 140, or 150 contiguous nucleotides of SEQ ID NO: 5 and 33-37.

In certain exemplary embodiments, the translatable oligomer encoding AGL comprises a 5' UTR sequence of SEQ ID NO: 3 and a 3' UTR sequence selected from SEQ ID NOs: 5 and 33-37. In some embodiments, the translatable oligomer encoding AGL further comprises a polyA tail shown in SEQ ID NO: 6, SEQ ID NO: 38, or SEQ ID NO: 39. In some embodiments, the mRNA coding sequence of AGL comprises a sequence selected from SEQ ID NOs: 7-32 or SEQ ID NOs: 41-45.

Triple Stop Codon

In some embodiments, the translatable oligomer encoding AGL may comprise a sequence immediately downstream of the CDS that creates a triple stop codon. The triple stop codon may be incorporated to enhance the efficiency of translation. In some embodiments, the transatable oligomer may comprise the sequence AUAAGUGAA (SEQ ID NO: 40) immediately downstream of a PAH CDS described herein, as exemplified in SEQ ID NOs: 7-32 or SEQ ID NOs: 41-45.

Translation Initiation Sites

In some embodiments, the translatable oligomer encoding AGL may comprise a translation initiation site. Such sequences are known in the art and include the Kozak sequence. See, for example, Kozak, Marilyn (1988) Mol. and Cell Biol., 8:2737-2744; Kozak, Marilyn (1991) J. Biol. Chem., 266:19867-19870; Kozak, Marilyn (1990) Proc Natl. Acad. Sci. USA, 87:8301-8305; and Kozak, Marilyn (1989) J. Cell Biol., 108:229-241; and the references cited therein. As is understood in the art, a Kozak sequence is a short consensus sequence centered around the translational initiation site of eukaryotic mRNAs that allows for efficient initiation of translation of the mRNA. The ribosomal translation machinery recognizes the AUG initiation codon in the context of the Kozak sequence.

In some embodiments, the translation initiation site, e.g., a Kozak sequence, is inserted upstream of the coding sequence for AGL. In some embodiments, the translation initiation site is inserted downstream of a 5' UTR. In certain exemplary embodiments, the translation initiation site is inserted upstream of the coding sequence for AGL and downstream of a 5' UTR.

As is understood in the art, the length of the Kozak sequence may vary. Generally, increasing the length of the leader sequence enhances translation.

In some embodiments, the translatable oligomer encoding AGL comprises a Kozak sequence having the sequence of SEQ ID NO: 4. In certain exemplary embodiments, the translatable oligomer encoding AGL comprises a Kozak sequence having the sequence of SEQ ID NO: 4, wherein the Kozak sequence is immediately downstream of a 5' UTR and immediately upstream of the coding sequence for AGL.

Synthesis Methods

In various aspects, this invention provides methods for synthesis of translatable messenger molecules.

Translatable molecules of this invention can be synthesized and isolated using methods disclosed herein, as well as any pertinent techniques known in the art.

Some methods for preparing nucleic acids are given in, for example, Merino, Chemical Synthesis of Nucleoside Analogues, (2013); Gait, Oligonucleotide synthesis: a practical approach (1984); Herdewijn, Oligonucleotide Synthesis, Methods in Molecular Biology, Vol. 288 (2005).

In some embodiments, a translatable molecule can be made by in vitro transcription (IVT) reaction. A mix of nucleoside triphosphates (NTP) can be polymerized using T7 reagents, for example, to yield RNA from a DNA template. The DNA template can be degraded with RNase-free DNase, and the RNA column-separated.

In some embodiments, a ligase can be used to link a synthetic oligomer to the 3' end of an RNA molecule or an RNA transcript to form a translatable molecule. The synthetic oligomer that is ligated to the 3' end can provide the functionality of a polyA tail, and advantageously provide resistance to its removal by 3'-exoribonucleases. The ligated product translatable molecule can have increased specific activity and provide increased levels of ectopic protein expression.

In certain embodiments, the ligated product of the translatable molecules of this invention can be made with an RNA transcript that has native specificity. The ligated product can be a synthetic molecule that retains the structure of the RNA transcript at the 5' end to ensure compatibility with the native specificity.

In further embodiments, the ligated product of the translatable molecules of this invention can be made with an exogenous RNA transcript or non-natural RNA. The ligated product can be a synthetic molecule that retains the structure of the RNA.

Without wishing to be bound by theory, the canonical mRNA degradation pathway in cells includes the steps: (i) the polyA tail is gradually cut back to a stub by 3' exonucleases, shutting down the looping interaction required for efficient translation and leaving the cap open to attack; (ii) decapping complexes remove the 5' cap; (iii) the unprotected and translationally incompetent residuum of the transcript is degraded by 5' and 3' exonuclease activity.

Embodiments of this invention involve new translatable structures which can have increased translational activity over a native transcript. Among other things, translatable molecules herein may prevent exonucleases from trimming back the polyA tail in the process of de-adenylation.

Embodiments of this invention provide structures, compositions and methods for translatable molecules. Embodiments of this invention can provide translatable molecules containing one or more UNA monomers and having increased functional half-life.

It has been found that ligation of a synthetic oligomer to the 3' end of an mRNA transcript can surprisingly be accomplished with high conversion of the mRNA transcript to the ligation product.

As used herein, the terms polyA tail and polyA oligomer refer to an oligomer of monomers, wherein the monomers can include nucleotides based on adenine, UNA monomers, naturally-occurring nucleotides, modified nucleotides, or nucleotide analogues.

Oligomers for ligation to the 3' end of an RNA may be from 2 to 120 monomers in length, or from 3 to 120 monomers in length, or from 4 to 120 monomers in length, or from 5 to 120 monomers in length, or longer. In an exemplary embodiment, the oligomer for ligation is about 30 monomers in length.

Lipid-Based Formulations

Lipid-based formulations have been increasingly recognized as one of the most promising delivery systems for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and to deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin R A-shRNA). Cationic lipids, such as DOTAP, (1,2-dioleoyl-3-trimethylammonium-propane) and DOTMA (N-[1-(2,3-dioleoyloxy)propyl]-N,N,N-trimethyl-ammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv Rev. 2014 February; 66: 110-116.)

According to some embodiments, the expressible polynucleotides and heterologous mRNA constructs described herein are lipid formulated. The lipid formulation is preferably selected from, but not limited to, liposomes, lipoplexes, copolymers, such as PLGA, and lipid nanoparticles. In one preferred embodiment, a lipid nanoparticle (LNP) comprises:

(a) a nucleic acid,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In one embodiment, the lipid nanoparticle formulation consists of (i) at least one cationic lipid; (ii) a neutral lipid; (iii) a sterol, e.g., cholesterol; and (iv) a PEG-lipid, in a molar ratio of about 20-60% cationic lipid:5-25% neutral lipid:25-55% sterol; 0.5-15% PEG-lipid.

Thiocarbamate and Carbamate-Containing Lipid Formulations

Some examples of lipids and lipid compositions for delivery of an active molecule of this invention are given in WO/2015/074085 and U.S. Ser. No. 15/387,067, each of which is hereby incorporated by reference in its entirety. In certain embodiments, the lipid is a compound of the following formula:

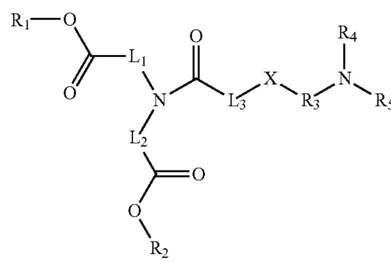

wherein $R_1$ and $R_2$ both consist of a linear alkyl consisting of 1 to 14 carbons, or an alkenyl or alkynyl consisting of 2 to 14 carbons;

$L_1$ and $L_2$ both consist of a linear alkylene or alkenylene consisting of 5 to 18 carbons, or forming a heterocycle with N;

X is S;

$L_3$ consists of a bond or a linear alkylene consisting of 1 to 6 carbons, or forming a heterocycle with N;

$R_3$ consists of a linear or branched alkylene consisting of 1 to 6 carbons; and $R_4$ and $R_5$ are the same or different, each consisting of a hydrogen or a linear or branched alkyl consisting of 1 to 6 carbons;

or a pharmaceutically acceptable salt thereof.

The lipid formulation may contain one or more ionizable cationic lipids selected from among the following:

ATX-001

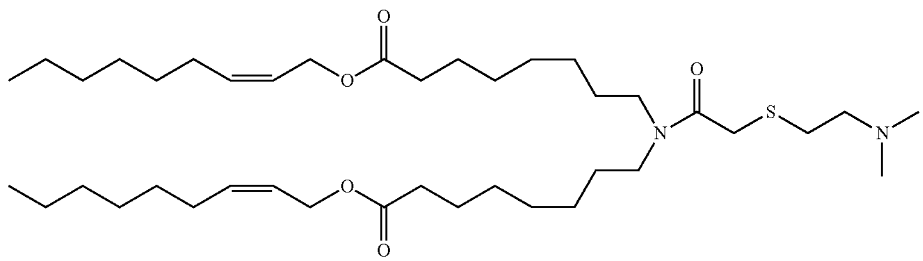

ATX-002

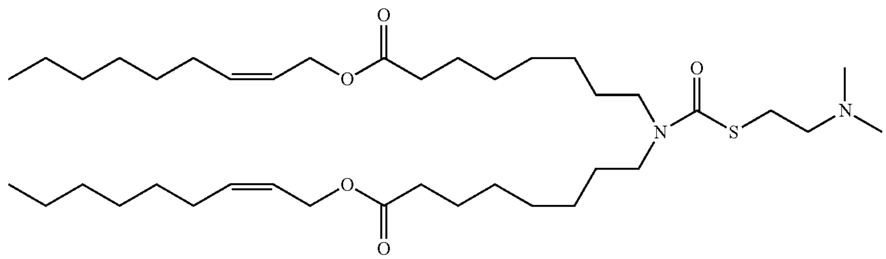

ATX-003

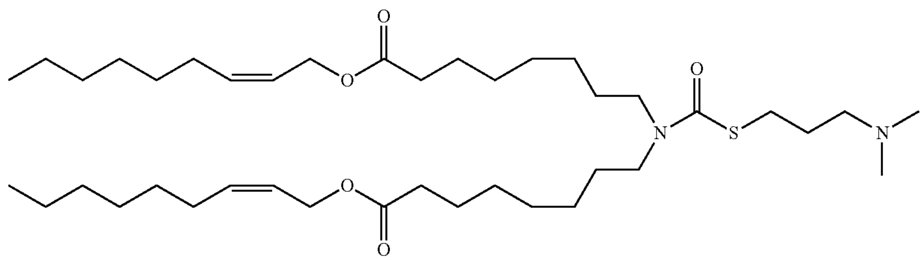

-continued
ATX-004
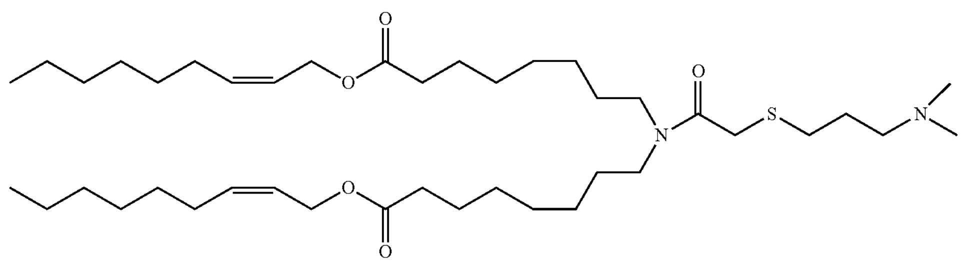
ATX-005
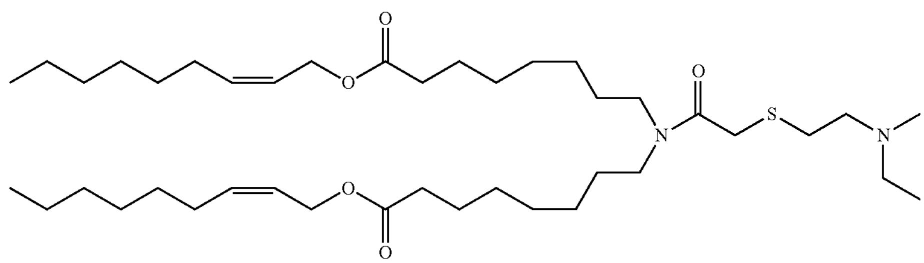
ATX-006
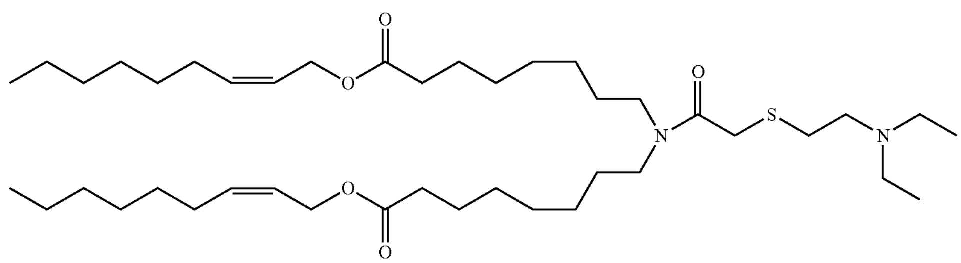
ATX-007
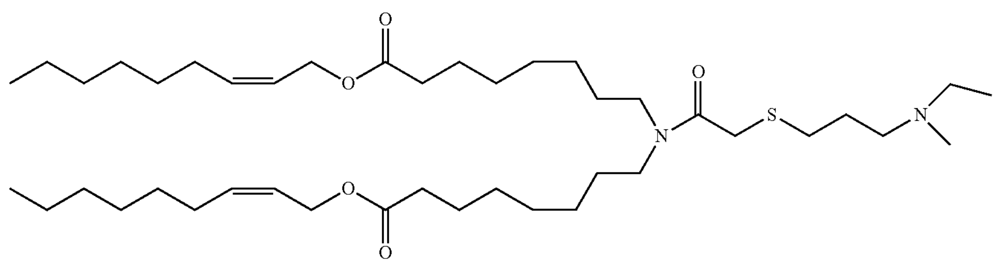
ATX-008
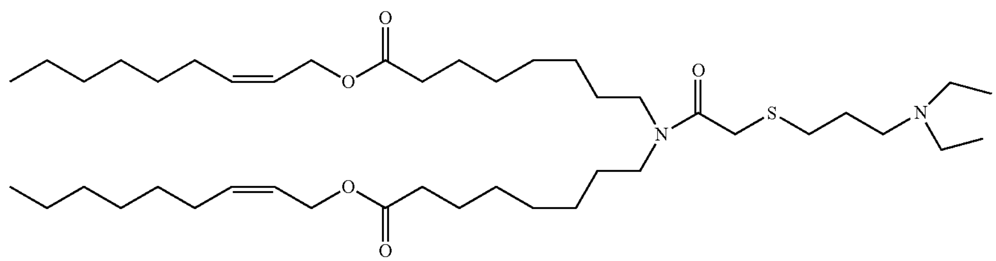
ATX-009
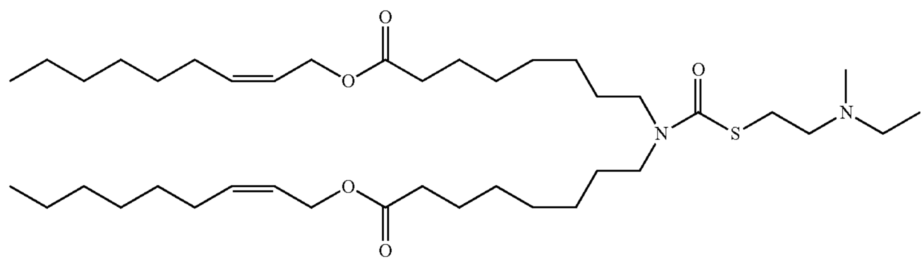

-continued
ATX-010
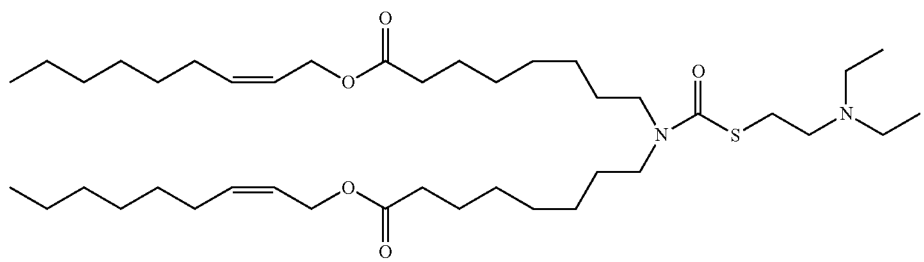
ATX-011
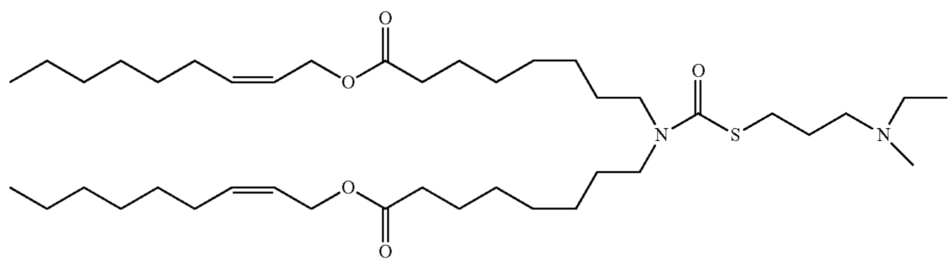
ATX-012
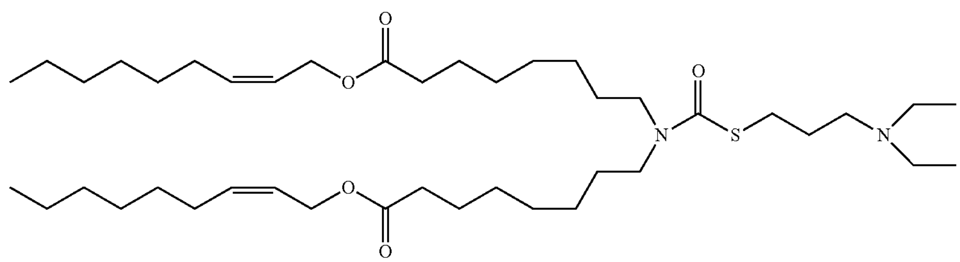
ATX-013
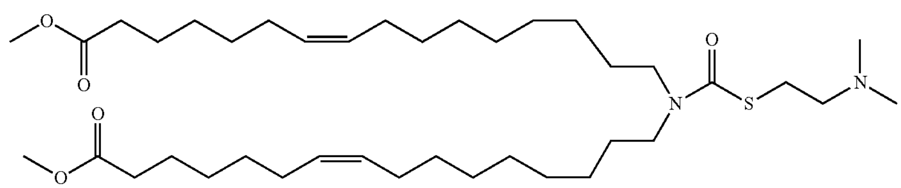
ATX-014
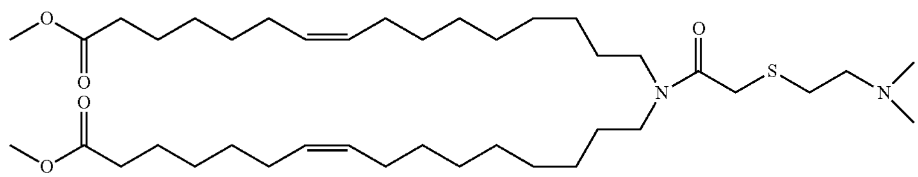
ATX-015
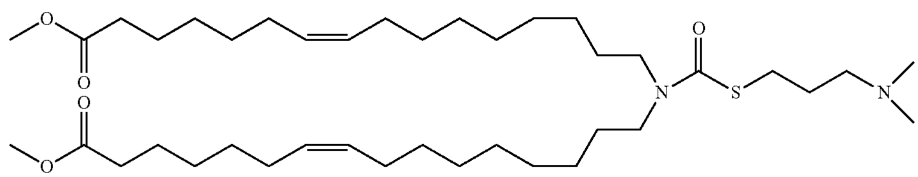
ATX-016
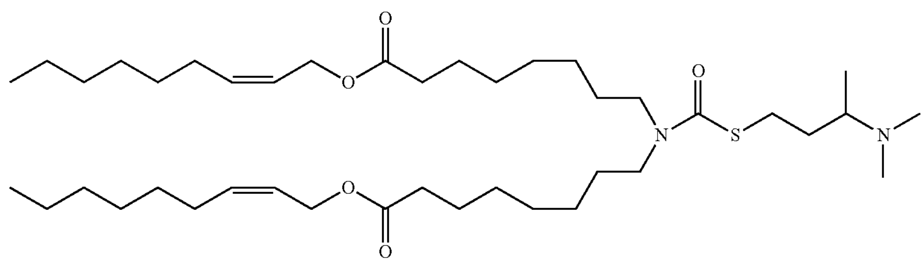

-continued
ATX-017
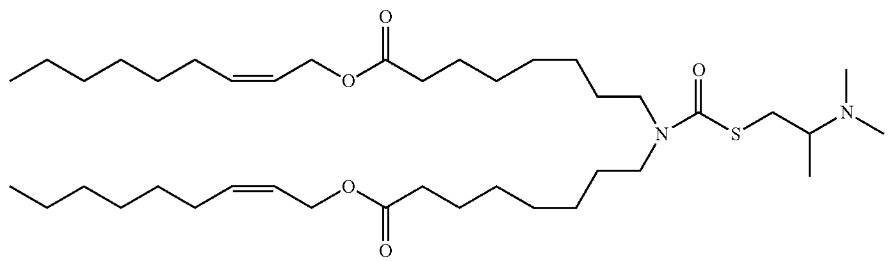
ATX-018
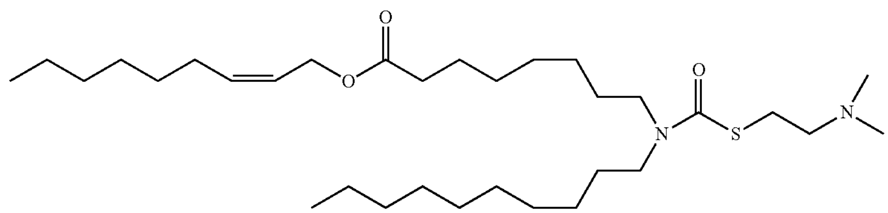
ATX-019
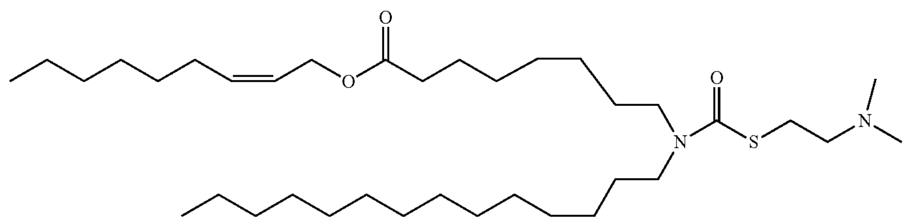
ATX-020
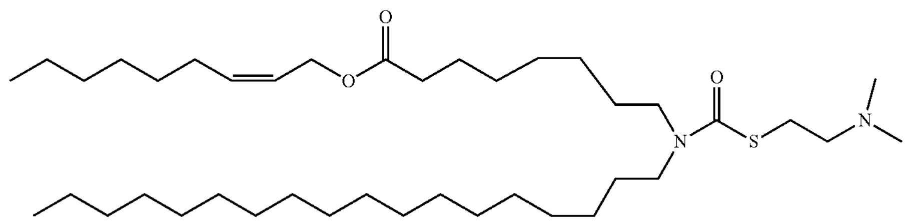
ATX-021
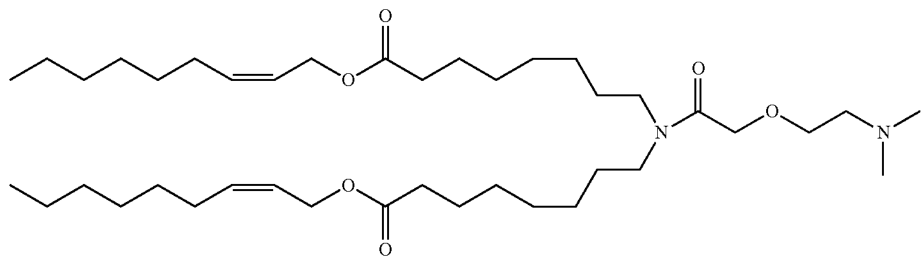
ATX-022
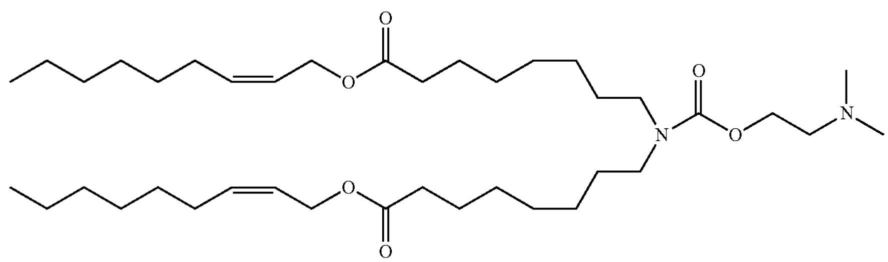

-continued
ATX-023
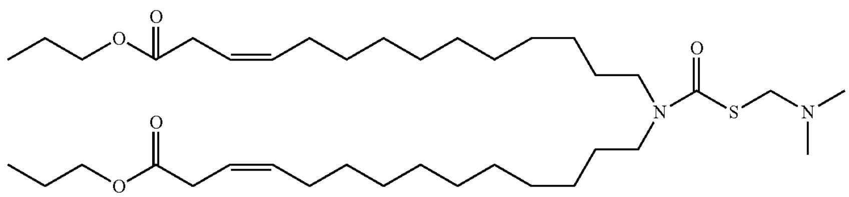
ATX-024
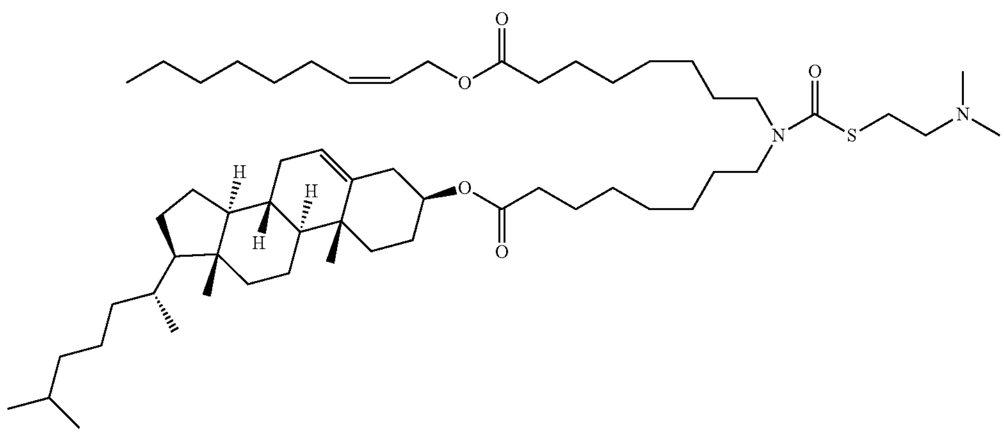
ATX-025
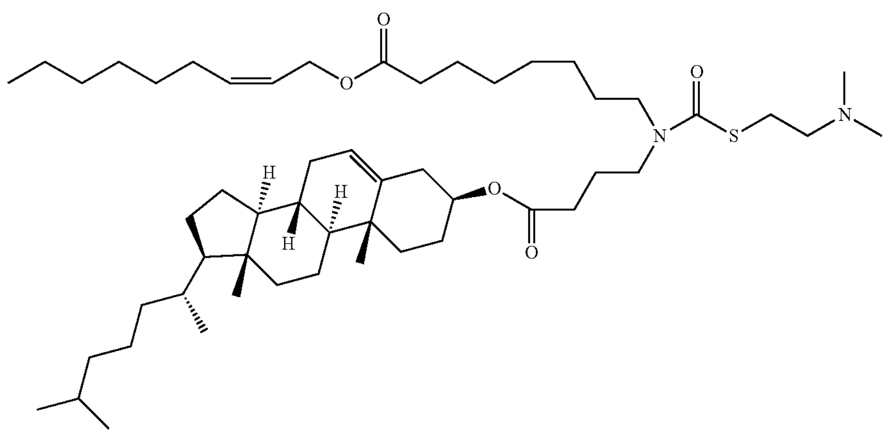
ATX-026
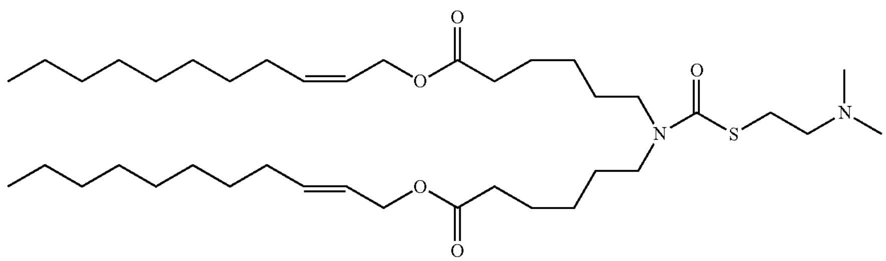
ATX-027
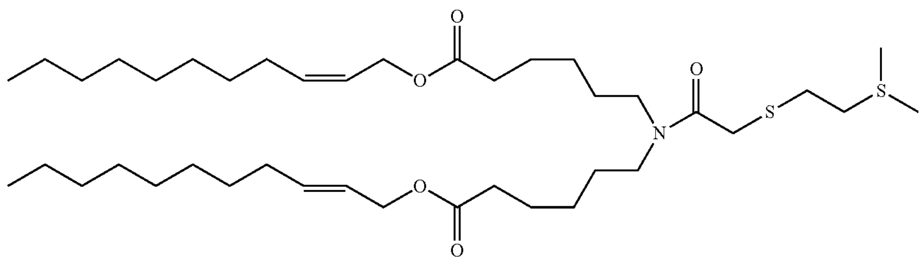

-continued
ATX-028
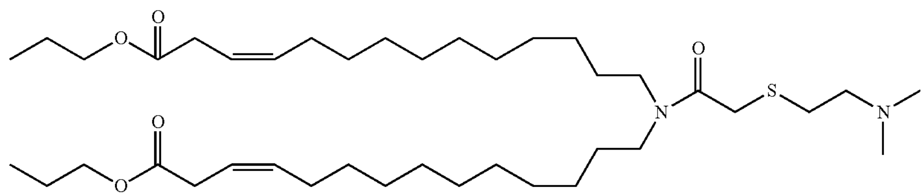
ATX-031
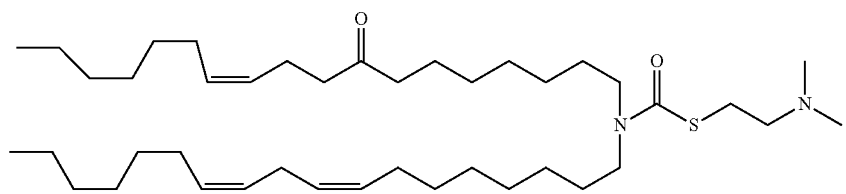
ATX-032
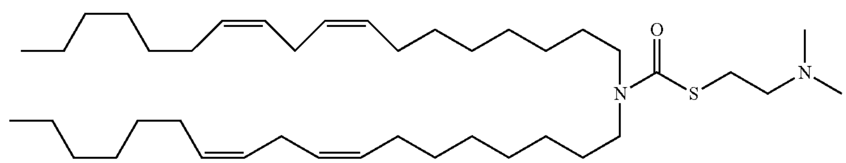
ATX-081
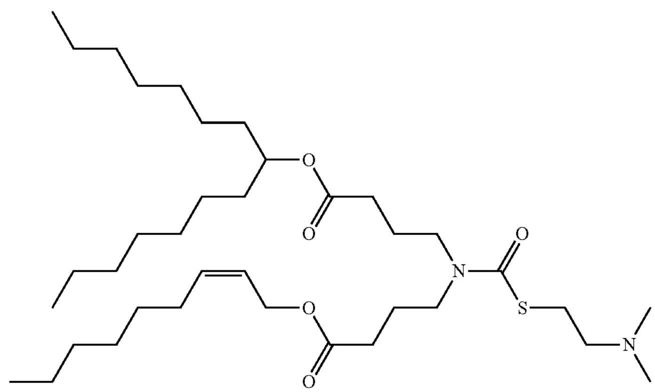
ATX-095
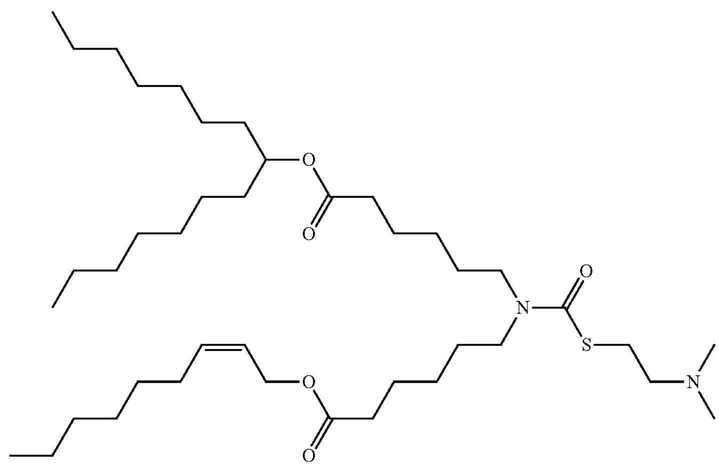

-continued

ATX-0126

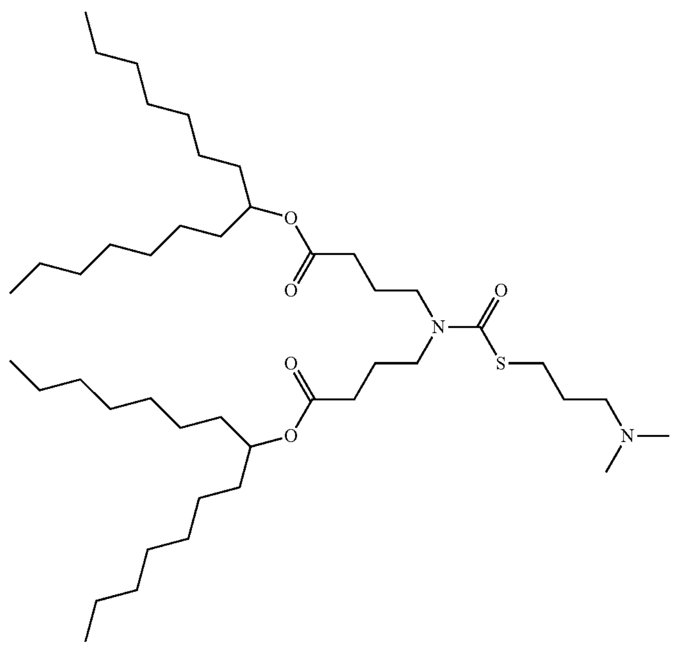

Cationic Lipids

The lipid nanoparticle preferably includes a cationic lipid suitable for forming a lipid nanoparticle. Preferably, the cationic lipid carries a net positive charge at about physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.CI), 1,2-Dilinoleoyl-3-trimethylaminopropane chloride salt (DLin-TAP.CI), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DM A), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination of any of the foregoing. Other cationic lipids include, but are not limited to, N,N-distearyl-N,N-dimethylammonium bromide (DDAB), 3P—(N—(N',N'-dimethylaminoethane)-carbamoyl)cholesterol (DC-Choi), N-(1-(2,3-dioleyloxy)propyl)-N-2-(spermine-carboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al, PNAS, 107(5), 1864-69, 2010. Other suitable amino lipids include those having alternative fatty acid groups and other dialkylamino groups, including those, in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In a further preferred embodiment, the LNP comprises the cationic lipid with formula (III) according to the patent application PCT/EP2017/064066. In this context, the disclosure of PCT/EP2017/064066 is also incorporated herein by reference.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention. In certain embodiments, the protonatable lipids have a pKa of the protonatable group in the range of about 4 to about 11, e.g., a pKa of about 5 to about 7.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.10%, about 50% or about 40% on a molar basis (based upon 100% total moles of lipid in the lipid nanoparticle). In one embodiment, the ratio of cationic lipid to nucleic acid is from about 3 to about 15, such as from about 5 to about 13 or from about 7 to about 11.

Pharmaceutical Compositions

In some aspects, this invention provides pharmaceutical compositions containing a translatable compound and a pharmaceutically acceptable carrier.

A pharmaceutical composition can be capable of local or systemic administration. In some aspects, a pharmaceutical composition can be capable of any modality of administration. In certain aspects, the administration can be by any route, including intravenous, subcutaneous, pulmonary, intramuscular, intraperitoneal, dermal, oral, inhalation or nasal administration.

Embodiments of this invention include pharmaceutical compositions containing a translatable compound in a lipid formulation.

In some embodiments, a pharmaceutical composition may comprise one or more lipids selected from cationic lipids, anionic lipids, sterols, pegylated lipids, and any combination of the foregoing. In some embodiments, the pharmaceutical composition containing a translatable compound comprises a cationic lipid, a phospholipid, cholesterol, and a pegylated lipid.

In certain embodiments, a pharmaceutical composition can be substantially free of liposomes.

In further embodiments, a pharmaceutical composition can include nanoparticles.

Some examples of lipids and lipid compositions for delivery of an active molecule of this invention are given in WO/2015/074085, which is hereby incorporated by reference in its entirety. In certain embodiments, the lipid is a cationic lipid. In some embodiment, the cationic lipid comprises a compound of formula II:

Formula II

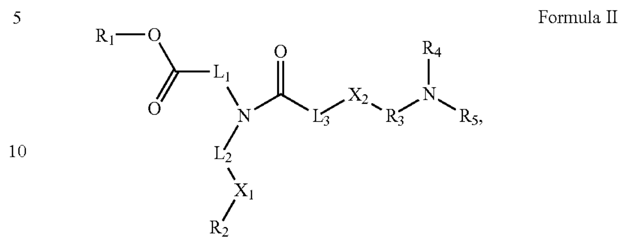

in which $R_1$ and $R_2$ are the same or different, each a linear or branched alkyl, alkenyl, or alkynyl, $L_1$ and $L_2$ are the same or different, each a linear alkyl having at least five carbon atoms, or form a heterocycle with the N, $X_1$ is a bond, or is —CO—O— whereby $L_2$-CO—O—$R_2$ is formed $X_2$ is S or O, $L_3$ is a bond or a lower alkyl, $R_3$ is a lower alkyl, $R_4$ and $R_5$ are the same or different, each a lower alkyl. What is also described herein is the compound of formula II, in which $L_3$ is absent, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is absent, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is absent, $R_1$ and $R_2$ each consists of an alkenyl of at least nine carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is methylene, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is methylene, $R_1$ and $R_2$ each consists of at least nine carbon atoms, $R_3$ is ethylene or n-propylene, $R_4$ and $R_5$ are each methyl, $L_1$ and $L_2$ each consists of a linear alkyl having at least seven carbon atoms. What is also described herein is the compound of formula II, in which $L_3$ is methylene, $R_1$ consists of an alkenyl having at least nine carbon atoms and $R_2$ consists of an alkenyl having at least seven carbon atoms, $R_3$ is n-propylene, $R_4$ and $R_5$ are each methyl, $L_1$ and $L_2$ each consists of a linear alkyl having at least seven carbon atoms. What is also described herein is the compound of formula II, in which $L_3$ is methylene, $R_1$ and $R_2$ each consists of an alkenyl having at least nine carbon atoms, $R_3$ is ethylene, $R_4$ and $R_5$ are each methyl, $L_1$ and $L_2$ each consists of a linear alkyl having at least seven carbon atoms.

In exemplary embodiments, the cationic lipid comprises a compound of selected from the group consisting of ATX-001, ATX-002, ATX-003, ATX-004, ATX-005, ATX-006, ATX-007, ATX-008, ATX-009, ATX-010, ATX-011, ATX-012, ATX-013, ATX-014, ATX-015, ATX-016, ATX-017, ATX-018, ATX-019, ATX-020, ATX-021, ATX-022, ATX-023, ATX-024, ATX-025, ATX-026, ATX-027, ATX-028, ATX-029, ATX-030, ATX-031, ATX-032, ATX-081, ATX-095, and ATX-126, or a pharmaceutically acceptable salt thereof.

In certain exemplary embodiments, the cationic lipid comprises ATX-002, ATX-081, ATX-095, or ATX-126.

In some embodiments, the cationic lipid or a pharmaceutically acceptable salt thereof, may be presented in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a translatable compound of the present invention. The lipid composition preferably further comprises a translatable compound of the present invention and a neutral lipid or a polymer. The lipid composition preferably encapsulates the translatable compound.

In further embodiments, the cationic lipid comprises a compound of formula III:

Formula III

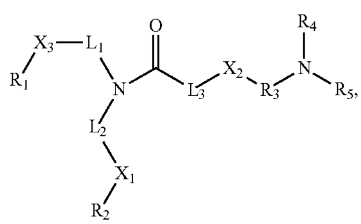

wherein $R_1$ and $R_2$ are the same or different, each a linear or branched alkyl consisting of 1 to 9 carbons, an alkenyl or alkynyl consisting of 2 to 11 carbons, or cholesteryl, $L_1$ and $L_2$ are the same or different, each a linear alkylene or alkenylene consisting of 5 to 18 carbons, $X_1$ is —CO—O— whereby $-L_2$-CO—O—$R_2$ is formed, $X_2$ is S or O, $X_3$ is —CO—O— whereby $-L_1$-CO—O—$R_1$ is formed, $L_3$ is a bond, $R_3$ is a linear or branched alkylene consisting of 1 to 6 carbons, and $R_4$ and $R_5$ are the same or different, each hydrogen or a linear or branched alkyl consisting of 1 to 6 carbons; or a pharmaceutically acceptable salt thereof. In one embodiment, $X_2$ is S. In another embodiment, $R_3$ is selected from ethylene, n-propylene, or isobutylene. In yet another embodiment, $R_4$ and $R_5$ are separately methyl, ethyl, or isopropyl. In yet another embodiment, $L_1$ and $L_2$ are the same. In yet another embodiment, $L_1$ and $L_2$ differ. In yet another embodiment, $L_1$ or $L_2$ consists of a linear alkylene having seven carbons. In yet another embodiment, $L_1$ or $L_2$ consists of a linear alkylene having nine carbons. In yet another embodiment, $R_1$ and $R_2$ are the same. In yet another embodiment, $R_1$ and $R_2$ differ. In yet another embodiment, $R_1$ and $R_2$ each consists of an alkenyl. In yet another embodiment, $R_1$ and $R_2$ each consists of an alkyl. In yet another embodiment, the alkenyl consists of a single double bond. In yet another embodiment, $R_1$ or $R_2$ consists of nine carbons. In yet another embodiment, $R_1$ or $R_2$ consists of eleven carbons. In yet another embodiment, $R_1$ or $R_2$ consists of seven carbons. In yet another embodiment, $L_3$ is a bond, $R_3$ is ethylene, $X_2$ is S, and $R_4$ and $R_5$ are each methyl. In yet another embodiment, $L_3$ is a bond, $R_3$ is n-propylene, $X_2$ is S, $R_4$ and $R_5$ are each methyl. In yet another embodiment, $L_3$ is a bond, $R_3$ is ethylene, $X_2$ is S, and $R_4$ and $R_5$ are each ethyl.

As would be appreciated by the skilled artisan, the compounds of formulas II and III form salts that are also within the scope of this disclosure. Reference to a compound of formulas II and III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula II or III contains both a basic moiety, such as, but not limited to, a pyridine or imidazole, and an acidic moiety, such as, but not limited to, a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of the formula II or III may be formed, for example, by reacting a compound of formula II or III with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, J. Pharmaceutical Sciences (1977) 66(1)1-19; P. Gould, International J. Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like. Basic nitrogen-containing groups may be quartemized with agents such as lower alkyl halides (e.g., methyl, ethyl, propyl, and butyl chlorides, bromides, and iodides), dialkyl sulfates (e g, dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure. Compounds of formula II or III can exist in unsolvated and solvated forms, including hydrated forms. In general, the solvated forms, with pharmaceutically acceptable solvents such as water, ethanol, and the like, are equivalent to the unsolvated forms for the purposes of this disclosure. Compounds of formula II or III and salts, solvates thereof, may exist in their tautomeric form (for example, as an amide or imino ether). All such tautomeric forms are contemplated herein as part of the present disclosure.

The cationic lipid compounds described herein may be combined with a translatable compound of the invention to form microparticles, nanoparticles, liposomes, or micelles. The translatable compound of the invention to be delivered by the particles, liposomes, or micelles may be in the form of a gas, liquid, or solid. The cationic lipid compound and the translatable compound may be combined with other cationic lipid compounds, polymers (synthetic or natural), surfactants, cholesterol, carbohydrates, proteins, lipids, etc. to form the particles. These particles may then optionally be combined with a pharmaceutical excipient to form a pharmaceutical composition.

In certain embodiments, the cationic lipid compounds are relatively non-cytotoxic. The cationic lipid compounds may be biocompatible and biodegradable. The cationic lipid may have a pKa in the range of approximately 5.5 to approximately 7.5, more preferably between approximately 6.0 and approximately 7.0. It may be designed to have a desired pKa between approximately 3.0 and approximately 9.0, or between approximately 5.0 and approximately 8.0.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5 to 10% phospholipid, and 1-10% PEG. The composition may contain 60-70% cationic lipid compound, 25-35% cholesterol, and 5-10% PEG. The composition may contain up to 90% cationic lipid compound and 2 to 15% helper lipid. The formulation may be a lipid particle formulation, for example containing 8-30% compound, 5-30% helper lipid, and 0-20% cholesterol; 4-25% cationic lipid, 4-25% helper lipid, 2 to 25% cholesterol, 10 to 35% cholesterol-PEG, and 5% cholesterol-amine; or 2-30% cationic lipid, 2-30% helper lipid, 1 to 15% cholesterol, 2 to 35% cholesterol-PEG, and 1-20% cholesterol-amine; or up to 90% cationic lipid and 2-10% helper lipids, or even 100% cationic lipid.

In some embodiments, the one or more cholesterol-based lipids are selected from cholesterol, PEGylated cholesterol and DC-Chol (N,N-dimethyl-N-ethylcarboxamidocholesterol), and 1,4-bis(3-N-oleylamino-propyl)piperazine. In an exemplary embodiment, the cholesterol-based lipid is cholesterol.

In some embodiments, the one or more pegylated lipids, i.e., PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K. In an exemplary embodiment, the PEG-modified lipid is PEGylated cholesterol.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions and methods are described, for example, in Remington's Pharmaceutical Sciences, Mack Publishing Co. (A. R. Gennaro ed. 1985), and Remington, The Science and Practice of Pharmacy, 21st Edition (2005).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause translation of a translatable molecule in a cell.

A therapeutically effective dose can be an amount of an agent or formulation that is sufficient to cause a therapeutic effect. A therapeutically effective dose can be administered in one or more separate administrations, and by different routes. As will be appreciated in the art, a therapeutically effective dose or a therapeutically effective amount is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating GSD III). For example, a therapeutically effective amount may be an amount sufficient to achieve a desired therapeutic and/or prophylactic effect. Generally, the amount of a therapeutic agent (e.g., a translatable oligomer encoding AGL) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

Methods provided herein contemplate single as well as multiple administrations of a therapeutically effective amount of the translatable compound (e.g., a translatable oligomer encoding AGL) described herein. Pharmaceutical compositions comprising a translatable compound encoding AGL can be administered at regular intervals, depending on the nature, severity and extent of the subject's condition (e.g., the severity of a subject's GSD III disease state and the associated symptoms of GSD III, and/or the subject's AGL activity levels). In some embodiments, a therapeutically effective amount of the translatable compound (e.g., a translatable oligomer encoding AGL) of the present invention may be administered periodically at regular intervals (e.g., once every year, once every six months, once every four months, once every three months, once every two months, once a month), biweekly, weekly, daily, twice a day, three times a day, four times a day, five times a day, six times a day, or continuously.

In some embodiments, the pharmaceutical compositions of the present invention are formulated such that they are suitable for extended-release of the translatable compound encoding AGL contained therein. Such extended-release compositions may be conveniently administered to a subject at extended dosing intervals. For instance, in one embodiment, the pharmaceutical compositions of the present invention are administered to a subject twice a day, daily or every other day. In some embodiments, the pharmaceutical compositions of the present invention are administered to a subject twice a week, once a week, every 10 days, every two weeks, every 28 days, every month, every six weeks, every eight weeks, every other month, every three months, every four months, every six months, every nine months or once a year. Also contemplated herein are pharmaceutical compositions which are formulated for depot administration (e.g., subcutaneously, intramuscularly) to either deliver or release a translatable compound encoding AGL over extended periods of time. Preferably, the extended-release means employed are combined with modifications made to the translatable compound encoding AGL to enhance stability.

In some embodiments, a therapeutically effective dose, upon administration, can result in serum or plasma levels of AGL of 1-1000 μg/ml, or 1-1000 ng/ml, or 1-1000 μg/ml, or more.

In some embodiments, administering a therapeutically effective dose of a composition comprising a translatable molecule of the invention can result in increased liver AGL protein levels in a treated subject. In some embodiments, administering a composition comprising a translatable molecule of the invention results in a 5%, 10%, 20%, 30%, 40%, 50%, 60%, 70%, 80%, 90%, or 95% increase in liver AGL protein levels relative to a baseline AGL protein level in the subject prior to treatment. In certain embodiments, administering a therapeutically effective dose of a composition comprising a translatable molecule of the invention will result an increase in liver AGL levels relative to baseline liver AGL levels in the subject prior to treatment. In some embodiments, the increase in liver AGL levels relative to baseline liver AGL levels will be at least 5%, 10%, 20%, 30%, 40%, 50%, 100%, 200%, or more.

In some embodiments, a therapeutically effective dose, when administered regularly, results in increased expression of AGL in the liver as compared to baseline levels prior to treatment. In some embodiments, administering a therapeutically effective dose of a composition comprising a translatable molecule of the invention results in the expression of a AGL protein level at or above about 10 ng/mg, about 20 ng/mg, about 50 ng/mg, about 100 ng/mg, about 150 ng/mg, about 200 ng/mg, about 250 ng/mg, about 300 ng/mg, about 350 ng/mg, about 400 ng/mg, about 450 ng/mg, about 500 ng/mg, about 600 ng/mg, about 700 ng/mg, about 800 ng/mg, about 900 ng/mg, about 1000 ng/mg, about 1200 ng/mg or about 1500 ng/mg of the total protein in the liver of a treated subject.

In some embodiments, administering a therapeutically effective dose of a composition comprising a translatable oligomer encoding AGL will result in reduced levels of one or more of markers selected from alanine transaminase (ALT), aspartate transaminase (AST), alkaline phosphatase (ALP), creatine phosphokinase (CPK), glycogen, and limit dextrin (i.e., a low-molecular carbohydrate produced by the hydrolysis of glycogen).

In some embodiments, a therapeutically effective dose, when administered regularly, results in a reduction of ALT, AST, ALP, and/or CPK levels in a biological sample. In some embodiments, administering a therapeutically effective dose of a composition comprising a translatable molecule of this invention results in a reduction of ALT, AST, ALP, and/or CPK levels in a biological sample (e.g., a plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline ALT, AST, ALP, and/or CPK levels before treatment. In some embodiments, the biological sample is selected from plasma, serum, whole blood, urine, or cerebrospinal fluid.

In certain exemplary embodiments, a therapeutically effective dose, when administered regularly, results in a reduction of ALT levels, e.g., as measured in units of ALT activity/liter (U/l), in a serum or plasma sample. In some embodiments, administering a therapeutically effective dose of a composition comprising a translatable molecule of this invention results in a reduction of ALT levels in a biological sample (e.g., a plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline ALT levels before treatment. In an exemplary embodiment, administering a therapeutically effective dose of a composition comprising a translatable molecule of this invention results in a reduction of ALT levels in a biological sample (e.g., a plasma or serum sample) by at least about 50% as compared to baseline ALT levels before treatment. In a further exemplary embodiment, ALT levels are measured after fasting, e.g., after 6, 8, 10, 12, 18, or 24 hours of fasting.

In other exemplary embodiments, a therapeutically effective dose, when administered regularly, results in a reduction of AST levels, e.g., as measured in units of AST activity/liter (U/l), in a serum or plasma sample. In some embodiments, administering a therapeutically effective dose of a composition comprising a translatable molecule of this invention results in a reduction of AST levels in a biological sample (e.g., a plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline AST levels before treatment. In an exemplary embodiment, administering a therapeutically effective dose of a composition comprising a translatable molecule of this invention results in a reduction of AST levels in a biological sample (e.g., a plasma or serum sample) by at least about 50% as compared to baseline AST levels before treatment. In a further exemplary embodiment, AST levels are measured after fasting, e.g., after 6, 8, 10, 12, 18, or 24 hours of fasting.

Measurements of ALT, AST, ALP, and/or CPK levels can be made using any method known in the art, e.g., using a Fuji Dri-Chem Clinical Chemistry Analyzer FDC 3500 as described in Liu et al., 2014, *Mol Genet andMetabolism* 111: 467-76.

In other exemplary embodiments, a therapeutically effective dose, when administered regularly, results in a reduction of glycogen levels in a biological sample. In some embodiments, administering a therapeutically effective dose of a composition comprising a translatable molecule of this invention results in a reduction of glycogen accumulation in a biological sample (e.g., a liver sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline glycogen levels before treatment. In some embodiments, the biological sample is a portion of an organ selected from liver, heart, diaphragm, quadriceps, and gastrocnemius. In an exemplary embodiment, the biological sample is a liver section, e.g., a section of hepatocytes.

In other exemplary embodiments, a therapeutically effective dose, when administered regularly, results in a reduction of limit dextrin levels in a biological sample. In some embodiments, administering a therapeutically effective dose of a composition comprising a translatable molecule of this invention results in a reduction of limit dextrin accumulation in a biological sample (e.g., a liver sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline limit dextrin levels before treatment. In some embodiments, the biological sample is a portion of an organ selected from liver, heart, diaphragm, quadriceps, and gastrocnemius. In an exemplary embodiment, the biological sample is a liver section, e.g., a section of hepatocytes. In a further exemplary embodiment, a therapeutically effective dose, when administered regularly, results in at least a 50%, 60%, 70%, or 80% reduction of limit dextrin levels in a liver sample as compared to baseline limit dextrin levels before treatment.

In further embodiments, a therapeutically effective dose, when administered regularly, delays the onset of liver fibrosis in a treated subject. In some embodiments, a therapeutically effective dose, when administered regularly, slows the development of liver fibrosis or reduces the amount of liver fibrosis in a subject afflicted with GSD III.

A therapeutically effective dose of an active agent (e.g., a translatable oligomer encoding AGL) in vivo can be a dose of about 0.001 to about 500 mg/kg body weight. For instance, the therapeutically effective dose may be about 0.001-0.01 mg/kg body weight, or 0.01-0.1 mg/kg, or 0.1-1 mg/kg, or 1-10 mg/kg, or 10-100 mg/kg. In some embodiments, a translatable oligomer encoding AGL is provided at a dose ranging from about 0.1 to about 10 mg/kg body weight, e.g., from about 0.5 to about 5 mg/kg, from about 1 to about 4.5 mg/kg, or from about 2 to about 4 mg/kg.

A therapeutically effective dose of an active agent (e.g., a translatable oligomer encoding AGL) in vivo can be a dose of at least about 0.001 mg/kg body weight, or at least about 0.01 mg/kg, or at least about 0.1 mg/kg, or at least about 1 mg/kg, or at least about 2 mg/kg, or at least about 3 mg/kg, or at least about 4 mg/kg, or at least about 5 mg/kg, at least about 10 mg/kg, at least about 20 mg/kg, at least about 50 mg/kg, or more. In some embodiments, a translatable oligomer encoding AGL is provided at a dose of about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 5 mg/kg, or about 6, 7, 8, 9, 10, 15, 20, 25, 50, 75, or 100 mg/kg.

Nucleobase sequences shown herein are from left to right, 5' to 3', unless stated otherwise.

Transfections

In some experiments, translatable messenger molecules were transfected into Hepa1-6 or AML12 cells in 96 well plates. The MessengerMAX transfection reagent (Thermo Fisher Scientific) was used by manufacture instruction for all transfections. Other suitable cell lines include HEK293 and Hep3B cells.

An example transfection protocol in vitro was as follows:

Plate hepatocyte Hepa1-6 cells 5000 cells per well in 96 well plate at least 8 hours before transfection.

Replace 90 μL DMEM medium containing 10% FBS and Non-essential amino acid) adding 90 μL into each well of 96 well plate immediately before beginning the transfection experiment.

Prepare MessengerMAX transfection reagent (Thermo Fisher Scientific) translatable molecule complex according to manufacturer's instruction.

Transfer 10 μL of the complex into a well containing the cells in the 96-well plate.

Collect the medium after desired time points and add 100 μL fresh medium into each well. Medium will be kept at −80° C. until an ELISA assay for AGL is performed using the standard manufacturer protocol.

An example of a transfection protocol in vivo was as follows:

The translatable molecule is formulated with nanoparticles.

Inject the nanoparticle-formulated translatable molecule (1 mg/kg) into BL57BL/c mice (4-6 week-old) via standard i.v. injection in the lateral tail vein.

Collect approximately 50 μL of blood in a Heparin-coated microcentrifuge tube at a suitable time post-injection.

Centrifuge at 3,000×g for 10 minutes at 4° C.

Transfer the supernatant (plasma) into a fresh microcentrifuge tube. Plasma will be kept at −80° C. until an ELISA assay for AGL is performed using the standard manufacturer protocol.

Nanoparticle Formulations

Lipid nanoparticles can be prepared containing an mRNA, using appropriate volumes of lipids in an ethanol/aqueous buffer containing the mRNA. A Nanossemblr microfluidic device can be used for this purpose, followed by downstream processing. For example, to prepare nanoparticles, a desired amount of targeted mRNA can be dissolved into 5 mM Citric Acid buffer (pH 3.5). The lipids can be dissolved at the adequate molar ratio, in ethanol. The molar percentage ratio for the constituent lipids can be, for example, 50% ionizable lipid, 7% DSPC (1,2-distearoyl-sn-glycero-3-phosphocholine; Avanti Polar Lipids), 40% cholesterol (Avanti Polar Lipids), and 3% DMG-PEG (1,2-Dimyristoyl-sn-glycerol, methoxypolyethylene glycol, PEG chain molecular weight: 2000; NOF America Corporation). Next, the lipid and mRNA solutions can be combined in the microfluidic device (Precision NanoSystems) at a flow ratio of 1:3 (ethanol:aqueous phase). The total combined flow rate can be 12 mL/min. Lipid nanoparticles can be formed and subsequently purified by overnight dialysis using a phosphate buffer in a dialysis device (Float-a-lyzer, Spectrum Labs), followed by concentration using Amicon Ultra-15 centrifugal filters (Merck Millipore). The particle size can be determined by dynamic light scattering (ZEN3600, Malvern Instruments). An "encapsulation" efficiency can be calculated by determining the un-encapsulated mRNA content measured by the fluorescence upon the addition of RiboGreen (Molecular Probes) to the LNP slurry (Fi); then, the value was compared to the total mRNA content that is obtained upon lysis of the LNPs by 1% Triton X-100 (Ft), where percentage of "encapsulation"=(Ft−Fi)/Ft×100. Encapsulation can refer to inclusion of the mRNA in the nanoparticle, regardless of form.

In-Cell Western 96-well collagen plates were used to seed the cells at the appropriate density in DMEM/FBS culture media. At the optimal confluence, cells were transfected with the targeted mRNAs diluted in the transfection reagent mix (Messenger-Max and Opti-MEM). Cells were placed in the CO2 incubator and let them grow. At the desire timepoint, media was removed and cells were fixed in 4% fresh PFA for 20 min. After that, fixative was removed and cells were permeabilized in TBST for 5 minutes several times. When permeabilization washes are complete, cells were incubated with the blocking buffer for 45 min. Primary antibody was then added and incubated for 1 h at room temperature. Following that, cells were washed several times in TBST, and then incubated for 1 h with the secondary antibody diluted in blocking buffer and containing the CellTag 700 stain. To finalize, cells were washed several times in TBST followed by a last wash in TBS. Then, plate was imaged using the Licor detection system and data was normalized to the total number of cells labeled by the CellTag 700.

Generating Tail PCR Products

Plasmid DNA (10 ng) containing each mRNA expression construct can be used to generate the poly A tail 120 PCR products in a 50 µl PCR reaction with 2×KAPA HiFi PCR mix (KR0370) as per the manufacturer's instructions. The product can be then checked on a 2% gel from Thermo Fisher Scientific and approximately quantified based on the intensity of the low molecular weight ladder (Thermo Fisher Scientific, 10068-013), and cleaned with the Qiagen PCR purification kit and resuspended in 50 ul water.

In vitro Transcription (IVT) for Synthesis

The following protocol is for a 200 µl IVT reaction using NEB HiScribe T7 RNA polymerase reagents, which should yield about 1 mg of RNA. 2.5×NTP mix was prepared as required by thawing individual 100 mM NTP stocks (ATP, GTP, CTP, and UTP nucleotides, or chemically modified counterparts) and pooling them together. For the IVT reaction, about 2-4 µg of the template was used for a 200 µl reaction. The 10×IVT reaction buffer, the 2.5× dNTP mix, the template DNA and the T7 RNA polymerase are mixed well by pipetting and incubated at 37° C. for 4 hours. To degrade the DNA template, the IVT reaction is diluted with 700 ul of nuclease-free water and then 10× DNase I buffer and 20 ul of the RNase-free DNase I are added to the IVT mix and incubated at 37° C. for 15 minutes. The diluted (to 1 ml) and DNase treated reaction is then purified by a Qiagen RNeasy Maxi columns as per the manufacturer's instructions with a final elution in RNase-free water. The purified RNA is then quantified by UV absorbance where the A260/A280 should be about 1.8-2.2, depending on the resuspension buffer used.

Enzymatic Capping of IVT RNA

For enzymatic capping, a 50× scaled-up version of NEB's one-step capping and 2'O-methylation reaction can be used, that is suitable for treating up to 1 mg of IVT transcripts. A 10 µg RNA in a 20 µl reaction is recommended, based on the assumption that transcript length would be as short as 100 nt. However, a higher substrate-to-reaction volume is acceptable for transcripts, which can be generally longer (about 300-600 nt) in length. Before initiating the capping reaction, the RNA is denatured at 65° C. for 5 minutes and then snap chilled to relieve any secondary conformations. For the total 1 ml capping reaction, 1 mg denatured RNA in 700 µl of nuclease-free water is used along with 100 µl (10×) capping buffer, 50 µl (10 mM) GTP, 50 µl (4 mM) SAM, 50 µl of (10 U/µl) Vaccinia capping enzyme and 50 µl of mRNA cap 2'-O-methyltransferase at (50 U/µl) are combined and incubated at 37° C. for 1 hour. The resulting capped mRNA is eluted using RNase free water, re-purified on an RNeasy column, quantified by nanodrop. The mRNA is also visualized on the gel by running 500 ng of the purified product per lane in a denaturing gel after denaturation and snap-chill to remove secondary structures.

EXAMPLES

Example 1: Reference Translatable Molecule 534

In this example, a reference translatable molecule 534 was made and used for expressing human WT amylo-alpha-1, 6-glucosidase, 4-alpha-glucanotransferase (AGL). The translatable molecule comprised a 5' cap (7mGpppG), a 5' UTR of TEV, a Kozak sequence, a WT AGL CDS (SEQ ID NO: 1), a 3'UTR of *Xenopus* beta-globin, and a Poly(A) tail region consisting of 114 As (i.e., "Poly(A) 114 tail region"). The reference translatable molecule further comprised the sequence of SEQ ID NO: 40 immediately downstream of the AGL CDS. This reference translatable molecule was synthesized with $N^1$-methylpseudouridine in place of uridine.

Details of the structure of this reference translatable molecule are as follows: Tobacco Etch Virus (TEV) 5' UTR of SEQ ID NO: 3, a Kozak Sequence of SEQ ID NO: 4, a *Xenopus* beta-globin (XBG) 3' UTR of SEQ ID NO: 5, and a Poly(A) 114 Tail of SEQ ID NO: 6.

Translatable molecules in the examples below can be synthesized with the 5' cap being a m7GpppGm cap. The translatable molecules in the examples below can contain a 5'-UTR (e.g., a 5' UTR of TEV (SEQ ID NO: 3)), a translation initiation sequence (e.g., a Kozak sequence of SEQ ID NO: 4), a sequence of SEQ ID NO: 40, a 3' UTR (e.g., a 3' UTR of *Xenopus* beta-globin (SEQ ID NO: 5)), and a poly(A) tail (e.g., a polyA tail of SEQ ID NO: 6, SEQ ID NO: 38, or SEQ ID NO: 39).

Example 2: Translatable Molecules Encoding AGL

In this example, translatable molecules 522-533, 546, 730-740, and 1783-1784 were made and used for expressing human amylo-alpha-1, 6-glucosidase, 4-alpha-glucanotransferase (AGL) with advantageously increased efficiency of translation. These translatable molecules expressing human amylo-alpha-1, 6-glucosidase, 4-alpha-glucanotransferase (AGL) exhibited activity suitable for use in methods for ameliorating or treating GSD III. These translatable molecules comprised a 5' cap (7mGpppG), a 5' UTR of TEV, a Kozak sequence, an AGL CDS, and a 3'UTR of *Xenopus* beta-globin. Translatable molecules 522-533, 546, and 1783-1784 further comprise a Poly(A) 114 tail region. Translatable molecule 730 further comprises a Poly(A) 100 tail region, while translatable molecules 731-740 further comprise a Poly(A) 110 tail region. Translatable molecules 522-533, 546, 730-740, and 1783-1784 further comprise the sequence of SEQ ID NO: 40 immediately downstream of the AGL CDS. Two additional translatable molecules—2258 and 2259—were developed that are identical to 546 and 1783, respectively, except that they contain a Poly(A) 100 tail region as opposed to a Poly(A) 114 tail region. The coding sequence of 1783 and 2259 may optionally be modified to contain 12 nucleotide differences, as reflected in SEQ ID NO: 45. The translatable molecules described in this example were synthesized with $N^1$-methylpseudouridine in place of uridine The AGL CDS in each of the translatable molecules is comprised of the following sequences:

| Molecule | AGL CDS |
|---|---|
| 522 | SEQ ID NO: 7 |
| 523 | SEQ ID NO: 8 |
| 524 | SEQ ID NO: 9 |

-continued

| Molecule | AGL CDS |
|---|---|
| 525 | SEQ ID NO: 10 |
| 526 | SEQ ID NO: 11 |
| 527 | SEQ ID NO: 12 |
| 528 | SEQ ID NO: 13 |
| 529 | SEQ ID NO: 14 |
| 530 | SEQ ID NO: 15 |
| 531 | SEQ ID NO: 16 |
| 532 | SEQ ID NO: 17 |
| 533 | SEQ ID NO: 18 |
| 546 & 2258 | SEQ ID NO: 19 |
| 730 | SEQ ID NO: 20 |
| 731 | SEQ ID NO: 21 |
| 732 | SEQ ID NO: 22 |
| 733 | SEQ ID NO: 23 |
| 734 | SEQ ID NO: 24 |
| 735 | SEQ ID NO: 25 |
| 736 | SEQ ID NO: 26 |
| 737 | SEQ ID NO: 27 |
| 738 | SEQ ID NO: 28 |
| 739 | SEQ ID NO: 29 |
| 740 | SEQ ID NO: 30 |
| 1783 & 2259 | SEQ ID NO: 31 |
| 1784 | SEQ ID NO: 32 |

The translatable molecules of this example were translated in AML12 and C2C12 cells to produce human AGL.

Example 3: Translation Enhancer Based on *Xenopus* Beta-Globin 3'UTR

In this example, the structures of 3' UTR sequences for use in enhancing translational efficiency of a translatable molecule are shown.

The base sequences shown in SEQ ID NOs: 33-37 are the portion of the translatable molecule that may correspond in functionality to the 3'-UTR of *Xenopus* beta-globin. The complete translatable molecule comprises a 5' cap (m7GpppGm), 5'-UTR, and coding region (CDS) upstream of the sequence below, and a polyA tail downstream of the sequence below, each of which corresponds to the structure of a native human mRNA. As shown above, a Kozak sequence may optionally be used. Thus, a translatable molecule incorporating the fragment below can have enhanced translational efficiency. The *Xenopus* beta-globin gene sequence is shown in accession no. NM_001096347.1

Example 4: AGL Expression in Human Primary Hepatocytes

Figure 5:
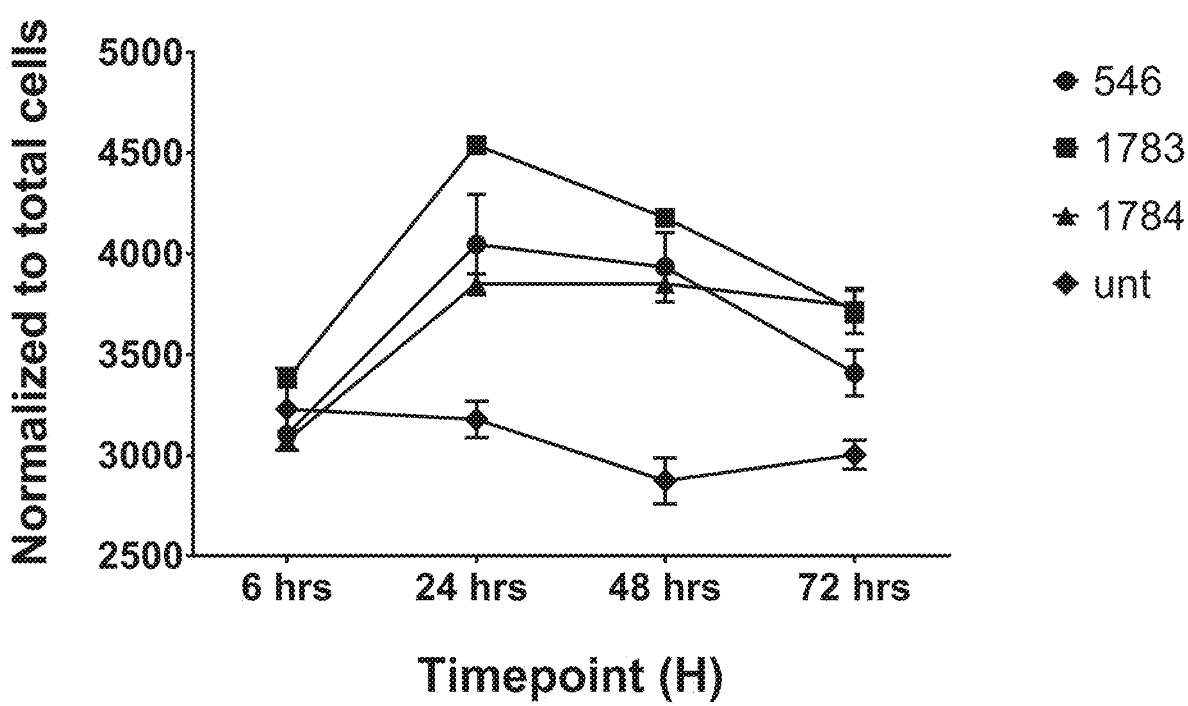
FIG. 5 shows the result of expressing human AGL from three translatable molecules: 546, 1783, and 1784. Human primary hepatocytes were transfected with codon-optimized mRNA and AGL protein expression was measured by In-Cell Western™ at 6, 24, 48, and 72 hours post-transfection. The expression of the mRNA sequences was compared with an untreated control ("unt").

In this example, human primary hepatocytes were transfected with codon-optimized mRNA molecules 546, 1783, and 1784. AGL protein expression was measured by In-Cell Western™ at 6, 24, 48, and 72 hours post-transfection. The expression of the mRNA sequences as compared with an untreated control ("unt") is shown in FIG. 5.

Example 5: In Vivo Analysis of AGL Protein Expression in Wild-Type Mice

Figure 6:
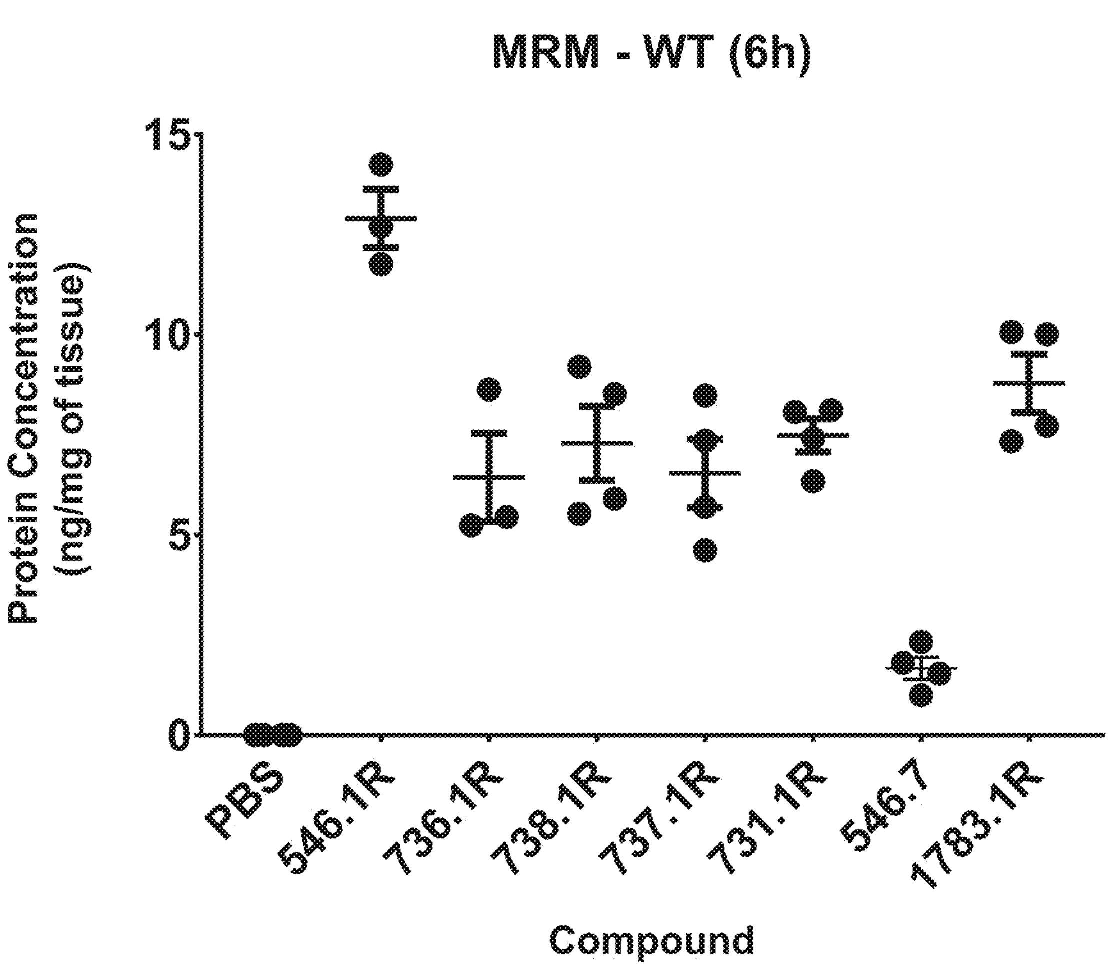
FIG. 6 shows expression of human AGL from various mRNA molecules formulated with lipid nanoparticles in wild-type C57BL/6 mice. The protein concentration (ng/mg) of exogenous human AGL expressed from the mRNA molecules in homogenates from liver biopsy samples was determined by a multiple reaction monitoring assay. The translatable molecules shown in the graph as 546.1, 736.1, 738.1, 737.1, 731.1, and 1783.1 are the same as 546, 736, 738, 737, 731, and 1783, respectively, as described in Example 2. Meanwhile, the translatable molecule 546.7 has the same nucleobase sequence as 546, which is described in Example 2, but was synthesized with 5-methoxyuridine in place of uridine instead of $N^1$-methylpseudouridine, which was used to synthesize translatable molecule 546.
Figure 7:
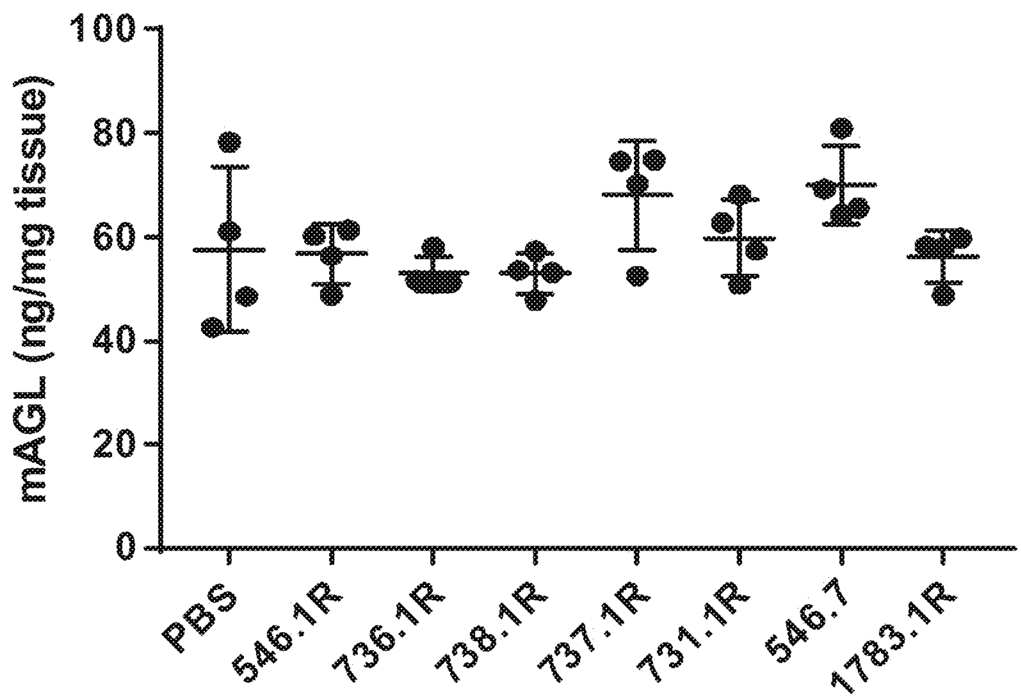
FIG. 7 shows expression of endogenous mouse AGL in wild-type C57BL/6 mice treated with various mRNA molecules formulated with lipid nanoparticles. The protein concentration (ng/mg) of endogenous mouse AGL expressed in homogenates from liver biopsy samples was determined by a multiple reaction monitoring assay. The translatable molecules shown in the graph as 546.1, 736.1, 738.1, 737.1, 731.1, and 1783.1 are the same as 546, 736, 738, 737, 731, and 1783, respectively, as described in Example 2. Meanwhile, the translatable molecule 546.7 has the same nucleobase sequence as 546, which is described in Example 2, but was synthesized with 5-methoxyuridine in place of uridine instead of $N^1$-methylpseudouridine, which was used to synthesize translatable molecule 546.

In this example, wild-type C57BL/6 mice were injected with human AGL mRNA formulated with lipid nanoparticles. Mice were sacrificed 6 hours post-injection. Liver biopsy samples were taken from mice, and human and mouse AGL protein expression in liver homogenates was analyzed. FIG. 6. shows ectopic expression of human AGL protein from various mRNA molecules. FIG. 7. shows mouse AGL protein levels, indicating similar levels of endogenous expression of mouse AGL protein across the treated mice. Translatable molecule 546.7—as shown in FIGS. 6 and 7—has an identical nucleobase sequence to translatable molecule 546, but was synthesized with 5-methoxyuridine in place of uridine instead of $N^1$-methylpseudouridine.

Example 6: mRNA Treatment Reduces Glycogen Accumulation in GSD3 Mice

Figure 8:
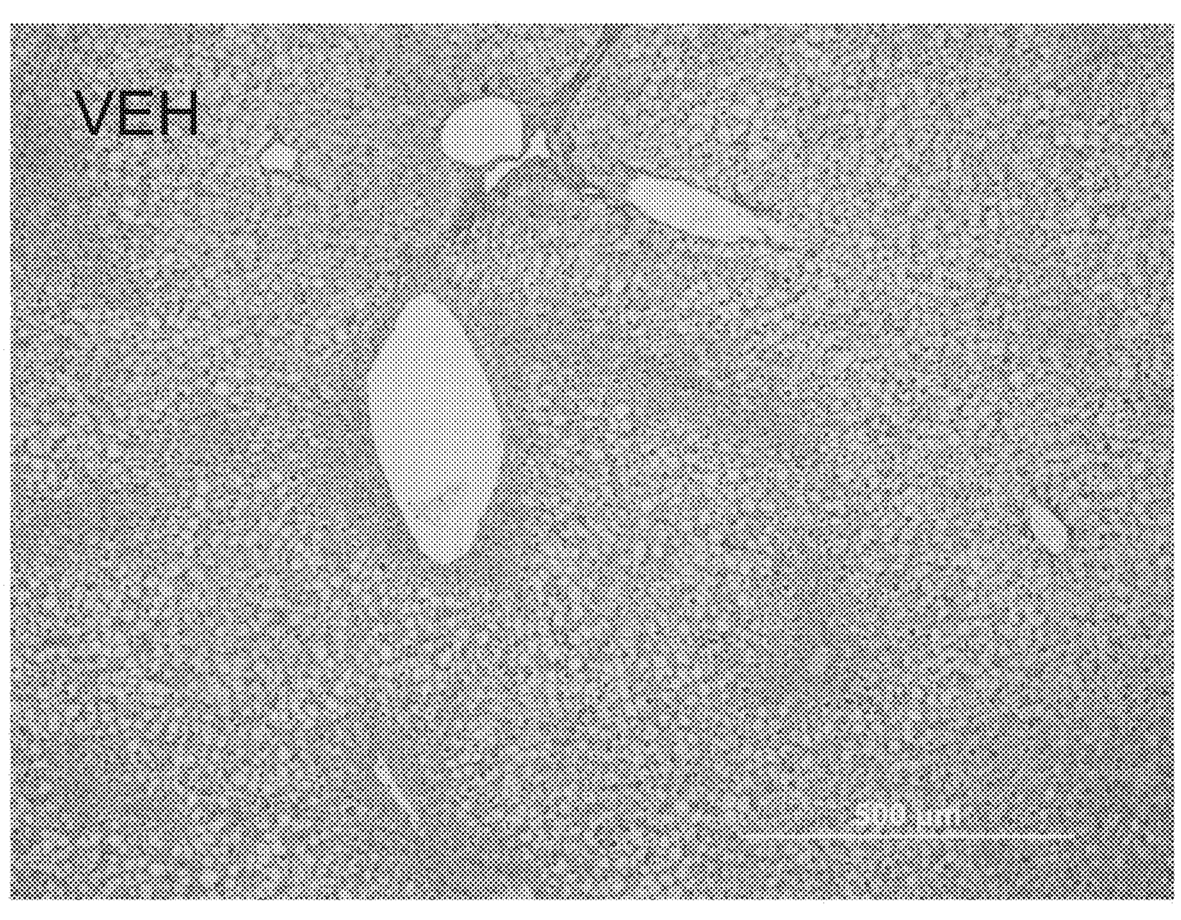
FIG. 8 shows the histopathology of a liver from an AGL knockout mice treated with vehicle ("VEH"). Marked to severe vacuolation of hepatocytes and moderate to marked increases in glycogen accumulation was observed within hepatocytes treated with vehicle.
Figure 9:
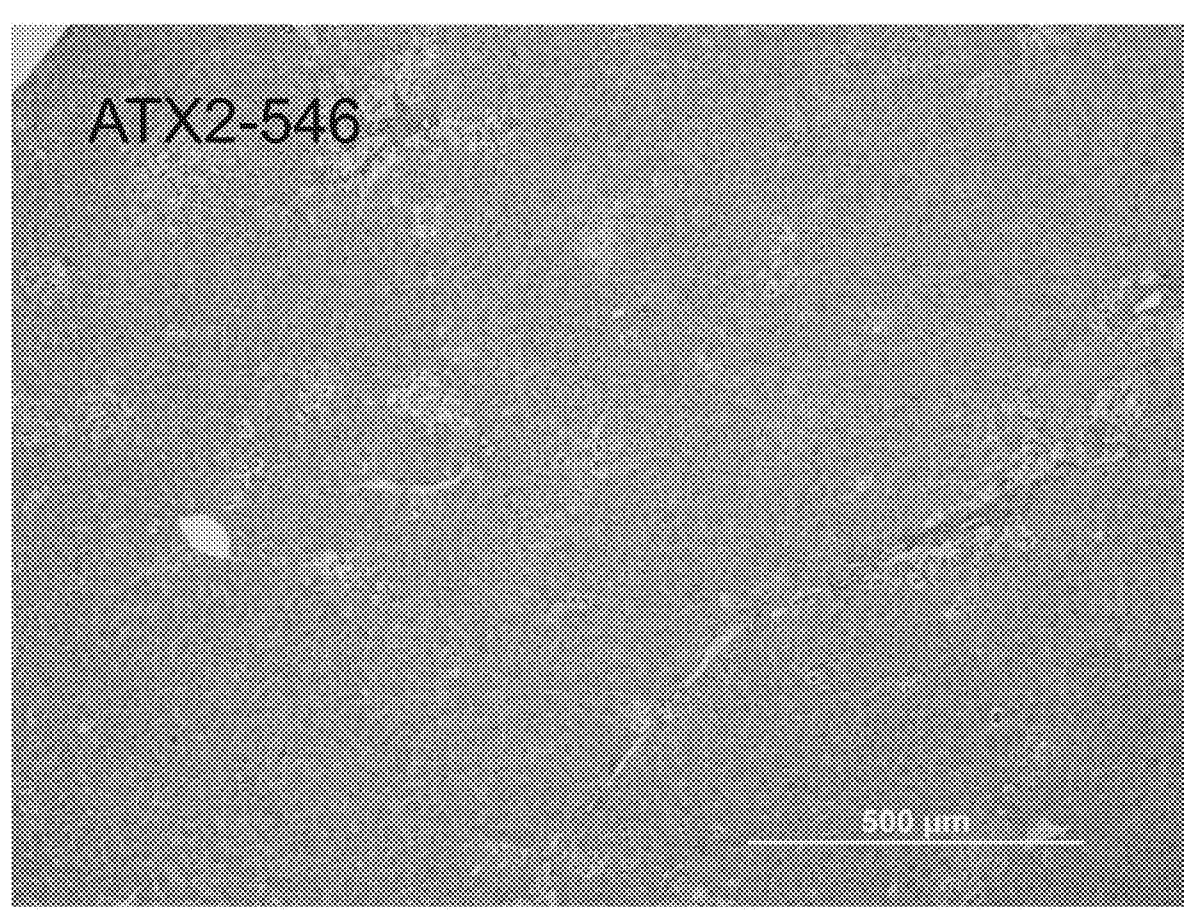
FIG. 9 shows the histopathology of a liver from an AGL knockout mice treated with translatable molecule 546 formulated with ATX2 lipid nanoparticles. Only mild to moderate vacuolation of hepatocytes and only mild to moderate increases in glycogen accumulation within hepatocytes was observed within hepatocytes treated with translatable molecule 546 formulated with ATX2 lipid nanoparticles.

In this example, AGL knockout mice were treated with vehicle or translatable molecule 546 formulated with ATX2 lipid nanoparticles. Livers from knockout mice treated with vehicle ("VEH") showed marked to severe vacuolation of hepatocytes and moderate to marked increases in glycogen accumulation within hepatocytes (FIG. 8). In contrast, livers from knockout mice treated with translatable molecule 546 formulated with ATX2 lipid nanoparticles had only mild to moderate vacuolation of hepatocytes and only mild to moderate increases in glycogen accumulation within hepatocytes (FIG. 9). Based upon the histopathology results shown in this example, there appears to be a reduction in the severity of hepatocellular vacuolization and glycogen accumulation in livers from knockout mice treated with mRNA compared with KO mice treated with vehicle.

Example 7: Additional Translatable Molecules Expressing AGL

Four additional translatable molecules—1970, 1987, SD1, and SD2—were designed with additionally modified codon-optimized human AGL coding sequences shown in SEQ ID NOs: 41, 42, 43, and 44, respectively. Translatable molecules 1970, 1987, SD1, and SD2 further comprise a 5' cap (7mGpppG), a 5' UTR of TEV, a Kozak sequence, a sequence of SEQ ID NO: 40 immediately downstream of the coding sequence, a 3' UTR of *Xenopus* beta-globin, and a Poly(A) tail region (e.g., a poly(A) 100, 110, or 114 tail region). These translatable molecules may optionally be synthesized with either $N^1$-methylpseudouridine or 5-methoxyuridine in place of uridine.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A lipid nanoparticle (LNP) comprising: (a) a polynucleotide comprising a nucleobase sequence encoding a human amylo-alpha-1, 6-glucosidase, 4-alpha-glucanotransferase (hAGL) of SEQ ID NO: 2, wherein the nucleobase sequence encoding hAGL is at least 97% identical to SEQ ID NO: 41, and wherein the polynucleotide comprises a 5' cap, a 5' untranslated region (5' UTR), a 3' untranslated region (3' UTR), and a 3' polyA tail; (b) a cationic lipid; (c) a neutral lipid; (d) a PEG-modified lipid; and (e) a sterol.

2. The LNP of claim 1, wherein at least one uridine residue in the polynucleotide is replaced with an $N^1$-methylpseudouridine residue.

3. The LNP of claim 1, wherein all uridine residues in the polynucleotide are replaced with $N^1$-methylpseudouridine residues.

4. The LNP of claim 1, wherein the 5' UTR is derived from a tobacco etch virus (TEV).

5. The LNP of claim 1, wherein the 5' UTR comprises SEQ ID NO: 3.

6. The LNP of claim 1, wherein the 3' UTR is derived from a *Xenopus* beta globin.

7. The LNP of claim 1, wherein the 3' UTR comprises SEQ ID NO: 5.

8. The LNP of claim 1, wherein the 3' polyA tail is 60 to 220 adenosine nucleotides in length.

9. The LNP of claim 1, wherein the 3' polyA tail is 100 adenosine nucleotides in length.

10. The LNP of claim 1, wherein the cationic lipid is selected from ATX-002, ATX-081, ATX-095, and ATX-126.

11. The LNP of claim 1, wherein the neutral lipid is 1,2-distearoyl-sn-glycero-3-phosphocholine (DSPC).

12. The LNP of claim 1, wherein the PEG-modified lipid is dimyristoylglycerol (DMG)-PEG-2K.

13. The LNP of claim 1, wherein the sterol is cholesterol.

14. The LNP of claim 1, wherein the lipids are provided in a molar ratio of 20-60% cationic lipid:5-25% neutral lipid:25-55% sterol:0.5-15% PEG-modified lipid.

15. A method of treating glycogen storage disease type III (GSDIII), the method comprising administering to a subject a LNP of claim 1.

16. The method of claim 15, wherein the administration is daily, weekly, biweekly, or monthly.

17. The method of claim 15, wherein the administration is intravenous or subcutaneous.

18. The method of claim 15, wherein the method comprises administration of a dose of the polynucleotide of 0.01 mg/kg to 10 mg/kg.

19. The method of claim 15, wherein the method comprises administration of a dose of the polynucleotide of at least 0.1 mg/kg.

20. The method of claim 19, wherein the administration is biweekly.

* * * * *